United States Patent
Glezer et al.

(10) Patent No.: US 11,649,452 B2
(45) Date of Patent: May 16, 2023

(54) HIGH DENSITY SEQUENCING AND MULTIPLEXED PRIMING

(71) Applicant: SINGULAR GENOMICS SYSTEMS, INC., San Diego, CA (US)

(72) Inventors: Eli N. Glezer, Del Mar, CA (US); Daan Witters, San Diego, CA (US); Niek Van Wietmarschen, San Diego, CA (US)

(73) Assignee: SINGULAR GENOMICS SYSTEMS, INC., San Diego, CA (US)

(*) Notice: Subject to any disclaimer, the term of this patent is extended or adjusted under 35 U.S.C. 154(b) by 0 days.

(21) Appl. No.: 18/046,458

(22) Filed: Oct. 13, 2022

(65) Prior Publication Data

US 2023/0111099 A1 Apr. 13, 2023

Related U.S. Application Data

(63) Continuation of application No. PCT/US2022/026587, filed on Apr. 27, 2022.

(60) Provisional application No. 63/315,339, filed on Mar. 1, 2022, provisional application No. 63/255,300, filed on Oct. 13, 2021, provisional application No. 63/180,588, filed on Apr. 27, 2021.

(51) Int. Cl.
*C12N 15/10* (2006.01)
*C12Q 1/6874* (2018.01)
*C12Q 1/6806* (2018.01)

(52) U.S. Cl.
CPC ....... *C12N 15/1068* (2013.01); *C12Q 1/6874* (2013.01); *C12Q 1/6806* (2013.01)

(58) Field of Classification Search
CPC . C12N 15/1068; C12Q 1/6806; C12Q 1/6874
See application file for complete search history.

(56) References Cited

U.S. PATENT DOCUMENTS

| | | |
|---|---|---|
| 4,318,846 A | 3/1982 | Khanna et al. |
| 4,882,245 A | 11/1989 | Gelorme et al. |
| 4,970,276 A | 11/1990 | Das et al. |
| 5,034,506 A | 7/1991 | Summerton et al. |
| 5,066,580 A | 11/1991 | Lee |
| 5,188,934 A | 2/1993 | Menchen et al. |
| 5,235,033 A | 8/1993 | Summerton et al. |
| 5,270,163 A | 12/1993 | Gold et al. |
| 5,366,860 A | 11/1994 | Bergot et al. |
| 5,475,096 A | 12/1995 | Gold et al. |
| 5,599,675 A | 2/1997 | Brenner |
| 5,688,648 A | 11/1997 | Mathies et al. |

(Continued)

FOREIGN PATENT DOCUMENTS

| | | |
|---|---|---|
| WO | WO-1989/010977 A1 | 11/1989 |
| WO | WO-1996/007669 A1 | 3/1996 |

(Continued)

OTHER PUBLICATIONS

Bains, W et al. (Dec. 7, 1988). "A novel method for nucleic acid sequence determination," *Journal of Theoretical Biology* 135(3): 303-307.

(Continued)

*Primary Examiner* — Jeremy C Flinders
(74) *Attorney, Agent, or Firm* — Mintz, Levin, Cohn, Ferris, Glovsky, Popeo, P.C.

(57) ABSTRACT

Disclosed herein, inter alia, are methods and compositions for sequencing a plurality of template nucleic acids.

21 Claims, 13 Drawing Sheets

Specification includes a Sequence Listing.

(56) References Cited

U.S. PATENT DOCUMENTS

| | | | |
|---|---|---|---|
| 5,750,341 | A | 5/1998 | Macevicz |
| 5,763,594 | A | 6/1998 | Hiatt et al. |
| 5,800,996 | A | 9/1998 | Lee et al. |
| 5,808,045 | A | 9/1998 | Hiatt et al. |
| 5,847,162 | A | 12/1998 | Lee et al. |
| 5,872,244 | A | 2/1999 | Hiatt et al. |
| 6,210,891 | B1 | 4/2001 | Nyren et al. |
| 6,232,465 | B1 | 5/2001 | Hiatt et al. |
| 6,258,568 | B1 | 7/2001 | Nyren |
| 6,274,320 | B1 | 8/2001 | Rothberg et al. |
| 6,664,079 | B2 | 12/2003 | Ju et al. |
| 6,897,012 | B2 | 5/2005 | Hada et al. |
| 6,991,888 | B2 | 1/2006 | Padmanaban et al. |
| 7,057,026 | B2 | 6/2006 | Barnes et al. |
| 7,467,632 | B2 | 12/2008 | Lee et al. |
| 7,541,444 | B2 | 6/2009 | Milton et al. |
| 7,855,054 | B2 | 12/2010 | Schneider et al. |
| 7,947,447 | B2 | 5/2011 | Zichi et al. |
| 7,964,356 | B2 | 6/2011 | Zichi et al. |
| 8,178,360 | B2 | 5/2012 | Barnes et al. |
| 10,738,072 | B1 | 8/2020 | Graham et al. |
| 2008/0000373 | A1 | 1/2008 | Petrucci-Samija et al. |
| 2010/0160478 | A1 | 6/2010 | Nilsson et al. |
| 2011/0136099 | A1 | 6/2011 | Schneider et al. |
| 2012/0115752 | A1 | 5/2012 | Zichi et al. |
| 2013/0012399 | A1 | 1/2013 | Myers et al. |
| 2015/0079351 | A1 | 3/2015 | Atasoy et al. |
| 2017/0022553 | A1 | 1/2017 | Vijayan et al. |
| 2018/0258472 | A1 | 9/2018 | Glezer |
| 2018/0274024 | A1 | 9/2018 | Ju et al. |
| 2018/0312917 | A1 | 11/2018 | Trepagnier et al. |
| 2019/0048404 | A1 | 2/2019 | Dambacher |
| 2020/0208214 | A1 | 7/2020 | Fisher et al. |
| 2021/0190668 | A1 | 6/2021 | Kovacs et al. |
| 2021/0239692 | A1 | 8/2021 | Sanders et al. |
| 2022/0259648 | A1 | 8/2022 | Witters et al. |

FOREIGN PATENT DOCUMENTS

| | | |
|---|---|---|
| WO | WO-2004/018497 A2 | 3/2004 |
| WO | WO-2004/018497 A3 | 3/2004 |
| WO | WO-2017/205336 A1 | 11/2017 |
| WO | WO-2018/148723 A1 | 8/2018 |
| WO | WO-2020/056044 A1 | 3/2020 |
| WO | WO-2020/163630 A1 | 8/2020 |

OTHER PUBLICATIONS

Beattie, WG et al. (Dec. 1995). "Hybridization of DNA targets to glass-tethered oligonucleotide probes," *Molecular Biotechnology* 4(3): 213-225.

Bentley, DR et al. (Nov. 6, 2008). "Accurate whole human genome sequencing using reversible terminator chemistry," *Nature* 456(7218): 53-59.

Bergen, K et al. (Jun. 17, 2013, e-published Jun. 3, 2013). "Structures of KOD and 9° N DNA polymerases complexed with primer template duplex," *ChemBioChem* 14(9): 1058-1062.

Bianchi, DW et al. (May 2012). "Genome-wide fetal aneuploidy detection by maternal plasma DNA sequencing," *Obstetrics & Gynecology* 119(5): 890-901.

Cayer, DM et al. (Oct. 1, 2016, e-published Jul. 20, 2016). "Mission critical: the need for proteomics in the era of next-generation sequencing and precision medicine," *Human Molecular Genetics* 25(R2): R182-R189.

Drmanac, S et al. (Jan. 1998). "Accurate sequencing by hybridization for DNA diagnostics and individual genomics," *Nature Biotechnology* 16(1): 54-58.

Eminaga, S et al. (e-published Jul. 2013). "Quantification of microRNA expression with next-generation sequencing," *Current Protocols in Molecular Biology* 103: 4.17.1-4.17.14.

Feeney, R et al. (Apr. 1, 1982). "Modification of Proteins," *Advances in Chemistry* 198: 3-55, American Chemical Society, Washington, D.C.

Fodor, Spa et al. (Feb. 15, 1991). "Light-directed, spatially addressable parallel chemical synthesis," *Science* 251(4995): 767-773.

Fuller, CW et al. (Mar. 18, 2016, e-published Apr. 18, 2016). "Real-time single-molecule electronic DNA sequencing by synthesis using polymer-tagged nucleotides on a nanopore array," *PNAS* 113(19): 5233-5238.

GenBank Accession No. DN169254 "LH_Ea04M05.f LH_Ea Solanum habrochaites cDNA clone LH_Ea04M05 5', mRNA sequence", https://www.ncbi.nlm.nih.gov/nuccore/DN169254.

Guo, J et al. (Jul. 8, 2008, e-published Jun. 30, 2008). "Four-color DNA sequencing with 3'-O-modified nucleotide reversible terminators and chemically cleavable fluorescent dideoxynucleotides," *PNAS* 105(27): 9145-9150.

Haas, K-H et al. (Aug. 30, 1999). "Functionalized coating materials based on inorganic-organic polymers," *Thin Solid Films* 351(1-2): 198-203.

International Search report dated Feb. 8, 2021, for PCT application PCT/US2020/058916, filed Nov. 4, 2020, 4 pages.

Kannan, K et al. (May 31, 2011, e-published May 12, 2011). "Recurrent chimeric RNAs enriched in human prostate cancer identified by deep sequencing," *PNAS* 108(22): 9172-77.

Kucharik, M et al. (Aug. 26, 2020). "Non-invasive prenatal testing (NIPT) by low coverage genomic sequencing: Detection limits of screened chromosomal microdeletions," *PLoS One* 15(8): e0238245.

Kukurba, KR et al. (Apr. 13, 2015). "RNA sequencing and analysis," *Cold Spring Harbor Protocols* 2015(11): 951-969.

Kumar, S et al. (Sep. 21, 2012). "PEG-labeled nucleotides and nanopore detection for single molecule DNA sequencing by synthesis," *Scientific reports* 2:684.

Maarten Altelaar, AF et al. (Dec. 4, 2012). "Next-generation proteomics: towards an integrative view of proteome dynamics," *Nature Reviews Genetics* 14: 35-48.

Maher, CA et al. (Jan. 11, 2009). "Transcriptome sequencing to detect gene fusions in cancer," *Nature* 458(7234): 97-101.

Mag, M et al. (Nov. 24, 1992). "Synthesis and selective cleavage of an oligodeoxynucleotide containing a bridged non-chiral internucleotide 3'-phosphoramidate linkage," *Tetrahedron Letters* 33(48): 7319-7322.

Norton, ME et al. (Apr. 23, 2015). "Cell-free DNA analysis for noninvasive examination of trisomy," *New England Journal of Medicine* 372(17): 1589-1597.

Raman, L et al. (Feb. 28, 2019). "WisecondorX: improved copy number detection for routine shallow whole-genome sequencing," *Nucleic Acids Research* 47(4): 1605-1614.

Ronaghi, M et al. (published Nov. 1, 1996). "Real-time DNA sequencing using detection of pyrophosphate release," *Analytical Biochemistry* 242(1): 84-89.

Ronaghi, M et al. (Jul. 17, 1998). "A sequencing method based on real-time pyrophosphate," *Science* 281(5375): 363-365.

Ronaghi, M (Jan. 2001). "Pyrosequencing sheds light on DNA sequencing," *Genome Research* 11: 3-11.

Shendure, J et al. (Sep. 9, 2005) "Accurate multiplex polony sequencing of an evolved bacterial genome," *Science* 309(5741): 1728-1732.

Southworth, MW et al. (published May 28, 1996). "Cloning of thermostable DNA polymerases from hyperthermophilic marine Archaea with emphasis on Thermococcus sp. 9 degrees N-7 and mutations affecting 3'-5' exonuclease activity," *PNAS USA* 93(11):5281-5285.

Tsao, DS et al. (Sep. 11, 2019, e-published Oct. 7, 2019). "A novel high-throughput molecular counting method with single base-pair resolution enables accurate single-gene NIPT," *Scientific Reports* 9: 14382, pp. 1-14.

Van Schendel, RV et al. (e-published Sep. 19, 2017). "Implementing non-invasive prenatal testing for aneuploidy in a national healthcare system: global challenges and national solutions," *BMC Health Services Research* 17: 1-10.

Walker, JW et al. (Oct. 1, 1988). "Photolabile 1-(2-nitrophenyl) ethyl phosphate esters of adenine nucleotide analogs. Synthesis and mechanism of photolysis," *Journal of the American Chemical Society* 110(21): 7170-7177.

Wang, Z et al. (Jan. 2009). "RNA-Seq: a revolutionary tool for transcriptomics," *Nature Reviews Genetics* 10: 57-63.

(56) References Cited

OTHER PUBLICATIONS

Written Opinion dated Oct. 24, 2019, for PCT Application No. PCT/US2019/32907, filed May 17, 2019, 12 pages.
Zhao, Q-Y et al. (e-published Dec. 14, 2011). "Optimizing de novo transcriptome assembly from short-read RNA-Seq data: a comparative study," *BMC Bioinformatics* 12(14): 1-12.

FIG. 6A

| Lane 1 | 10pM M1-Clostridium |
| --- | --- |
| Lane 2 | 10pM M5-EColi |
| Lane 3 | 10pM SP-Salmonella |
| Lane 4 | 30pM Mixed library |

FIG. 6B

Seq w/ M5b primer (E. Coli)

NaOH stripping (FC1 only)
3'-OH blocking
Primer annealing

Seq w/ M1b primer (Clostridium)

NaOH stripping (FC1 only)
3'-OH blocking
Primer annealing

Seq w/ SP primer (Salmonella)

SEQUENCE LISTING

```
Sequence total quantity: 96
SEQ ID NO: 1              moltype = DNA  length = 33
FEATURE                   Location/Qualifiers
misc_feature              1..33
                          note = Synthetic Nucleotide
source                    1..33
                          mol_type = other DNA
                          organism = synthetic construct
SEQUENCE: 1
aacgccaaac ctacggcttt acttcctgtg gct                                        33

SEQ ID NO: 2              moltype = DNA  length = 33
FEATURE                   Location/Qualifiers
misc_feature              1..33
                          note = Synthetic Nucleotide
source                    1..33
                          mol_type = other DNA
                          organism = synthetic construct
SEQUENCE: 2
tcttgagtca ttcgcagggc atgtgccaga cct                                        33

SEQ ID NO: 3              moltype = DNA  length = 33
FEATURE                   Location/Qualifiers
misc_feature              1..33
                          note = Synthetic Nucleotide
source                    1..33
```

```
                                mol_type = other DNA
                                organism = synthetic construct
SEQUENCE: 3
tcggcgttgt ctgctatcgt tcttggcact cct                              33

SEQ ID NO: 4                    moltype = DNA   length = 33
FEATURE                         Location/Qualifiers
misc_feature                    1..33
                                note = Synthetic Nucleotide
source                          1..33
                                mol_type = other DNA
                                organism = synthetic construct
SEQUENCE: 4
ggagcaataa ccataaggcc gttgacaagc cct                              33

SEQ ID NO: 5                    moltype = DNA   length = 33
FEATURE                         Location/Qualifiers
misc_feature                    1..33
                                note = Synthetic Nucleotide
source                          1..33
                                mol_type = other DNA
                                organism = synthetic construct
SEQUENCE: 5
ggcgtattgc cttggttctg gcagcctcat tgt                              33

SEQ ID NO: 6                    moltype = DNA   length = 33
FEATURE                         Location/Qualifiers
misc_feature                    1..33
                                note = Synthetic Nucleotide
source                          1..33
                                mol_type = other DNA
                                organism = synthetic construct
SEQUENCE: 6
cagcagaggg aacgatttca acttcctgtg gct                              33

SEQ ID NO: 7                    moltype = DNA   length = 33
FEATURE                         Location/Qualifiers
misc_feature                    1..33
                                note = Synthetic Nucleotide
source                          1..33
                                mol_type = other DNA
                                organism = synthetic construct
SEQUENCE: 7
ctactgcaag ggtgtctaga atgtgccaga cct                              33

SEQ ID NO: 8                    moltype = DNA   length = 33
FEATURE                         Location/Qualifiers
misc_feature                    1..33
                                note = Synthetic Nucleotide
source                          1..33
                                mol_type = other DNA
                                organism = synthetic construct
SEQUENCE: 8
gaccgactcg tgaaacgtaa tcttggcact cct                              33

SEQ ID NO: 9                    moltype = DNA   length = 33
FEATURE                         Location/Qualifiers
misc_feature                    1..33
                                note = Synthetic Nucleotide
source                          1..33
                                mol_type = other DNA
                                organism = synthetic construct
SEQUENCE: 9
acacattctt tgcgcccaga gttgacaagc cct                              33

SEQ ID NO: 10                   moltype = DNA   length = 33
FEATURE                         Location/Qualifiers
misc_feature                    1..33
                                note = Synthetic Nucleotide
source                          1..33
                                mol_type = other DNA
                                organism = synthetic construct
SEQUENCE: 10
atttcattcg acacccggtc gcagcctcat tgt                              33

SEQ ID NO: 11                   moltype = DNA   length = 33
FEATURE                         Location/Qualifiers
misc_feature                    1..33
                                note = Synthetic Nucleotide
```

```
source                   1..33
                         mol_type = other DNA
                         organism = synthetic construct
SEQUENCE: 11
tcggtgtcct tcatttcggc atccaaaccg caa                                 33

SEQ ID NO: 12            moltype = DNA  length = 33
FEATURE                  Location/Qualifiers
misc_feature             1..33
                         note = Synthetic Nucleotide
source                   1..33
                         mol_type = other DNA
                         organism = synthetic construct
SEQUENCE: 12
tccagaccgt gtacgggacg cttactgagt tct                                 33

SEQ ID NO: 13            moltype = DNA  length = 33
FEATURE                  Location/Qualifiers
misc_feature             1..33
                         note = Synthetic Nucleotide
source                   1..33
                         mol_type = other DNA
                         organism = synthetic construct
SEQUENCE: 13
tcctcacggt tcttgctatc gtctgttgcg gct                                 33

SEQ ID NO: 14            moltype = DNA  length = 33
FEATURE                  Location/Qualifiers
misc_feature             1..33
                         note = Synthetic Nucleotide
source                   1..33
                         mol_type = other DNA
                         organism = synthetic construct
SEQUENCE: 14
tcccgaacag ttgccggaat accaataacg agg                                 33

SEQ ID NO: 15            moltype = DNA  length = 33
FEATURE                  Location/Qualifiers
misc_feature             1..33
                         note = Synthetic Nucleotide
source                   1..33
                         mol_type = other DNA
                         organism = synthetic construct
SEQUENCE: 15
tgttactccg acggtcttgg ttccgttatg cgg                                 33

SEQ ID NO: 16            moltype = DNA  length = 33
FEATURE                  Location/Qualifiers
misc_feature             1..33
                         note = Synthetic Nucleotide
source                   1..33
                         mol_type = other DNA
                         organism = synthetic construct
SEQUENCE: 16
tcggtgtcct tcaactttag caagggagac gac                                 33

SEQ ID NO: 17            moltype = DNA  length = 33
FEATURE                  Location/Qualifiers
misc_feature             1..33
                         note = Synthetic Nucleotide
source                   1..33
                         mol_type = other DNA
                         organism = synthetic construct
SEQUENCE: 17
tccagaccgt gtaagatctg tgggaacgtc atc                                 33

SEQ ID NO: 18            moltype = DNA  length = 33
FEATURE                  Location/Qualifiers
misc_feature             1..33
                         note = Synthetic Nucleotide
source                   1..33
                         mol_type = other DNA
                         organism = synthetic construct
SEQUENCE: 18
tcctcacggt tctaatgcaa agtgctcagc cag                                 33

SEQ ID NO: 19            moltype = DNA  length = 33
FEATURE                  Location/Qualifiers
misc_feature             1..33
```

```
                    note = Synthetic Nucleotide
source              1..33
                    mol_type = other DNA
                    organism = synthetic construct
SEQUENCE: 19
tcccgaacag ttgagacccg cgtttcttac aca                                   33

SEQ ID NO: 20       moltype = DNA  length = 33
FEATURE             Location/Qualifiers
misc_feature        1..33
                    note = Synthetic Nucleotide
source              1..33
                    mol_type = other DNA
                    organism = synthetic construct
SEQUENCE: 20
tgttactccg acgctggccc acagcttact tta                                   33

SEQ ID NO: 21       moltype = DNA  length = 33
FEATURE             Location/Qualifiers
misc_feature        1..33
                    note = Synthetic Nucleotide
source              1..33
                    mol_type = other DNA
                    organism = synthetic construct
SEQUENCE: 21
ttgcggtttg gatgccgaaa tgaaggacac cga                                   33

SEQ ID NO: 22       moltype = DNA  length = 33
FEATURE             Location/Qualifiers
misc_feature        1..33
                    note = Synthetic Nucleotide
source              1..33
                    mol_type = other DNA
                    organism = synthetic construct
SEQUENCE: 22
agaactcagt aagcgtcccg tacacggtct gga                                   33

SEQ ID NO: 23       moltype = DNA  length = 33
FEATURE             Location/Qualifiers
misc_feature        1..33
                    note = Synthetic Nucleotide
source              1..33
                    mol_type = other DNA
                    organism = synthetic construct
SEQUENCE: 23
agccgcaaca gacgatagca agaaccgtga gga                                   33

SEQ ID NO: 24       moltype = DNA  length = 33
FEATURE             Location/Qualifiers
misc_feature        1..33
                    note = Synthetic Nucleotide
source              1..33
                    mol_type = other DNA
                    organism = synthetic construct
SEQUENCE: 24
cctcgttatt ggtattccgg caactgttcg gga                                   33

SEQ ID NO: 25       moltype = DNA  length = 33
FEATURE             Location/Qualifiers
misc_feature        1..33
                    note = Synthetic Nucleotide
source              1..33
                    mol_type = other DNA
                    organism = synthetic construct
SEQUENCE: 25
ccgcataacg gaaccaagac cgtcggagta aca                                   33

SEQ ID NO: 26       moltype = DNA  length = 33
FEATURE             Location/Qualifiers
misc_feature        1..33
                    note = Synthetic Nucleotide
source              1..33
                    mol_type = other DNA
                    organism = synthetic construct
SEQUENCE: 26
gtcgtctccc ttgctaaagt tgaaggacac cga                                   33

SEQ ID NO: 27       moltype = DNA  length = 33
FEATURE             Location/Qualifiers
```

```
misc_feature              1..33
                          note = Synthetic Nucleotide
source                    1..33
                          mol_type = other DNA
                          organism = synthetic construct
SEQUENCE: 27
gatgacgttc ccacagatct tacacggtct gga                                 33

SEQ ID NO: 28             moltype = DNA  length = 33
FEATURE                   Location/Qualifiers
misc_feature              1..33
                          note = Synthetic Nucleotide
source                    1..33
                          mol_type = other DNA
                          organism = synthetic construct
SEQUENCE: 28
ctggctgagc actttgcatt agaaccgtga gga                                 33

SEQ ID NO: 29             moltype = DNA  length = 33
FEATURE                   Location/Qualifiers
misc_feature              1..33
                          note = Synthetic Nucleotide
source                    1..33
                          mol_type = other DNA
                          organism = synthetic construct
SEQUENCE: 29
tgtgtaagaa acgcgggtct caactgttcg gga                                 33

SEQ ID NO: 30             moltype = DNA  length = 33
FEATURE                   Location/Qualifiers
misc_feature              1..33
                          note = Synthetic Nucleotide
source                    1..33
                          mol_type = other DNA
                          organism = synthetic construct
SEQUENCE: 30
taaagtaagc tgtgggccag cgtcggagta aca                                 33

SEQ ID NO: 31             moltype = DNA  length = 33
FEATURE                   Location/Qualifiers
misc_feature              1..33
                          note = Synthetic Nucleotide
source                    1..33
                          mol_type = other DNA
                          organism = synthetic construct
SEQUENCE: 31
agccacagga agtaaagccg taggtttggc gtt                                 33

SEQ ID NO: 32             moltype = DNA  length = 33
FEATURE                   Location/Qualifiers
misc_feature              1..33
                          note = Synthetic Nucleotide
source                    1..33
                          mol_type = other DNA
                          organism = synthetic construct
SEQUENCE: 32
aggtctggca catgccctgc gaatgactca aga                                 33

SEQ ID NO: 33             moltype = DNA  length = 33
FEATURE                   Location/Qualifiers
misc_feature              1..33
                          note = Synthetic Nucleotide
source                    1..33
                          mol_type = other DNA
                          organism = synthetic construct
SEQUENCE: 33
aggagtgcca agaacgatag cagacaacgc cga                                 33

SEQ ID NO: 34             moltype = DNA  length = 33
FEATURE                   Location/Qualifiers
misc_feature              1..33
                          note = Synthetic Nucleotide
source                    1..33
                          mol_type = other DNA
                          organism = synthetic construct
SEQUENCE: 34
agggcttgtc aacggcctta tggttattgc tcc                                 33

SEQ ID NO: 35             moltype = DNA  length = 33
```

```
FEATURE                 Location/Qualifiers
misc_feature            1..33
                        note = Synthetic Nucleotide
source                  1..33
                        mol_type = other DNA
                        organism = synthetic construct
SEQUENCE: 35
acaatgaggc tgccagaacc aaggcaatac gcc                                      33

SEQ ID NO: 36           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 36
agccacagga agttgaaatc gttccctctg ctg                                      33

SEQ ID NO: 37           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 37
aggtctggca cattctagac accttgcag tag                                       33

SEQ ID NO: 38           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 38
aggagtgcca agattacgtt tcacgagtcg gtc                                      33

SEQ ID NO: 39           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 39
agggcttgtc aactctgggc gcaaagaatg tgt                                      33

SEQ ID NO: 40           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 40
acaatgaggc tgcgaccggg tgtcgaatga aat                                      33

SEQ ID NO: 41           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 41
tgttgcatct ccacccggat tgagccttca gct                                      33

SEQ ID NO: 42           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 42
cacaacggga gctgtggaat tggttcacct ggt                                      33
```

```
SEQ ID NO: 43           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 43
tggactaaga ctcgtcctcc agcggaccta agt                                   33

SEQ ID NO: 44           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 44
gtatgatggt gttgcggctt ctcgcttaac gct                                   33

SEQ ID NO: 45           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 45
tctgagtgcc agtgacttca cgcattcgct tgt                                   33

SEQ ID NO: 46           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 46
tacgacacac tcgggctcta tgggcttcat ggt                                   33

SEQ ID NO: 47           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 47
gtttgagtga aggcggtcca acccttagtg cgt                                   33

SEQ ID NO: 48           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 48
ctataagttt gtcgtgcccg tgagccttca gct                                   33

SEQ ID NO: 49           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 49
ggagtgacac tgactacgtt tggttcacct ggt                                   33

SEQ ID NO: 50           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 50
gtcaacgccc tagcagacat agcggaccta agt                                   33
```

```
SEQ ID NO: 51            moltype = DNA   length = 33
FEATURE                  Location/Qualifiers
misc_feature             1..33
                         note = Synthetic Nucleotide
source                   1..33
                         mol_type = other DNA
                         organism = synthetic construct
SEQUENCE: 51
ccagaaccta ttgagcctga ctcgcttaac gct                                         33

SEQ ID NO: 52            moltype = DNA   length = 33
FEATURE                  Location/Qualifiers
misc_feature             1..33
                         note = Synthetic Nucleotide
source                   1..33
                         mol_type = other DNA
                         organism = synthetic construct
SEQUENCE: 52
aggtgttcgt acaatgaggc cgcattcgct tgt                                         33

SEQ ID NO: 53            moltype = DNA   length = 33
FEATURE                  Location/Qualifiers
misc_feature             1..33
                         note = Synthetic Nucleotide
source                   1..33
                         mol_type = other DNA
                         organism = synthetic construct
SEQUENCE: 53
tggtcaaggg caactaatcc tgggcttcat ggt                                         33

SEQ ID NO: 54            moltype = DNA   length = 33
FEATURE                  Location/Qualifiers
misc_feature             1..33
                         note = Synthetic Nucleotide
source                   1..33
                         mol_type = other DNA
                         organism = synthetic construct
SEQUENCE: 54
acaattaccc gtttaccggc acccttagtg cgt                                         33

SEQ ID NO: 55            moltype = DNA   length = 33
FEATURE                  Location/Qualifiers
misc_feature             1..33
                         note = Synthetic Nucleotide
source                   1..33
                         mol_type = other DNA
                         organism = synthetic construct
SEQUENCE: 55
tcgacttccg agttaggccc acctctacgt tgt                                         33

SEQ ID NO: 56            moltype = DNA   length = 33
FEATURE                  Location/Qualifiers
misc_feature             1..33
                         note = Synthetic Nucleotide
source                   1..33
                         mol_type = other DNA
                         organism = synthetic construct
SEQUENCE: 56
tggtccactt ggttaaggtg tcgagggcaa cac                                         33

SEQ ID NO: 57            moltype = DNA   length = 33
FEATURE                  Location/Qualifiers
misc_feature             1..33
                         note = Synthetic Nucleotide
source                   1..33
                         mol_type = other DNA
                         organism = synthetic construct
SEQUENCE: 57
tgaatccagg cgacctcctg ctcagaatca ggt                                         33

SEQ ID NO: 58            moltype = DNA   length = 33
FEATURE                  Location/Qualifiers
misc_feature             1..33
                         note = Synthetic Nucleotide
source                   1..33
                         mol_type = other DNA
                         organism = synthetic construct
SEQUENCE: 58
```

```
tcgcaattcg ctcttcggcg ttgtggtagt atg                              33

SEQ ID NO: 59         moltype = DNA  length = 33
FEATURE               Location/Qualifiers
misc_feature          1..33
                      note = Synthetic Nucleotide
source                1..33
                      mol_type = other DNA
                      organism = synthetic construct
SEQUENCE: 59
tgttcgctta cgcacttcag tgaccgtgag tct                              33

SEQ ID NO: 60         moltype = DNA  length = 33
FEATURE               Location/Qualifiers
misc_feature          1..33
                      note = Synthetic Nucleotide
source                1..33
                      mol_type = other DNA
                      organism = synthetic construct
SEQUENCE: 60
tggtacttcg ggtatctcgg gctcacacag cat                              33

SEQ ID NO: 61         moltype = DNA  length = 33
FEATURE               Location/Qualifiers
misc_feature          1..33
                      note = Synthetic Nucleotide
source                1..33
                      mol_type = other DNA
                      organism = synthetic construct
SEQUENCE: 61
tgcgtgattc ccaacctggc ggaagtgagt ttg                              33

SEQ ID NO: 62         moltype = DNA  length = 33
FEATURE               Location/Qualifiers
misc_feature          1..33
                      note = Synthetic Nucleotide
source                1..33
                      mol_type = other DNA
                      organism = synthetic construct
SEQUENCE: 62
tcgacttccg agtgcccgtg ctgtttgaat atc                              33

SEQ ID NO: 63         moltype = DNA  length = 33
FEATURE               Location/Qualifiers
misc_feature          1..33
                      note = Synthetic Nucleotide
source                1..33
                      mol_type = other DNA
                      organism = synthetic construct
SEQUENCE: 63
tggtccactt ggtttgcatc agtcacagtg agg                              33

SEQ ID NO: 64         moltype = DNA  length = 33
FEATURE               Location/Qualifiers
misc_feature          1..33
                      note = Synthetic Nucleotide
source                1..33
                      mol_type = other DNA
                      organism = synthetic construct
SEQUENCE: 64
tgaatccagg cgatacagac gatcccgcaa ctg                              33

SEQ ID NO: 65         moltype = DNA  length = 33
FEATURE               Location/Qualifiers
misc_feature          1..33
                      note = Synthetic Nucleotide
source                1..33
                      mol_type = other DNA
                      organism = synthetic construct
SEQUENCE: 65
tcgcaattcg ctcagtccga gttatccaag acc                              33

SEQ ID NO: 66         moltype = DNA  length = 33
FEATURE               Location/Qualifiers
misc_feature          1..33
                      note = Synthetic Nucleotide
source                1..33
                      mol_type = other DNA
                      organism = synthetic construct
```

```
SEQUENCE: 66
tgttcgctta cgccggagta acatgcttgt gga                              33

SEQ ID NO: 67           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 67
tggtacttcg ggtcctaatc aacgggaact ggt                              33

SEQ ID NO: 68           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 68
tgcgtgattc ccacggccat ttgcccatta aca                              33

SEQ ID NO: 69           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 69
acaacgtaga ggtgggccta actcggaagt cga                              33

SEQ ID NO: 70           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 70
gtgttgccct cgacacctta accaagtgga cca                              33

SEQ ID NO: 71           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 71
acctgattct gagcaggagg tcgcctggat tca                              33

SEQ ID NO: 72           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 72
catactacca caacgccgaa gagcgaattg cga                              33

SEQ ID NO: 73           moltype = DNA  length = 33
FEATURE                 Location/Qualifiers
misc_feature            1..33
                        note = Artificial Sequence
source                  1..33
                        mol_type = other DNA
                        organism = synthetic construct
SEQUENCE: 73
agactcacgg tcactgaagt gcgtaagcga aca                              33

SEQ ID NO: 74           moltype = DNA  length = 33
FEATURE                 Location/Qualifiers
misc_feature            1..33
                        note = Synthetic Nucleotide
source                  1..33
                        mol_type = other DNA
```

```
                        organism = synthetic construct
SEQUENCE: 74
atgctgtgtg agcccgagat acccgaagta cca                                   33

SEQ ID NO: 75           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 75
caaactcact tccgccaggt tgggaatcac gca                                   33

SEQ ID NO: 76           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 76
gatattcaaa cagcacgggc actcggaagt cga                                   33

SEQ ID NO: 77           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 77
cctcactgtg actgatgcaa accaagtgga cca                                   33

SEQ ID NO: 78           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 78
cagttgcggg atcgtctgta tcgcctggat tca                                   33

SEQ ID NO: 79           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 79
ggtcttggat aactcggact gagcgaattg cga                                   33

SEQ ID NO: 80           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 80
tccacaagca tgttactccg gcgtaagcga aca                                   33

SEQ ID NO: 81           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 81
accagttccc gttgattagg acccgaagta cca                                   33

SEQ ID NO: 82           moltype = DNA  length = 33
FEATURE                 Location/Qualifiers
misc_feature            1..33
                        note = Synthetic Nucleotide
source                  1..33
```

-continued

```
                            mol_type = other DNA
                            organism = synthetic construct
SEQUENCE: 82
tgttaatggg caaatggccg tgggaatcac gca                              33

SEQ ID NO: 83           moltype = DNA   length = 33
FEATURE                 Location/Qualifiers
misc_feature            1..33
                        note = Synthetic Nucleotide
source                  1..33
                        mol_type = other DNA
                        organism = synthetic construct
SEQUENCE: 83
agctgaaggc tcaatccggg tggagatgca aca                              33

SEQ ID NO: 84           moltype = DNA   length = 33
FEATURE                 Location/Qualifiers
misc_feature            1..33
                        note = Synthetic Nucleotide
source                  1..33
                        mol_type = other DNA
                        organism = synthetic construct
SEQUENCE: 84
accaggtgaa ccaattccac agctcccgtt gtg                              33

SEQ ID NO: 85           moltype = DNA   length = 33
FEATURE                 Location/Qualifiers
misc_feature            1..33
                        note = Synthetic Nucleotide
source                  1..33
                        mol_type = other DNA
                        organism = synthetic construct
SEQUENCE: 85
acttaggtcc gctggaggac gagtcttagt cca                              33

SEQ ID NO: 86           moltype = DNA   length = 33
FEATURE                 Location/Qualifiers
misc_feature            1..33
                        note = Synthetic Nucleotide
source                  1..33
                        mol_type = other DNA
                        organism = synthetic construct
SEQUENCE: 86
agcgttaagc gagaagccgc aacaccatca tac                              33

SEQ ID NO: 87           moltype = DNA   length = 33
FEATURE                 Location/Qualifiers
misc_feature            1..33
                        note = Synthetic Nucleotide
source                  1..33
                        mol_type = other DNA
                        organism = synthetic construct
SEQUENCE: 87
acaagcgaat gcgtgaagtc actggcactc aga                              33

SEQ ID NO: 88           moltype = DNA   length = 33
FEATURE                 Location/Qualifiers
misc_feature            1..33
                        note = Synthetic Nucleotide
source                  1..33
                        mol_type = other DNA
                        organism = synthetic construct
SEQUENCE: 88
accatgaagc ccatagagcc cgagtgtgtc gta                              33

SEQ ID NO: 89           moltype = DNA   length = 33
FEATURE                 Location/Qualifiers
misc_feature            1..33
                        note = Synthetic Nucleotide
source                  1..33
                        mol_type = other DNA
                        organism = synthetic construct
SEQUENCE: 89
acgcactaag ggttggaccg ccttcactca aac                              33

SEQ ID NO: 90           moltype = DNA   length = 33
FEATURE                 Location/Qualifiers
misc_feature            1..33
                        note = Synthetic Nucleotide
```

```
source                  1..33
                        mol_type = other DNA
                        organism = synthetic construct
SEQUENCE: 90
agctgaaggc tcacgggcac gacaaactta tag                          33

SEQ ID NO: 91           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 91
accaggtgaa ccaaacgtag tcagtgtcac tcc                          33

SEQ ID NO: 92           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 92
acttaggtcc gctatgtctg ctagggcgtt gac                          33

SEQ ID NO: 93           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 93
agcgttaagc gagtcaggct caataggttc tgg                          33

SEQ ID NO: 94           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 94
acaagcgaat gcggcctcat tgtacgaaca cct                          33

SEQ ID NO: 95           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 95
accatgaagc ccaggattag ttgcccttga cca                          33

SEQ ID NO: 96           moltype = DNA  length = 33
FEATURE                 Location/Qualifiers
misc_feature            1..33
                        note = Synthetic Nucleotide
source                  1..33
                        mol_type = other DNA
                        organism = synthetic construct
SEQUENCE: 96
acgcactaag ggtgccggta aacgggtaat tgt                          33
```

HIGH DENSITY SEQUENCING AND MULTIPLEXED PRIMING

CROSS-REFERENCES TO RELATED APPLICATIONS

This application is a continuation of International Application No. PCT/US22/26587, filed Apr. 27, 2022, and which claims the benefit of U.S. Provisional Application No. 63/180,588, filed Apr. 27, 2021; U.S. Provisional Application No. 63/255,300, filed Oct. 13, 2021; and U.S. Provisional Application No. 63/315,339, filed Mar. 1, 2022; each of which are incorporated herein by reference in their entirety and for all purposes.

REFERENCE TO SEQUENCE LISTING SUBMITTED ELECTRONICALLY

The Sequence Listing titled 051385-547001WO SEQUENCE LISTING ST26.XML, was created on Oct. 3, 2022 in machine format IBM-PC, MS-Windows operating system, is 123,787 bytes in size, and is hereby incorporated by reference in its entirety for all purposes.

BACKGROUND

RNA sequencing experiments (e.g., RNA-Seq, infectious disease diagnostics) typically sequence between 25 to 75 base pairs in a single run to obtain clinically significant data. Commercial sequencing platforms provide flow cells and associated sequencing reagents suitable for a range of sequencing experiments (e.g., sequencing greater than 100-300 base pairs). Short read experiments underutilize the available sequencing space, and overuse reagents and resources. Disclosed herein, inter alia, are solutions to these and other problems in the art.

BRIEF SUMMARY

In an aspect is provided a method of sequencing different populations of polynucleotides (e.g., different libraries of polynucleotides) immobilized on a solid support, the method including: contacting a first population of polynucleotides annealed to a first sequencing primer with a first sequencing solution including a plurality of modified nucleotides including a reversible terminator and monitoring the sequential incorporation of complementary nucleotides to generate a first sequencing read, wherein the reversible terminator is removed prior to the introduction of the next complementary nucleotide; contacting a second population of polynucleotides annealed to a second sequencing primer with a second sequencing solution including a plurality of modified nucleotides including a reversible terminator and monitoring the sequential incorporation of complementary nucleotides to generate a second sequencing read, wherein the reversible terminator is removed prior to the introduction of the next complementary nucleotide; contacting a third population of polynucleotides annealed to a third sequencing primer with a third sequencing solution comprising a plurality of modified nucleotides comprising a reversible terminator and monitoring the sequential incorporation of complementary nucleotides to generate a third sequencing read, wherein the reversible terminator is removed prior to the introduction of the next complementary nucleotide; wherein the first sequencing primer, second sequencing primer, and third sequencing primer are different.

In an aspect is provided a method of sequencing a plurality of template polynucleotides on a solid support, the method including: (a) amplifying a first template polynucleotide including a first adapter sequence and a second adapter sequence, and amplifying a second template polynucleotide including a third adapter sequence and a fourth adapter sequence to generate a plurality of overlapping amplification clusters on the solid support, wherein the first adapter sequence includes a first platform primer binding sequence and a first sequencing primer binding sequence; the second adapter sequence includes a second platform primer binding sequence and a second sequencing primer binding sequence; the third adapter sequence includes the first platform primer binding sequence and a third sequencing primer binding sequence; the fourth adapter sequence includes the second platform primer binding sequence and a fourth sequencing primer binding sequence; (b) sequentially sequencing the overlapping amplification clusters by i) hybridizing a first sequencing primer to the first sequencing primer binding sequence and generating a first sequencing read; ii) hybridizing a second sequencing primer to the second sequencing primer binding sequence and generating a second sequencing read; iii) hybridizing a third sequencing primer to the third sequencing primer binding sequence and generating a third sequencing read; iv) hybridizing a fourth sequencing primer to the fourth sequencing primer binding sequence and generating a fourth sequencing read.

In an aspect is provided a method of amplifying a plurality of template polynucleotides, the method including: (a) contacting a solid support with a first template polynucleotide including a first adapter sequence thereby forming a first complex attached to the solid support and contacting the solid support with a second template polynucleotide including a second adapter sequence thereby forming a second complex attached to the solid support, wherein: the first adapter sequence includes a first platform primer binding sequence complementary to a first amplification primer, and a first sequencing primer binding sequence, and the second adapter sequence includes the first platform primer binding sequence and a second sequencing primer binding sequence; the first complex includes a first amplification primer attached to the solid support hybridized to the first adapter sequence; and the second complex includes a second amplification primer attached to the solid support hybridized to the second adapter sequence, wherein the first and second amplification primer include the same sequence; and the first sequencing primer binding sequence is different from the second sequencing primer binding sequence; (b) amplifying the first template polynucleotide and the second template polynucleotide to form a plurality of first amplification products and plurality of second amplification products that form overlapping amplification clusters on the solid support.

In an aspect is provided a method for amplifying polynucleotides, the method including: contacting a solid support with a first population of polynucleotides including a first sequencing primer binding sequence thereby forming a first complex, and contacting the solid support with a second population of polynucleotides including a second sequencing primer binding sequence thereby forming a second complex, wherein the first complex includes a first polynucleotide including the first sequencing primer binding sequence hybridized to a first oligonucleotide attached to the solid support and wherein the second complex includes a second polynucleotide including the second sequencing primer binding sequence hybridized to a second oligonucleotide attached to the solid support; and contacting the first complex with a polymerase and extending the first oligonucleotide thereby forming a plurality of first amplification products and contacting the second complex with the polymerase and extending the second oligonucleotide thereby forming a plurality of second amplification products.

In an aspect is provided a substrate including: (a) a plurality of amplification clusters on a solid support, wherein: (i) one or more amplification clusters including one or more copies of a first template polynucleotide including a first adapter sequence, and one or more copies of a second template polynucleotide including a second adapter sequence, wherein the first and second template polynucleotides are not substantially complementary to each other; and (ii) the first adapter sequence includes a first platform primer binding sequence and a first sequencing primer binding sequence; and the second adapter sequence includes the first platform primer binding sequence and a second sequencing primer binding sequence, wherein the first sequencing primer binding sequence is different from the second sequencing primer binding sequence and wherein the first platform primer binding sequence includes a sequence complementary to a first amplification primer attached to the solid support; and (b) a plurality of first sequencing primers hybridized to the first adapter sequences of the amplification clusters.

In an aspect is provided a kit including an adapter composition, the adapter composition including: a first adapter including a first platform primer binding sequence and a first sequencing primer binding sequence; a second adapter including a second platform primer binding sequence and a second sequencing primer binding sequence; a third adapter including the third platform primer binding sequence and a third sequencing primer binding sequence, wherein the first sequencing primer binding sequence, second sequencing primer binding sequence, and the third sequencing primer binding sequence are different.

BRIEF DESCRIPTION OF THE DRAWINGS

FIG. 1 shows examples of the adapter sequences, referred to as P1, P2, P3, and P4 adapters, respectively. The P1 adapter contains a platform primer 1 (pp1), which is a sequence complementary to a first surface-immobilized primer, an optional index sequence (i) for multiplexing samples, and a region complementary to a first sequencing primer (SP1). The P2 adapter contains a platform primer 2 (pp2), which is a sequence complementary to a second surface-immobilized primer, an optional index sequence (i) for multiplexing samples, and a region complementary to a second sequencing primer (SP2). The P3 adapter contains a platform primer 1 (pp1), which is a sequence complementary to the first surface-immobilized primer, an optional index sequence (i) for multiplexing samples, and a region complementary to a third sequencing primer (SP3). The P4 adapter contains a platform primer 2 (pp2), which is a sequence complementary to the second surface-immobilized primer, an optional index sequence (i) for multiplexing samples, and a region complementary to a fourth sequencing primer (SP4). The illustrations depict embodiments of the oligo sequences wherein there are two different platform primer binding sequences, pp1 and pp2, in combination with four different sequencing primer binding sites: SP1, SP2, SP3, and SP4. The dashed lines are indicative of regions within the adapter and are included to aid the eye in the different arrangement of the sequences and are not indicative of the overall size/length (i.e., the index sequence may not be the same length as the sequencing primer despite the illustration showing the index sequence and sequencing primer as being the same size). It is understood that any P1 adapter, or the complement thereof, may be combined with any P2 or P4 adapter, or complement thereof, when preparing the template nucleic acid sequence. It is understood that any P3 adapter, or the complement thereof, may be combined with any P2 or P4 adapter, or complement thereof, when preparing the template nucleic acid sequence. The 5' end of any of the illustrated adapters (or a portion thereof, for example only the platform primer binding sequence) may be covalently attached to a solid surface via a linker (not shown). It is understood that color is not an indication of a different sequence; for example, the pp1 sequence of one color may be similar or substantially identical to the pp1 sequence of a different color. As illustrated, two Y-shaped adapters are ligated to the sample polynucleotide, however it is understood that alternative shaped adapters are contemplated herein (e.g., hairpin adapters, blunt end adapters, bubble adapters, and the like). In embodiments, each end of the sample polynucleotide is ligated to adapters having the same shape (e.g., both ends include a Y-adapter). In embodiments, each end of the sample polynucleotide is ligated to adapters having different shapes (e.g., the first adapter is a Y adapter and the second adapter is a hairpin adapter).

FIG. 2A shows a DNA template with P1 and P2' adapters ligated to the ends. FIG. 2B shows a DNA template with P3 and P4' adapters ligated to the ends. It is understood that color is not an indication of a different sequence; for example, the pp1 sequence of one color may be similar or substantially identical to the pp1 sequence of a different color. The two libraries (i.e., the two populations) include common platform primer binding sequences (e.g., pp1 and pp2') to facilitate a single amplification process and distinct sequencing primer binding sites (e.g., SP1, SP2', SP3, and SP4').

FIG. 3A shows an example of a cluster of immobilized nucleic acids, each nucleic acid comprising a first and a second sequencing primer binding site. From left to right, the illustration of the cluster contains, from 5'-3', 5'-(P1')-template-(P2); 5'-(P2)-template-(P1); 5'-(P2)-template-(P1); 5'-(P1')-template-(P2); 5'-(P4)-template-(P3'); and 5'-(P3')-template-(P4). A first sequencing primer complementary to SP2 hybridizes to the template and is extended in the presence of a polymerase and detectable nucleotides, illustrated as a dashed line and star. Following a first plurality of sequencing cycles, the immobilized strands are optionally removed, and a second plurality of sequencing cycles on the same cluster (i.e., the same optically resolvable feature) may commence in a similar fashion. FIG. 3B shows a second sequencing primer complementary to SP4 hybridizing to the template, and is then extended in the presence of a polymerase and detectable nucleotides, illustrated as a dashed line and star. The remaining templates may be sequenced as outlined above, e.g., by hybridizing a third and fourth sequencing primer to the respective template and sequencing.

FIG. 5A depicts a 4×4 patterned array, wherein each polyclonal cluster (alternatively referred to herein as a feature) includes template nucleic acids that include two to four different sequencing primer complements, depicted as four different colors. In embodiments, each polyclonal cluster contains a plurality of templates having more than two (e.g., four) different primer binding sites. Sequencing is initiated by hybridizing a sequencing primer to one of four different sequencing primer binding sites SP1, SP2, SP3, and SP4, or a complement thereof. A plurality of sequencing cycles then occurs, each cycle comprising extension and detection of the incorporated nucleotide. Illustrated in FIG. 5B is the multiplexed array wherein each cluster (depicted as a shaded circle) is active when the appropriate sequencing primer hybridizes and is extended, allowing for selective sequencing of an entire array. Depicted in FIG. 5B, when the cluster contains a plurality of templates having different primer binding sites, e.g., regions complementary to SP1, SP2, and SP3, only the clusters containing complementarity to the appropriate sequencing primer is active during each plurality of sequencing cycles. For example, when a first sequencing primer SP1 hybridizes to each of the complementary templates in the array, only a subset of the array is detected during that round of sequencing. A second round of sequencing then occurs by hybridizing a second sequencing primer, SP2, to each of the complementary templates in the array, and so on. The same clusters may be active and detectable during multiple rounds of sequencing if the cluster includes templates with two or more different sequencing primer binding sites.

FIGS. 6A-6B provide an overview of the multiplexed bacterial genomic libraries sequencing experiment described in Example 3. FIG. 6A is a diagram of the genomic samples contained in each lane of the two four-lane (alternatively referred to as four channel) flow cells (referred to herein as FC1 and FC2, respectively) prepared and sequenced. Lane 1 includes a genomic library from *Clostridium*, Lane 2 includes a library from *E. coli*, Lane 3 includes a library from *Salmonella*, and Lane 4 includes a mixture of all three of the *Clostridium*, *E. coli*, and *Salmonella* bacterial genomic library samples, referred to as a mixed library. Each library was prepared with a unique adapter sequence to allow for selective sequencing (e.g., each library includes an adapter referred to as an M1 adapter, M5 adapter, or SP adapter). Each adapter includes a unique, independent sequence that is complementary to the corresponding sequencing primer. FIG. 6B is an illustration of the selective sequencing workflow performed for the mixed library sample. The *E. coli* library was first sequenced with the M5b primer followed by NaOH stripping of extended and residual primers (flow cell 1 (FC1) only), 3'-OH blocking of extended and residual primers with a dideoxynucleotide triphosphate (ddNTP), and annealing of the second primer (e.g., M1b primer for *Clostridium* genome sequencing). The primer stripping/blocking and annealing process was subsequently repeated for the SP primer for *Salmonella* genome sequencing in FC1.

FIG. 7B illustrates an unpatterned solid support including a polymer (e.g., a hydrophilic polymer) including the plurality of platform primer oligonucleotides randomly distributed throughout the polymer (e.g., the plurality of platform primer oligonucleotides are covalently attached to the polymer in a random distribution). In embodiments, the platform primer oligonucleotides are present at a density of at least 1,000 molecules per squared micrometer ($\mu m^2$).

FIG. 8A. The prepared library molecules (i.e., nucleic acids having the appropriate adapters on each end) are allowed to contact the solid support and may contact a single feature. For example, if one molecule seeds (i.e., hybridizes to the surface-immobilized oligonucleotide) a single feature and is amplified it is referred to as a monoclonal colony. Colony formation, alternatively referred to as a cluster, for a P1'-template-P2 molecule and a P3'-template-P4 molecule is illustrated in FIGS. 8A-8B, where an initial molecule anneals to a first immobilized oligonucleotide and is extended to form an immobilized extension product (FIG. 8A). The initial seeding molecule is removed and the immobilized extension product hybridizes to a second immobilized oligonucleotide, and with a polymerase is extended to form a second immobilized extension product (FIG. 8B). Under suitable amplification conditions, the process is repeated to form a plurality of immobilized extension products, as illustrated in FIG. 8C, wherein each extension product is capable of being sequenced by hybridizing the appropriate sequencing primer: SP1, SP2, SP3, or SP4. A similar process occurs on unpatterned solid supports, as illustrated in FIGS. 8D-8F.

As illustrated in FIG. 9B, a splint oligonucleotide hybridizes to both ends of the library molecule, and following ligation, a circular template molecule is annealed to the primer. A nucleic acid polymerase (e.g., a strand-displacing polymerase, depicted as a cloud) then extends the primer that is hybridized to the circular nucleic acid template by continuously progressing around the circular nucleic acid template to replicate the sequence of the nucleic acid template over and over again (rolling circle mechanism). The rolling circle amplification typically produces concatemers comprising tandem repeat units of the circular nucleic acid template sequence, as illustrated in FIG. 9C. The solid support optionally may include a second immobilized oligonucleotide as illustrated in FIG. 9A and FIG. 9B to permit non-linear circular amplification modalities such as exponential rolling circle amplification (eRCA).

DETAILED DESCRIPTION

Figure 1:
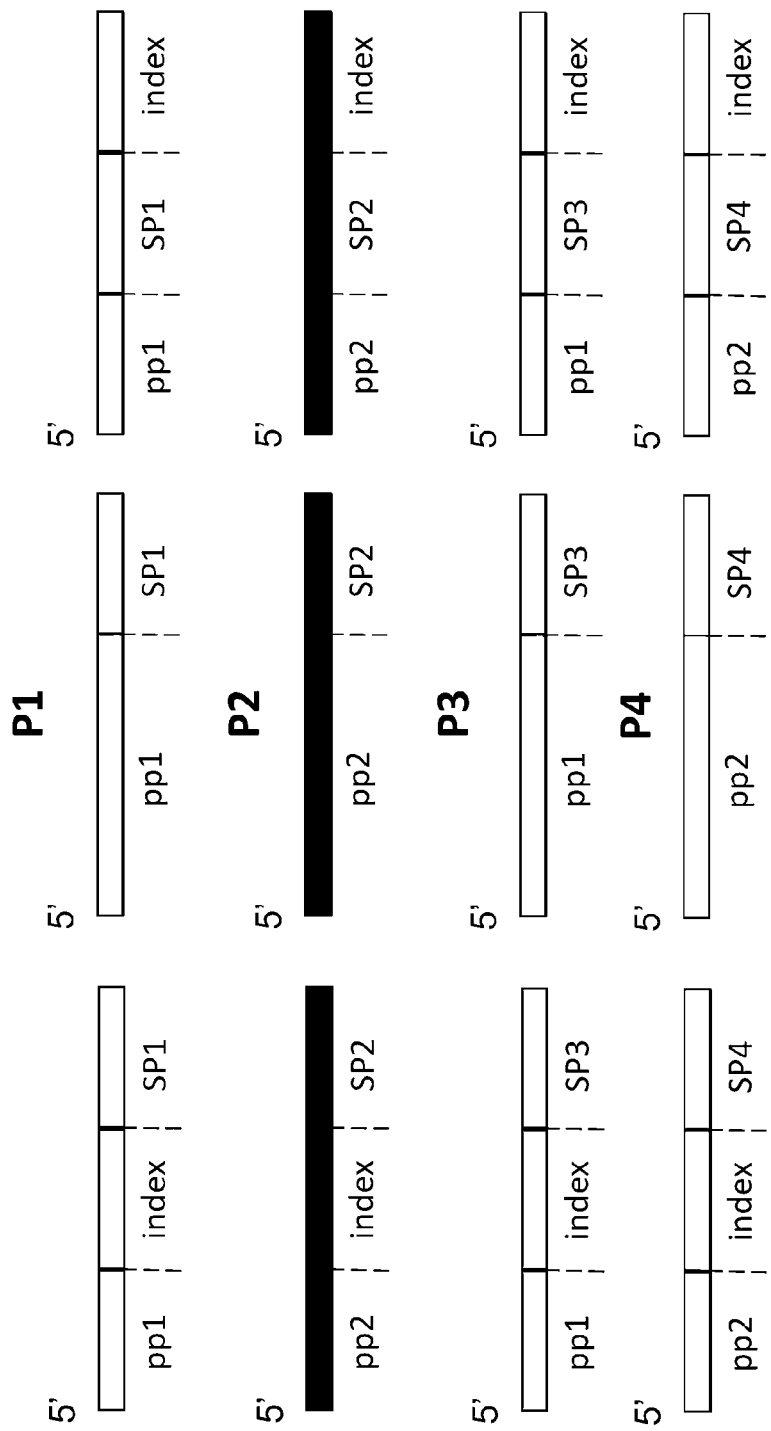
FIG. 1 is a schematic of the adapter sequences used in some embodiments.

The aspects and embodiments described herein relate to sequencing a plurality of template polynucleotides on a solid support (e.g., on a flow cell). In embodiments, the method includes making and amplifying the plurality of template polynucleotides to generate a plurality of overlapping amplification clusters on a surface. Described herein is an elegant solution to a complex problem, and taking advantage of polyclonal clusters.

I. Definitions

All patents, patent applications, articles and publications mentioned herein, both supra and infra, are hereby expressly incorporated herein by reference in their entireties. The practice of the technology described herein will employ, unless indicated specifically to the contrary, conventional methods of chemistry, biochemistry, organic chemistry, molecular biology, bioinformatics, microbiology, recombinant DNA techniques, genetics, immunology, and cell biology that are within the skill of the art, many of which are described below for the purpose of illustration. Examples of such techniques are available in the literature. See, e.g., Singleton et al., DICTIONARY OF MICROBIOLOGY AND MOLECULAR BIOLOGY 2nd ed., J. Wiley & Sons (New York, N.Y. 1994); and Sambrook and Green, Molecular Cloning: A Laboratory Manual, 4th Edition (2012). Methods, devices and materials similar or equivalent to those described herein can be used in the practice of this invention.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise. Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the term "control" or "control experiment" is used in accordance with its plain and ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

As used herein, the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association.

As used herein, the term "complementary" or "substantially complementary" refers to the hybridization, base pairing, or the formation of a duplex between nucleotides or nucleic acids. For example, complementarity exists between the two strands of a double-stranded DNA molecule or between an oligonucleotide primer and a primer binding site on a single-stranded nucleic acid when a nucleotide (e.g., RNA or DNA) or a sequence of nucleotides is capable of base pairing with a respective cognate nucleotide or cognate sequence of nucleotides. As described herein and commonly known in the art the complementary (matching) nucleotide of adenosine (A) is thymidine (T) and the complementary (matching) nucleotide of guanosine (G) is cytosine (C). Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. "Duplex" means at least two oligonucleotides and/or polynucleotides that are fully or partially complementary undergo Watson-Crick type base pairing among all or most of their nucleotides so that a stable complex is formed. In embodiments, a first template polynucleotide and a second template polynucleotide of an overlapping cluster are not substantially complementary (e.g., are at least 50%, 75%, 90%, or more non-complementary to each other).

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin or loop structure, with or without an overhang) or portions of separate polynucleotides. In embodiments, one or both sequences in a pair of complementary sequences form portions of longer polynucleotides, which may or may not include additional regions of complementarity.

As used herein, the term "contacting" is used in accordance with its plain ordinary meaning and refers to the process of allowing at least two distinct species (e.g., chemical compounds including biomolecules or cells) to become sufficiently proximal to react, interact or physically touch. However, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound, nucleic acid, a protein, or enzyme (e.g., a DNA polymerase).

As may be used herein, the terms "nucleic acid," "nucleic acid molecule," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences. As may be used herein, the terms "nucleic acid oligomer" and "oligonucleotide" are used interchangeably and are intended to include, but are not limited to, nucleic acids having a length of 200 nucleotides or less. In some embodiments, an oligonucleotide is a nucleic acid having a length of 2 to 200 nucleotides, 2 to 150 nucleotides, 5 to 150 nucleotides or 5 to 100 nucleotides. The terms "polynucleotide," "oligonucleotide," "oligo" or the like refer, in the usual and customary sense, to a linear sequence of nucleotides. Oligonucleotides are typically from about 5, 6, 7, 8, 9, 10, 12, 15, 25, 30, 40, 50 or more nucleotides in length, up to about 100 nucleotides in length. In some embodiments, an oligonucleotide is a primer configured for extension by a polymerase when the primer is annealed completely or partially to a complementary nucleic acid template. A primer is often a single stranded nucleic acid. In certain embodiments, a primer, or portion thereof, is substantially complementary to a portion of an adapter. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. In some embodiments, an oligonucleotide may be immobilized to a solid support.

As used herein, the terms "library", "RNA library" or "DNA library" or "library of DNA molecules" are used in accordance with their plain ordinary meaning and refer to a collection or a population of similarly sized nucleic acid fragments with known adapter sequences (e.g., known adapters attached to the 5' and 3' ends of each of the fragments). In embodiments, the library includes a plurality of nucleic acid fragments including one or more adapter sequences. In embodiments, the library includes circular nucleic acid templates. Libraries are typically prepared from input RNA, DNA, or cDNA and are processed by fragmentation, size selection, end-repair, adapter ligation, amplification, and purification. Alternative amplification-free (i.e., PCR free) methods for preparing a library of molecules include shearing input polynucleotides, size selecting and ligating adapters. A library may correspond to a single sample or a single origin. Multiple libraries, each with their own unique adapter sequences, may be pooled and sequenced in the same sequencing run using the methods described herein.

As used herein, the terms "polynucleotide primer" and "primer" refers to any polynucleotide molecule that may hybridize to a polynucleotide template, be bound by a polymerase, and be extended in a template-directed process for nucleic acid synthesis. The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin). Primers (e.g., forward or reverse primers) may be attached to a solid support. A primer can be of any length depending on the particular technique it will be used for. For example, PCR primers are generally between 10 and 40 nucleotides in length. The length and complexity of the nucleic acid fixed onto the nucleic acid template may vary. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target polynucleotide. A "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

As used herein, the terms "solid support" and "substrate" and "solid surface" are used interchangeably and refers to discrete solid or semi-solid surfaces to which a plurality of nucleic acid (e.g., primers) may be attached. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. Solid supports may be in the form of discrete particles, which alone does not imply or require any particular shape. The term "particle" means a small body made of a rigid or semi-rigid material. The body can have a shape characterized, for example, as a sphere, oval, microsphere, or other recognized particle shape whether having regular or irregular dimensions. As used herein, the term "discrete particles" refers to physically distinct particles having discernible boundaries. The term "particle" does not indicate any particular shape. The shapes and sizes of a collection of particles may be different or about the same (e.g., within a desired range of dimensions, or having a desired average or minimum dimension). A particle may be substantially spherical (e.g., microspheres) or have a non-spherical or irregular shape, such as cubic, cuboid, pyramidal, cylindrical, conical, oblong, or disc-shaped, and the like. In embodiments, the particle has the shape of a sphere, cylinder, spherocylinder, or ellipsoid. Discrete particles collected in a container and contacting one another will define a bulk volume containing the particles, and will typically leave some internal fraction of that bulk volume unoccupied by the particles, even when packed closely together. In embodiments, cores and/or core-shell particles are approximately spherical. As used herein the term "spherical" refers to structures which appear substantially or generally of spherical shape to the human eye, and does not require a sphere to a mathematical standard. In other words, "spherical" cores or particles are generally spheroidal in the sense of resembling or approximating to a sphere. In embodiments, the diameter of a spherical core or particle is substantially uniform, e.g., about the same at any point, but may contain imperfections, such as deviations of up to 1, 2, 3, 4, 5 or up to 10%. Because cores or particles may deviate from a perfect sphere, the term "diameter" refers to the longest dimension of a given core or particle. Likewise, polymer shells are not necessarily of perfect uniform thickness all around a given core. Thus, the term "thickness" in relation to a polymer structure (e.g., a shell polymer of a core-shell particle) refers to the average thickness of the polymer layer.

Figure 8A:
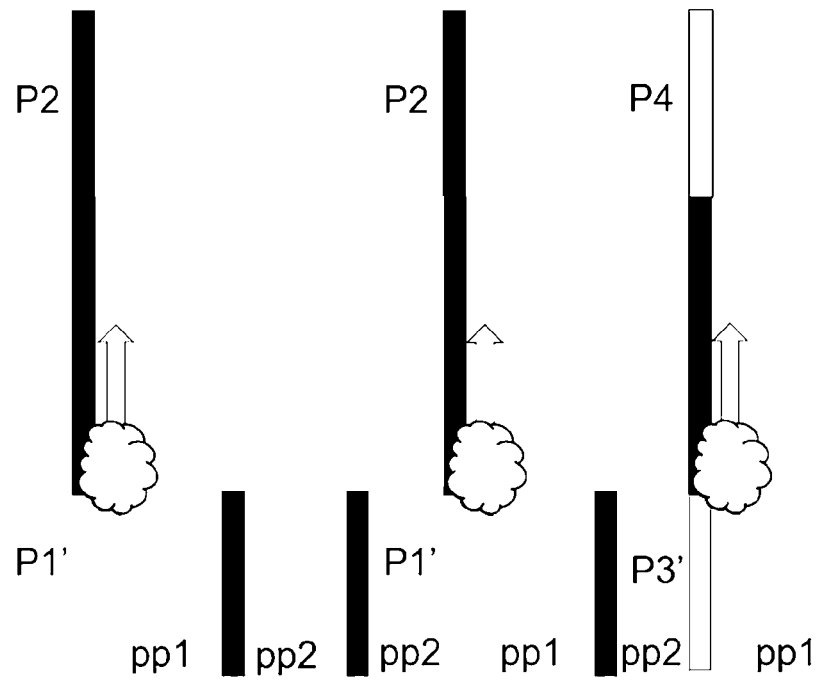
FIGS. 8A-8F. Seeding and amplification of two different libraries of nucleic acid molecules.
Figure 8B:
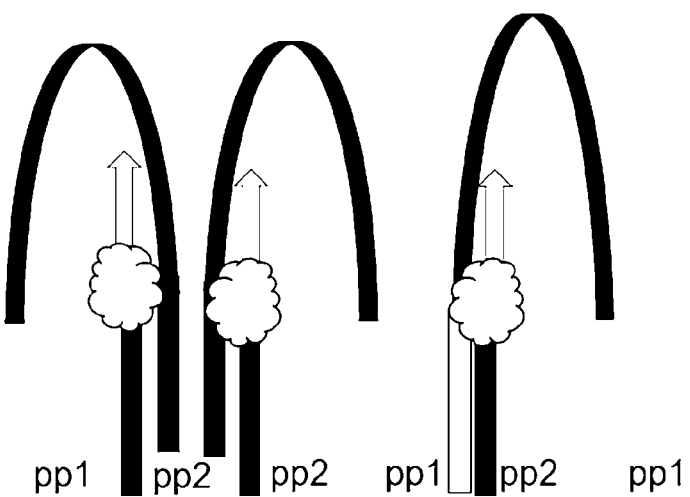
Figure 8C:
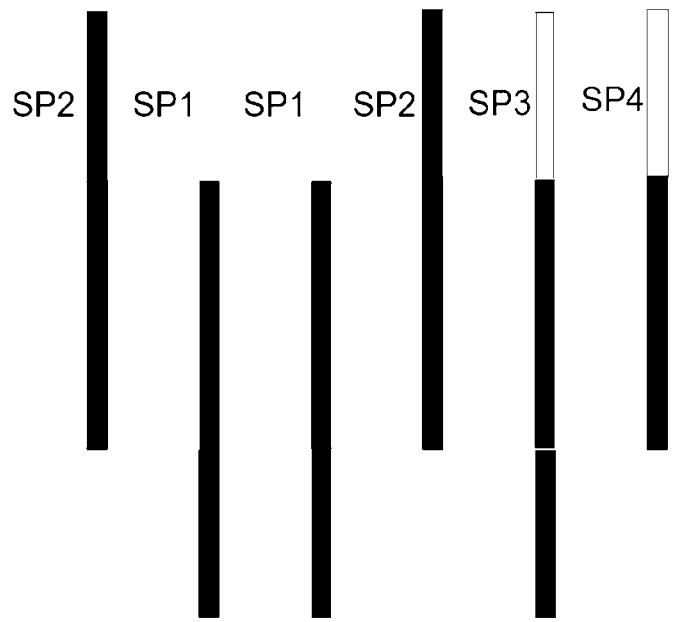
Figure 8D:
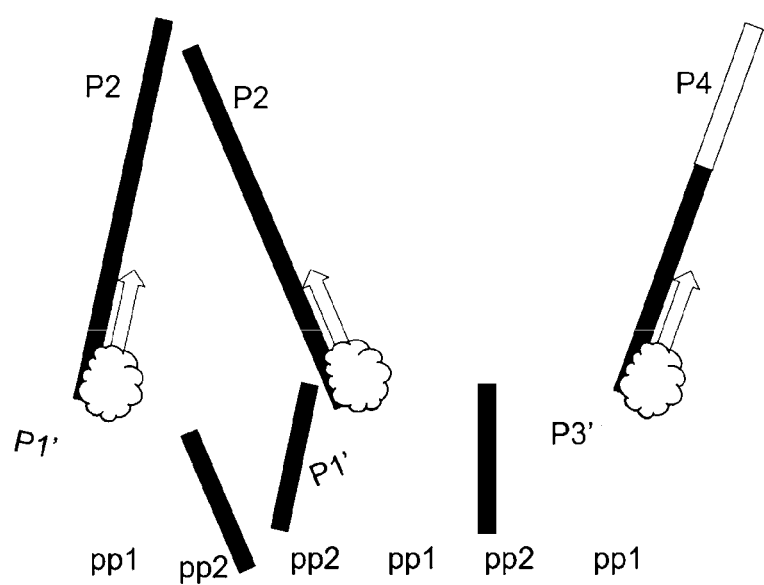
Figure 8E:
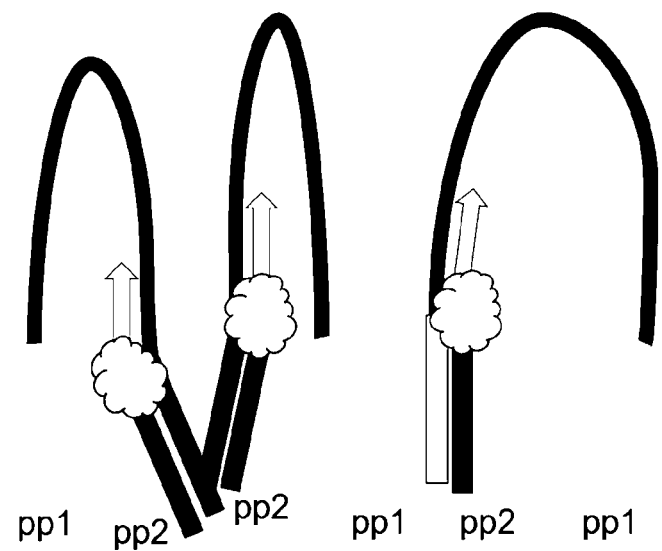
Figure 8F:
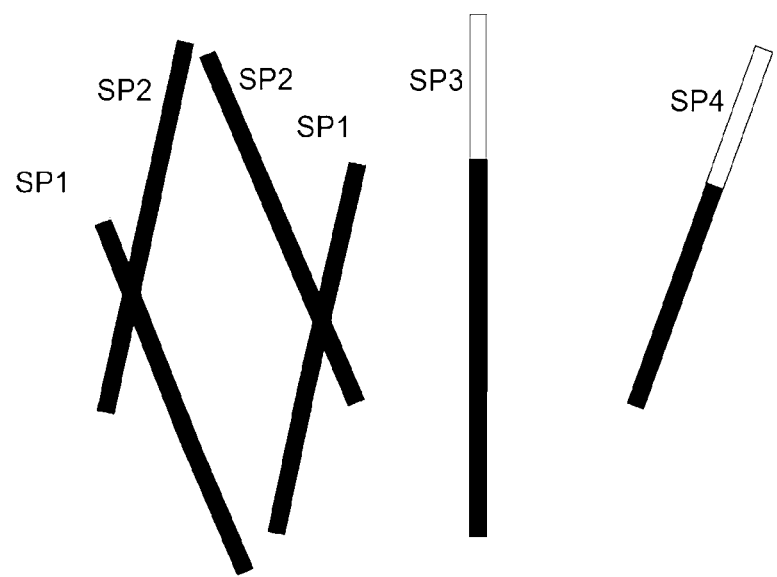

A solid support may further comprise a polymer or hydrogel on the surface to which the primers are attached (e.g., the primers are covalently attached to the polymer, wherein the polymer is in direct contact with the solid support). Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. The solid supports for some embodiments have at least one surface located within a flow cell. The solid support, or regions thereof, can be substantially flat. The solid support can have surface features such as wells, pits, channels, ridges, raised regions, pegs, posts or the like. The term solid support is encompassing of a substrate (e.g., a flow cell) having a surface comprising a polymer coating covalently attached thereto. In embodiments, the solid support is a flow cell. The term "flow cell" as used herein refers to a chamber including a solid surface across which one or more fluid reagents can be flowed. Examples of flow cells and related fluidic systems and detection platforms that can be readily used in the methods of the present disclosure are described, for example, in Bentley et al., Nature 456:53-59 (2008). In certain embodiments a substrate comprises a surface (e.g., a surface of a flow cell, a surface of a tube, a surface of a chip), for example a metal surface (e.g., steel, gold, silver, aluminum, silicon and copper). In some embodiments a substrate (e.g., a substrate surface) is coated and/or comprises functional groups and/or inert materials. In certain embodiments a substrate comprises a bead, a chip, a capillary, a plate, a membrane, a wafer (e.g., silicon wafers), a comb, or a pin for example. In some embodiments a substrate comprises a bead and/or a nanoparticle. A substrate can be made of a suitable material, non-limiting examples of which include a plastic or a suitable polymer (e.g., polycarbonate, poly(vinyl alcohol), poly(divinylbenzene), polystyrene, polyamide, polyester, polyvinylidene difluoride (PVDF), polyethylene, polyurethane, polypropylene, and the like), borosilicate, glass, nylon, Wang resin, Merrifield resin, metal (e.g., iron, a metal alloy, sepharose, agarose, polyacrylamide, dextran, cellulose and the like or combinations thereof. In some embodiments a substrate comprises a magnetic material (e.g., iron, nickel, cobalt, platinum, aluminum, and the like). In certain embodiments a substrate comprises a magnetic bead (e.g., DYNABEADS®, hematite, AMPure XP). Magnets can be used to purify and/or capture nucleic acids bound to certain substrates (e.g., substrates comprising a metal or magnetic material). In embodiments, the solid support is an unpatterned solid support. The term "unpatterned solid support" as used herein refers to a solid support with a uniform polymer surface including, for example, amplification primers randomly distributed throughout the polymer surface. This is in contrast to a patterned solid support, wherein amplification primers, for example, as localized to specific regions of the surface, such as to wells in an array. In embodiments, an unpatterned solid support does not include organized surface features such as wells, pits, channels, ridges, raised regions, pegs, posts or the like. In embodiments, the surface of an unpatterned solid support does not contain interstitial regions. In embodiments, an unpatterned solid support includes a polymer (e.g., a hydrophilic polymer). In certain embodiments, the unpatterned solid support includes a plurality of oligonucleotides (e.g., primer oligonucleotides) randomly distributed throughout the polymer (e.g., the plurality of primer oligonucleotides are covalently attached to the polymer in a random distribution, as illustrated in FIGS. 8D-8F). An unpatterned solid support may be, for example, a glass slide including a polymer coating (a hydrophilic polymer coating).

As used herein, the term "channel" refers to a passage in or on a substrate material that directs the flow of a fluid. A channel may run along the surface of a substrate, or may run through the substrate between openings in the substrate. A channel can have a cross section that is partially or fully surrounded by substrate material (e.g., a fluid impermeable substrate material). For example, a partially surrounded cross section can be a groove, trough, furrow or gutter that inhibits lateral flow of a fluid. The transverse cross section of an open channel can be, for example, U-shaped, V-shaped, curved, angular, polygonal, or hyperbolic. A channel can have a fully surrounded cross section such as a tunnel, tube, or pipe. A fully surrounded channel can have a rounded, circular, elliptical, square, rectangular, or polygonal cross section. A microfluidic flow channel is characterized by cross-sectional dimensions less than 1000 microns. Usually at least one, and preferably all, cross-sectional dimensions are greater than 500 microns.

As used herein, the term "polymer" refers to macromolecules having one or more structurally unique repeating units. The repeating units are referred to as "monomers," which are polymerized for the polymer. Typically, a polymer is formed by monomers linked in a chain-like structure. A polymer formed entirely from a single type of monomer is referred to as a "homopolymer." A polymer formed from two or more unique repeating structural units may be referred to as a "copolymer." A polymer may be linear or branched, and may be random, block, polymer brush, hyperbranched polymer, bottlebrush polymer, dendritic polymer, or polymer micelles. The term "polymer" includes homopolymers, copolymers, tripolymers, tetra polymers and other polymeric molecules made from monomeric subunits. Copolymers include alternating copolymers, periodic copolymers, statistical copolymers, random copolymers, block copolymers, linear copolymers and branched copolymers. The term "polymerizable monomer" is used in accordance with its meaning in the art of polymer chemistry and refers to a compound that may covalently bind chemically to other monomer molecules (such as other polymerizable monomers that are the same or different) to form a polymer.

Polymers can be hydrophilic, hydrophobic, or amphiphilic, as known in the art. Thus, "hydrophilic polymers" are substantially miscible with water and include, but are not limited to, polyethylene glycol and the like. "Hydrophobic polymers" are substantially immiscible with water and include, but are not limited to, polyethylene, polypropylene, polybutadiene, polystyrene, polymers disclosed herein, and the like. "Amphiphilic polymers" have both hydrophilic and hydrophobic properties and are typically copolymers having hydrophilic segment(s) and hydrophobic segment(s). Polymers include homopolymers, random copolymers, and block copolymers, as known in the art. The term "homopolymer" refers, in the usual and customary sense, to a polymer having a single monomeric unit. The term "copolymer" refers to a polymer derived from two or more monomeric species. The term "random copolymer" refers to a polymer derived from two or more monomeric species with no preferred ordering of the monomeric species. The term "block copolymer" refers to polymers having two or homopolymer subunits linked by covalent bond. Thus, the term "hydrophobic homopolymer" refers to a homopolymer which is hydrophobic. The term "hydrophobic block copolymer" refers to two or more homopolymer subunits linked by covalent bonds and which is hydrophobic.

As used herein, the term "hydrogel" refers to a three-dimensional polymeric structure that is substantially insoluble in water, but which is capable of absorbing and retaining large quantities of water to form a substantially stable, often soft and pliable, structure. In embodiments, water can penetrate in between polymer chains of a polymer network, subsequently causing swelling and the formation of a hydrogel. In embodiments, hydrogels are super-absorbent (e.g., containing more than about 90% water) and can be comprised of natural or synthetic polymers. In some embodiments, the hydrogel polymer includes 60-90% fluid, such as water, and 10-30% polymer. In certain embodiments, the water content of hydrogel is about 70-80%.

Hydrogels may be prepared by cross-linking hydrophilic biopolymers or synthetic polymers. Thus, in some embodiments, the hydrogel may include a crosslinker. As used herein, the term "crosslinker" refers to a molecule that can form a three-dimensional network when reacted with the appropriate base monomers. Examples of the hydrogel polymers, which may include one or more crosslinkers, include but are not limited to, hyaluronans, chitosans, agar, heparin, sulfate, cellulose, alginates (including alginate sulfate), collagen, dextrans (including dextran sulfate), pectin, carrageenan, polylysine, gelatins (including gelatin type A), agarose, (meth)acrylate-oligolactide-PEO-oligolactide-(meth)acrylate, PEO—PPO-PEO copolymers (Pluronics), poly(phosphazene), poly(methacrylates), poly(N-vinylpyrrolidone), PL(G)A-PEO-PL(G)A copolymers, poly(ethylene imine), polyethylene glycol (PEG)-thiol, PEG-acrylate, acrylamide, N,N'-bis(acryloyl)cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetracrylate, or combinations thereof. Thus, for example, a combination may include a polymer and a crosslinker, for example polyethylene glycol (PEG)-thiol/PEG-acrylate, acrylamide/N,N'-bis(acryloyl)cystamine (BACy), or PEG/polypropylene oxide (PPO).

The term "surface" is intended to mean an external part or external layer of a substrate. The surface can be in contact with another material such as a gas, liquid, gel, polymer, organic polymer, second surface of a similar or different material, metal, or coat. The surface, or regions thereof, can be substantially flat. The substrate and/or the surface can have surface features such as wells, pits, channels, ridges, raised regions, pegs, posts or the like.

As used herein, the terms "cluster" and "colony" are used interchangeably to refer to a site (e.g., a discrete site) on a solid support that includes a plurality of immobilized polynucleotides and a plurality of immobilized complementary polynucleotides. In embodiments, the polynucleotides consist of amplicons of a single species (e.g., "monoclonal"), thereby forming a homogenous cluster. However, in preferred embodiments, the polynucleotides at a given site are heterogeneous (e.g., "polyclonal"), such that individual molecules having different sequences are present at the site or feature. In some embodiments, a polyclonal cluster includes template polynucleotides including the same template sequence but containing different adapter sequences compared to other substantially identical template polynucleotides (e.g., the same target polynucleotide sequence from different samples, prepared with the different adapter sequences). The term "clustered array" refers to an array formed from such clusters or colonies. In this context the term "array" is not to be understood as requiring an ordered arrangement of clusters. The term "array" is used in accordance with its ordinary meaning in the art and refers to a population of different molecules that are attached to one or more solid-phase substrates such that different molecules can be differentiated from each other according to their relative location. An array can include different molecules that are each located at different addressable features on a solid-phase substrate. In some embodiments, an array of sites is provided, wherein each of a plurality of the sites includes a first nucleic acid template and a second nucleic acid template and wherein the first nucleic acid template has a sequence that is different from the sequence of the second nucleic acid template. There can be greater than two different templates (e.g., greater than three different templates, greater than four different templates, etc.) at each of a plurality of sites, in some embodiments. The molecules of the array can be nucleic acid primers, nucleic acid probes, nucleic acid templates, or nucleic acid enzymes such as polymerases or ligases. Arrays useful in embodiments of the invention can have densities that range from about 2 different features to many millions, billions, or higher. The density of an array can be from 2 to as many as a billion or more different features per square cm. For example, an array can have at least about 100 features/cm$^2$, at least about 1,000 features/cm$^2$, at least about 10,000 features/cm$^2$, at least about 100,000 features/cm$^2$, at least about 10,000,000 features/cm$^2$, at least about 100,000,000 features/cm$^2$, at least about 1,000,000,000 features/cm$^2$, at least about 2,000,000,000 features/cm$^2$ or higher. In embodiments, the arrays have features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

As used herein, the terms "overlapping amplification cluster" and "overlapping cluster" refer to a site (e.g., a discrete site) on a solid support that includes a plurality of polyclonal immobilized polynucleotides, and a plurality of immobilized complementary polynucleotides. In embodiments, to generate an overlapping amplification cluster, multiple template polynucleotides are immobilized within one spot of an array and subsequently amplified. In an overlapping amplification cluster, a fraction of the surface is occupied by copies of one template polynucleotide species, and other fractions of the surface are occupied of copies of a different template polynucleotide. In embodiments, each immobilized polynucleotide in an overlapping amplification cluster is included in a detection region. In embodiments, an overlapping amplification cluster is included in one or more detection regions. As used herein, the term "detection region" refers to a location in an array where at least one analyte molecule is present. A site can contain only a single analyte molecule or it can contain a population of several analyte molecules of the same species. In some embodiments, a site can include multiple different analyte molecule species, each species being present in one or more copies. Sites of an array are typically discrete. The discrete sites can be contiguous, or they can have spaces between each other. In embodiments, the same template polynucleotide sequence may be present in the same location (e.g., same x-y coordinates and/or geographic location). In embodiments, the same template polynucleotide sequence may be present in different locations (e.g., different x-y coordinates and/or geographic location). In embodiments, the overlapping cluster may be referred to as a feature. In embodiments, multiple template polynucleotides seed one spot (i.e., a feature) of a patterned array or unpatterned solid support. In embodiments, a fraction of the surface area within the feature is occupied by copies of one template, and another fraction of the patterned spot can be occupied by copies of another template. The fractions of the template polynucleotides within the feature are inherently stochastic and governed by Poisson statistics.

Detection can be carried out at ensemble or single molecule levels on an array. Ensemble level detection is detection that occurs in a way that several copies of a single template sequence (e.g. multiple amplicons of a template) are detected at each individual site and individual copies at the site are not distinguished from each other. Thus, ensemble detection provides an average signal from many copies of a particular template sequence at the site. For example, the site can contain at least 10, 100, 1000 or more copies of a particular template sequence. Of course, a site can contain multiple different template sequences each of which is present as an ensemble. Alternatively, detection at a single molecule level includes detection that occurs in a way that individual template sequences are individually resolved on the array, each at a different site. Thus, single molecule detection provides a signal from an individual molecule that is distinguished from one or more signals that may arise from a population of molecules within which the individual molecule is present. Of course, even in a single molecule array, a site can contain several different template sequences (e.g., two or more template sequence regions located along a single nucleic acid molecule).

An array of sites (e.g., an array of features) can appear as a grid of spots or patches. The sites can be located in a repeating pattern or in an irregular non-repeating pattern. Particularly useful patterns are hexagonal patterns, rectilinear patterns, grid patterns, patterns having reflective symmetry, patterns having rotational symmetry, or the like. Asymmetric patterns can also be useful; in embodiments, the array of features are present in an asymmetric pattern.

The size of the sites and/or spacing between the sites in an array can vary to achieve high density, medium density, or lower density. High density arrays are characterized as having sites with a pitch that is less than about 15 μm. Medium density arrays have sites with a pitch that is about 15 to 30 μm, while low density arrays have a pitch that is greater than 30 μm. An array useful in some embodiments can have sites with a pitch that is less than 100 μm, 50 μm, 10 μm, 5 μm, 1 μm, or 0.5 μm. An embodiment of the methods set forth herein can be used to image an array at a resolution sufficient to distinguish sites at the above densities or density ranges. However, the detecting step will typically use a detector having a spatial resolution that is too low to resolve points at a distance equivalent to the spacing between a first template (or first primer extension product hybridized thereto) and a second template (or second primer extension product hybridized thereto) of an overlapping cluster at an individual site. In particular embodiments, sites of an array can each have an area that is larger than about 100 nm$^2$, 250 nm$^2$, 500 nm$^2$, 1 μm$^2$, 2.5 μm$^2$, 5 μm$^2$, 10 μm$^2$, 100 μm$^2$, or 500 μm$^2$. Alternatively or additionally, sites of an array can each have an area that is smaller than about 1 mm$^2$, 500 μm$^2$, 100 μm$^2$, 25 μm$^2$, 10 μm$^2$, 5 μm$^2$, 1 μm$^2$, 500 μm$^2$, or 100 μm$^2$. Indeed, a site can have a size that is in a range between an upper and lower limit selected from those exemplified above.

Generally, an array will have sites with different nucleic acid sequence content. In embodiments, each of a plurality of sites of the array contains different ratios of a population of template polynucleotides, wherein each population of template polynucleotides contains different sequencing primer binding sites. Accordingly, each of the sites in an array can contain a nucleic acid sequence that is unique compared to the nucleic acid sequences at the other sites in the array. However, in some cases an array can have redundancy such that two or more sites have the same nucleic acid content.

As used herein, the term "each," when used in reference to a collection of items, is intended to identify an individual item in the collection but does not necessarily refer to every item in the collection. Exceptions can occur if explicit disclosure or context clearly dictates otherwise.

Nucleic acids, including e.g., nucleic acids with a phosphorothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

As used herein, the term "template polynucleotide" refers to any polynucleotide molecule that may be bound by a polymerase and utilized as a template for nucleic acid synthesis. A template polynucleotide may be a target polynucleotide. In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s). In the context of selective sequencing, "target polynucleotide(s)" refers to the subset of polynucleotide(s) to be sequenced from within a starting population of polynucleotides.

In embodiments, a target polynucleotide is a cell-free polynucleotide. In general, the terms "cell-free," "circulating," and "extracellular" as applied to polynucleotides (e.g. "cell-free DNA" (cfDNA) and "cell-free RNA" (cfRNA)) are used interchangeably to refer to polynucleotides present in a sample from a subject or portion thereof that can be isolated or otherwise manipulated without applying a lysis step to the sample as originally collected (e.g., as in extraction from cells or viruses). Cell-free polynucleotides are thus unencapsulated or "free" from the cells or viruses from which they originate, even before a sample of the subject is collected. Cell-free polynucleotides may be produced as a byproduct of cell death (e.g. apoptosis or necrosis) or cell shedding, releasing polynucleotides into surrounding body fluids or into circulation. Accordingly, cell-free polynucleotides may be isolated from a non-cellular fraction of blood (e.g. serum or plasma), from other bodily fluids (e.g. urine), or from non-cellular fractions of other types of samples.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the terms "analogue" and "analog", in reference to a chemical compound, refers to compound having a structure similar to that of another one, but differing from it in respect of one or more different atoms, functional groups, or substructures that are replaced with one or more other atoms, functional groups, or substructures. In the context of a nucleotide, a nucleotide analog refers to a compound that, like the nucleotide of which it is an analog, can be incorporated into a nucleic acid molecule (e.g., an extension product) by a suitable polymerase, for example, a DNA polymerase in the context of a nucleotide analogue. The terms also encompass nucleic acids containing known nucleotide analogs or modified backbone residues or linkages, which are synthetic, naturally occurring, or non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphorothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, a "native" nucleotide is used in accordance with its plain and ordinary meaning and refers to a naturally occurring nucleotide that does not include an exogenous label (e.g., a fluorescent dye, or other label) or chemical modification such as may characterize a nucleotide analog (e.g., a reversible terminating moiety). Examples of native nucleotides useful for carrying out procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate). A "canonical" nucleotide is an unmodified nucleotide.

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety (alternatively referred to herein as a reversible terminator moiety) and/or a label moiety. A blocking moiety (e.g., a reversible terminator) on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. In embodiments, the blocking moiety is attached to the 3' oxygen of the nucleotide and is independently —NH$_2$, —CN, —CH$_3$, C$_2$-C$_6$ allyl (e.g., —CH$_2$—CH=CH$_2$), methoxyalkyl (e.g., —CH$_2$—O—CH$_3$), or —CH$_2$N$_3$. In embodiments, the blocking moiety is attached to the 3' oxygen of the nucleotide and is independently

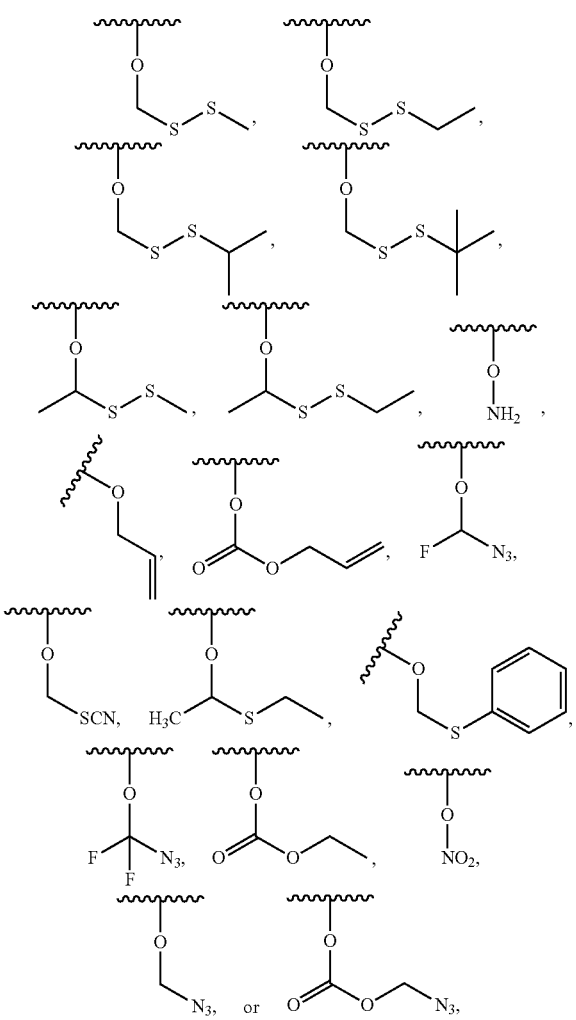

wherein the 3' oxygen of the nucleotide is explicitly shown in the formulae above. A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the OH group at the 3'-position of deoxyribose. Nucleotide analogues and DNA polymerase-based DNA sequencing are also described in U.S. Pat. No. 6,664,079, which is incorporated herein by reference in its entirety for all purposes. Non-limiting examples of detectable labels include labels comprising fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.). In embodiments, the label is a fluorophore.

In embodiments, the nucleotides of the present disclosure use a cleavable linker to attach the label to the nucleotide. The use of a cleavable linker ensures that the label can, if required, be removed after detection, avoiding any interfering signal with any labelled nucleotide incorporated subsequently. The use of the term "cleavable linker" is not meant to imply that the whole linker is required to be removed from the nucleotide base. The cleavage site can be located at a position on the linker that ensures that part of the linker remains attached to the nucleotide base after cleavage. The linker can be attached at any position on the nucleotide base provided that Watson-Crick base pairing can still be carried out. In the context of purine bases, it is preferred if the linker is attached via the 7-position of the purine or the preferred deazapurine analogue, via an 8-modified purine, via an N-6 modified adenosine or an N-2 modified guanine. For pyrimidines, attachment is preferably via the 5-position on cytidine, thymidine or uracil and the N-4 position on cytosine.

The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is a phosphine containing reagent (e.g., TCEP or THPP), sodium dithionite ($Na_2S_2O_4$), weak acid, hydrazine ($N_2H_4$), Pd(0), or light-irradiation (e.g., ultraviolet radiation). In embodiments, cleaving includes removing. A "cleavable site" or "scissile linkage" in the context of a polynucleotide is a site which allows controlled cleavage of the polynucleotide strand (e.g., the linker, the primer, or the polynucleotide) by chemical, enzymatic, or photochemical means known in the art and described herein. A scissile site may refer to the linkage of a nucleotide between two other nucleotides in a nucleotide strand (i.e., an internucleosidic linkage). In embodiments, the scissile linkage can be located at any position within the one or more nucleic acid molecules, including at or near a terminal end (e.g., the 3' end of an oligonucleotide) or in an interior portion of the one or more nucleic acid molecules. In embodiments, conditions suitable for separating a scissile linkage include a modulating the pH and/or the temperature. In embodiments, a scissile site can include at least one acid-labile linkage. For example, an acid-labile linkage may include a phosphoramidate linkage. In embodiments, a phosphoramidate linkage can be hydrolysable under acidic conditions, including mild acidic conditions such as trifluoroacetic acid and a suitable temperature (e.g., 30° C.), or other conditions known in the art, for example Matthias Mag, et al Tetrahedron Letters, Volume 33, Issue 48, 1992, 7319-7322. In embodiments, the scissile site can include at least one photolabile internucleosidic linkage (e.g., o-nitrobenzyl linkages, as described in Walker et al, J. Am. Chem. Soc. 1988, 110, 21, 7170-7177), such as o-nitrobenzyloxymethyl or p-nitrobenzyloxymethyl group(s). In embodiments, the scissile site includes at least one uracil nucleobase. In embodiments, a uracil nucleobase can be cleaved with a uracil DNA glycosylase (UDG) or Formamidopyrimidine DNA Glycosylase Fpg. In embodiments, the scissile linkage site includes a sequence-specific nicking site having a nucleotide sequence that is recognized and nicked by a nicking endonuclease enzyme or a uracil DNA glycosylase.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site blast.ncbi.nlm.nih.gov/Blast.cgi or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

As used herein, the term "removable" group, e.g., a label or a blocking group or protecting group, is used in accordance with its plain and ordinary meaning and refers to a chemical group that can be removed from a nucleotide analogue such that a DNA polymerase can extend the nucleic acid (e.g., a primer or extension product) by the incorporation of at least one additional nucleotide. Removal may be by any suitable method, including enzymatic, chemical, or photolytic cleavage. Removal of a removable group, e.g., a blocking group, does not require that the entire removable group be removed, only that a sufficient portion of it be removed such that a DNA polymerase can extend a nucleic acid by incorporation of at least one additional nucleotide using a nucleotide or nucleotide analogue. In general, the conditions under which a removable group is removed are compatible with a process employing the removable group (e.g., an amplification process or sequencing process).

As used herein, the terms "reversible blocking groups" and "reversible terminators" are used in accordance with their plain and ordinary meanings and refer to a blocking moiety located, for example, at the 3' position of the nucleotide and may be a chemically cleavable moiety such as an allyl group, an azidomethyl group or a methoxymethyl group, or may be an enzymatically cleavable group such as a phosphate ester. Non-limiting examples of nucleotide blocking moieties are described in applications WO 2004/018497, U.S. Pat. Nos. 7,057,026, 7,541,444, WO 96/07669, U.S. Pat. Nos. 5,763,594, 5,808,045, 5,872,244 and 6,232,465 the contents of which are incorporated herein by reference in their entirety. The nucleotides may be labelled or unlabeled. They may be modified with reversible terminators useful in methods provided herein and may be 3'-O-blocked reversible or 3'-unblocked reversible terminators. In nucleotides with 3'-O-blocked reversible terminators, the blocking group —OR [reversible terminating (capping) group] is linked to the oxygen atom of the 3'-OH of the pentose, while the label is linked to the base, which acts as a reporter and can be cleaved. The 3'-O-blocked reversible terminators are known in the art, and may be, for instance, a 3'-ONH₂ reversible terminator, a 3'-O-allyl reversible terminator, or a 3'-O-azidomethyl reversible terminator. In embodiments, the reversible terminator moiety is attached to the 3'-oxygen of the nucleotide, having the formula:

wherein the 3' oxygen of the nucleotide is not shown in the formulae above. The term "allyl" as described herein refers to an unsubstituted methylene attached to a vinyl group (i.e., —CH=CH₂), having the formula

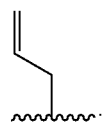

In embodiments, the reversible terminator moiety is

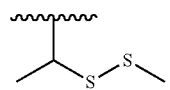

as described in U.S. Pat. No. 10,738,072, which is incorporated herein by reference for all purposes. For example, a nucleotide including a reversible terminator moiety may be represented by the formula:

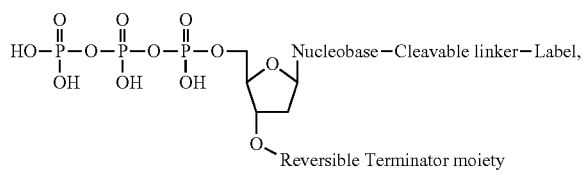

where the nucleobase is adenine or adenine analogue, thymine or thymine analogue, guanine or guanine analogue, or cytosine or cytosine analogue.

In some embodiments, a nucleic acid (e.g., an immobilized oligonucleotide) comprises a molecular identifier or a molecular barcode. As used herein, the term "barcode" or "index" or "unique molecular identifier (UMI)" refers to a known nucleic acid sequence that allows some feature with which the barcode is associated to be identified. Typically, a barcode is unique to a particular feature in a pool of barcodes that differ from one another in sequence, and each of which is associated with a different feature. In embodiments, a barcode is unique in a pool of barcodes that differ from one another in sequence, or is uniquely associated with a particular sample polynucleotide in a pool of sample polynucleotides. In embodiments, every barcode in a pool of adapters is unique, such that sequencing reads comprising the barcode can be identified as originating from a single sample polynucleotide molecule on the basis of the barcode alone. In other embodiments, individual barcode sequences may be used more than once, but adapters comprising the duplicate barcodes are associated with different sequences and/or in different combinations of barcoded adaptors, such that sequence reads may still be uniquely distinguished as originating from a single sample polynucleotide molecule on the basis of a barcode and adjacent sequence information (e.g., sample polynucleotide sequence, and/or one or more adjacent barcodes). In embodiments, barcodes are about or at least about 5, 6, 7, 8, 9, 10, 15, 20, 25, 30, 40, 50, 75 or more nucleotides in length. In embodiments, barcodes are shorter than 20, 15, 10, 9, 8, 7, 6, or 5 nucleotides in length. In embodiments, barcodes are about 10 to about 50 nucleotides in length, such as about 15 to about 40 or about 20 to about 30 nucleotides in length. In a pool of different barcodes, barcodes may have the same or different lengths. In general, barcodes are of sufficient length and comprise sequences that are sufficiently different to allow the identification of associated features (e.g., a binding moiety or analyte) based on barcodes with which they are associated. In embodiments, a barcode can be identified accurately after the mutation, insertion, or deletion of one or more nucleotides in the barcode sequence, such as the mutation, insertion, or deletion of 1, 2, 3, 4, 5, or more nucleotides. In embodiments, each barcode in a plurality of barcodes differs from every other barcode in the plurality by at least three nucleotide positions, such as at least 3, 4, 5, 6, 7, 8, 9, 10, or more nucleotide positions. In some embodiments, substantially degenerate barcodes may be known as random.

In some embodiments, a nucleic acid comprises a label. As used herein, the term "label" or "labels" are used in accordance with their plain and ordinary meanings and refer to molecules that can directly or indirectly produce or result in a detectable signal either by themselves or upon interaction with another molecule. Non-limiting examples of detectable labels include fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the label is a dye. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.). In embodiments, a particular nucleotide type is associated with a particular label, such that identifying the label identifies the nucleotide with which it is associated. In embodiments, the label is luciferin that reacts with luciferase to produce a detectable signal in response to one or more bases being incorporated into an elongated complementary strand, such as in pyrosequencing. In embodiment, a nucleotide comprises a label (such as a dye). In embodiments, the label is not associated with any particular nucleotide, but detection of the label identifies whether one or more nucleotides having a known identity were added during an extension step (such as in the case of pyrosequencing).

In embodiments, the detectable label is a fluorescent dye. In embodiments, the detectable label is a fluorescent dye capable of exchanging energy with another fluorescent dye (e.g., fluorescence resonance energy transfer (FRET) chromophores). Examples of detectable agents include imaging agents, including fluorescent and luminescent substances, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). In embodiments, the detectable moiety is a moiety of a derivative of one of the detectable moieties described immediately above, wherein the derivative differs from one of the detectable moieties immediately above by a modification resulting from the conjugation of the detectable moiety to a compound described herein. The term "cyanine" or "cyanine moiety" as described herein refers to a detectable moiety containing two nitrogen groups separated by a polymethine chain. In embodiments, the cyanine moiety has 3 methine structures (i.e., cyanine 3 or Cy3). In embodiments, the cyanine moiety has 5 methine structures (i.e., cyanine 5 or Cy5). In embodiments, the cyanine moiety has 7 methine structures (i.e., cyanine 7 or Cy7).

As used herein, the term "DNA polymerase" and "nucleic acid polymerase" are used in accordance with their plain ordinary meanings and refer to enzymes capable of synthesizing nucleic acid molecules from nucleotides (e.g., deoxyribonucleotides). Exemplary types of polymerases that may be used in the compositions and methods of the present disclosure include the nucleic acid polymerases such as DNA polymerase, DNA- or RNA-dependent RNA polymerase, and reverse transcriptase. In some cases, the DNA polymerase is 9°N polymerase or a variant thereof, *E. coli* DNA polymerase I, Bacteriophage T4 DNA polymerase, Sequenase, Taq DNA polymerase, DNA polymerase from *Bacillus stearothermophilus*, Bst 2.0 DNA polymerase, 9°N polymerase (exo-) A485L/Y409V, Phi29 DNA Polymerase (φ29 DNA Polymerase), T7 DNA polymerase, DNA polymerase II, DNA polymerase III holoenzyme, DNA polymerase IV, DNA polymerase V, VentR DNA polymerase, Therminator™ II DNA Polymerase, Therminator™ III DNA Polymerase, or or Therminator™ IX DNA Polymerase. In embodiments, the polymerase is a protein polymerase. Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ, DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g. Therminator γ, 9°N polymerase (exo-), Therminator II, Therminator III, or Therminator IX). In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044). In embodiments, the polymerase is an enzyme described in US 2021/0139884.

As used herein, the term "thermophilic nucleic acid polymerase" refers to a family of DNA polymerases (e.g., 9°N™) and mutants thereof derived from the DNA polymerase originally isolated from the hyperthermophilic archaea, *Thermococcus* sp. 9 degrees N-7, found in hydrothermal vents at that latitude (East Pacific Rise) (Southworth M W, et al. PNAS. 1996; 93(11):5281-5285). A thermophilic nucleic acid polymerase is a member of the family B DNA polymerases. Site-directed mutagenesis of the 3'-5' exo motif I (Asp-Ile-Glu or DIE) to AIA, AIE, EIE, EID or DIA yielded polymerase with no detectable 3' exonuclease activity. Mutation to Asp-Ile-Asp (DID) resulted in reduction of 3'-5' exonuclease specific activity to <1% of wild type, while maintaining other properties of the polymerase including its high strand displacement activity. The sequence AIA (D141A, E143A) was chosen for reducing exonuclease. Subsequent mutagenesis of key amino acids results in an increased ability of the enzyme to incorporate dideoxynucleotides, ribonucleotides and acyclonucleotides (e.g., Therminator II enzyme from New England Biolabs with D141A/E143A/Y409V/A485L mutations); 3'-amino-dNTPs, 3'-azido-dNTPs and other 3'-modified nucleotides (e.g., NEB Therminator III DNA Polymerase with D141A/E143A/L408S/Y409A/P410V mutations, NEB Therminator IX DNA polymerase), or γ-phosphate labeled nucleotides (e.g., Therminator γ: D141A/E143A/W355A/L408W/R460A/Q461S/K464E/D480V/R484W/A485L). Typically, these enzymes do not have 5'-3' exonuclease activity. Additional information about thermophilic nucleic acid polymerases may be found in (Southworth M W, et al. PNAS. 1996; 93(11):5281-5285; Bergen K, et al. ChemBioChem. 2013; 14(9):1058-1062; Kumar S, et al. Scientific Reports. 2012; 2:684; Fuller C W, et al. 2016; 113(19):5233-5238; Guo J, et al. Proceedings of the National Academy of Sciences of the United States of America. 2008; 105(27): 9145-9150), which are incorporated herein in their entirety for all purposes.

As used herein, the term "exonuclease activity" is used in accordance with its ordinary meaning in the art, and refers to the removal of a nucleotide from a nucleic acid by a DNA polymerase. For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at the 3' end of a polynucleotide chain to excise the nucleotide. In embodiments, 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, see for example Southworth et al, PNAS Vol 93, 8281-8285 (1996).

As used herein, the term "incorporating" or "chemically incorporating," when used in reference to a primer and cognate nucleotide, refers to the process of joining the cognate nucleotide to the primer or extension product thereof by formation of a phosphodiester bond. In embodiments, incorporating a nucleotide is catalyzed by an enzyme (e.g., a polymerase).

As used herein, the term "selective" or "selectivity" or the like of a compound refers to the compound's ability to discriminate between molecular targets. For example, a chemical reagent may selectively modify one nucleotide type in that it reacts with one nucleotide type (e.g., cytosines) and not other nucleotide types (e.g., adenine, thymine, or guanine). When used in the context of sequencing, such as in "selectively sequencing," this term refers to sequencing one or more target polynucleotides from an original starting population of polynucleotides, and not sequencing non-target polynucleotides from the starting population. Typically, selectively sequencing one or more target polynucleotides involves differentially manipulating the target polynucleotides based on known sequence. For example, target polynucleotides may be hybridized to a probe oligonucleotide that may be labeled (such as with a member of a binding pair) or bound to a surface. In embodiments, hybridizing a target polynucleotide to a probe oligonucleotide includes the step of displacing one strand of a double-stranded nucleic acid. Probe-hybridized target polynucleotides may then be separated from non-hybridized polynucleotides, such as by removing probe-bound polynucleotides from the starting population or by washing away polynucleotides that are not bound to a probe. The result is a selected subset of the starting population of polynucleotides, which is then subjected to sequencing, thereby selectively sequencing the one or more target polynucleotides.

As used herein, the terms "specific", "specifically", "specificity", or the like of a compound refers to the agent's ability to cause a particular action, such as binding, to a particular molecular target with minimal or no action to other proteins in the cell.

As used herein, the terms "bind" and "bound" are used in accordance with their plain and ordinary meanings and refer to an association between atoms or molecules. The association can be direct or indirect. For example, bound atoms or molecules may be directly bound to one another, e.g., by a covalent bond or non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). As a further example, two molecules may be bound indirectly to one another by way of direct binding to one or more intermediate molecules, thereby forming a complex.

As used herein, the term "rolling circle amplification (RCA)" refers to a nucleic acid amplification reaction that amplifies a circular nucleic acid template (e.g., single-stranded DNA circles) via a rolling circle mechanism. Rolling circle amplification reaction is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatemers comprising tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyperbranched concatemers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. The rolling circle amplification may be performed in-vitro under isothermal conditions using a suitable nucleic acid polymerase such as Phi29 DNA polymerase. RCA may be performed by using any of the DNA polymerases that are known in the art (e.g., a Phi29 DNA polymerase, a Bst DNA polymerase, or SD polymerase).

As used herein, the terms "sequencing", "sequence determination", "determining a nucleotide sequence", and the like include determination of a partial or complete sequence information, including the identification, ordering, or locations of the nucleotides that comprise the polynucleotide being sequenced, and inclusive of the physical processes for generating such sequence information. That is, the term includes sequence comparisons, consensus sequence determination, contig assembly, fingerprinting, and like levels of information about a target polynucleotide, as well as the express identification and ordering of nucleotides in a target polynucleotide. The term also includes the determination of the identification, ordering, and locations of one, two, or three of the four types of nucleotides within a target polynucleotide. In some embodiments, a sequencing process described herein comprises contacting a template and an annealed primer with a suitable polymerase under conditions suitable for polymerase extension and/or sequencing. The sequencing methods are preferably carried out with the target polynucleotide arrayed on a solid substrate. Multiple target polynucleotides can be immobilized on the solid support through linker molecules, or can be attached to particles, e.g., microspheres, which can also be attached to a solid substrate. In embodiments, the solid substrate is in the form of a chip, a bead, a well, a capillary tube, a slide, a wafer, a filter, a fiber, a porous media, or a column. In embodiments, the solid substrate is gold, quartz, silica, plastic, glass, diamond, silver, metal, or polypropylene. In embodiments, the solid substrate is porous.

As used herein, the term "sequencing cycle" is used in accordance with its plain and ordinary meaning and refers to incorporating one or more nucleotides (e.g., nucleotide analogues) to the 3' end of a polynucleotide with a polymerase, and detecting one or more labels that identify the one or more nucleotides incorporated. In embodiments, one nucleotide (e.g., a modified nucleotide) is incorporated per sequencing cycle. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes, and other substances can be removed between steps by washing. Cycles may include repeating these steps, and the sequence of each cluster is read over the multiple repetitions.

As used herein, the term "sequencing reaction mixture" is used in accordance with its plain and ordinary meaning and refers to an aqueous mixture that contains the reagents necessary to allow a nucleotide or nucleotide analogue to be added to a DNA strand by a DNA polymerase. In embodiments, the sequencing reaction mixture includes a buffer. In embodiments, the buffer includes an acetate buffer, 3-(N-morpholino)propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer. In embodiments, the sequencing reaction mixture includes nucleotides, wherein the nucleotides include a reversible terminating moiety and a label covalently linked to the nucleotide via a cleavable linker. In embodiments, the sequencing reaction mixture includes a buffer, DNA polymerase, detergent (e.g., Triton X), a chelator (e.g., EDTA), and/or salts (e.g., ammonium sulfate, magnesium chloride, sodium chloride, or potassium chloride). As used herein, the term "invasion-reaction mixture" is used in accordance with its plain and ordinary meaning and refers to an aqueous mixture that contains the reagents sufficient to allow a nucleotide or nucleotide analogue to be added to a DNA strand by a DNA polymerase that extends the invasion primer.

As used herein, the term "extension" or "elongation" is used in accordance with their plain and ordinary meanings and refer to synthesis by a polymerase of a new polynucleotide strand (e.g., an "extension strand") complementary to a template strand by adding free nucleotides (e.g., dNTPs) from a reaction mixture that are complementary to the template in a 5'-to-3' direction, including condensing a 5'-phosphate group of a dNTPs with a 3'-hydroxy group at the end of the nascent (elongating) DNA strand.

As used herein, the term "sequencing read" is used in accordance with its plain and ordinary meaning and refers to an inferred sequence of nucleotide bases (or nucleotide base probabilities) corresponding to all or part of a single polynucleotide fragment. A sequencing read may include 10, 20, 30, 40, 50, 60, 70, 80, 90, 100, 150, 200, 250, or more nucleotide bases. In embodiments, a sequencing read includes reading a barcode and a template nucleotide sequence. In embodiments, a sequencing read includes reading a template nucleotide sequence. In embodiments, a sequencing read includes reading a barcode and not a template nucleotide sequence. In embodiments, a sequencing read is about 25 nucleotide bases. In embodiments, a sequencing read is about 35 nucleotide bases. In embodiments, a sequencing read is about 45 nucleotide bases. In embodiments, a sequencing read is about 55 nucleotide bases. In embodiments, a sequencing read is about 65 nucleotide bases. In embodiments, a sequencing read is about 75 nucleotide bases. In embodiments, a sequencing read is about 85 nucleotide bases. In embodiments, a sequencing read is a string of characters representing the sequence of nucleotides. In embodiments, the length of a sequencing read corresponds to the length of the target sequence. In embodiments, the length of a sequencing read corresponds to the number of sequencing cycles. A sequencing read may be subjected to initial processing (often termed "pre-processing") prior to annotation. Pre-processing includes filtering out low-quality sequences, sequence trimming to remove continuous low-quality nucleotides, merging paired-end sequences, or identifying and filtering out PCR repeats using known techniques in the art. The sequenced reads may then be assembled and aligned using bioinformatic algorithms known in the art. A sequencing read may be aligned to a reference sequence. In embodiments, a sequencing read includes a computationally derived string corresponding to the detected complementary nucleotide (e.g., a labeled nucleotide). The sequence reads are optionally stored in an appropriate data structure for further evaluation. In embodiments, a first sequencing reaction can generate a first sequencing read. The first sequencing read can provide the sequence of a first region of the polynucleotide fragment. In some embodiments, the nucleic acid template is optionally subjected to one or more additional rounds of sequencing using additional sequencing primers, thereby generating additional sequencing reads.

The term "multiplexing" as used herein refers to an analytical method in which the presence and/or amount of multiple targets, e.g., multiple nucleic acid target sequences, can be assayed simultaneously by using the methods and devices as described herein, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

Complementary single stranded nucleic acids and/or substantially complementary single stranded nucleic acids can hybridize to each other under hybridization conditions, thereby forming a nucleic acid that is partially or fully double stranded. All or a portion of a nucleic acid sequence may be substantially complementary to another nucleic acid sequence, in some embodiments. As referred to herein, "substantially complementary" refers to nucleotide sequences that can hybridize with each other under suitable hybridization conditions. Hybridization conditions can be altered to tolerate varying amounts of sequence mismatch within complementary nucleic acids that are substantially complementary.

Substantially complementary portions of nucleic acids that can hybridize to each other can be 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other. In some embodiments substantially complementary portions of nucleic acids that can hybridize to each other are 100% complementary. Nucleic acids, or portions thereof, that are configured to hybridize to each other often comprise nucleic acid sequences that are substantially complementary to each other.

As used herein, the term "hybridize" or "specifically hybridize" refers to a process where two complementary nucleic acid strands anneal to each other under appropriately stringent conditions. Hybridizations are typically and preferably conducted with oligonucleotides. The terms "annealing" and "hybridization" are used interchangeably to mean the formation of a stable duplex. The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). Those skilled in the art understand how to estimate and adjust the stringency of hybridization conditions such that sequences having at least a desired level of complementarity will stably hybridize, while those having lower complementarity will not. As used herein, hybridization of a primer, or of a DNA extension product, respectively, is extendable by creation of a phosphodiester bond with an available nucleotide or nucleotide analogue capable of forming a phosphodiester bond, therewith. For example, hybridization can be performed at a temperature ranging from 15° C. to 95° C. In some embodiments, the hybridization is performed at a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or about 95° C. In other embodiments, the stringency of the hybridization can be further altered by the addition or removal of components of the buffered solution.

As used herein, the term "stringent condition" refers to condition(s) under which a polynucleotide probe or primer will hybridize preferentially to its target sequence, and to a lesser extent to, or not at all to, other sequences. As used herein, "specifically hybridizes" refers to preferential hybridization under hybridization conditions where two nucleic acids, or portions thereof, that are substantially complementary, hybridize to each other and not to other nucleic acids that are not substantially complementary to either of the two nucleic acids. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands that are hybridized to each other can form a duplex which comprises a double-stranded portion of nucleic acid.

A nucleic acid can be amplified by a suitable method. The term "amplified" as used herein refers to subjecting a target nucleic acid in a sample to a process that linearly or exponentially generates amplicon nucleic acids having the same or substantially the same (e.g., substantially identical) nucleotide sequence as the target nucleic acid, or segment thereof, and/or a complement thereof. In some embodiments an amplification reaction comprises a suitable thermal stable polymerase. Thermal stable polymerases are known in the art and are stable for prolonged periods of time, at temperature greater than 80° C. when compared to common polymerases found in most mammals. In certain embodiments the term "amplified" refers to a method that comprises a polymerase chain reaction (PCR). Conditions conducive to amplification (i.e., amplification conditions) are known and often comprise at least a suitable polymerase, a suitable template, a suitable primer or set of primers, suitable nucleotides (e.g., dNTPs), a suitable buffer, and application of suitable annealing, hybridization and/or extension times and temperatures. In certain embodiments an amplified product (e.g., an amplicon) can contain one or more additional and/or different nucleotides than the template sequence, or portion thereof, from which the amplicon was generated (e.g., a primer can contain "extra" nucleotides (such as a 5' portion that does not hybridize to the template), or one or more mismatched bases within a hybridizing portion of the primer).

A nucleic acid can be amplified by a thermocycling method or by an isothermal amplification method. In some embodiments, a rolling circle amplification method is used.

In some embodiments, amplification takes place on a solid support (e.g., within a flow cell) where a nucleic acid, nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification comprises a nucleic acid amplification reaction comprising only one species of oligonucleotide primer (e.g., an amplification primer) immobilized to a surface or substrate. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution-based primers can be used. Non-limiting examples of solid phase nucleic acid amplification reactions include interfacial amplification, bridge amplification, emulsion PCR, WildFire amplification (e.g., US patent publication US2013/0012399), the like or combinations thereof.

Provided herein are methods and compositions for analyzing a sample (e.g., sequencing nucleic acids within a sample). A sample (e.g., a sample comprising nucleic acid) can be obtained from a suitable subject. A sample can be isolated or obtained directly from a subject or part thereof. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. A fluid or tissue sample from which nucleic acid is extracted may be acellular (e.g., cell-free). Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may comprise cells or tissues that are normal, healthy, diseased (e.g., infected), and/or cancerous (e.g., cancer cells). A sample obtained from a subject may comprise cells or cellular material (e.g., nucleic acids) of multiple organisms (e.g., virus nucleic acid, fetal nucleic acid, bacterial nucleic acid, parasite nucleic acid).

In some embodiments, a sample includes nucleic acid, or fragments thereof. A sample can include nucleic acids obtained from one or more subjects. In some embodiments a sample includes nucleic acid obtained from a single subject. In some embodiments, a sample includes a mixture of nucleic acids. A mixture of nucleic acids can include two or more nucleic acid species having different nucleotide sequences, different fragment lengths, different origins (e.g., genomic origins, cell or tissue origins, subject origins, the like or combinations thereof), or combinations thereof. A sample may include synthetic nucleic acid.

A subject can be any living or non-living organism, including but not limited to a human, non-human animal, plant, bacterium, fungus, virus or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a human subject. A subject can be a patient (e.g., a human patient). In some embodiments a subject is suspected of having a genetic variation or a disease or condition associated with a genetic variation.

The methods and kits of the present disclosure may be applied, mutatis mutandis, to the sequencing of RNA, or to determining the identity of a ribonucleotide.

The terms "bioconjugate group," "bioconjugate reactive moiety," and "bioconjugate reactive group" refer to a chemical moiety which participates in a reaction to form a bioconjugate linker (e.g., covalent linker). Non-limiting examples of bioconjugate groups include —NH$_2$, —COOH, —COOCH$_3$, —N-hydroxysuccinimide, —N$_3$, -dibenzylcyclooctyne (DBCO), alkyne, -maleimide,

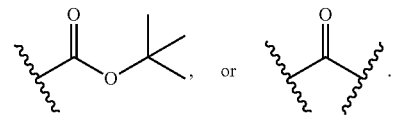

In embodiments, the bioconjugate reactive group may be protected (e.g., with a protecting group). In embodiments, the bioconjugate reactive moiety is

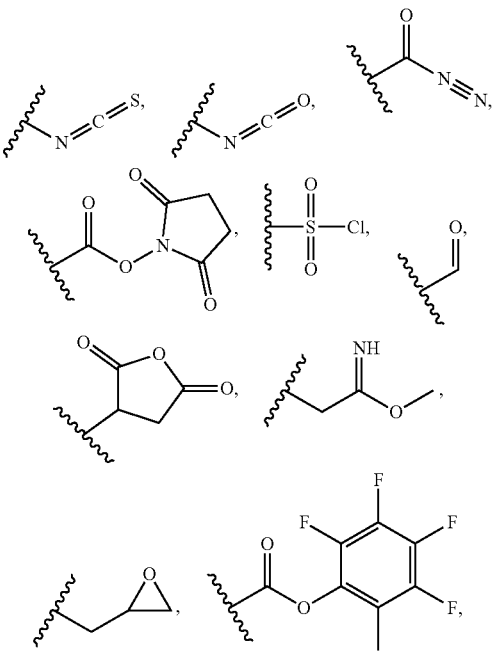

or —NH$_2$. Additional examples of bioconjugate reactive groups and the resulting bioconjugate reactive linkers may be found in the Bioconjugate Table below:

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotri azines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g., —NH₂, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine). In embodiments, the first bioconjugate reactive group (e.g., —COOH) is covalently attached to the second bioconjugate reactive group (e.g.,

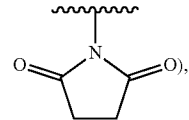

thereby forming a bioconjugate (e.g.,

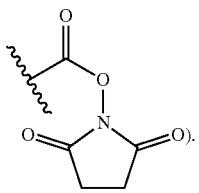

In embodiments, the first bioconjugate reactive group (e.g., —NH₂) is covalently attached to the second bioconjugate reactive group (e.g.,

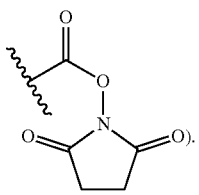

thereby forming a bioconjugate (e.g.,

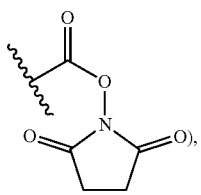

O),

In embodiments, the first bioconjugate reactive group (e.g., a coupling reagent) is covalently attached to the second bioconjugate reactive group (e.g.,

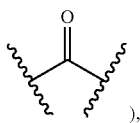

), thereby forming a bioconjugate (e.g.,

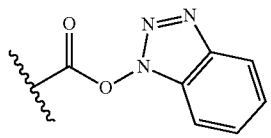 [SMILES: *C(=O)On1nnc2ccccc21]

In embodiments, the first bioconjugate reactive group (e.g., azide moiety) is covalently attached to the second bioconjugate reactive group (e.g., an alkyne moiety) to form a 5-membered heteroatom ring. In embodiments, the first bioconjugate reactive group (e.g., azide moiety) is covalently attached to the second bioconjugate reactive group (e.g., an DBCO moiety) to form a bioconjugate linker.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; (o) biotin conjugate can react with avidin or streptavidin to form a avidin-biotin complex or streptavidin-biotin complex.

The term "covalent linker" is used in accordance with its ordinary meaning and refers to a divalent moiety which connects at least two moieties to form a molecule. The term "non-covalent linker" is used in accordance with its ordinary meaning and refers to a divalent moiety which includes at least two molecules that are not covalently linked to each other but are capable of interacting with each other via a non-covalent bond (e.g., electrostatic interactions (e.g., ionic bond, hydrogen bond, halogen bond) or van der Waals interactions (e.g., dipole-dipole, dipole-induced dipole, London dispersion). In embodiments, the non-covalent linker is the result of two molecules that are not covalently linked to each other that interact with each other via a non-covalent bond.

The term "adapter" as used herein refers to any linear oligonucleotide that can be ligated to a nucleic acid molecule, thereby generating nucleic acid products that can be sequenced on a sequencing platform (e.g., an Illumina or Singular Genomics sequencing platform). In embodiments, adapters include two reverse complementary oligonucleotides forming a double-stranded structure. In embodiments, an adapter includes two oligonucleotides that are complementary at one portion and mismatched at another portion, forming a Y-shaped or fork-shaped adapter that is double stranded at the complementary portion and has two overhangs at the mismatched portion. Since Y-shaped adapters have a complementary, double-stranded region, they can be considered a special form of double-stranded adapters. When this disclosure contrasts Y-shaped adapters and double stranded adapters, the term "double-stranded adapter" or "blunt-ended" is used to refer to an adapter having two strands that are fully complementary, substantially (e.g., more than 90% or 95%) complementary, or partially complementary. In embodiments, adapters include sequences that bind to sequencing primers. In embodiments, adapters include sequences that bind to immobilized oligonucleotides (e.g., P7 and P5 sequences, or S1 and S2 sequences) or reverse complements thereof. In embodiments, the adapter is substantially non-complementary to the 3' end or the 5' end of any target polynucleotide present in the sample. In embodiments, the adapter can include a sequence that is substantially identical, or substantially complementary, to at least a portion of a primer, for example a universal primer. In embodiments, the adapter can include an index sequence (also referred to as barcode or tag) to assist with downstream error correction, identification or sequencing. In embodiments, greater than four types of adapters are contemplated herein, for example 5, 6, 7, 8, 9, 10, 11, or 12 adapters.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

"Synthetic" agents refer to non-naturally occurring agents, such as enzymes or nucleotides.

A "blocking element" refers to an agent (e.g., polynucleotide, protein, nucleotide) that reduces and/or inhibits nucleotide incorporation (i.e., extension of a primer) relative to the absence of the blocking element. In embodiments, the blocking element is a non-extendable oligomer (e.g., an oligonucleotide including a non-extendible nucleotide at the 3' end, for example a 3'-blocked oligo). A blocking element on a nucleotide can be reversible, whereby the blocking moiety can be removed or modified to allow the 3' hydroxyl to form a covalent bond with the 5' phosphate of another nucleotide. For example, a reversible terminator may refer to a blocking moiety located, for example, at the 3' position of the nucleotide and may be a chemically cleavable moiety such as an allyl group, an azidomethyl group or a methoxymethyl group. In embodiments the blocking moiety is not reversible (e.g., the blocking element including a blocking moiety irreversibly prevents extension). In embodiments, the blocking element includes an oligo having a 3' dideoxynucleotide or similar modification to prevent extension by a polymerase and is used in conjunction with a non-strand displacing polymerase. In another example implementation, the blocking element includes one or more modified nucleotides comprising a cleavable linker (e.g., linked to the 5', 3', or the nucleobase) containing PEG, thereby blocking the extension. In another example implementation, the blocking element includes one or more modified nucleotides linked to biotin, to which a protein (e.g., streptavidin) can be bound, thereby blocking polymerase extension. In another example implementation, the blocking element includes a modified nucleotide, such as iso dGTP or iso dCTP, which are complementary to each other. In a reaction of polymerization lacking the appropriate complementary modified nucleotides, the extension of a primer is halted. In another example implementation, the blocking element comprises one or more sequences which is recognized and bound by one or more single-stranded DNA-binding proteins, thereby blocking polymerase extension at the bound site. In another example implementation, the blocking element includes one or more sequences which are recognized and bound by one or more short RNA or PNA oligos, thereby blocking the extension by a DNA polymerase that cannot strand displace RNA or PNA.

As used herein, the term "feature" refers a site (i.e., a physical location) on a solid support for one or more molecule(s). A feature can contain only a single molecule or it can contain a population of several molecules of the same species (i.e., a cluster). Features of an array are typically discrete. The discrete features can be contiguous, or they can have spaces between each other. An "optically resolvable feature" refers to a feature capable of being distinguished from other features. Optics and sensor resolution has a finite limit as to a resolvable area. The Rayleigh criterion for the diffraction limit to resolution states that two images are just resolvable when the center of the diffraction pattern of one object is directly over the first minimum of the diffraction pattern of the other object. The minimal distance between two resolvable objects, r, is proportional to the wavelength of light and inversely proportional to the numerical aperture (NA). That is, the minimal distance between two resolvable objects is provided as r=0.61 wavelength/NA. If detecting light in the UV-vis spectrum (about 100 nm to about 900 nm), the remaining mutable variable to increase the resolution is the NA of the objective lens. A lens with a large NA will be able to resolve finer details. For example, a lens with larger NA is capable of detecting more light and so it produces a brighter image. Thus, a large NA lens provides more information to form a clear image, and so its resolving power will be higher. Typical dry objectives have an NA of about 0.80 to about 0.95. Higher NAs may be obtained by increasing the imaging medium refractive index between the object and the objective front lens for example immersing the lens in water (refractive index=1.33), glycerin (refractive index=1.47), or immersion oil (refractive index=1.51). Most oil immersion objectives have a maximum numerical aperture of 1.4, with the typical objectives having an NA ranging from 1.0 to 1.35.

It will be understood that the steps of the methods set forth herein can be carried out in a manner to expose an entire site or a plurality of sites of an array with the treatment. For example, a step that involves extension of a primer can be carried out by delivering primer extension reagents to an array such that multiple nucleic acids (e.g. different nucleic acids in a mixture) at each of one or more sites of the array are contacted with the primer extension reagents. Similarly, a step of deblocking a blocked primer extension product can be carried out by exposing an array with a deblocking treatment such that multiple nucleic acids (e.g. different nucleic acids in a mixture) at each of one or more sites of the array are contacted with the treatment.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

II. Compositions & Kits

In an aspect is provided a substrate including: (a) a plurality of amplification clusters on a solid support, wherein: (i) one or more amplification clusters includes one or more copies of a first template polynucleotide including a first adapter sequence, and one or more copies of a second template polynucleotide including a second adapter sequence, wherein the first and second template polynucleotides are not substantially complementary to each other; and (ii) the first adapter sequence includes a first platform primer binding sequence and a first sequencing primer binding sequence; and the second adapter sequence includes the first platform primer binding sequence and a second sequencing primer binding sequence, wherein the first sequencing primer binding sequence is different from the second sequencing primer binding sequence and wherein the first platform primer binding sequence includes a sequence complementary to a first amplification primer attached to the solid support; (b) a plurality of first sequencing primers hybridized to the first adapter sequences of the amplification clusters. In embodiments, the substrate further includes a plurality of second sequencing primers hybridized to the second adapter sequences of the amplification clusters.

In embodiments, the substrate further includes one or more amplification clusters on the solid support, wherein: (i) one or more amplification clusters includes one or more copies of a third template polynucleotide including a third adapter sequence, and one or more copies of a fourth template polynucleotide including a fourth adapter sequence, wherein the third and fourth template polynucleotides are not substantially complementary to each other; and (ii) the third adapter sequence includes a second platform primer binding sequence and a third sequencing primer binding sequence; and the fourth adapter sequence includes the second platform primer binding sequence and a fourth sequencing primer binding sequence, wherein the third sequencing primer binding sequence is different from the fourth sequencing primer binding sequence and wherein the second platform primer binding sequence includes a sequence complementary to a second amplification primer attached to the solid support; (b) a plurality of third sequencing primers hybridized to the third adapter sequences of the amplification clusters. In embodiments, the substrate further includes a plurality of fourth sequencing primers hybridized to the fourth adapter sequences of the amplification clusters.

In an aspect is provided a substrate including: (a) a plurality of amplification clusters on a solid support, wherein: (i) one or more amplification clusters includes one or more copies of a first template polynucleotide including a first adapter sequence, one or more copies of a second template polynucleotide including a second adapter sequence, one or more copies of a third template polynucleotide including a third adapter sequence, and one or more copies of a fourth template polynucleotide including a fourth adapter sequence, wherein the first, second, third, and fourth template polynucleotides are not substantially complementary to each other; and (ii) the first adapter sequence includes a first platform primer binding sequence and a first sequencing primer binding sequence; the second adapter sequence includes the first platform primer binding sequence and a second sequencing primer binding sequence; the third adapter sequence includes a second platform primer binding sequence and a third sequencing primer binding sequence; and the fourth adapter sequence includes the second platform primer binding sequence and a fourth sequencing primer binding sequence, wherein the first sequencing primer binding sequence is different from the second sequencing primer binding sequence and the third sequencing primer binding sequence is different from the fourth sequencing primer binding sequence, and wherein the first platform primer binding sequence includes a sequence complementary to a first amplification primer attached to the solid support and the second platform primer binding sequence includes a sequence complementary to a second amplification primer attached to the solid support; (b) a plurality of first sequencing primers hybridized to the first adapter sequences of the amplification clusters. In embodiments, the substrate further includes a plurality of second sequencing primers hybridized to the second adapter sequences of the amplification clusters. In embodiments, the substrate further includes a plurality of third sequencing primers hybridized to the third adapter sequences of the amplification clusters. In embodiments, the substrate further includes a plurality of fourth sequencing primers hybridized to the fourth adapter sequences of the amplification clusters. In embodiments, the first sequencing primer binding sequence, the second sequencing primer binding sequence, the third sequencing primer binding sequence, and the fourth sequencing primer binding sequence are different from each other.

In an aspect is provided a substrate including: (a) a plurality of amplification clusters on a solid support, wherein: (i) one or more amplification clusters includes one or more copies of a first template polynucleotide including a first adapter sequence, one or more copies of a second template polynucleotide including a second adapter sequence, one or more copies of a third template polynucleotide including a third adapter sequence, one or more copies of a fourth template polynucleotide including a fourth adapter sequence, one or more copies of a fifth template polynucleotide including a fifth adapter sequence, one or more copies of a sixth template polynucleotide including a sixth adapter sequence, one or more copies of a seventh template polynucleotide including a seventh adapter sequence, and one or more copies of an eighth template polynucleotide including an eighth adapter sequence, wherein the first, second, third, fourth, fifth, sixth, seventh, and eighth template polynucleotides are not substantially complementary to each other; and (ii) the first adapter sequence includes a first platform primer binding sequence and a first sequencing primer binding sequence; the second adapter sequence includes the first platform primer binding sequence and a second sequencing primer binding sequence; the third adapter sequence includes a second platform primer binding sequence and a third sequencing primer binding sequence; the fourth adapter sequence includes the second platform primer binding sequence and a fourth sequencing primer binding sequence, the fifth adapter sequence includes a third platform primer binding sequence and a fifth sequencing primer binding sequence, the sixth adapter sequence includes the third platform primer binding sequence and a sixth sequencing primer binding sequence, the seventh adapter sequence includes a fourth platform primer binding sequence and a seventh sequencing primer binding sequence, and the eighth adapter sequence includes the fourth platform primer binding sequence and an eighth sequencing primer binding sequence, wherein the first sequencing primer binding sequence is different from the second sequencing primer binding sequence, the third sequencing primer binding sequence is different from the fourth sequencing primer binding sequence, the fifth sequencing primer binding sequence is different from the sixth sequencing primer binding sequence, and the seventh sequencing primer binding sequence is different from the eighth sequencing primer binding sequence, and wherein the first platform primer binding sequence includes a sequence complementary to a first amplification primer attached to the solid support, the second platform primer binding sequence includes a sequence complementary to a second amplification primer attached to the solid support, the third platform primer binding sequence includes a sequence complementary to a third amplification primer attached to the solid support, and the fourth platform primer binding sequence includes a sequence complementary to a fourth amplification primer attached to the solid support; (b) a plurality of first sequencing primers hybridized to the first adapter sequences of the amplification clusters. In embodiments, the substrate further includes a plurality of second sequencing primers hybridized to the second adapter sequences of the amplification clusters. In embodiments, the substrate further includes a plurality of third sequencing primers hybridized to the third adapter sequences of the amplification clusters. In embodiments, the substrate further includes a plurality of fourth sequencing primers hybridized to the fourth adapter sequences of the amplification clusters. In embodiments, the substrate further includes a plurality of fifth sequencing primers hybridized to the fifth adapter sequences of the amplification clusters. In embodiments, the substrate further includes a plurality of sixth sequencing primers hybridized to the sixth adapter sequences of the amplification clusters. In embodiments, the substrate further includes a plurality of seventh sequencing primers hybridized to the seventh adapter sequences of the amplification clusters. In embodiments, the substrate further includes a plurality of eighth sequencing primers hybridized to the eighth adapter sequences of the amplification clusters. In embodiments, the first sequencing primer binding sequence, the second sequencing primer binding sequence, the third sequencing primer binding sequence, the fourth sequencing primer binding sequence, the fifth sequencing primer binding sequence, the sixth sequencing primer binding sequence, the seventh sequencing primer binding sequence, and the eighth sequencing primer binding sequence are different from each other.

In an aspect is provided a substrate including: (a) a plurality of amplification clusters on a solid support, wherein: (i) one or more amplification clusters includes one or more copies of a first template polynucleotide including a first adapter sequence, one or more copies of a second template polynucleotide including a second adapter sequence, one or more copies of a third template polynucleotide including a third adapter sequence, one or more copies of a fourth template polynucleotide including a fourth adapter sequence, one or more copies of a fifth template polynucleotide including a fifth adapter sequence, one or more copies of a sixth template polynucleotide including a sixth adapter sequence, one or more copies of a seventh template polynucleotide including a seventh adapter sequence, one or more copies of an eighth template polynucleotide including an eighth adapter sequence, one or more copies of a ninth template polynucleotide including a ninth adapter sequence, one or more copies of a tenth template polynucleotide including a tenth adapter sequence, one or more copies of an eleventh template polynucleotide including an eleventh adapter sequence, and one or more copies of a twelfth template polynucleotide including a twelfth adapter sequence, wherein the first, second, third, fourth, fifth, sixth, seventh, eighth, ninth, tenth, eleventh, and twelfth template polynucleotides are not substantially complementary to each other; and (ii) the first adapter sequence includes a first platform primer binding sequence and a first sequencing primer binding sequence; the second adapter sequence includes the first platform primer binding sequence and a second sequencing primer binding sequence; the third adapter sequence includes a second platform primer binding sequence and a third sequencing primer binding sequence; the fourth adapter sequence includes the second platform primer binding sequence and a fourth sequencing primer binding sequence, the fifth adapter sequence includes a third platform primer binding sequence and a fifth sequencing primer binding sequence, the sixth adapter sequence includes the third platform primer binding sequence and a sixth sequencing primer binding sequence, the seventh adapter sequence includes a fourth platform primer binding sequence and a seventh sequencing primer binding sequence, the eighth adapter sequence includes the fourth platform primer binding sequence and an eighth sequencing primer binding sequence, the ninth adapter sequence includes a fifth platform primer binding sequence and a ninth sequencing primer binding sequence, the tenth adapter sequence includes the fifth platform primer binding sequence and a tenth sequencing primer binding sequence, the eleventh adapter sequence includes a sixth platform primer binding sequence and an eleventh sequencing primer binding sequence, and the twelfth adapter sequence includes the sixth platform primer binding sequence and a twelfth sequencing primer binding sequence, wherein the first sequencing primer binding sequence is different from the second sequencing primer binding sequence, the third sequencing primer binding sequence is different from the fourth sequencing primer binding sequence, the fifth sequencing primer binding sequence is different from the sixth sequencing primer binding sequence, the seventh sequencing primer binding sequence is different from the eighth sequencing primer binding sequence, the ninth sequencing primer binding sequence is different from the tenth sequencing primer binding sequence, and the eleventh sequencing primer binding sequence is different from the twelfth sequencing primer binding sequence, and wherein the first platform primer binding sequence includes a sequence complementary to a first amplification primer attached to the solid support, the second platform primer binding sequence includes a sequence complementary to a second amplification primer attached to the solid support, the third platform primer binding sequence includes a sequence complementary to a third amplification primer attached to the solid support, the fourth platform primer binding sequence includes a sequence complementary to a fourth amplification primer attached to the solid support, the fifth platform primer binding sequence includes a sequence complementary to a fifth amplification primer attached to the solid support, and the sixth platform primer binding sequence includes a sequence complementary to a sixth amplification primer attached to the solid support; (b) a plurality of first sequencing primers hybridized to the first adapter sequences of the amplification clusters. In embodiments, the substrate further includes a plurality of second sequencing primers hybridized to the second adapter sequences of the amplification clusters. In embodiments, the substrate further includes a plurality of third sequencing primers hybridized to the third adapter sequences of the amplification clusters. In embodiments, the substrate further includes a plurality of fourth sequencing primers hybridized to the fourth adapter sequences of the amplification clusters. In embodiments, the substrate further includes a plurality of fifth sequencing primers hybridized to the fifth adapter sequences of the amplification clusters. In embodiments, the substrate further includes a plurality of sixth sequencing primers hybridized to the sixth adapter sequences of the amplification clusters. In embodiments, the substrate further includes a plurality of seventh sequencing primers hybridized to the seventh adapter sequences of the amplification clusters. In embodiments, the substrate further includes a plurality of eighth sequencing primers hybridized to the eighth adapter sequences of the amplification clusters. In embodiments, the substrate further includes a plurality of ninth sequencing primers hybridized to the ninth adapter sequences of the amplification clusters. In embodiments, the substrate further includes a plurality of tenth sequencing primers hybridized to the tenth adapter sequences of the amplification clusters. In embodiments, the substrate further includes a plurality of eleventh sequencing primers hybridized to the eleventh adapter sequences of the amplification clusters. In embodiments, the substrate further includes a plurality of twelfth sequencing primers hybridized to the twelfth adapter sequences of the amplification clusters. In embodiments, the first sequencing primer binding sequence, the second sequencing primer binding sequence, the third sequencing primer binding sequence, the fourth sequencing primer binding sequence, the fifth sequencing primer binding sequence, the sixth sequencing primer binding sequence, the seventh sequencing primer binding sequence, the eighth sequencing primer binding sequence, the ninth sequencing primer binding sequence, the tenth sequencing primer binding sequence, the eleventh sequencing primer binding sequence, and the twelfth sequencing primer binding sequence are different from each other.

In an aspect is provided a substrate including amplification products of a first population of polynucleotides, or complements thereof, and amplification products of a second population of polynucleotides, or complements thereof, on a solid support, wherein the solid support includes a first plurality of oligonucleotides attached to the solid support and a second plurality of oligonucleotides attached to the solid support, wherein: (i) the first and second populations are not substantially complementary to each other; and (ii) the polynucleotides of each population include a first platform primer binding sequence complementary to the first plurality of oligonucleotides attached to the solid support and a second platform primer binding sequence complementary to the second plurality of oligonucleotides attached to the solid support.

In an aspect is provided a substrate including at least two different populations, for example 2, 3, 4, 5, 6, 7, or 8 different libraries, of polynucleotides at a single feature (e.g., a discrete area) of a solid support, wherein the feature includes: a first complex including a first population of polynucleotides including a first adapter sequence attached to the solid support and a second complex including a second population of polynucleotides including a second adapter sequence attached to the solid support; wherein: the first adapter sequence includes a first platform primer binding sequence complementary to a first amplification primer, and a first sequencing primer binding sequence and the second adapter sequence includes the first platform primer binding sequence and a second sequencing primer binding sequence; the first complex includes a first amplification primer attached to the solid support hybridized to the first adapter sequence; and the second complex includes a second amplification primer attached to the solid support hybridized to the second adapter sequence, wherein the first and second amplification primer include the same sequence; and the first sequencing primer binding sequence is different from the second sequencing primer binding sequence. In embodiments, the substrate includes a plurality of features. In embodiments, the feature is about 0.2 µm to about 2 µm in diameter. In embodiments, the feature is about 0.2-1.5 µm in diameter. In some embodiments, the diameter of the feature is less than 700 nm, less than 600 nm, less than 500 nm, less than 400 nm, less than 300 nm, less than 200 nm, or less than 100 nm. It is also understood that the size of the features on the array can be of various sizes and will ultimately depend on the systems and/or apparatus used to analyze later reactions.

In embodiments, the substrate includes at least 3, 4, 5, 6, 7, 8, 9 10, 11, or 12 different populations of polynucleotides at a single feature of a solid support. In embodiments, the substrate includes 3, 4, 5, 6, 7, 8, 9 10, 11, or 12 different populations of polynucleotides at a single feature of a solid support. In embodiments, the substrate includes 3 different populations of polynucleotides at a single feature of a solid support. In embodiments, the substrate includes 4 different populations of polynucleotides at a single feature of a solid support. In embodiments, the substrate includes 5 different populations of polynucleotides at a single feature of a solid support. In embodiments, the substrate includes 6 different populations of polynucleotides at a single feature of a solid support. In embodiments, the substrate includes 7 different populations of polynucleotides at a single feature of a solid support. In embodiments, the substrate includes 8 different populations of polynucleotides at a single feature of a solid support. In embodiments, the substrate includes 9 different populations of polynucleotides at a single feature of a solid support. In embodiments, the substrate includes 10 different populations of polynucleotides at a single feature of a solid support. In embodiments, the substrate includes 11 different populations of polynucleotides at a single feature of a solid support. In embodiments, the substrate includes 12 different populations of polynucleotides at a single feature of a solid support.

In embodiments, the first and second populations of polynucleotides have heterogenic sequences except for the first sequencing primer binding sequence. In embodiments, the first and second populations of polynucleotides have heterogenic sequences except for the second sequencing primer binding sequence. In embodiments, the third and fourth populations of polynucleotides have heterogenic sequences except for the third sequencing primer binding sequence. In embodiments, the third and fourth populations of polynucleotides have heterogenic sequences except for the fourth sequencing primer binding sequence. In embodiments, the fifth and sixth populations of polynucleotides have heterogenic sequences except for the fifth sequencing primer binding sequence. In embodiments, the fifth and sixth populations of polynucleotides have heterogenic sequences except for the sixth sequencing primer binding sequence. In embodiments, the seventh and eighth populations of polynucleotides have heterogenic sequences except for the seventh sequencing primer binding sequence. In embodiments, the seventh and eighth populations of polynucleotides have heterogenic sequences except for the eighth sequencing primer binding sequence. In embodiments, the ninth and tenth populations of polynucleotides have heterogenic sequences except for the ninth sequencing primer binding sequence. In embodiments, the ninth and tenth populations of polynucleotides have heterogenic sequences except for the tenth sequencing primer binding sequence. In embodiments, the eleventh and twelfth populations of polynucleotides have heterogenic sequences except for the eleventh sequencing primer binding sequence. In embodiments, the eleventh and twelfth populations of polynucleotides have heterogenic sequences except for the twelfth sequencing primer binding sequence.

In an aspect is provided a substrate including four different populations (e.g., four different libraries) of polynucleotides at a single feature of a solid support, wherein the feature includes: a first complex including a first population of polynucleotides including a first adapter sequence attached to the solid support, a second complex including a second population of polynucleotides including a second adapter sequence attached to the solid support, a third complex including a third population of polynucleotides including a third adapter sequence attached to the solid support, and a fourth complex including a fourth population of polynucleotides including a fourth adapter sequence attached to the solid support; wherein: the first adapter sequence includes a first platform primer binding sequence complementary to a first amplification primer, and a first sequencing primer binding sequence, the second adapter sequence includes the first platform primer binding sequence and a second sequencing primer binding sequence, the third adapter sequence includes a second platform primer binding sequence complementary to a second amplification primer, and a third sequencing primer binding sequence, and the fourth adapter sequence includes the second platform primer binding sequence and a fourth sequencing primer binding sequence; the first complex includes a first amplification primer attached to the solid support hybridized to the first adapter sequence; the second complex includes a second amplification primer attached to the solid support hybridized to the second adapter sequence, wherein the first and second amplification primer include the same sequence; the third complex includes a third amplification primer attached to the solid support hybridized to the third adapter sequence; and the fourth complex includes a fourth amplification primer attached to the solid support hybridized to the fourth adapter sequence, wherein the third and fourth amplification primer include the same sequence; and the first sequencing primer binding sequence, the second sequencing primer binding sequence, the third sequencing primer binding sequence, and the fourth sequencing primer binding sequence are different from each other.

In an aspect is provided a substrate including eight different populations of polynucleotides at a single feature of a solid support, wherein the feature includes: a first complex including a first population of polynucleotides including a first adapter sequence attached to the solid support, a second complex including a second population of polynucleotides including a second adapter sequence attached to the solid support, a third complex including a third population of polynucleotides including a third adapter sequence attached to the solid support, a fourth complex including a fourth population of polynucleotides including a fourth adapter sequence attached to the solid support, a fifth complex including a fifth population of polynucleotides including a fifth adapter sequence attached to the solid support, a sixth complex including a sixth population of polynucleotides including a sixth adapter sequence attached to the solid support, a seventh complex including a seventh population of polynucleotides including a seventh adapter sequence attached to the solid support, and an eight complex including an eighth population of polynucleotides including an eighth adapter sequence attached to the solid support; wherein: the first adapter sequence includes a first platform primer binding sequence complementary to a first amplification primer, and a first sequencing primer binding sequence, the second adapter sequence includes the first platform primer binding sequence and a second sequencing primer binding sequence, the third adapter sequence includes a second platform primer binding sequence complementary to a second amplification primer, and a third sequencing primer binding sequence, the fourth adapter sequence includes the second platform primer binding sequence and a fourth sequencing primer binding sequence, the fifth adapter sequence includes a third platform primer binding sequence and a fifth sequencing primer binding sequence, the sixth adapter sequence includes the third platform primer binding sequence and a sixth sequencing primer binding sequence, the seventh adapter sequence includes a fourth platform primer binding sequence and a seventh sequencing primer binding sequence, and the eighth adapter sequence includes the fourth platform primer binding sequence and an eighth sequencing primer binding sequence; the first complex includes a first amplification primer attached to the solid support hybridized to the first adapter sequence; the second complex includes a second amplification primer attached to the solid support hybridized to the second adapter sequence, wherein the first and second amplification primer include the same sequence; the third complex includes a third amplification primer attached to the solid support hybridized to the third adapter sequence; the fourth complex includes a fourth amplification primer attached to the solid support hybridized to the fourth adapter sequence, wherein the third and fourth amplification primer include the same sequence; the fifth complex includes a fifth amplification primer attached to the solid support hybridized to the fifth adapter sequence; the sixth complex includes a sixth amplification primer attached to the solid support hybridized to the sixth adapter sequence, wherein the fifth and sixth amplification primer include the same sequence; the seventh complex includes a seventh amplification primer attached to the solid support hybridized to the seventh adapter sequence; and the eighth complex includes an eighth amplification primer attached to the solid support hybridized to the eighth adapter sequence, wherein the seventh and eighth amplification primer include the same sequence; and the first sequencing primer binding sequence, the second sequencing primer binding sequence, the third sequencing primer binding sequence, the fourth sequencing primer binding sequence, the fifth sequencing primer binding sequence, the sixth sequencing primer binding sequence, the seventh sequencing primer binding sequence, and the eighth sequencing primer binding sequence are different from each other.

In an aspect is provided a substrate including twelve different populations of polynucleotides at a single feature of a solid support, wherein the feature includes: a first complex including a first population of polynucleotides including a first adapter sequence attached to the solid support, a second complex including a second population of polynucleotides including a second adapter sequence attached to the solid support, a third complex including a third population of polynucleotides including a third adapter sequence attached to the solid support, a fourth complex including a fourth population of polynucleotides including a fourth adapter sequence attached to the solid support, a fifth complex including a fifth population of polynucleotides including a fifth adapter sequence attached to the solid support, a sixth complex including a sixth population of polynucleotides including a sixth adapter sequence attached to the solid support, a seventh complex including a seventh population of polynucleotides including a seventh adapter sequence attached to the solid support, an eight complex including an eighth population of polynucleotides including an eighth adapter sequence attached to the solid support, a ninth complex including a ninth population of polynucleotides including a ninth adapter sequence attached to the solid support; a tenth complex including a tenth population of polynucleotides including a tenth adapter sequence attached to the solid support; an eleventh complex including an eleventh population of polynucleotides including an eleventh adapter sequence attached to the solid support; and a twelfth complex including a twelfth population of polynucleotides including a twelfth adapter sequence attached to the solid support; wherein: the first adapter sequence includes a first platform primer binding sequence complementary to a first amplification primer, and a first sequencing primer binding sequence, the second adapter sequence includes the first platform primer binding sequence and a second sequencing primer binding sequence, the third adapter sequence includes a second platform primer binding sequence complementary to a second amplification primer, and a third sequencing primer binding sequence, the fourth adapter sequence includes the second platform primer binding sequence and a fourth sequencing primer binding sequence, the fifth adapter sequence includes a third platform primer binding sequence and a fifth sequencing primer binding sequence, the sixth adapter sequence includes the third platform primer binding sequence and a sixth sequencing primer binding sequence, the seventh adapter sequence includes a fourth platform primer binding sequence and a seventh sequencing primer binding sequence, the eighth adapter sequence includes the fourth platform primer binding sequence and an eighth sequencing primer binding sequence, the ninth adapter sequence includes a fifth platform primer binding sequence and a ninth sequencing primer binding sequence, the tenth adapter sequence includes the fifth platform primer binding sequence and a tenth sequencing primer binding sequence, the eleventh adapter sequence includes a sixth platform primer binding sequence and an eleventh sequencing primer binding sequence, and the twelfth adapter sequence includes the sixth platform primer binding sequence and a twelfth sequencing primer binding sequence; the first complex includes a first amplification primer attached to the solid support hybridized to the first adapter sequence; the second complex includes a second amplification primer attached to the solid support hybridized to the second adapter sequence, wherein the first and second amplification primer include the same sequence; the third complex includes a third amplification primer attached to the solid support hybridized to the third adapter sequence; the fourth complex includes a fourth amplification primer attached to the solid support hybridized to the fourth adapter sequence, wherein the third and fourth amplification primer include the same sequence; the fifth complex includes a fifth amplification primer attached to the solid support hybridized to the fifth adapter sequence; the sixth complex includes a sixth amplification primer attached to the solid support hybridized to the sixth adapter sequence, wherein the fifth and sixth amplification primer include the same sequence; the seventh complex includes a seventh amplification primer attached to the solid support hybridized to the seventh adapter sequence; the eighth complex includes an eighth amplification primer attached to the solid support hybridized to the eighth adapter sequence, wherein the seventh and eighth amplification primer include the same sequence; the ninth complex includes a ninth amplification primer attached to the solid support hybridized to the ninth adapter sequence; the tenth complex includes a tenth amplification primer attached to the solid support hybridized to the tenth adapter sequence, wherein the ninth and tenth amplification primer include the same sequence; the eleventh complex includes an eleventh amplification primer attached to the solid support hybridized to the eleventh adapter sequence; and the twelfth complex includes a twelfth amplification primer attached to the solid support hybridized to the twelfth adapter sequence, wherein the eleventh and twelfth amplification primer include the same sequence; and the first sequencing primer binding sequence, the second sequencing primer binding sequence, the third sequencing primer binding sequence, the fourth sequencing primer binding sequence, the fifth sequencing primer binding sequence, the sixth sequencing primer binding sequence, the seventh sequencing primer binding sequence, the eighth sequencing primer binding sequence, the ninth sequencing primer binding sequence, the tenth sequencing primer binding sequence, the eleventh sequencing primer binding sequence, and the twelfth sequencing primer binding sequence are different from each other.

Figure 2A:
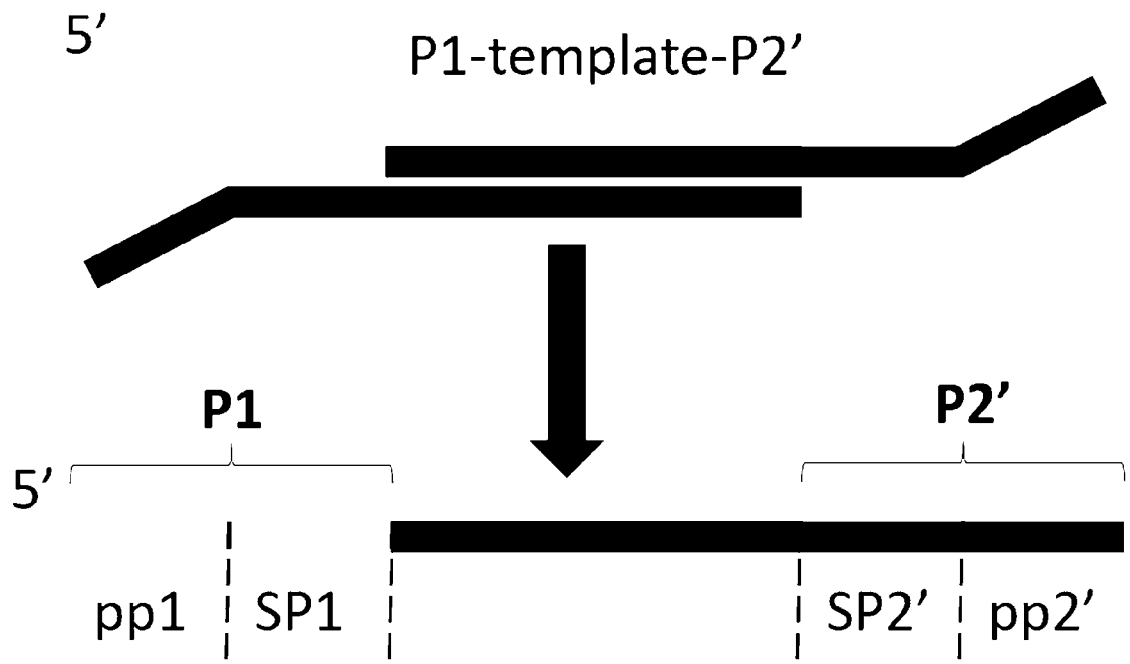
FIGS. 2A-2B shows an example of the library of DNA molecules prepared according to an embodiment of the methods described herein.

In embodiments, polynucleotides of each population include a different pair of sequencing primer binding sequences. For example, as illustrated in FIG. 2A, the first library of polynucleotides may include an SP1-SP2' pair. Alternatively, as illustrated in FIG. 2A, the second library of polynucleotides may include an SP3-SP4' pair.

In embodiments, a first population of polynucleotides includes a first and a second sequencing primer binding sequence and a second population of polynucleotides includes a first and a third sequencing primer binding sequence. In embodiments, a first population of polynucleotides includes a first and a second sequencing primer binding sequence and a second population of polynucleotides includes a third and a fourth sequencing primer binding sequence.

In an aspect is provided a substrate including overlapping amplification clusters on a solid support including a plurality of first amplification products and plurality of second amplification products. In embodiments, the first amplification products include a first template polynucleotide including a first adapter sequence attached to the solid support and the second amplification products include a second template polynucleotide including a second adapter sequence attached to the solid support. In embodiments, the first adapter sequence includes a first platform primer binding sequence complementary to a first amplification primer, and a first sequencing primer binding sequence, and the second adapter sequence includes the first platform primer binding sequence and a second sequencing primer binding sequence, and wherein the first sequencing primer binding sequence is different from the second sequencing primer binding sequence.

In embodiments, the substrate further includes overlapping amplification clusters on the solid support including a plurality of third amplification products and a plurality of fourth amplification products, wherein: the third amplification products include a third template polynucleotide including a third adapter sequence attached to the solid support and the fourth amplification products include a fourth template polynucleotide including a fourth adapter sequence attached to the solid support, wherein: the third adapter sequence includes a second platform primer binding sequence complementary to a second amplification primer, and a third sequencing primer binding sequence, and the fourth adapter sequence includes the second platform primer binding sequence and a fourth sequencing primer binding sequence, and wherein the third sequencing primer binding sequence is different from the fourth sequencing primer binding sequence.

In an aspect is provided a substrate including a first complex attached to a solid support and a second complex attached to the solid support, wherein: the first complex includes a first template polynucleotide including a first adapter sequence and the second complex includes a second template polynucleotide including a second adapter sequence, wherein: the first adapter sequence includes a first platform primer binding sequence complementary to a first amplification primer, and a first sequencing primer binding sequence, and the second adapter sequence includes the first platform primer binding sequence and a second sequencing primer binding sequence; the first complex includes a first amplification primer attached to the solid support hybridized to the first adapter sequence; and the second complex includes a second amplification primer attached to the solid support hybridized to the second adapter sequence; and the first sequencing primer binding sequence is different from the second sequencing primer binding sequence.

In embodiments the substrate further includes a third complex attached to a solid support and a fourth complex attached to the solid support, wherein: the third complex includes a third template polynucleotide including a third adapter sequence and the fourth complex includes a fourth template polynucleotide including a fourth adapter sequence, wherein: the third adapter sequence includes a second platform primer binding sequence complementary to a second amplification primer, and a third sequencing primer binding sequence, and the fourth adapter sequence includes the second platform primer binding sequence and a fourth sequencing primer binding sequence; the third complex includes a second amplification primer attached to the solid support hybridized to the third adapter sequence; and the fourth complex includes a second amplification primer attached to the solid support hybridized to the fourth adapter sequence; and the third sequencing primer binding sequence is different from the fourth sequencing primer binding sequence.

In embodiments, the first, second, third, and fourth sequencing primer binding sequences are different from each other. In embodiments, the first, second, third, and fourth sequencing primer binding sequences are non-complementary. In embodiments, the first, second, third, and fourth sequencing primer binding sequences each comprise a different sequence.

In an aspect is provided a substrate including: (a) a plurality of amplification clusters on a surface of the substrate, wherein: (i) an amplification cluster includes amplicons of a first template polynucleotide including a first adapter sequence, and amplicons of a second template polynucleotide including a second adapter sequence, wherein the first and second template polynucleotides are not substantially complementary to each other; (ii) the first adapter sequence includes a first platform primer binding sequence (e.g., pp1 as depicted in FIG. 1) and a first sequencing primer binding sequence (e.g., SP1 as depicted in FIG. 1); (iii) the second adapter sequence includes a second platform primer binding sequence (e.g., pp2 as depicted in FIG. 1) and a second sequencing primer binding sequence (e.g., SP2 as depicted in FIG. 1); (iv) the first platform primer binding sequence includes a sequence complementary to a first amplification primer attached to the surface; (v) the second platform primer binding sequence includes a sequence complementary to a second amplification primer attached to the surface; (vi) the first platform primer binding sequence is different from the second platform primer binding sequence, the first sequencing primer binding sequence is different from the second sequencing primer binding sequence and the first amplification primer is different from the second amplification primer; and (b) a plurality of first sequencing primers hybridized to the first adapter sequences of the amplification clusters. In embodiments, the plurality of amplification clusters include overlapping amplification clusters.

In an aspect is provided a substrate including: (a) a plurality of overlapping amplification clusters on a surface of the substrate, wherein: (i) an overlapping amplification cluster includes amplicons of a first template polynucleotide including a first adapter sequence, and amplicons of a second template polynucleotide including a second adapter sequence, wherein the first and second template polynucleotides are not substantially complementary to each other; (ii) the first adapter sequence includes a first platform primer binding sequence (e.g., pp1 as depicted in FIG. 1) and a first sequencing primer binding sequence (e.g., SP1 as depicted in FIG. 1); (iii) the second adapter sequence includes a second platform primer binding sequence (e.g., pp2 as depicted in FIG. 1) and a second sequencing primer binding sequence (e.g., SP2 as depicted in FIG. 1); (iv) the first platform primer binding sequence includes a sequence complementary to a first amplification primer attached to the surface; (v) the second platform primer binding sequence includes a sequence complementary to a second amplification primer attached to the surface; (vi) the first platform primer binding sequence is different from the second platform primer binding sequence, the first sequencing primer binding sequence is different from the second sequencing primer binding sequence and the first amplification primer is different from the second amplification primer; and (b) a plurality of first sequencing primers hybridized to the first adapter sequences of the overlapping amplification clusters.

In an aspect is provided a substrate including: (a) a plurality of overlapping amplification clusters on a surface of the substrate, wherein: (i) an overlapping amplification cluster includes amplicons of a first template polynucleotide including a first adapter sequence, and amplicons of a second template polynucleotide including a second adapter sequence; (ii) the first adapter sequence and second adapter sequence include a sequence complementary to an amplification primer attached to the surface (e.g., pp1 and pp2, respectively, as depicted in FIG. 1); (iii) the first adapter sequence includes a sequence complementary to a first sequencing primer (e.g., SP1 as depicted in FIG. 1); and (iv) the second adapter sequence includes a sequence complementary to a second sequencing primer that is different from the first sequencing primer (e.g., SP2 as depicted in FIG. 1); and (b) a plurality of first sequencing primers hybridized to the first adapter sequences of the overlapping amplification clusters. In embodiments, the first and second template polynucleotides are not substantially complementary to each other.

In an aspect is provided a substrate including: (a) a plurality of overlapping amplification clusters on a surface of the substrate, wherein: (i) an overlapping amplification cluster includes double-stranded amplicons of a first template polynucleotide including a first adapter sequence, and double-stranded amplicons of a second template polynucleotide including a second adapter sequence; (ii) the first adapter sequence and second adapter sequence include a sequence complementary to an amplification primer attached to the surface (e.g., pp1 and pp2, respectively, as depicted in FIG. 1); (iii) the first adapter sequence includes a sequence complementary to a first sequencing primer (e.g., SP1 as depicted in FIG. 1); and (iv) the second adapter sequence includes a sequence complementary to a second sequencing primer that is different from the first sequencing primer (e.g., SP2 as depicted in FIG. 1); and (b) a plurality of first sequencing primers hybridized to the first adapter sequences of the overlapping amplification clusters. In embodiments, the first and second template polynucleotides are not substantially complementary to each other.

In an aspect is provided an array (e.g., a multiwell container), including: (a) a plurality of overlapping amplification clusters on surface of a solid support, wherein the surface includes a plurality of wells separated from each other by interstitial regions on the surface, wherein one or more wells, wherein: (i) an overlapping amplification cluster includes double-stranded amplicons of a first template polynucleotide including a first adapter sequence, and double-stranded amplicons of a second template polynucleotide including a second adapter sequence; (ii) the first adapter sequence and second adapter sequence include a sequence complementary to an amplification primer attached to the surface(e.g., pp1 and pp2, respectively, as depicted in FIG. 1); (iii) the first adapter sequence includes a sequence complementary to a first sequencing primer (e.g., SP1 as depicted in FIG. 1); and (iv) the second adapter sequence includes a sequence complementary to a second sequencing primer that is different from the first sequencing primer (e.g., SP2 as depicted in FIG. 1); and (b) a plurality of first sequencing primers hybridized to the first adapter sequences of the overlapping amplification clusters. In embodiments, the first and second template polynucleotides are not substantially complementary to each other. In embodiments, the surface comprises a polymer layer.

In an aspect is provided a solid support (e.g., a patterned glass slide or planar support) including two or more wells, wherein each well includes a plurality of overlapping amplification clusters, wherein: (i) an overlapping amplification cluster includes double-stranded amplicons of a first template polynucleotide including a first adapter sequence, and double-stranded amplicons of a second template polynucleotide including a second adapter sequence; (ii) the first adapter sequence and second adapter sequence include a sequence complementary to an amplification primer attached to the surface(e.g., pp1 and pp2, respectively, as depicted in FIG. 1); (iii) the first adapter sequence includes a sequence complementary to a first sequencing primer (e.g., SP1 as depicted in FIG. 1); and (iv) the second adapter sequence includes a sequence complementary to a second sequencing primer that is different from the first sequencing primer (e.g., SP2 as depicted in FIG. 1); and (b) a plurality of first sequencing primers hybridized to the first adapter sequences of the overlapping amplification clusters. In embodiments, the solid support includes a plurality of wells (e.g., a billion or more wells). In embodiments, the wells (e.g., each well) is separated by about 0.1 µm to about 5.0 µm. In embodiments, the wells (e.g., each well) is separated by about 0.2 µm to about 2.0 µm. In embodiments, the wells (e.g., each well) is separated by about 0.5 µm to about 1.5 µm. In embodiments, the wells of the solid support are all the same size. In embodiments, one or more wells are different sizes (e.g., one population of wells are 1.0 µm in diameter, and a second population are 0.5 µm in diameter). In embodiments, the solid support is a glass slide about 75 mm by about 25 mm. In embodiments, the solid support includes a resist (e.g., a photoresist or nanoimprint resist including a crosslinked polymer matrix attached to the solid support).

In embodiments, the first template polynucleotide further includes a third adapter sequence, wherein the third adapter sequence includes: i) a first platform primer binding sequence complementary to a first amplification primer attached to the surface, and ii) a third sequencing primer binding sequence; and wherein the second template polynucleotide further includes a fourth adapter sequence, wherein the fourth adapter sequence includes: i) a second platform primer binding sequence complementary to a second amplification primer attached to the surface, and ii) a fourth sequencing primer binding sequence.

In embodiments, the plurality of amplification clusters include overlapping amplification clusters. In embodiments, the plurality of amplification clusters do not include overlapping amplification clusters.

In embodiments, density of wells on the solid support may be tuned. For example, in embodiments, the multiwell container includes a density of at least about 100 wells per mm$^2$, about 1,000 wells per mm$^2$, about 0.1 million wells per mm$^2$, about 1 million wells per mm$^2$, about 2 million wells per mm$^2$, about 5 million wells per mm$^2$, about 10 million wells per mm$^2$, about 50 million wells per mm$^2$, or more. In embodiments, the multiwell container includes no more than about 50 million wells per mm$^2$, about 10 million wells per mm$^2$, about 5 million wells per mm$^2$, about 2 million wells per mm$^2$, about 1 million wells per mm$^2$, about 0.1 million wells per mm$^2$, about 1,000 wells per mm$^2$, about 100 wells per mm$^2$, or less. In embodiments, the solid support includes about 500, 1,000, 2,500, 5,000, or about 25,000 wells per mm$^2$. In embodiments, the solid support includes about $1 \times 10^6$ to about $1 \times 10^{12}$ wells. In embodiments, the solid support includes about $1 \times 10^7$ to about $1 \times 10^{12}$ wells. In embodiments, the solid support includes about $1 \times 10^8$ to about $1 \times 10^{12}$ wells. In embodiments, the solid support includes about $1 \times 10^6$ to about $1 \times 10^9$ wells. In embodiments, the solid support includes about $1 \times 10^9$ to about $1 \times 10^{10}$ wells. In embodiments, the solid support includes about $1 \times 10^7$ to about $1 \times 10^9$ wells. In embodiments, the solid support includes about $1 \times 10^8$ to about $1 \times 10^8$ wells. In embodiments, the solid support includes about $1 \times 10^6$ to about $1 \times 10^8$ wells. In embodiments, the solid support includes about $1 \times 10^6$, $1 \times 10^7$, $1 \times 10^8$, $1 \times 10^9$, $1 \times 10^{10}$, $1 \times 10^{11}$, $1 \times 10^{12}$, $5 \times 10^{12}$, or more wells. In embodiments, the solid support includes about $1.8 \times 10^9$, $3.7 \times 10^9$, $9.4 \times 10^9$, $1.9 \times 10^{10}$, or about $9.4 \times 10^{10}$ wells. In embodiments, the solid support includes about $1 \times 10^6$ or more wells. In embodiments, the solid support includes about $1 \times 10^7$ or more wells. In embodiments, the solid support includes about $1 \times 10^8$ or more wells. In embodiments, the solid support includes about $1 \times 10^9$ or more wells. In embodiments, the solid support includes about $1 \times 10^{10}$ or more wells. In embodiments, the solid support includes about $1 \times 10^{11}$ or more wells. In embodiments, the solid support includes about $1 \times 10^{12}$ or more wells. In embodiments, the solid support is a glass slide. In embodiments, the solid support is a about 75 mm by about 25 mm. In embodiments, the solid support includes one, two, three, or four channels.

In embodiments, the solid support includes a polymer layer. In embodiments, the polymer layer includes polymerized units of alkoxysilyl methacrylate, alkoxysilyl acrylate, alkoxysilyl methacrylamide, alkoxysilyl methylacrylamide, or a copolymer thereof. In embodiments, the polymer layer includes polymerized units of alkoxysilyl methacrylate. In embodiments, the polymer layer includes polymerized units of alkoxysilyl acrylate. In embodiments, the polymer layer includes polymerized units of alkoxysilyl methacrylamide. In embodiments, the polymer layer includes polymerized units of alkoxysilyl methylacrylamide. In embodiments, the polymer layer includes glycidyloxypropyl-trimethyloxysilane. In embodiments, the polymer layer includes methacryloxypropyl-trimethoxysilane. In embodiments, the polymer layer includes polymerized units of

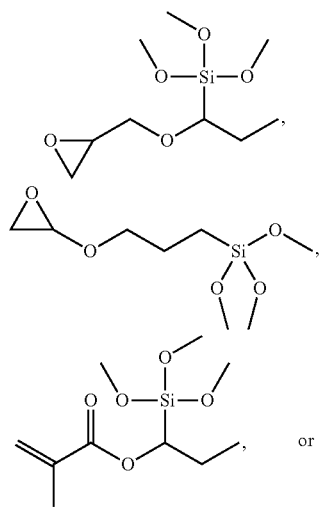

-continued

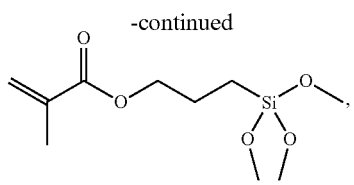

or a copolymer thereof.

In embodiments, the solid support includes a photoresist, alternatively referred to herein as a resist. A "resist" as used herein is used in accordance with its ordinary meaning in the art of lithography and refers to a polymer matrix (e.g., a polymer network). In embodiments, the photoresist is a silsesquioxane resist, an epoxy-based polymer resist, poly(vinylpyrrolidone-vinyl acrylic acid) copolymer resist, an Off-stoichiometry thiol-enes (OSTE) resist, amorphous fluoropolymer resist, a crystalline fluoropolymer resist, polysiloxane resist, or a organically modified ceramic polymer resist. In embodiments, the photoresist is a silsesquioxane resist. In embodiments, the photoresist is an epoxy-based polymer resist. In embodiments, the photoresist is a poly(vinylpyrrolidone-vinyl acrylic acid) copolymer resist. In embodiments, the photoresist is an Off-stoichiometry thiol-enes (OSTE) resist. In embodiments, the photoresist is an amorphous fluoropolymer resist. In embodiments, the photoresist is a crystalline fluoropolymer resist. In embodiments, the photoresist is a polysiloxane resist. In embodiments, the photoresist is an organically modified ceramic polymer resist. In embodiments, the photoresist includes polymerized alkoxysilyl methacrylate polymers and metal oxides (e.g., $SiO_2$, ZrO, MgO, $Al_2O_3$, $TiO_2$ or $Ta_2O_5$). In embodiments, the photoresist includes polymerized alkoxysilyl acrylate polymers and metal oxides (e.g., $SiO_2$, ZrO, MgO, $Al_2O_3$, $TiO_2$ or $Ta_2O_5$). In embodiments, the photoresist includes metal atoms, such as Si, Zr, Mg, Al, Ti or Ta atoms.

In embodiments, the wells are separated from each other by interstitial regions including a polymer layer as described herein (e.g., an amphiphilic copolymer). In embodiments, the solid support further includes a photoresist, wherein the photoresist does not contact the bottom of the well. In embodiments, the polymer layer is substantially free of overlapping amplification clusters. In embodiments, the solid support does not include a polymer (e.g., the solid support is a patterned glass slide). In embodiments, the wells do not include a polymer (e.g., an amphiphilic polymer as described herein). In embodiments, the solid support further includes a photoresist, wherein the photoresist is in contact the bottom of the well and the interstitial space. In embodiments, the wells include a polymer (e.g., an amphiphilic polymer and/or resist as described herein).

In embodiments, the features and/or the wells have a mean or median separation from one another of about 0.5-5 µm. In embodiments, the mean or median separation is about 0.1-10 microns, 0.25-5 microns, 0.5-2 microns, 1 micron, or a number or a range between any two of these values. In embodiments, the mean or median separation is about or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 µm, or a number or a range between any two of these values. In embodiments, the mean or median separation is about or at least about 0.1 µm. In embodiments, the mean or median separation is about or at least about 0.2 µm. In embodiments, the mean or median separation is about or at least about 0.3 µm. In embodiments, the mean or median separation is about or at least about 0.4 µm. In embodiments, the mean or median separation is about or at least about 0.5 µm. In embodiments, the mean or median separation is about or at least about 0.6 µm. In embodiments, the mean or median separation is about or at least about 0.7 µm. In embodiments, the mean or median separation is about or at least about 0.8 µm. In embodiments, the mean or median separation is about or at least about 0.9 µm. In embodiments, the mean or median separation is about or at least about 1.0 µm. In embodiments, the mean or median separation is about or at least about 1.1 µm. In embodiments, the mean or median separation is about or at least about 1.2 µm. In embodiments, the mean or median separation is about or at least about 1.3 µm. In embodiments, the mean or median separation is about or at least about 1.4 µm. In embodiments, the mean or median separation is about or at least about 1.5 µm. In embodiments, the mean or median separation is about or at least about 1.6 µm. In embodiments, the mean or median separation is about or at least about 1.7 µm. In embodiments, the mean or median separation is about or at least about 1.8 µm. In embodiments, the mean or median separation is about or at least about 1.9 µm. In embodiments, the mean or median separation is about or at least about 2.0 µm. In embodiments, the mean or median separation is about or at least about 2.1 µm. In embodiments, the mean or median separation is about or at least about 2.2 µm. In embodiments, the mean or median separation is about or at least about 2.3 µm. In embodiments, the mean or median separation is about or at least about 2.4 µm. In embodiments, the mean or median separation is about or at least about 2.5 µm. In embodiments, the mean or median separation is about or at least about 2.6 µm. In embodiments, the mean or median separation is about or at least about 2.7 µm. In embodiments, the mean or median separation is about or at least about 2.8 µm. In embodiments, the mean or median separation is about or at least about 2.9 µm. In embodiments, the mean or median separation is about or at least about 3.0 µm. In embodiments, the mean or median separation is about or at least about 3.1 µm. In embodiments, the mean or median separation is about or at least about 3.2 µm. In embodiments, the mean or median separation is about or at least about 3.3 µm. In embodiments, the mean or median separation is about or at least about 3.4 µm. In embodiments, the mean or median separation is about or at least about 3.5 µm. In embodiments, the mean or median separation is about or at least about 3.6 µm. In embodiments, the mean or median separation is about or at least about 3.7 µm. In embodiments, the mean or median separation is about or at least about 3.8 µm. In embodiments, the mean or median separation is about or at least about 3.9 µm. In embodiments, the mean or median separation is about or at least about 4.0 µm. In embodiments, the mean or median separation is about or at least about 4.1 µm. In embodiments, the mean or median separation is about or at least about 4.2 µm. In embodiments, the mean or median separation is about or at least about 4.3 µm. In embodiments, the mean or median separation is about or at least about 4.4 µm. In embodiments, the mean or median separation is about or at least about 4.5 µm. In embodiments, the mean or median separation is about or at least about 4.6 µm. In embodiments, the mean or median separation is about or at least about 4.7 µm. In embodiments, the mean or median separation is about or at least about 4.8 µm. In embodiments, the mean or median separation is about or at least about 4.9 µm. In embodiments, the mean or median separation is about or at least about 5.0 µm. The mean or median separation may be measured center-to-center (i.e., the center of one well to the center of a second well). In embodiments of the methods provided herein, the wells have a mean or median separation (measured center-to-center) from one another of about 0.5-5 µm. The mean or median separation may be measured edge-to-edge (i.e., the edge of well to the edge of a second well). In embodiments, the wells have a mean or median separation (measured edge-to-edge) from one another of about 0.2-1.5 µm. In embodiments, the wells have a mean or median separation (measured center-to-center) from one another of about 0.7-1.5 µm.

Neighboring features of an array can be discrete one from the other in that they do not overlap. Accordingly, the features can be adjacent to each other or separated by a gap (e.g., an interstitial space). In embodiments where features are spaced apart, neighboring sites can be separated, for example, by a distance of less than 10 µm, 5 µm, 1 µm, 0.9 µm, 0.8 µm, 0.7 µm, 0.6 µm, 0.5 µm, or less. The layout of features on an array can also be understood in terms of center-to-center distances between neighboring features. An array useful in the invention can have neighboring features with center-to-center spacing of less than about 10 µm, 5 µm, 1 µm, 0.9 µm, 0.8 µm, 0.7 µm, 0.6 µm, 0.5 µm, 0.4 µm, or less. In embodiments, the array has neighboring features with center-to-center spacing of less than about 10 µm. In embodiments, the array has neighboring features with center-to-center spacing of less than about 5 µm. In embodiments, the array has neighboring features with center-to-center spacing of less than about 1 In embodiments, the array has neighboring features with center-to-center spacing of less than about 0.9 µm. In embodiments, the array has neighboring features with center-to-center spacing of less than about 0.8 µm. In embodiments, the array has neighboring features with center-to-center spacing of less than about 0.7 µm. In embodiments, the array has neighboring features with center-to-center spacing of less than about 0.6 µm. In embodiments, the array has neighboring features with center-to-center spacing of less than about 0.5 µm. In embodiments, the array has neighboring features with center-to-center spacing of less than about 0.4 Furthermore, it will be understood that the distance values described above and elsewhere herein can represent an average distance between neighboring features of an array. As such, not all neighboring features need to fall in the specified range unless specifically indicated to the contrary, for example, by a specific statement that the distance constitutes a threshold distance between all neighboring features of an array.

The arrays and solid supports for some embodiments have at least one surface located within a flow cell. Flow cells provide a convenient format for housing an array of clusters produced by the methods described herein, in particular when subjected to an SBS or other detection technique that involves repeated delivery of reagents in cycles.

In embodiments, the solid support is a multiwell container or an unpatterned solid support (e.g., an unpatterned surface). In embodiments, the solid support is a glass slide including a polymer coating (e.g., a hydrophilic polymer coating). In embodiments, the polymer coating includes a plurality of immobilized oligonucleotides (e.g., an oligonucleotide complementary to the platform primer binding sequence of the adapter).

In embodiments, the solid support includes a plurality of immobilized oligonucleotides. In embodiments, the solid support includes a plurality of oligonucleotides immobilized to a polymer. In embodiments, the solid support includes a plurality of particles. In embodiments, the solid support includes a first plurality of immobilized oligonucleotides. In embodiments, the solid support includes a first and a second plurality of immobilized oligonucleotides, wherein the immobilized oligonucleotides of each plurality are different (e.g., S1 or S2).

In embodiments, the plurality of oligonucleotides is present at a density of about 100 oligonucleotides per $\mu m^2$ to about 1,000,000 oligonucleotides per $\mu m^2$. In embodiments, the plurality of oligonucleotides is present at a density of about 100 oligonucleotides per $\mu m^2$ to about 1,000 oligonucleotides per $\mu m^2$. In embodiments, the plurality of oligonucleotides is present at a density of about 100 oligonucleotides per $\mu m^2$ to about 10,000 oligonucleotides per $\mu m^2$. In embodiments, the plurality of oligonucleotides is present at a density of about 100 oligonucleotides per $\mu m^2$ to about 100,000 oligonucleotides per $\mu m^2$. In embodiments, the plurality of oligonucleotides is present at a density of about 100 oligonucleotides per $\mu m^2$ to about 500,000 oligonucleotides per $\mu m^2$. In embodiments, the plurality of oligonucleotides is present at a density of about 100, 1,000, 10,000, 50,000, 100,000, 250,000, 500,000, 750,000, or 1,000,000 oligonucleotides per $\mu m^2$.

In another aspect is provided a substrate including: (a) a plurality of overlapping amplification clusters on a surface of the substrate, wherein an amplification cluster includes amplicons of a first template polynucleotide including a first adapter sequence, and amplicons of a second template polynucleotide including a second adapter sequence, wherein the first and second template polynucleotides are not substantially complementary to each other; and (b) a plurality of first sequencing primers hybridized to the first adapter sequences of the overlapping amplification clusters.

In embodiments, the overlapping amplification cluster includes a plurality amplicons of different template polynucleotides. In embodiments, the substrate includes at least 3 different populations of amplicons, each population of amplicons including a different sequence complementary to a sequencing primer. In embodiments, the substrate includes at least 4 different populations of amplicons, each population of amplicons including a different sequence complementary to a sequencing primer. In embodiments, the substrate includes at least 5 different populations of amplicons, each population of amplicons including a different sequence complementary to a sequencing primer. In embodiments, the substrate includes at least 6 different populations of amplicons, each population of amplicons including a different sequence complementary to a sequencing primer. In embodiments, the substrate includes at most 3 different populations of amplicons, each population of amplicons including a different sequence complementary to a sequencing primer. In embodiments, the substrate includes at most 4 different populations of amplicons, each population of amplicons including a different sequence complementary to a sequencing primer. In embodiments, the substrate includes at most 5 different populations of amplicons, each population of amplicons including a different sequence complementary to a sequencing primer. In embodiments, the substrate includes at most 6 different populations of amplicons, each population of amplicons including a different sequence complementary to a sequencing primer.

In embodiments, the first template polynucleotide further includes a third adapter sequence, wherein the third adapter sequence includes: i) a first platform primer binding sequence complementary to a first amplification primer attached to the surface (e.g., pp1 as depicted in FIG. 1), and ii) a third sequencing primer binding sequence (e.g., SP3 as depicted in FIG. 1); and wherein the second template polynucleotide further includes a fourth adapter sequence, wherein the fourth adapter sequence includes: i) a second platform primer binding sequence complementary to a second amplification primer attached to the surface (e.g., pp2 as depicted in FIG. 1), and ii) a fourth sequencing primer binding sequence (e.g., SP4 as depicted in FIG. 1).

In embodiments, the substrate further includes template polynucleotides including a third adapter sequence, wherein the third adapter sequence includes i) a sequence complementary to an amplification primer attached to the surface (e.g., pp1 as depicted in FIG. 1), and ii) a sequence complementary to a third sequencing primer (e.g., SP3 as depicted in FIG. 1). In embodiments, the substrate further includes template polynucleotides including a fourth adapter sequence, wherein the fourth adapter sequence includes i) a sequence complementary to an amplification primer attached to the surface (e.g., pp2 as depicted in FIG. 1), and ii) a sequence complementary to a fourth sequencing primer (e.g., SP4 as depicted in FIG. 1).

In some embodiments, the first template polynucleotide further includes a third adapter sequence, wherein the third adapter sequence includes i) a sequence complementary to an amplification primer attached to the surface (e.g., pp1 as depicted in FIG. 1), and ii) a sequence complementary to a third sequencing primer (e.g., SP3 as depicted in FIG. 1); and wherein the second template polynucleotide further includes a fourth adapter sequence, wherein the fourth adapter sequence includes i) a sequence complementary to an amplification primer attached to the surface (e.g., pp2 as depicted in FIG. 1), and ii) a sequence complementary to a fourth sequencing primer (e.g., SP4 as depicted in FIG. 1). In embodiments, the first adapter sequence and third adapter sequence each include a sequence complementary to the same amplification primer attached to the surface (e.g., pp1). In embodiments, the second adapter sequence and fourth adapter sequence each include a sequence complementary to the same amplification primer attached to the surface (e.g., pp2). For example, as depicted in FIG. 1, the adapters described herein may contain a platform primer 1 or platform primer 2 (pp1 or pp2) sequence, which is a sequence complementary to a first surface-immobilized primer, an optional index sequence (i) for multiplexing samples, and a region complementary to a sequencing primer (SP1, SP2, SP3, SP4, etc). The P2 adapter contains a platform primer 2 (pp2) sequence, which is a sequence complementary to a second surface-immobilized primer, an optional index sequence (i) for multiplexing samples, and a region complementary to a second sequencing primer (SP2). The P3 adapter contains a platform primer 1 (pp1) sequence, which is a sequence complementary to the first surface-immobilized primer, an optional index sequence (i) for multiplexing samples, and a region complementary to a third sequencing primer (SP3). The P4 adapter contains a platform primer 2 (pp2) sequence, which is a sequence complementary to the second surface-immobilized primer, an optional index sequence (i) for multiplexing samples, and a region complementary to a fourth sequencing primer (SP4). The illustrations depict embodiments of the oligo sequences wherein there are two different platform primer binding sequences, pp1 and pp2, in combination with four different sequencing primer binding sites: SP1, SP2, SP3, and SP4.

In embodiments, the surface includes a glass surface including a polymer coating. In embodiments, the surface is glass or quartz, such as a microscope slide, having a surface that is uniformly silanized. This may be accomplished using conventional protocols, such as those described in Beattie et al (1995), Molecular Biotechnology, 4: 213. Such a surface is readily treated to permit end-attachment of oligonucleotides (e.g., forward and reverse primers) prior to amplification. In embodiments the surface further includes a polymer coating, which contains functional groups capable of immobilizing primers. In some embodiments, the surface includes a patterned surface suitable for immobilization of primers in an ordered pattern. A patterned surface refers to an arrangement of different regions in or on an exposed layer of a substrate. For example, one or more of the regions can be features (e.g., overlapping clusters) where one or more primers are present. The features can be separated by interstitial regions where capture primers are not present. In some embodiments, the pattern can be an x-y format of features that are in rows and columns. In some embodiments, the pattern can be a repeating arrangement of features and/or interstitial regions. In some embodiments, the pattern can be a random arrangement of features (e.g., overlapping clusters) and/or interstitial regions. In some embodiments, the primers are randomly distributed upon the surface. In some embodiments, the primers are distributed on a patterned surface.

In embodiments, the immobilized primers are immobilized on the substrate via a linker. The linker may also include spacer nucleotides. Including spacer nucleotides in the linker puts the polynucleotide in an environment having a greater resemblance to free solution. This can be beneficial, for example, in enzyme-mediated reactions such as sequencing-by-synthesis. It is believed that such reactions suffer less steric hindrance issues that can occur when the polynucleotide is directly attached to the solid support or is attached through a very short linker (e.g., a linker comprising about 1 to 3 carbon atoms). Spacer nucleotides form part of the polynucleotide but do not participate in any reaction carried out on or with the polynucleotide (e.g. a hybridization or amplification reaction). In embodiments, the spacer nucleotides include 1 to 20 nucleotides. In embodiments, the linker includes 10 spacer nucleotides. In embodiments, the linker includes 12 spacer nucleotides. In embodiments, the linker includes 15 spacer nucleotides. It is preferred to use polyT spacers, although other nucleotides and combinations thereof can be used. In embodiments, the linker includes 10, 11, 12, 13, 14, or 15 T spacer nucleotides. In embodiments, the linker includes 12 T spacer nucleotides. Spacer nucleotides are typically included at the 5' ends of polynucleotides which are attached to a suitable support. Attachment can be achieved via a phosphorothioate present at the 5' end of the polynucleotide, an azide moiety, a dibenzocyclooctyne (DBCO) moiety, or any other bioconjugate reactive moiety. The linker may be a carbon-containing chain such as those of formula $-(CH_2)_n-$ wherein "n" is from 1 to about 1000. However, a variety of other linkers may be used so long as the linkers are stable under conditions used in DNA sequencing. In embodiments, the linker includes polyethylene glycol (PEG) having a general formula of $-(CH_2-CH_2-O)_m-$, wherein m is from about 1 to 500. In embodiments, m is 8 to 24. In embodiments, m is 10 to 12.

In embodiments, the linker, or the immobilized oligonucleotides (e.g., primers) include a cleavable site. In embodiments, a cleavable site is a location which allows controlled cleavage of the immobilized polynucleotide strand (e.g., the linker, the primer, or the polynucleotide) by chemical, enzymatic or photochemical means. In embodiments, the cleavable site includes one or more deoxyuracil nucleobases (dUs).

Any suitable enzymatic, chemical, or photochemical cleavage reaction may be used to cleave the cleavable site. The cleavage reaction may result in removal of a part or the whole of the strand being cleaved. Suitable cleavage means include, for example, restriction enzyme digestion, in which case the cleavable site is an appropriate restriction site for the enzyme which directs cleavage of one or both strands of a duplex template; Rnase digestion or chemical cleavage of a bond between a deoxyribonucleotide and a ribonucleotide, in which case the cleavable site may include one or more ribonucleotides; chemical reduction of a disulfide linkage with a reducing agent (e.g., THPP or TCEP), in which case the cleavable site should include an appropriate disulfide linkage; chemical cleavage of a diol linkage with periodate, in which case the cleavable site should include a diol linkage; generation of an abasic site and subsequent hydrolysis, etc. In embodiments, the cleavable site is included in the surface immobilized primer (e.g., within the polynucleotide sequence of the primer). In embodiments, the linker, the primer, or the template polynucleotide includes a diol linkage which permits cleavage by treatment with periodate (e.g., sodium periodate). It will be appreciated that more than one diol can be included at the cleavable site. One or more diol units may be incorporated into a polynucleotide using standard methods for automated chemical DNA synthesis. Polynucleotide primers including one or more diol linkers can be conveniently prepared by chemical synthesis. The diol linker is cleaved by treatment with any substance which promotes cleavage of the diol (e.g., a diol-cleaving agent). In embodiments, the diol-cleaving agent is periodate, e.g., aqueous sodium periodate ($NaIO_4$). Following treatment with the diol-cleaving agent (e.g., periodate) to cleave the diol, the cleaved product may be treated with a "capping agent" In order to neutralize reactive species generated in the cleavage reaction. Suitable capping agents for this purpose include amines, e.g., ethanolamine or propanolamine. In embodiments, cleavage may be accomplished by using a modified nucleotide as the cleavable site (e.g., uracil, 8oxoG, 5-mC, 5-hmC) that is removed or nicked via a corresponding DNA glycosylase, endonuclease, or combination thereof.

In embodiments, each of the plurality of immobilized oligonucleotides (e.g., immobilized primers) is about 5 to about 25 nucleotides in length. In embodiments, each of the plurality of immobilized oligonucleotides (e.g., immobilized primers) is about 10 to about 40 nucleotides in length. In embodiments, each of the plurality of immobilized oligonucleotides (e.g., immobilized primers) is about 5 to about 100 nucleotides in length. In embodiments, each of the plurality of immobilized oligonucleotides (e.g., immobilized primers) is about 20 to 200 nucleotides in length. In embodiments, each of the plurality of immobilized oligonucleotides (e.g., immobilized primers) about or at least about 5, 6, 7, 8, 9, 10, 12, 15, 18, 20, 25, 30, 35, 40, 50 or more nucleotides in length.

In embodiments, the immobilized oligonucleotides include one or more phosphorothioate nucleotides. In embodiments, the immobilized oligonucleotides include a plurality of phosphorothioate nucleotides. In embodiments, about or at least about 20%, 30%, 40%, 50%, 60%, 70%, 80%, 90%, or about 100% of the nucleotides in the immobilized oligonucleotides are phosphorothioate nucleotides. In embodiments, most of the nucleotides in the immobilized oligonucleotides are phosphorothioate nucleotides. In embodiments, all of the nucleotides in the immobilized oligonucleotides are phosphorothioate nucleotides. In embodiments, none of the nucleotides in the immobilized oligonucleotides are phosphorothioate nucleotides. In embodiments, the 5' end of the immobilized oligonucleotide includes one or more phosphorothioate nucleotides. In embodiments, the 5' end of the immobilized oligonucleotide includes between one and five phosphorothioate nucleotides.

In embodiments, the amplification primers are each attached to the solid support (i.e., immobilized on the surface of a solid support). The polynucleotide molecules can be fixed to surface by a variety of techniques, including covalent attachment and non-covalent attachment. In embodiments, the polynucleotides are confined to an area of a discrete region (referred to as a cluster). The discrete regions may have defined locations in a regular array, which may correspond to a rectilinear pattern, circular pattern, hexagonal pattern, or the like. A regular array of such regions is advantageous for detection and data analysis of signals collected from the arrays during an analysis. These discrete regions are separated by interstitial regions. As used herein, the term "interstitial region" refers to an area in a substrate or on a surface that separates other areas (e.g., overlapping clusters) of the substrate or surface. For example, an interstitial region can separate one concave feature of an array from another concave feature of the array. The two regions that are separated from each other can be discrete, lacking contact with each other. In another example, an interstitial region can separate a first portion of a feature from a second portion of a feature. In embodiments the interstitial region is continuous whereas the features are discrete, for example, as is the case for an array of wells in an otherwise continuous surface. The separation provided by an interstitial region can be partial or full separation. Interstitial regions will typically have a surface material that differs from the surface material of the features on the surface. For example, features of an array can have polynucleotides that exceeds the amount or concentration present at the interstitial regions. In some embodiments the polynucleotides and/or primers may not be present at the interstitial regions. In embodiments, at least two different primers are attached to the solid support (e.g., a forward and a reverse primer), which facilitates generating multiple amplification products from the first extension product or a complement thereof.

In embodiments, the clusters (e.g., overlapping clusters) have a mean or median separation from one another of about 0.5-5 μm. In embodiments, the mean or median separation is about 0.1-10 microns, 0.25-5 microns, 0.5-2 microns, 1 micron, or a number or a range between any two of these values. In embodiments, the mean or median separation is about or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4., 4.5, 4.6, 4.7, 4.8, 4.9, 5.0 μm or a number or a range between any two of these values. In embodiments, the mean or median separation is about 0.1-10 microns. In embodiments, the mean or median separation is about 0.25-5 microns. In embodiments, the mean or median separation is about 0.5-2 microns. In embodiments, the mean or median separation is about or at least about 0.1 μm. In embodiments, the mean or median separation is about or at least about 0.25 μm. In embodiments, the mean or median separation is about or at least about 0.5 μm. In embodiments, the mean or median separation is about or at least about 1.0 μm. In embodiments, the mean or median separation is about or at least about 1.5 μm. In embodiments, the mean or median separation is about or at least about 2.0 μm. In embodiments, the mean or median separation is about or at least about 5.0 μm. In embodiments, the mean or median separation is about or at least about 10 μm. The mean or median separation may be measured center-to-center (i.e., the center of one cluster to the center of a second cluster).

In embodiments of the methods provided herein, the amplicon clusters have a mean or median separation (measured center-to-center) from one another of about 0.5-5 µm. The mean or median separation may be measured edge-to-edge (i.e., the edge of one amplicon cluster to the edge of a second amplicon cluster). In embodiments of the methods provided herein, the amplicon clusters have a mean or median separation (measured edge-to-edge) from one another of about 0.2-5 µm. In embodiments, the mean or median separation is about or at least about 1.0, 1.1, 1.2, 1.3, 1.4, 1.5, 1.6, 1.7, 1.8, 1.9, or 2.0 µm. In embodiments, the mean or median separation is about 1.0, 1.1, 1.2, 1.3, 1.4, 1.5, 1.6, 1.7, 1.8, 1.9, or 2.0 µm.

In embodiments of the methods provided herein, the amplicon clusters have a mean or median diameter of about 100-2000 nm, or about 200-1000 nm. In embodiments, the mean or median diameter is about 100-3000 nanometers, about 500-2500 nanometers, about 1000-2000 nanometers, or a number or a range between any two of these values. In embodiments, the mean or median diameter is about or at most about 100, 200, 300, 400, 500, 600, 700, 800, 900, 1,000, 1,100, 1,200, 1,300, 1,400, 1,500, 1,600, 1,700, 1,800, 1,900, 2000 nanometers or a number or a range between any two of these values. In embodiments, the mean or median diameter is about 100-3,000 nanometers. In embodiments, the mean or median diameter is about 100-2,000 nanometers. In embodiments, the mean or median diameter is about 500-2500 nanometers. In embodiments, the mean or median diameter is about 200-1000 nanometers. In embodiments, the mean or median diameter is about 1,000-2,000 nanometers. In embodiments, the mean or median diameter is about or at most about 100 nanometers. In embodiments, the mean or median diameter is about or at most about 200 nanometers. In embodiments, the mean or median diameter is about or at most about 500 nanometers. In embodiments, the mean or median diameter is about or at most about 1,000 nanometers. In embodiments, the mean or median diameter is about or at most about 2,000 nanometers. In embodiments, the mean or median diameter is about or at most about 2,500 nanometers. In embodiments, the mean or median diameter is about or at most about 3,000 nanometers.

In some embodiments, the first and second detection regions overlap by at least 25%. In embodiments, the first and second detection regions overlap by at least 50%. In other embodiments, the first and second detection regions overlap by at least 75%. In some embodiments, the first and second detection regions overlap by between at least 25% to 100%. In some embodiments, the first and second detection regions overlap by between at least 50% to 100%. In some embodiments, the first and second detection regions overlap by between at least 75% to 100%. In embodiments, a detection region is a feature. In embodiments, a detection region is a cluster. In embodiments, the first and second detection regions are the same feature.

In embodiments, the plurality of amplifications clusters include overlapping amplification clusters (e.g., overlapping amplification clusters on a patterned array or multiwell solid support). In embodiments, the plurality of amplification clusters do not include overlapping amplification clusters.

In some embodiments, the overlapping amplification cluster includes a total cluster density per unit area of about 100,000 to about 2,000,000 amplicons per $mm^2$. In embodiments, the overlapping amplification cluster includes a total cluster density per unit area of about 200,000 to about 1,750,000 amplicons per $mm^2$. In embodiments, the overlapping amplification cluster includes a total cluster density per unit area of about 300,000 to about 1,500,000 amplicons per $mm^2$. In embodiments, the overlapping amplification cluster includes a total cluster density per unit area of about 400,000 to about 1,250,000 amplicons per $mm^2$. In embodiments, the overlapping amplification cluster includes a total cluster density per unit area of about 500,000 to about 1,000,000 amplicons per $mm^2$. In embodiments, the overlapping amplification cluster includes a total cluster density per unit area of about 100,000 to about 750,000 amplicons per $mm^2$. In embodiments, the overlapping amplification cluster includes a total cluster density per unit area of about 50,000 to about 500,000 amplicons per $mm^2$.

In embodiments, the cluster is monoclonal (i.e., one template polynucleotide (e.g., a first template polynucleotide) binds and is amplified within the feature). In embodiments, the cluster is polyclonal (i.e., more than one template polynucleotide type (e.g., a first template polynucleotide and a second template polynucleotide) binds and is amplified within the feature). In embodiments, the array contains a ratio of monoclonal (e.g., one template polynucleotide (e.g., a first template polynucleotide)), diclonal (e.g., two template polynucleotides (e.g., a first and a second template polynucleotide)), triclonal (e.g., three template polynucleotides (e.g., a first, second, and a third template polynucleotide)), quadraclonal (e.g., four template polynucleotides (e.g., a first, second, third, and fourth template polynucleotide)), etc. clusters. In embodiments, multiple different template polynucleotides seed one spot (i.e., a feature) of a patterned array, and is referred to herein as a polyclonal feature. In embodiments, a fraction of the surface area within the feature is occupied by copies of one template type, and another fraction of the patterned spot can be occupied by copies of another template type (e.g., a first template polynucleotide and a second template polynucleotide, wherein each template polynucleotide is different). The fractions of the template polynucleotides within the feature are inherently stochastic and governed by Poisson statistics, however the ratios may be influenced by underseeing or overseeding (i.e., providing less or more template polynucleotides relative to the number of available sites on the array). In some embodiments, the ratio of overlapping amplification clusters to monoclonal amplification clusters is at least about 1:1. In some embodiments, the ratio of overlapping amplification clusters to monoclonal amplification clusters is at least about 2:1. In embodiments, the ratio of overlapping amplification clusters to monoclonal amplification clusters is at least about 2.5:1. In embodiments, the ratio of overlapping amplification clusters to monoclonal amplification clusters is at least about 3:1. In some embodiments, the ratio of overlapping amplification clusters to monoclonal amplification clusters is about 1:1. In some embodiments, the ratio of overlapping amplification clusters to monoclonal amplification clusters is about 2:1. In embodiments, the ratio of overlapping amplification clusters to monoclonal amplification clusters is about 2.5:1. In embodiments, the ratio of overlapping amplification clusters to monoclonal amplification clusters is about 3:1.

In some embodiments, fewer than 35% of all of the clusters are monoclonal amplification clusters. In some embodiments, fewer than 30% of all of the clusters are monoclonal amplification clusters. In some embodiments, fewer than 25% of all of the clusters are monoclonal amplification clusters. In some embodiments, fewer than 20% of all of the clusters are monoclonal amplification clusters. In some embodiments, fewer than 15% of all of the clusters are monoclonal amplification clusters. In some embodiments, fewer than 10% of all of the clusters are monoclonal amplification clusters.

In embodiments, the method includes contacting a solid support with 2, 3, 4, 5, 6, 7, 8, 9, 10, 11, or 12 populations of polynucleotides. In embodiments, the method includes contacting a solid support with 2 populations of polynucleotides. In embodiments, the method includes contacting a solid support with 3 populations of polynucleotides. In embodiments, the method includes contacting a solid support with 4 populations of polynucleotides. In embodiments, the method includes contacting a solid support with 5 populations of polynucleotides. In embodiments, the method includes contacting a solid support with 6 populations of polynucleotides. In embodiments, the method includes contacting a solid support with 7 populations of polynucleotides. In embodiments, the method includes contacting a solid support with 8 populations of polynucleotides. In embodiments, the method includes contacting a solid support with 9 populations of polynucleotides. In embodiments, the method includes contacting a solid support with 10 populations of polynucleotides. In embodiments, the method includes contacting a solid support with 11 populations of polynucleotides. In embodiments, the method includes contacting a solid support with 12 populations of polynucleotides.

In some embodiments, at least 30% of all of the clusters are overlapping amplification clusters. In some embodiments, at least 35% of all of the clusters are overlapping amplification clusters. In some embodiments, at least 40% of all of the clusters are overlapping amplification clusters. In some embodiments, at least 45% of all of the clusters are overlapping amplification clusters. In some embodiments, at least 50% of all of the clusters are overlapping amplification clusters. In some embodiments, at least 55% of all of the clusters are overlapping amplification clusters. In some embodiments, at least 60% of all of the clusters are overlapping amplification clusters. In some embodiments, at least 65% of all of the clusters are overlapping amplification clusters. In some embodiments, at least 70% of all of the clusters are overlapping amplification clusters. In some embodiments, at least 75% of all of the clusters are overlapping amplification clusters. In some embodiments, at least 80% of all of the clusters are overlapping amplification clusters. In some embodiments, at least 85% of all of the clusters are overlapping amplification clusters. In some embodiments, at least 90% of all of the clusters are overlapping amplification clusters. In some embodiments, at least 95% of all of the clusters are overlapping amplification clusters. In some embodiments, 100% of all of the clusters are overlapping amplification clusters.

In some embodiments, the first and second template polynucleotides include substantially identical template sequences or complements thereof, i.e., the first template polynucleotide and the second template polynucleotide include the same template sequence or complement thereof and are each ligated to distinct combinations of first and second adapter sequences, or first, second, third, and fourth adapter sequences. For example, a first template polynucleotide includes a template polynucleotide sequence and a first adapter sequence, and a second template polynucleotide includes the same template polynucleotide sequence as the first template polynucleotide, and further includes a second adapter sequence.

In embodiments, the first adapter sequence and the second adapter sequence include different sequencing primer binding regions (i.e., a polynucleotide sequence complementary to a first sequencing primer and a polynucleotide sequence complementary to a second sequencing primer, respectively).

In some embodiments, the first and second template polynucleotides include different template sequences, i.e., the first template polynucleotide and the second template polynucleotide include different template sequences and are each ligated to distinct combinations of first and second adapter sequences, or first, second, third, and fourth adapter sequences. For example, a first template polynucleotide includes a template polynucleotide sequence and a first adapter sequence, and a second template polynucleotide includes a different template polynucleotide sequence, and further includes a second adapter sequence. In embodiments, the first adapter sequence and the second adapter sequence include different sequencing primer binding regions (i.e., a polynucleotide sequence complementary to a first sequencing primer and a polynucleotide sequence complementary to a second sequencing primer, respectively).

In embodiments, the first template polynucleotide and the second template polynucleotide are less than 1% homologous (i.e., the first and second template polynucleotides include different template sequences). In embodiments, the first template polynucleotide and the second template polynucleotide are less than 1%, 2%, 3%, 4%, or 5% homologous.

In some embodiments, the first and second adapter sequences further include a barcode sequence. In embodiments, the first and second adapter sequences further include a barcode sequence that alone or in combination with a sequence of one or both of (a) the sample polynucleotide, or (b) one or more additional barcode sequences, uniquely distinguishing the template polynucleotide from other template polynucleotides in the plurality. In embodiments, each barcode sequence is selected from a set of barcode sequences represented by a random or partially random sequence. In other embodiments, each barcode sequence is selected from a set of barcode sequences represented by a random sequence. In other embodiments, each barcode sequence differs from every other barcode sequence by at least two nucleotide positions. In embodiments, each barcode sequence includes about 5 to about 20 nucleotides, or about 10 to about 20 nucleotides.

Figure 2B:
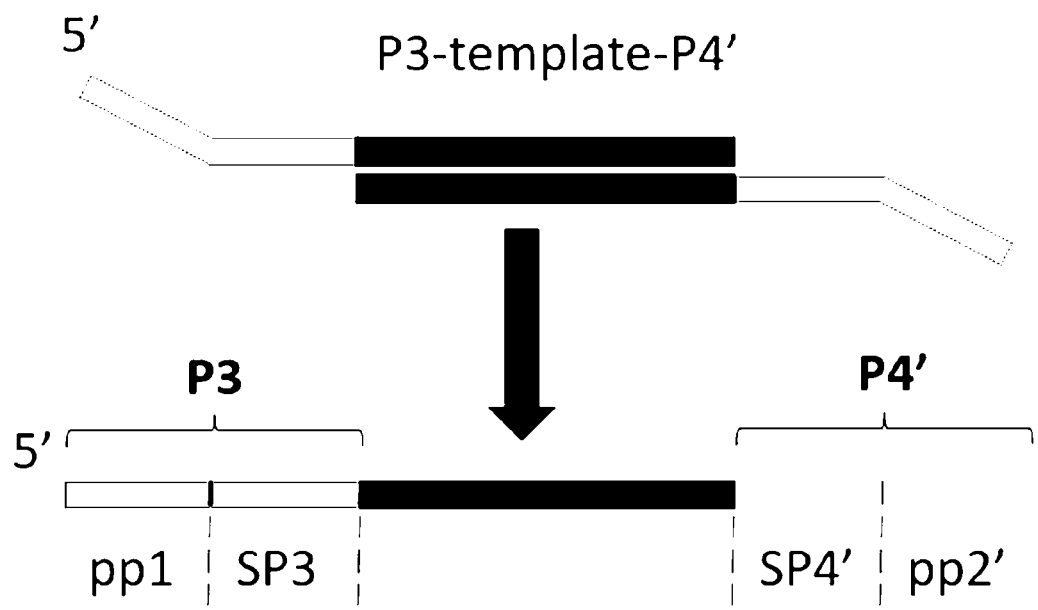

In embodiments, the template polynucleotide includes an adapter sequence flanking both ends (i.e., the 5' and the 3' end) of the template polynucleotide sequence (e.g., as depicted in FIGS. 2A-2B). In embodiments, the template polynucleotide includes a first adapter sequence one end of the template polynucleotide and a second adapter on the other end of the template polynucleotide. In embodiments, the template polynucleotide includes a third adapter sequence one end of the template polynucleotide and a fourth adapter on the other end of the template polynucleotide. It is understood that first, second, third, fourth, fifth, sixth, etc. may be interchanged when in reference to each other depending on the context.

In embodiments, the first adapter and/or second adapter is a Y-adapter. In some embodiments, the Y-adapter includes (i) a first strand having a 5'-arm and a 3'-portion, and (ii) a second strand having a 5'-portion and a 3'-arm, wherein the 3'-portion of the first strand is substantially complementary to the 5'-portion of the second strand, and the 5'-arm of the first strand is not substantially complementary to the 3'-arm of the second strand. In further embodiments, the ligating of the first adapter includes ligating a 3'-end of the first strand of the Y-adapter to a 5'-end of a forward strand of the first template polynucleotide, and ligating a 5'-end of the second strand of the Y-adapter to a 3'-end of a reverse strand of the first template polynucleotide.

In some embodiments, the first adapter and/or second adapter is a hairpin adapter. In some embodiments, the first adapter and/or second adapter is a hairpin adapter, wherein the hairpin adapter includes a cleavable site. In embodiments, the cleavable site includes a diol linker, disulfide linker, photocleavable linker, abasic site, deoxyuracil triphosphate (dUTP), deoxy-8-oxo-guanine triphosphate (d-8-oxoG), methylated nucleotide, ribonucleotide, or a sequence containing a modified or unmodified nucleotide that is specifically recognized by a cleaving agent.

In embodiments, the amplicons of a first template polynucleotide include at least one cleavable site. In embodiments, the cleavable site includes a diol linker, disulfide linker, photocleavable linker, abasic site, deoxyuracil triphosphate (dUTP), deoxy-8-oxo-guanine triphosphate (d-8-oxoG), methylated nucleotide, ribonucleotide, or a sequence containing a modified or unmodified nucleotide that is specifically recognized by a cleaving agent.

In some embodiments, the template polynucleotide includes genomic DNA, complementary DNA (cDNA), cell-free DNA (cfDNA), messenger RNA (mRNA), transfer RNA (tRNA), ribosomal RNA (rRNA), cell-free RNA (cfRNA), or noncoding RNA (ncRNA). In embodiments, the template polynucleotide is genomic DNA, complementary DNA (cDNA), cell-free DNA (cfDNA), messenger RNA (mRNA), transfer RNA (tRNA), ribosomal RNA (rRNA), cell-free RNA (cfRNA), or noncoding RNA (ncRNA). In embodiments, the template polynucleotide is genomic DNA. In embodiments, the template polynucleotide is complementary DNA (cDNA). In embodiments, the template polynucleotide is cell-free DNA (cfDNA). In embodiments, the template polynucleotide is messenger RNA (mRNA). In embodiments, the template polynucleotide is transfer RNA (tRNA). In embodiments, the template polynucleotide is ribosomal RNA (rRNA). In embodiments, the template polynucleotide is cell-free RNA (cfRNA). In embodiments, the template polynucleotide is noncoding RNA (ncRNA).

In embodiments, the template polynucleotide is about 20 to 100 nucleotides in length. In embodiments, the template polynucleotide is about 30 to 100 nucleotides in length. In embodiments, the template polynucleotide is about 40 to 100 nucleotides in length. In embodiments, the template polynucleotide is about 50 to 100 nucleotides in length. In embodiments, the template polynucleotide is about 60 to 100 nucleotides in length. In embodiments, the template polynucleotide is about 70 to 100 nucleotides in length. In embodiments, the template polynucleotide is about 80 to 100 nucleotides in length. In embodiments, the template polynucleotide is about 90 to 100 nucleotides in length. In embodiments, the template polynucleotide is about 20 to 200 nucleotides in length. In embodiments, the template polynucleotide is about 30 to 200 nucleotides in length. In embodiments, the template polynucleotide is about 40 to 200 nucleotides in length. In embodiments, the template polynucleotide is about 50 to 200 nucleotides in length. In embodiments, the template polynucleotide is about 60 to 200 nucleotides in length. In embodiments, the template polynucleotide is about 70 to 200 nucleotides in length. In embodiments, the template polynucleotide is about 80 to 200 nucleotides in length. In embodiments, the template polynucleotide is about 90 to 200 nucleotides in length. In embodiments, the template polynucleotide is about 100 to 200 nucleotides in length. In embodiments, the template polynucleotide is less than about 50 nucleotides in length. In embodiments, the template polynucleotide is less than about 75 nucleotides in length. In embodiments, the template polynucleotide is less than about 100 nucleotides in length.

In embodiments, the template polynucleotide is less than about 125 nucleotides in length. In embodiments, the template polynucleotide is less than about 150 nucleotides in length. In embodiments, the template polynucleotide is less than about 175 nucleotides in length. In embodiments, the template polynucleotide is less than about 200 nucleotides in length.

In embodiments, overlapping amplification clusters form an ordered array at discrete locations on the surface. In some embodiments, the surface does not include an ordered array of amplification sites. For example, the surface may be uniformly coated with amplification primers, rather than coating some areas (amplification sites) and not others (interstitial regions).

In an aspect is provided a substrate including: a plurality of oligonucleotides attached to a solid support, wherein each of the oligonucleotides includes a sequence complementary to a first platform primer binding sequence. In embodiments, the solid support includes a polymer, wherein the oligonucleotides are attached (e.g., covalently attached) to the polymer. In embodiments, the substrate includes a first plurality of oligonucleotides wherein each of the oligonucleotides includes a sequence complementary to a first platform primer binding sequence; and a second plurality of oligonucleotides, wherein each of the oligonucleotides includes a sequence complementary to a second platform primer binding sequence. In embodiments, the substrate includes two or more populations of polynucleotides, wherein each population of polynucleotides includes a different sequencing primer binding sequence or a different pair of primer binding sequences. In embodiments, the polynucleotides of each population include a first platform primer binding sequence complementary to the first plurality of oligonucleotides attached to the solid support and a second platform primer binding sequence complementary to the second plurality of oligonucleotides attached to the solid support. In embodiments, the substrate includes a polynucleotide from each population of polynucleotides hybridized to an oligonucleotide (e.g., the platform primer binding sequence hybridizes to the oligonucleotide attached to the solid support).

In an aspect is provided a kit, wherein the kit includes the substrate as described herein. In embodiments, the kit includes components necessary to perform the methods as described herein. Generally, the kit includes one or more containers providing a composition and one or more additional reagents (e.g., a buffer suitable for polynucleotide extension). The kit may also include a template nucleic acid (DNA and/or RNA), one or more primer polynucleotides, nucleoside triphosphates (including, e.g., deoxyribonucleotides, ribonucleotides, labeled nucleotides, and/or modified nucleotides), buffers, salts, and/or labels (e.g., fluorophores). In embodiments, the kit includes a substrate (e.g., a patterned substrate such as a flow cell), wherein the substrate includes a first plurality of immobilized oligonucleotides and a second plurality of immobilized oligonucleotides (e.g., the first plurality of immobilized oligonucleotides and the second plurality of immobilized oligonucleotides are each attached to the surface of the substrate). When the solid support includes an array of discrete sites of immobilized oligonucleotides, it may be referred to as an array. In embodiments, the substrate is in a container. The container may be a storage device or other readily usable vessel capable of storing and protecting the substrate. In embodiments the kit includes a substrate, at least 3 different sequencing primers, one or more polymerases, and one or more platform primers. In embodiments, the kit includes more than 3, more than 4, more than 5, more than 6, more than 7, more than 8, more than 9, or more than 10 different sequencing primers.

In an aspect is provided a kit, wherein the kit includes a substrate including: a plurality of oligonucleotides attached to a solid support, wherein each of the oligonucleotides includes a sequence complementary to a first platform primer binding sequence. In embodiments, the solid support includes a polymer, wherein the oligonucleotides are attached (e.g., covalently attached) to the polymer. In embodiments, the substrate includes a first plurality of oligonucleotides wherein each of the oligonucleotides includes a sequence complementary to a first platform primer binding sequence; and a second plurality of oligonucleotides, wherein each of the oligonucleotides includes a sequence complementary to a second platform primer binding sequence. In embodiments, the substrate includes two or more populations of polynucleotides, wherein each population of polynucleotides includes a different sequencing primer binding sequence or a different pair of primer binding sequences. In embodiments, the polynucleotides of each population include a first platform primer binding sequence complementary to the first plurality of oligonucleotides attached to the solid support and a second platform primer binding sequence complementary to the second plurality of oligonucleotides attached to the solid support. In embodiments, the substrate includes a polynucleotide from each population of polynucleotides hybridized to an oligonucleotide (e.g., the platform primer binding sequence hybridizes to the oligonucleotide attached to the solid support). In embodiments, the kit includes an adapter composition wherein the adapter composition includes a first adapter including a first platform primer binding sequence and a first sequencing primer binding sequence; a second adapter including a second platform primer binding sequence and a second sequencing primer binding sequence; a third adapter including the third platform primer binding sequence and a third sequencing primer binding sequence. In embodiments the adapter composition includes a fourth adapter, including the second platform primer binding sequence and a fourth sequencing primer binding sequence. In embodiments, the first sequencing primer binding sequence, second sequencing primer binding sequence, third sequencing primer binding sequence, and fourth sequencing primer binding sequence are different. In embodiments, the adapters are in separate reaction vessels or separate containers (e.g., individual buffered vials). In embodiments, the adapters are included in a single container (e.g., in a vial containing a buffered solution). In embodiments, the kit includes 3, 4, 5, 6, 7, 8, 9, 10 or more sequencing primers. In embodiments, all or a subset of sequencing primers are in separate containers. In embodiments, the sequencing primers are in a single container. In embodiments, a subset of the sequencing primers are in separate containers.

In embodiments, the kit includes an array with particles (e.g., particles including immobilized oligonucleotides) already loaded into the wells. In embodiments, the array is filled with a buffered solution. Alternatively, in embodiments, the array is not filled with a buffered solution. In embodiments, the array is dry. In embodiments, the array with particles already loaded into the wells is filled with a buffered solution. In embodiments, the particles are in a container. In embodiments, the particles are in aqueous suspension or as a powder within the container. The container may be a storage device or other readily usable vessel capable of storing and protecting the particles.

In embodiments, the kit includes a sequencing polymerase, and one or more amplification polymerases. In embodiments, the sequencing polymerase is capable of incorporating modified nucleotides. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g., Therminator γ, 9°N polymerase (exo-), Therminator II, Therminator III, or Therminator IX). In embodiments, the DNA polymerase is a thermophilic nucleic acid polymerase. In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044, each of which are incorporated herein by reference for all purposes). In embodiments, the kit includes a strand-displacing polymerase. In embodiments, the kit includes a strand-displacing polymerase, such as a phi29 polymerase, phi29 mutant polymerase or a thermostable phi29 mutant polymerase.

In embodiments, the kit includes a buffered solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, bicine, tricine, HEPES, TES, MOPS, MOPSO and PIPES. Additionally, other buffer agents that can be used in enzyme reactions, hybridization reactions, and detection reactions are known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can comprise one or more divalent cations. Examples of divalent cations can include, but are not limited to, $Mg^{2+}$, $Mn^{2+}$, $Zn^{2+}$, and $Ca^{2+}$. In embodiments, the buffered solution can contain one or more divalent cations at a concentration sufficient to permit hybridization of a nucleic acid. In embodiments, the buffered solution can contain one or more divalent cations at a concentration sufficient to permit hybridization of a nucleic acid. In embodiments, the buffered solution includes about 10 mM Tris, about 20 mM Tris, about 30 mM Tris, about 40 mM Tris, or about 50 mM Tris. In embodiments the buffered solution includes about 50 mM NaCl, about 75 mM NaCl, about 100 mM NaCl, about 125 mM NaCl, about 150 mM NaCl, about 200 mM NaCl, about 300 mM NaCl, about 400 mM NaCl, or about 500 mM NaCl. In embodiments, the buffered solution includes about 0.05 mM EDTA, about 0.1 mM EDTA, about 0.25 mM EDTA, about 0.5 mM EDTA, about 1.0 mM EDTA, about 1.5 mM EDTA or about 2.0 mM EDTA. In embodiments, the buffered solution includes about 0.01% Triton X-100, about 0.025% Triton X-100, about 0.05% Triton X-100, about 0.1% Triton X-100, or about 0.5% Triton X-100. In embodiments, the buffered solution includes 20 mM Tris pH 8.0, 100 mM NaCl, 0.1 mM EDTA, 0.025% Triton X-100. In embodiments, the buffered solution includes 20 mM Tris pH 8.0, 150 mM NaCl, 0.1 mM EDTA, 0.025% Triton X-100. In embodiments, the buffered solution includes 20 mM Tris pH 8.0, 300 mM NaCl, 0.1 mM EDTA, 0.025% Triton X-100. In embodiments, the buffered solution includes 20 mM Tris pH 8.0, 400 mM NaCl, 0.1 mM EDTA, 0.025% Triton X-100. In embodiments, the buffered solution includes 20 mM Tris pH 8.0, 500 mM NaCl, 0.1 mM EDTA, 0.025% Triton X-100.

In embodiments, the kit includes one or more sequencing reaction mixtures. In embodiments, the sequencing reaction mixture includes a buffer. In embodiments, the buffer includes an acetate buffer, 3-(N-morpholino)propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer. In embodiments, the sequencing reaction mixture includes nucleotides, wherein the nucleotides include a reversible terminating moiety and a label covalently linked to the nucleotide via a cleavable linker. In embodiments, the sequencing reaction mixture includes a buffer, DNA polymerase, detergent (e.g., Triton X), a chelator (e.g., EDTA), and/or salts (e.g., ammonium sulfate, magnesium chloride, sodium chloride, or potassium chloride).

In embodiments, the kit includes one or more sequencing reaction mixtures. In embodiments, the kit includes one sequencing reaction mixture for each sequencing primer included in the kit (e.g., the kit includes 1, 2, 3, 4, 5, 6, 7, 8, 9, 10, 11, or 12 sequencing reaction mixtures). In embodiments, the kit includes a sequencing reaction mixture including a plurality of different sequencing primer species, wherein all but one of the sequencing primer species is terminated with one or more ddNTPs (e.g., ddCTP, ddATP, ddGTP, or ddTTP) at the 3' end. In embodiments, a cleavable site is present next to the one or more ddNTPs on the 3' end, wherein the cleavable site precedes the ddNTPs. In embodiments, the number of different sequencing primer species corresponds to the number of unique adapter sequences and sequencing primer regions present on the template polynucleotides on the surface. For example, if 4 unique sequencing primer binding sites are present on the template polynucleotides, then the sequencing reaction mixture would contain 1 sequencing primer with an extendable 3' end (e.g., a 3'-OH), and 3 sequencing primers with a cleavable site and one or more ddNTPs at the 3' end.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the components). The term "kit" includes both fragmented and combined kits. In embodiments, the kit includes, without limitation, nucleic acid primers, probes, adapters, enzymes, and the like, and are each packaged in a container, such as, without limitation, a vial, tube or bottle, in a package suitable for commercial distribution, such as, without limitation, a box, a sealed pouch, a blister pack and a carton. The package typically contains a label or packaging insert indicating the uses of the packaged materials. As used herein, "packaging materials" includes any article used in the packaging for distribution of reagents in a kit, including without limitation containers, vials, tubes, bottles, pouches, blister packaging, labels, tags, instruction sheets and package inserts.

Adapters and/or primers may be supplied in the kits ready for use, as concentrates-requiring dilution before use, or in a lyophilized or dried form requiring reconstitution prior to use. If required, the kits may further include a supply of a suitable diluent for dilution or reconstitution of the primers and/or adapters. Optionally, the kits may further include supplies of reagents, buffers, enzymes, and dNTPs for use in carrying out nucleic acid amplification and/or sequencing. Further components which may optionally be supplied in the kit include sequencing primers suitable for sequencing templates prepared using the methods described herein.

In embodiments, the kit includes a first oligonucleotide (e.g., a first adapter) including any one of the sequences of SEQ ID NO:1 to SEQ ID NO:96. In embodiments, the kit further includes a second oligonucleotide (e.g., a second adapter) including any one of the sequences of SEQ ID NO:1 to SEQ ID NO:96. In embodiments, the first adapter and the second adapter sequences are different (i.e., the first adapter and the second adapter sequences include different sequences described in Table 1, having different SEQ ID NOs).

In embodiments, the kit includes an adapter including a first oligonucleotide including any one of the sequences of SEQ ID NO: 1, 11, 21, or 31, and a second oligonucleotide including any one of the sequences of SEQ ID NO: 6, 16, 26, or 36, wherein the first oligonucleotide can hybridize to the second oligonucleotide. In embodiments, the kit includes an adapter including a first oligonucleotide including any one of the sequences of SEQ ID NO: 2, 12, 22, or 32, and a second oligonucleotide including any one of the sequences of SEQ ID NO: 7, 17, 27, or 37, wherein the first oligonucleotide can hybridize to the second oligonucleotide. In embodiments, the kit includes an adapter including a first oligonucleotide including any one of the sequences of SEQ ID NO: 3, 13, 23, or 33, and a second oligonucleotide including any one of the sequences of SEQ ID NO: 8, 18, 28, or 38, wherein the first oligonucleotide can hybridize to the second oligonucleotide. In embodiments, the kit includes an adapter including a first oligonucleotide including any one of the sequences of SEQ ID NO: 4, 14, 24, or 34, and a second oligonucleotide including any one of the sequences of SEQ ID NO: 9, 19, 29, or 39, wherein the first oligonucleotide can hybridize to the second oligonucleotide. In embodiments, the kit includes an adapter including a first oligonucleotide including any one of the sequences of SEQ ID NO: 5, 15, 25, or 35, and a second oligonucleotide including any one of the sequences of SEQ ID NO: 10, 20, 30, or 40, wherein the first oligonucleotide can hybridize to the second oligonucleotide. In embodiments, the kit includes an adapter including a first oligonucleotide including any one of the sequences of SEQ ID NO: 41, 55, 69, or 83, and a second oligonucleotide including any one of the sequences of SEQ ID NO: 48, 62, 76, or 90, wherein the first oligonucleotide can hybridize to the second oligonucleotide. In embodiments, the kit includes an adapter including a first oligonucleotide including any one of the sequences of SEQ ID NO: 42, 56, 70, or 84, and a second oligonucleotide including any one of the sequences of SEQ ID NO: 49, 63, 77, or 91, wherein the first oligonucleotide can hybridize to the second oligonucleotide. In embodiments, the kit includes an adapter including a first oligonucleotide including any one of the sequences of SEQ ID NO: 43, 57, 71, or 85, and a second oligonucleotide including any one of the sequences of SEQ ID NO: 50, 64, 78, or 92, wherein the first oligonucleotide can hybridize to the second oligonucleotide. In embodiments, the kit includes an adapter including a first oligonucleotide including any one of the sequences of SEQ ID NO: 44, 58, 72, or 86, and a second oligonucleotide including any one of the sequences of SEQ ID NO: 51, 65, 79, or 93, wherein the first oligonucleotide can hybridize to the second oligonucleotide. In embodiments, the kit includes an adapter including a first oligonucleotide including any one of the sequences of SEQ ID NO: 45, 59, 73, or 87, and a second oligonucleotide including any one of the sequences of SEQ ID NO: 52, 66, 80, or 94, wherein the first oligonucleotide can hybridize to the second oligonucleotide. In embodiments, the kit includes an adapter including a first oligonucleotide including any one of the sequences of SEQ ID NO: 46, 60, 74, or 88, and a second oligonucleotide including any one of the sequences of SEQ ID NO: 53, 67, 81, or 95, wherein the first oligonucleotide can hybridize to the second oligonucleotide. In embodiments, the kit includes an adapter including a first oligonucleotide including any one of the sequences of SEQ ID NO: 47, 61, 75, or 89, and a second oligonucleotide including any one of the sequences of SEQ ID NO: 54, 68, 82, or 96, wherein the first oligonucleotide can hybridize to the second oligonucleotide.

In embodiments, the kit includes two primers each including a sequence described in Table 1 that may be hybridized to an adapter on one, or both ends of the double-stranded template. In embodiments, the kit includes a first primer including the sequence of any one of SEQ ID NO: 1, 11, 21, or 31 and a second primer including the sequence of any one of SEQ ID NO: 6, 16, 26, or 36, wherein the first primer is complementary to the first oligonucleotide of the adapter and the second primer is complementary to the second oligonucleotide of the adapter. In embodiments, the kit includes a first primer including the sequence of any one of SEQ ID NO: 2, 12, 22, or 32 and a second primer including the sequence of any one of SEQ ID NO: 7, 17, 27, or 37, wherein the first primer is complementary to the first oligonucleotide of the adapter and the second primer is complementary to the second oligonucleotide of the adapter. In embodiments, the kit includes a first primer including the sequence of any one of SEQ ID NO: 3, 13, 23, or 33 and a second primer including the sequence of any one of SEQ ID NO: 8, 18, 28, or 38, wherein the first primer is complementary to the first oligonucleotide of the adapter and the second primer is complementary to the second oligonucleotide of the adapter. In embodiments, the kit includes a first primer including the sequence of any one of SEQ ID NO: 4, 14, 24, or 34 and a second primer including the sequence of any one of SEQ ID NO: 9, 19, 29, or 39, wherein the first primer is complementary to the first oligonucleotide of the adapter and the second primer is complementary to the second oligonucleotide of the adapter. In embodiments, the kit includes a first primer including the sequence of any one of SEQ ID NO: 5, 15, 25, or 35 and a second primer including the sequence of any one of SEQ ID NO: 10, 20, 30, or 40, wherein the first primer is complementary to the first oligonucleotide of the adapter and the second primer is complementary to the second oligonucleotide of the adapter. In embodiments, the kit includes a first primer including the sequence of any one of SEQ ID NO: 41, 55, 69, or 83 and a second primer including the sequence of any one of SEQ ID NO: 48, 62, 76, or 90, wherein the first primer is complementary to the first oligonucleotide of the adapter and the second primer is complementary to the second oligonucleotide of the adapter. In embodiments, the kit includes a first primer including the sequence of any one of SEQ ID NO: 42, 56, 70, or 84 and a second primer including the sequence of any one of SEQ ID NO: 49, 63, 77, or 91, wherein the first primer is complementary to the first oligonucleotide of the adapter and the second primer is complementary to the second oligonucleotide of the adapter. In embodiments, the kit includes a first primer including the sequence of any one of SEQ ID NO: 43, 57, 71, or 85 and a second primer including the sequence of any one of SEQ ID NO: 50, 64, 78, or 92, wherein the first primer is complementary to the first oligonucleotide of the adapter and the second primer is complementary to the second oligonucleotide of the adapter. In embodiments, the kit includes a first primer including the sequence of any one of SEQ ID NO: 44, 58, 72, or 86 and a second primer including the sequence of any one of SEQ ID NO: 51, 65, 79, or 93, wherein the first primer is complementary to the first oligonucleotide of the adapter and the second primer is complementary to the second oligonucleotide of the adapter. In embodiments, the kit includes a first primer including the sequence of any one of SEQ ID NO: 45, 59, 73, or 87 and a second primer including the sequence of any one of SEQ ID NO: 52, 66, 80, or 94, wherein the first primer is complementary to the first oligonucleotide of the adapter and the second primer is complementary to the second oligonucleotide of the adapter. In embodiments, the kit includes a first primer including the sequence of any one of SEQ ID NO: 46, 60, 74, or 88 and a second primer including the sequence of any one of SEQ ID NO: 53, 67, 81, or 95, wherein the first primer is complementary to the first oligonucleotide of the adapter and the second primer is complementary to the second oligonucleotide of the adapter. In embodiments, the kit includes a first primer including the sequence of any one of SEQ ID NO: 47, 61, 75, or 89 and a second primer including the sequence of any one of SEQ ID NO: 54, 68, 82, or 96, wherein the first primer is complementary to the first oligonucleotide of the adapter and the second primer is complementary to the second oligonucleotide of the adapter.

In an aspect is provided a flow cell including a particle as described herein, wherein the particle is within a well of the flow cell.

In an aspect is provided a kit, including the array as described herein. In an aspect is provided a kit, including the solid support as described herein. Generally, the kit includes one or more containers providing a composition and one or more additional reagents (e.g., a buffer suitable for polynucleotide extension). The kit may also include a template nucleic acid (DNA and/or RNA), one or more primer polynucleotides, nucleoside triphosphates (including, e.g., deoxyribonucleotides, ribonucleotides, particles, labeled nucleotides, and/or modified nucleotides), buffers, salts, and/or labels (e.g., fluorophores). In embodiments, the kit includes an array with particles already loaded into the wells. In embodiments, the particles are in a container. In embodiments, the particles are in aqueous suspension or as a powder within the container. The container may be a storage device or other readily usable vessel capable of storing and protecting the particles. The kit may also include a flow cell. In embodiments, kit includes the solid support and a flow cell carrier (e.g., a flow cell carrier as described in US 2021/0190668, which is incorporated herein by reference for all purposes).

In an aspect is provided a kit, including the plurality of particles, adapters, primers, and enzymes as described herein. Generally, the kit includes one or more containers providing a composition and one or more additional reagents (e.g., a buffer suitable for polynucleotide extension and/or sequencing).

III. Methods

In as aspect is provided a method for amplifying different populations of polynucleotides (e.g., different libraries), wherein each population of polynucleotides includes a different sequencing primer binding sequence. In embodiments, the method includes simultaneously (i.e., concurrently in a single amplification protocol) amplifying different populations of polynucleotides. In embodiments, the method includes contacting a solid support with a first population of polynucleotides thereby forming a first complex, and contacting the solid support with a second population of polynucleotides thereby forming a second complex, wherein the complexes include a polynucleotide hybridized to an oligonucleotide attached to the solid support; contacting each complex with a polymerase and extending the oligonucleotide, thereby forming amplification products. In embodiments, the solid support includes a first plurality of oligonucleotides attached to the solid support. In embodiments, the solid support includes a second plurality of oligonucleotides attached to the solid support. In embodiments, the oligonucleotides of the first plurality are different than the oligonucleotides of the second plurality (e.g., a plurality of pp1 and a plurality of pp2, or complements thereof).

In an aspect is provided a method of sequencing different populations of polynucleotides immobilized on a solid support, the method including: contacting a first population of polynucleotides annealed to a first sequencing primer with a first sequencing solution including a plurality of modified nucleotides including a reversible terminator and monitoring the sequential incorporation of complementary nucleotides to generate a first sequencing read, wherein the reversible terminator is removed prior to the introduction of the next complementary nucleotide; contacting a second population of polynucleotides annealed to a second sequencing primer with a second sequencing solution including a plurality of modified nucleotides including a reversible terminator and monitoring the sequential incorporation of complementary nucleotides to generate a second sequencing read, wherein the reversible terminator is removed prior to the introduction of the next complementary nucleotide; contacting a third population of polynucleotides annealed to a third sequencing primer with a third sequencing solution including a plurality of modified nucleotides including a reversible terminator and monitoring the sequential incorporation of complementary nucleotides to generate a third sequencing read, wherein the reversible terminator is removed prior to the introduction of the next complementary nucleotide; wherein the first sequencing primer, second sequencing primer, and third sequencing primer are different.

In as aspect is provided a method for amplifying different populations of polynucleotides, wherein each population of polynucleotides includes a different sequencing primer binding sequence, the method including contacting a solid support with a first population of polynucleotides thereby forming a first complex, and contacting the solid support with a second population of polynucleotides thereby forming a second complex, wherein the complexes include a polynucleotide hybridized to an oligonucleotide attached to the solid support; contacting each complex with a polymerase and extending the oligonucleotide, thereby forming amplification products. In embodiments, the solid support includes a first plurality of oligonucleotides attached to the solid support. In embodiments, the solid support includes a second plurality of oligonucleotides attached to the solid support.

In as aspect is provided a method for amplifying different populations of polynucleotides, wherein each population of polynucleotides includes a different sequencing primer binding sequence, the method including contacting a solid support with a first population of polynucleotides thereby forming a first complex, contacting the solid support with a second population of polynucleotides thereby forming a second complex, contacting the solid support with a third population of polynucleotides thereby forming a third complex, and contacting the solid support with a fourth population of polynucleotides thereby forming a fourth complex, wherein the complexes include a polynucleotide hybridized to an oligonucleotide attached to the solid support; contacting each complex with a polymerase and extending the oligonucleotide, thereby forming amplification products. In embodiments, the solid support includes a first plurality of oligonucleotides attached to the solid support, a second plurality of oligonucleotides attached to the solid support, a third plurality of oligonucleotides attached to the solid support, and a fourth plurality of oligonucleotides attached to the solid support.

In as aspect is provided a method for amplifying different populations (e.g., different libraries) of polynucleotides, wherein each population of polynucleotides includes a different sequencing primer binding sequence, the method including contacting a solid support with a first population of polynucleotides thereby forming a first complex, contacting the solid support with a second population of polynucleotides thereby forming a second complex, contacting the solid support with a third population of polynucleotides thereby forming a third complex, contacting the solid support with a fourth population of polynucleotides thereby forming a fourth complex, contacting the solid support with a fifth population of polynucleotides thereby forming a fifth complex, contacting the solid support with a sixth population of polynucleotides thereby forming a sixth complex, contacting the solid support with a seventh population of polynucleotides thereby forming a seventh complex, and contacting the solid support with an eighth population of polynucleotides thereby forming an eighth complex, wherein the complexes include a polynucleotide hybridized to an oligonucleotide attached to the solid support; contacting each complex with a polymerase and extending the oligonucleotide, thereby forming amplification products. In embodiments, the solid support includes a first plurality of oligonucleotides attached to the solid support, a second plurality of oligonucleotides attached to the solid support, a third plurality of oligonucleotides attached to the solid support, a fourth plurality of oligonucleotides attached to the solid support, a fifth plurality of oligonucleotides attached to the solid support, a sixth plurality of oligonucleotides attached to the solid support, a seventh plurality of oligonucleotides attached to the solid support, and an eighth plurality of oligonucleotides attached to the solid support.

In as aspect is provided a method for amplifying different populations of polynucleotides, wherein each population of polynucleotides includes a different sequencing primer binding sequence, the method including contacting a solid support with a first population of polynucleotides thereby forming a first complex, contacting the solid support with a second population of polynucleotides thereby forming a second complex, contacting the solid support with a third population of polynucleotides thereby forming a third complex, contacting the solid support with a fourth population of polynucleotides thereby forming a fourth complex, contacting the solid support with a fifth population of polynucleotides thereby forming a fifth complex, contacting the solid support with a sixth population of polynucleotides thereby forming a sixth complex, contacting the solid support with a seventh population of polynucleotides thereby forming a seventh complex, contacting the solid support with an eighth population of polynucleotides thereby forming an eighth complex, contacting the solid support with a ninth population of polynucleotides thereby forming a ninth complex, contacting the solid support with a tenth population of polynucleotides thereby forming a tenth complex, contacting the solid support with an eleventh population of polynucleotides thereby forming an eleventh complex, contacting the solid support with a twelfth population of polynucleotides thereby forming a twelfth complex, wherein the complexes include a polynucleotide hybridized to an oligonucleotide attached to the solid support; contacting each complex with a polymerase and extending the oligonucleotide, thereby forming amplification products. In embodiments, the solid support includes a first plurality of oligonucleotides attached to the solid support, a second plurality of oligonucleotides attached to the solid support, a third plurality of oligonucleotides attached to the solid support, a fourth plurality of oligonucleotides attached to the solid support, a fifth plurality of oligonucleotides attached to the solid support, a sixth plurality of oligonucleotides attached to the solid support, a seventh plurality of oligonucleotides attached to the solid support, an eighth plurality of oligonucleotides attached to the solid support, a ninth plurality of oligonucleotides attached to the solid support, a tenth plurality of oligonucleotides attached to the solid support, an eleventh plurality of oligonucleotides attached to the solid support, and a twelfth plurality of oligonucleotides attached to the solid support.

Figure 9A:
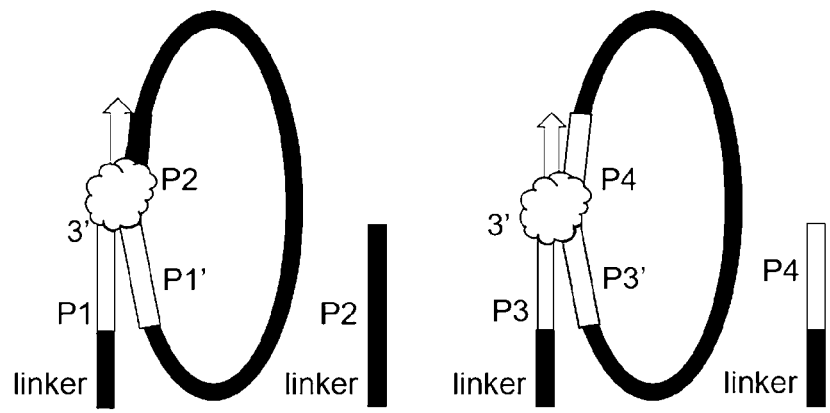
FIGS. 9A-9C. Seeding and amplification of two different circularized libraries. The prepared library molecules may be circularized in solution and annealed to a complementary immobilized oligonucleotide as illustrated in FIG. 9A, or a linear nucleic acid molecule may be circularized on the solid support, as illustrated in FIG. 9B.
Figure 9B:
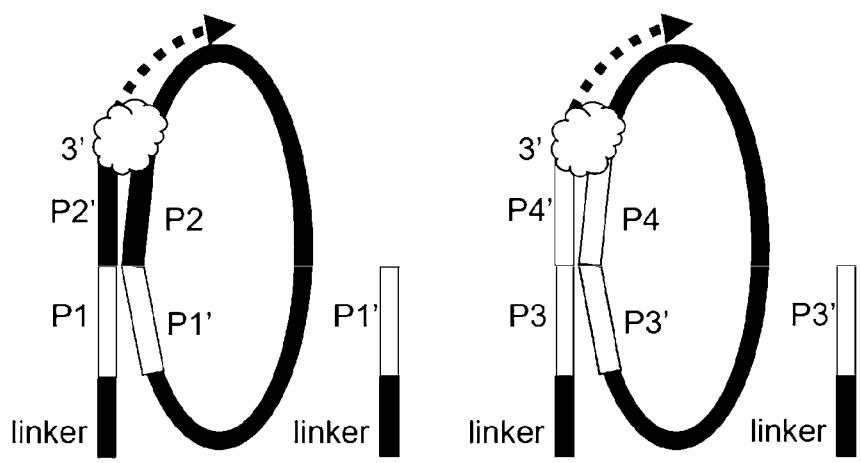
Figure 9C:
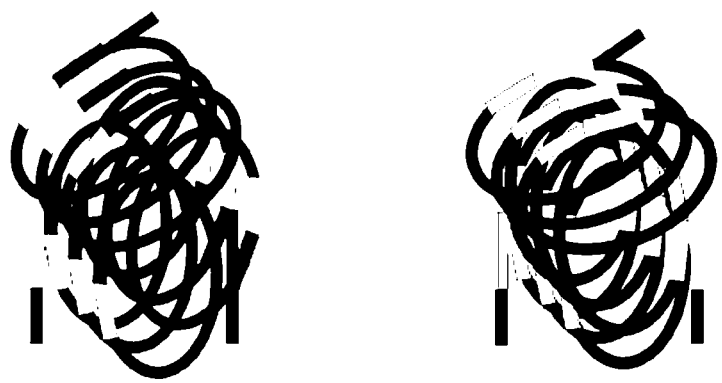

In embodiments, a plurality of oligonucleotides attached to the solid support is used to capture a population of circular polynucleotides (e.g., the population of circular polynucleotides is circularized in solution and annealed to complementary immobilized oligonucleotides, as shown in FIG. 9A), followed by rolling circle amplification (RCA), thereby generating a concatemer of amplification products including tandem repeat units of the circular polynucleotides (see, FIG. 9C). In embodiments, a plurality of oligonucleotides attached to the solid support is used to circularize a population of polynucleotides (e.g., the plurality of oligonucleotides are used as splint oligonucleotides to hybridize to both ends of the polynucleotides, and following ligation, the circular polynucleotides are annealed to the primer, as shown in FIG. 9B), followed by rolling circle amplification (RCA), thereby generating a concatemer of amplification products including tandem repeat units of the circular polynucleotides (see, FIG. 9C). In embodiments, a second oligonucleotide is attached to the solid support may be used to further amplify the concatemer of amplification products (e.g., used to perform exponential rolling circle amplification (eRCA)).

In an aspect is provided a method for amplifying different populations of polynucleotides, wherein each population of polynucleotides includes a different sequencing primer binding sequence. In embodiments, the method includes contacting a solid support with two or more populations of polynucleotides, wherein the solid support includes a first plurality of oligonucleotides attached to the solid support; hybridizing and extending with a polymerase the oligonucleotides of the first plurality hybridized to a polynucleotide; and hybridizing and extending with a polymerase the oligonucleotides of the second plurality hybridized to a polynucleotide; thereby forming amplification products of the first population of polynucleotides, or complements thereof, and the second population of polynucleotides, or complements thereof. In embodiments, the solid support includes a second plurality of oligonucleotides attached to the solid support, wherein the second plurality of oligonucleotides include different sequences relative to the first plurality of oligonucleotides.

In embodiments, the first and second populations of polynucleotides have heterogenic sequences except for the first sequencing primer binding sequence. In embodiments, the first and second populations of polynucleotides have heterogenic sequences except for the second sequencing primer binding sequence. In embodiments, the third and fourth populations of polynucleotides have heterogenic sequences except for the third sequencing primer binding sequence. In embodiments, the third and fourth populations of polynucleotides have heterogenic sequences except for the fourth sequencing primer binding sequence. In embodiments, the fifth and sixth populations of polynucleotides have heterogenic sequences except for the fifth sequencing primer binding sequence. In embodiments, the fifth and sixth populations of polynucleotides have heterogenic sequences except for the sixth sequencing primer binding sequence. In embodiments, the seventh and eighth populations of polynucleotides have heterogenic sequences except for the seventh sequencing primer binding sequence. In embodiments, the seventh and eighth populations of polynucleotides have heterogenic sequences except for the eighth sequencing primer binding sequence. In embodiments, the ninth and tenth populations of polynucleotides have heterogenic sequences except for the ninth sequencing primer binding sequence. In embodiments, the ninth and tenth populations of polynucleotides have heterogenic sequences except for the tenth sequencing primer binding sequence. In embodiments, the eleventh and twelfth populations of polynucleotides have heterogenic sequences except for the eleventh sequencing primer binding sequence. In embodiments, the eleventh and twelfth populations of polynucleotides have heterogenic sequences except for the twelfth sequencing primer binding sequence.

In embodiments, the method includes contacting a solid support with four or more populations of polynucleotides, wherein the solid support includes a first plurality of oligonucleotides attached to the solid support and a second plurality of oligonucleotides attached to the solid support; hybridizing and extending with a polymerase the oligonucleotides of the first plurality hybridized to a polynucleotide and hybridizing and extending with a polymerase the oligonucleotides of the second plurality hybridized to a polynucleotide; thereby forming amplification products of the first population of polynucleotides, or complements thereof, the second population of polynucleotides, or complements thereof, the third population of polynucleotides, or complements thereof, and the fourth population of polynucleotides, or complements thereof. In embodiments, each population includes a first and a second sequencing primer binding sequence, wherein both sequences together are not in other populations.

In embodiments, the method includes contacting a solid support with eight or more populations of polynucleotides, wherein the solid support includes a first plurality of oligonucleotides attached to the solid support, a second plurality of oligonucleotides attached to the solid support, a third plurality of oligonucleotides attached to the solid support, and a fourth plurality of oligonucleotides attached to the solid support; hybridizing and extending with a polymerase the oligonucleotides of the first plurality hybridized to a polynucleotide; hybridizing and extending with a polymerase the oligonucleotides of the second plurality hybridized to a polynucleotide, hybridizing and extending with a polymerase the oligonucleotides of the third plurality hybridized to a polynucleotide, and hybridizing and extending with a polymerase the oligonucleotides of the fourth plurality hybridized to a polynucleotide; thereby forming amplification products of the first population of polynucleotides, or complements thereof, the second population of polynucleotides, or complements thereof, the third population of polynucleotides, or complements thereof, the fourth population of polynucleotides, or complements thereof, the fifth population of polynucleotides, or complements thereof, the sixth population of polynucleotides, or complements thereof, the seventh population of polynucleotides, or complements thereof, and the eighth population of polynucleotides, or complements thereof.

In embodiments, the method includes contacting a solid support with twelve or more populations of polynucleotides, wherein the solid support includes a first plurality of oligonucleotides attached to the solid support, a second plurality of oligonucleotides attached to the solid support, a third plurality of oligonucleotides attached to the solid support, a fourth plurality of oligonucleotides attached to the solid support, a fifth plurality of oligonucleotides attached to the solid support, and a sixth plurality of oligonucleotides attached to the solid support; hybridizing and extending with a polymerase the oligonucleotides of the first plurality hybridized to a polynucleotide; hybridizing and extending with a polymerase the oligonucleotides of the second plurality hybridized to a polynucleotide, hybridizing and extending with a polymerase the oligonucleotides of the third plurality hybridized to a polynucleotide, hybridizing and extending with a polymerase the oligonucleotides of the fourth plurality hybridized to a polynucleotide, hybridizing and extending with a polymerase the oligonucleotides of the fifth plurality hybridized to a polynucleotide, and hybridizing and extending with a polymerase the oligonucleotides of the sixth plurality hybridized to a polynucleotide; thereby forming amplification products of the first population of polynucleotides, or complements thereof, the second population of polynucleotides, or complements thereof, the third population of polynucleotides, or complements thereof, the fourth population of polynucleotides, or complements thereof, the fifth population of polynucleotides, or complements thereof, the sixth population of polynucleotides, or complements thereof, the seventh population of polynucleotides, or complements thereof, the eighth population of polynucleotides, or complements thereof, the ninth population of polynucleotides, or complements thereof, the tenth population of polynucleotides, or complements thereof, the eleventh population of polynucleotides, or complements thereof, and the twelfth population of polynucleotides, or complements thereof.

In embodiments, the polynucleotides of each population include a first platform primer binding sequence complementary to the first plurality of oligonucleotides attached to the solid support and a second platform primer binding sequence complementary to the second plurality of oligonucleotides attached to the solid support.

In embodiments, the polynucleotides of each population include a different pair of sequencing primer binding sequences. For example, a first population may have a sequencing primer binding sequence 'A' and a second sequencing primer binding sequence 'B'. A second population may have the sequencing primer binding sequence 'A' and a different second sequencing primer binding sequence, 'C'. A third population may have a sequencing primer binding sequence 'D' and a sequencing primer binding sequence 'E'. In this example, there are three different libraries: i) 5'-A-template-B; ii) 5'-A-template-C; and iii) 5'-D-template-E. In embodiments, if the libraries are generated in a single reaction vessel (i.e., a one-pot reaction), multiple combinations are permitted. For example, if combining the fragments and adapters in a single reaction, multiple populations are generated: 5'-A-template-B; 5'-A-template-C; 5'-A-template-E; 5'-D-template-E; 5'-D-template-B; and 5'-D-template-C.

In embodiments, a first population of polynucleotides includes a first and a second sequencing primer binding sequence and a second population of polynucleotides includes a first and a third sequencing primer binding sequence. In embodiments, a first population of polynucleotides includes a first and a second sequencing primer binding sequence and a second population of polynucleotides includes a third and a fourth sequencing primer binding sequence. In embodiments, a third population of polynucleotides includes a fifth and a sixth sequencing primer binding sequence and a fourth population of polynucleotides includes a fifth and a seventh sequencing primer binding sequence. In embodiments, a third population of polynucleotides includes a fifth and a sixth sequencing primer binding sequence and a fourth population of polynucleotides includes a seventh and an eighth sequencing primer binding sequence. In embodiments, a fifth population of polynucleotides includes a ninth and a tenth sequencing primer binding sequence and a sixth population of polynucleotides includes a ninth and an eleventh sequencing primer binding sequence. In embodiments, a fifth population of polynucleotides includes a ninth and a tenth sequencing primer binding sequence and a sixth population of polynucleotides includes an eleventh and a twelfth sequencing primer binding sequence.

In embodiments, monitoring the sequential incorporation of complementary nucleotides includes a sequencing-by-synthesis, sequencing-by-ligation, or sequencing-by-binding process.

In embodiments, monitoring the sequential incorporation of complementary nucleotides includes incorporating one or more modified nucleotides into the sequencing primer with a polymerase to create an extension strand, and detecting the one or more incorporated nucleotides so as to identify each incorporated nucleotide in the extension strand, thereby generating one or more sequencing reads.

In embodiments, monitoring the sequential incorporation of complementary nucleotides includes incorporating one or more modified nucleotides into the first sequencing primer with a polymerase to create an extension strand, and detecting the one or more incorporated nucleotides in a first optically resolvable feature; incorporating one or more modified nucleotides into the second sequencing primer with a polymerase to create an extension strand, and detecting the one or more incorporated nucleotides in a second optically resolvable feature; incorporating one or more modified nucleotides into the third sequencing primer with a polymerase to create an extension strand, and detecting the one or more incorporated nucleotides in a third optically resolvable feature; and incorporating one or more modified nucleotides into the fourth sequencing primer with a polymerase to create an extension strand, and detecting the one or more incorporated nucleotides in a fourth optically resolvable feature; wherein the optically resolvable features overlap.

In embodiments, the method further includes sequencing the amplification products or complements thereof. In embodiments, sequencing includes a sequencing-by-synthesis or sequencing-by-binding process. In embodiments, sequencing includes hybridizing a sequencing primer to the amplification product, or a complement thereof, and contacting the sequencing primer with a sequencing solution including one or more modified nucleotides including a reversible terminator, and monitoring the sequential incorporation of complementary nucleotides to generate one or more sequencing reads, wherein the reversible terminator is removed prior to the introduction of the next complementary nucleotide. In embodiments, sequencing includes hybridizing a sequencing primer to the amplification product, or a complement thereof, incorporating one or more modified nucleotides including a reversible terminator into the sequencing primer with a polymerase to create an extension strand, and detecting the one or more incorporated nucleotides so as to identify each incorporated nucleotide in the extension strand, thereby generating one or more sequencing reads, wherein the reversible terminator is removed prior to the introduction of the next complementary nucleotide.

In an aspect is provided a method of sequencing different populations of polynucleotides immobilized on a solid support, the method including: contacting a first population of polynucleotides annealed to a first sequencing primer with a first sequencing solution including a plurality of modified nucleotides including a reversible terminator and monitoring the sequential incorporation of complementary nucleotides to generate a first sequencing read, wherein the reversible terminator is removed prior to the introduction of the next complementary nucleotide; contacting a second population of polynucleotides annealed to a second sequencing primer with a second sequencing solution including a plurality of modified nucleotides including a reversible terminator and monitoring the sequential incorporation of complementary nucleotides to generate a second sequencing read, wherein the reversible terminator is removed prior to the introduction of the next complementary nucleotide; contacting a third population of polynucleotides annealed to a third sequencing primer with a third sequencing solution including a plurality of modified nucleotides including a reversible terminator and monitoring the sequential incorporation of complementary nucleotides to generate a third sequencing read, wherein the reversible terminator is removed prior to the introduction of the next complementary nucleotide; wherein the first sequencing primer, second sequencing primer, and third sequencing primer are different.

In an aspect is provided a method of sequencing different populations of polynucleotides immobilized on a solid support, the method including: contacting a first population of polynucleotides annealed to a first sequencing primer with a first sequencing solution including a plurality of modified nucleotides including a reversible terminator and monitoring the sequential incorporation of complementary nucleotides to generate a first sequencing read, wherein the reversible terminator is removed prior to the introduction of the next complementary nucleotide; contacting a second population of polynucleotides annealed to a second sequencing primer with a second sequencing solution including a plurality of modified nucleotides including a reversible terminator and monitoring the sequential incorporation of complementary nucleotides to generate a second sequencing read, wherein the reversible terminator is removed prior to the introduction of the next complementary nucleotide; contacting a third population of polynucleotides annealed to a third sequencing primer with a third sequencing solution including a plurality of modified nucleotides including a reversible terminator and monitoring the sequential incorporation of complementary nucleotides to generate a third sequencing read, wherein the reversible terminator is removed prior to the introduction of the next complementary nucleotide;

contacting a fourth population of polynucleotides annealed to a fourth sequencing primer with a fourth sequencing solution including a plurality of modified nucleotides including a reversible terminator and monitoring the sequential incorporation of complementary nucleotides to generate a fourth sequencing read, wherein the reversible terminator is removed prior to the introduction of the next complementary nucleotide, contacting a fifth population of polynucleotides annealed to a fifth sequencing primer with a fifth sequencing solution including a plurality of modified nucleotides including a reversible terminator and monitoring the sequential incorporation of complementary nucleotides to generate a fifth sequencing read, wherein the reversible terminator is removed prior to the introduction of the next complementary nucleotide, contacting a sixth population of polynucleotides annealed to a sixth sequencing primer with a sixth sequencing solution including a plurality of modified nucleotides including a reversible terminator and monitoring the sequential incorporation of complementary nucleotides to generate a sixth sequencing read, wherein the reversible terminator is removed prior to the introduction of the next complementary nucleotide; wherein the first sequencing primer, second sequencing primer, third sequencing primer, fourth sequencing primer, fifth sequencing primer, and sixth sequencing primer are different.

In an aspect is provided a method of sequencing different populations of polynucleotides immobilized on a solid support, the method including: contacting a first population of polynucleotides annealed to a first sequencing primer with a first sequencing solution including a plurality of modified nucleotides including a reversible terminator and monitoring the sequential incorporation of complementary nucleotides to generate a first sequencing read, wherein the reversible terminator is removed prior to the introduction of the next complementary nucleotide; contacting a second population of polynucleotides annealed to a second sequencing primer with a second sequencing solution including a plurality of modified nucleotides including a reversible terminator and monitoring the sequential incorporation of complementary nucleotides to generate a second sequencing read, wherein the reversible terminator is removed prior to the introduction of the next complementary nucleotide; contacting a third population of polynucleotides annealed to a third sequencing primer with a third sequencing solution including a plurality of modified nucleotides including a reversible terminator and monitoring the sequential incorporation of complementary nucleotides to generate a third sequencing read, wherein the reversible terminator is removed prior to the introduction of the next complementary nucleotide; contacting a fourth population of polynucleotides annealed to a fourth sequencing primer with a fourth sequencing solution including a plurality of modified nucleotides including a reversible terminator and monitoring the sequential incorporation of complementary nucleotides to generate a fourth sequencing read, wherein the reversible terminator is removed prior to the introduction of the next complementary nucleotide, contacting a fifth population of polynucleotides annealed to a fifth sequencing primer with a fifth sequencing solution including a plurality of modified nucleotides including a reversible terminator and monitoring the sequential incorporation of complementary nucleotides to generate a fifth sequencing read, wherein the reversible terminator is removed prior to the introduction of the next complementary nucleotide, contacting a sixth population of polynucleotides annealed to a sixth sequencing primer with a sixth sequencing solution including a plurality of modified nucleotides including a reversible terminator and monitoring the sequential incorporation of complementary nucleotides to generate a sixth sequencing read, wherein the reversible terminator is removed prior to the introduction of the next complementary nucleotide, contacting a seventh population of polynucleotides annealed to a seventh sequencing primer with a seventh sequencing solution including a plurality of modified nucleotides including a reversible terminator and monitoring the sequential incorporation of complementary nucleotides to generate a seventh sequencing read, wherein the reversible terminator is removed prior to the introduction of the next complementary nucleotide, contacting an eighth population of polynucleotides annealed to an eighth sequencing primer with an eighth sequencing solution including a plurality of modified nucleotides including a reversible terminator and monitoring the sequential incorporation of complementary nucleotides to generate an eighth sequencing read, wherein the reversible terminator is removed prior to the introduction of the next complementary nucleotide, contacting a ninth population of polynucleotides annealed to a ninth sequencing primer with a ninth sequencing solution including a plurality of modified nucleotides including a reversible terminator and monitoring the sequential incorporation of complementary nucleotides to generate a ninth sequencing read, wherein the reversible terminator is removed prior to the introduction of the next complementary nucleotide; wherein the first sequencing primer, second sequencing primer, third sequencing primer, fourth sequencing primer, fifth sequencing primer, sixth sequencing primer, seventh sequencing primer, eighth sequencing primer, and ninth sequencing primer are different.

In an aspect is provided a method of sequencing different populations of polynucleotides immobilized on a solid support, the method including: contacting a first population of polynucleotides annealed to a first sequencing primer with a first sequencing solution including a plurality of modified nucleotides including a reversible terminator and monitoring the sequential incorporation of complementary nucleotides to generate a first sequencing read, wherein the reversible terminator is removed prior to the introduction of the next complementary nucleotide; contacting a second population of polynucleotides annealed to a second sequencing primer with a second sequencing solution including a plurality of modified nucleotides including a reversible terminator and monitoring the sequential incorporation of complementary nucleotides to generate a second sequencing read, wherein the reversible terminator is removed prior to the introduction of the next complementary nucleotide; contacting a third population of polynucleotides annealed to a third sequencing primer with a third sequencing solution including a plurality of modified nucleotides including a reversible terminator and monitoring the sequential incorporation of complementary nucleotides to generate a third sequencing read, wherein the reversible terminator is removed prior to the introduction of the next complementary nucleotide; contacting a fourth population of polynucleotides annealed to a fourth sequencing primer with a fourth sequencing solution including a plurality of modified nucleotides including a reversible terminator and monitoring the sequential incorporation of complementary nucleotides to generate a fourth sequencing read, wherein the reversible terminator is removed prior to the introduction of the next complementary nucleotide, contacting a fifth population of polynucleotides annealed to a fifth sequencing primer with a fifth sequencing solution including a plurality of modified nucleotides including a reversible terminator and monitoring the sequential incorporation of complementary nucleotides to generate a fifth sequencing read, wherein the reversible terminator is removed prior to the introduction of the next complementary nucleotide, contacting a sixth population of polynucleotides annealed to a sixth sequencing primer with a sixth sequencing solution including a plurality of modified nucleotides including a reversible terminator and monitoring the sequential incorporation of complementary nucleotides to generate a sixth sequencing read, wherein the reversible terminator is removed prior to the introduction of the next complementary nucleotide, contacting a seventh population of polynucleotides annealed to a seventh sequencing primer with a seventh sequencing solution including a plurality of modified nucleotides including a reversible terminator and monitoring the sequential incorporation of complementary nucleotides to generate a seventh sequencing read, wherein the reversible terminator is removed prior to the introduction of the next complementary nucleotide, contacting an eighth population of polynucleotides annealed to an eighth sequencing primer with an eighth sequencing solution including a plurality of modified nucleotides including a reversible terminator and monitoring the sequential incorporation of complementary nucleotides to generate an eighth sequencing read, wherein the reversible terminator is removed prior to the introduction of the next complementary nucleotide, contacting a ninth population of polynucleotides annealed to a ninth sequencing primer with a ninth sequencing solution including a plurality of modified nucleotides including a reversible terminator and monitoring the sequential incorporation of complementary nucleotides to generate a ninth sequencing read, wherein the reversible terminator is removed prior to the introduction of the next complementary nucleotide, contacting a tenth population of polynucleotides annealed to a tenth sequencing primer with a tenth sequencing solution including a plurality of modified nucleotides including a reversible terminator and monitoring the sequential incorporation of complementary nucleotides to generate a tenth sequencing read, wherein the reversible terminator is removed prior to the introduction of the next complementary nucleotide, contacting an eleventh population of polynucleotides annealed to an eleventh sequencing primer with an eleventh sequencing solution including a plurality of modified nucleotides including a reversible terminator and monitoring the sequential incorporation of complementary nucleotides to generate an eleventh sequencing read, wherein the reversible terminator is removed prior to the introduction of the next complementary nucleotide, contacting a twelfth population of polynucleotides annealed to a twelfth sequencing primer with a twelfth sequencing solution including a plurality of modified nucleotides including a reversible terminator and monitoring the sequential incorporation of complementary nucleotides to generate a twelfth sequencing read, wherein the reversible terminator is removed prior to the introduction of the next complementary nucleotide; wherein the first sequencing primer, second sequencing primer, third sequencing primer, fourth sequencing primer, fifth sequencing primer, sixth sequencing primer, seventh sequencing primer, eighth sequencing primer, ninth sequencing primer, tenth sequencing primer, eleventh sequencing primer, and twelfth sequencing primer are different.

In embodiments, the method includes sequencing a plurality of different populations of polynucleotides within overlapping optically resolvable features.

In embodiments, the first population of polynucleotides, the second population of polynucleotides, and the third population of polynucleotides are not substantially complementary. In embodiments, the first population of polynucleotides, the second population of polynucleotides, the third population of polynucleotides, the fourth population of polynucleotides, the fifth population of polynucleotides, and the sixth population of polynucleotides are not substantially complementary. In embodiments, the first population of polynucleotides, the second population of polynucleotides, the third population of polynucleotides, the fourth population of polynucleotides, the fifth population of polynucleotides, the sixth population of polynucleotides, the seventh population of polynucleotides, the eighth population of polynucleotides, and the ninth population of polynucleotides are not substantially complementary. In embodiments, the first population of polynucleotides, the second population of polynucleotides, the third population of polynucleotides, the fourth population of polynucleotides, the fifth population of polynucleotides, the sixth population of polynucleotides, the seventh population of polynucleotides, the eighth population of polynucleotides, the ninth population of polynucleotides, the tenth population of polynucleotides, the eleventh population of polynucleotides, and the twelfth population of polynucleotides are not substantially complementary.

In embodiments, the first population of polynucleotides and the second population of polynucleotides are not substantially complementary. In embodiments, the first population of polynucleotides, the second population of polynucleotides, the third population of polynucleotides, and the fourth population of polynucleotides are not substantially complementary. In embodiments, the first population of polynucleotides, the second population of polynucleotides, the third population of polynucleotides, the fourth population of polynucleotides, the fifth population of polynucleotides, the sixth population of polynucleotides, the seventh population of polynucleotides, and the eighth population of polynucleotides are not substantially complementary. In embodiments, the first population of polynucleotides, the second population of polynucleotides, the third population of polynucleotides, the fourth population of polynucleotides, the fifth population of polynucleotides, the sixth population of polynucleotides, the seventh population of polynucleotides, the eighth population of polynucleotides, the ninth population of polynucleotides, the tenth population of polynucleotides, the eleventh population of polynucleotides, and the twelfth population of polynucleotides are not substantially complementary.

In an aspect is provided a method of sequencing a plurality of different polynucleotides within overlapping optically resolvable features. In embodiments, the method includes: repeatedly contacting a first polynucleotide annealed to a first sequencing primer with a sequencing solution including one or more modified nucleotides including a reversible terminator, and monitoring the sequential incorporation of complementary nucleotides to generate a first sequencing read, wherein the reversible terminator is removed prior to the introduction of the next complementary nucleotide; repeatedly contacting a second polynucleotide annealed to a second sequencing primer with a sequencing solution including one or more modified nucleotides including a reversible terminator, and monitoring the sequential incorporation of complementary nucleotides to generate a second sequencing read, wherein the reversible terminator is removed prior to the introduction of the next complementary nucleotide; repeatedly contacting a third polynucleotide annealed to a third sequencing primer with a sequencing solution including one or more modified nucleotides including a reversible terminator, and monitoring the sequential incorporation of complementary nucleotides to generate a third sequencing read, wherein the reversible terminator is removed prior to the introduction of the next complementary nucleotide; wherein the first polynucleotide, the second polynucleotide, and the third polynucleotide are different. In embodiments, the first polynucleotide, the second polynucleotide, and the third polynucleotide are not substantially complementary.

In an aspect is provided a method of sequencing a plurality of template polynucleotides on a solid support, the method including: (a) amplifying a first template polynucleotide including a first adapter sequence and a second adapter sequence, and amplifying a second template polynucleotide including a third adapter sequence and a fourth adapter sequence to generate a plurality of overlapping amplification clusters on the solid support, wherein the first adapter sequence includes a first platform primer binding sequence and a first sequencing primer binding sequence; the second adapter sequence includes a second platform primer binding sequence and a second sequencing primer binding sequence; the third adapter sequence includes the first platform primer binding sequence and a third sequencing primer binding sequence; the fourth adapter sequence includes the second platform primer binding sequence and a fourth sequencing primer binding sequence; (b) sequentially sequencing the overlapping amplification clusters by i) hybridizing a first sequencing primer to the first sequencing primer binding sequence and generating a first sequencing read; ii) hybridizing a second sequencing primer to the second sequencing primer binding sequence and generating a second sequencing read; iii) hybridizing a third sequencing primer to the third sequencing primer binding sequence and generating a third sequencing read; iv) hybridizing a fourth sequencing primer to the fourth sequencing primer binding sequence and generating a fourth sequencing read. In embodiments, sequentially refers to a consecutive order, occurring in time. In embodiments, amplifying includes hybridizing the first template polynucleotide to a first immobilized oligonucleotide and hybridizing the second template polynucleotide to a second immobilized oligonucleotide and extending the first and second immobilized oligonucleotide to form a plurality of first amplification products and plurality of second amplification products. In embodiments, amplifying the first template polynucleotide and the second template polynucleotide occurs simultaneously.

In embodiments, sequentially sequencing the overlapping amplification clusters includes: i) hybridizing a first sequencing primer to the first sequencing primer binding sequence and generating a first sequencing read; and ii) hybridizing a second sequencing primer to the third sequencing primer binding sequence and generating a second sequencing read. In embodiments, sequentially sequencing the overlapping amplification clusters includes: i) hybridizing a first sequencing primer to the second sequencing primer binding sequence and generating a first sequencing read; and ii) hybridizing a second sequencing primer to the fourth sequencing primer binding sequence and generating a second sequencing read.

In an aspect is provided a method of sequencing a plurality of template polynucleotides on a solid support, the method including: (a) amplifying a first template polynucleotide including a first adapter sequence and a second adapter sequence, amplifying a second template polynucleotide including a third adapter sequence and a fourth adapter sequence, amplifying a third template polynucleotide including a fifth adapter sequence and a sixth adapter sequence, and amplifying a fourth template polynucleotide including a seventh adapter sequence and an eighth adapter sequence to generate a plurality of overlapping amplification clusters on the solid support, wherein the first adapter sequence includes a first platform primer binding sequence and a first sequencing primer binding sequence; the second adapter sequence includes a second platform primer binding sequence and a second sequencing primer binding sequence; the third adapter sequence includes the first platform primer binding sequence and a third sequencing primer binding sequence; the fourth adapter sequence includes the second platform primer binding sequence and a fourth sequencing primer binding sequence; the fifth adapter sequence includes a third platform primer binding sequence and a fifth sequencing primer binding sequence; the sixth adapter sequence includes a fourth platform primer binding sequence and a sixth sequencing primer binding sequence; the seventh adapter sequence includes the third platform primer binding sequence and a seventh sequencing primer binding sequence; and the eighth adapter sequence includes the fourth platform primer binding sequence and an eighth sequencing primer binding sequence; (b) sequentially sequencing the overlapping amplification clusters by i) hybridizing a first sequencing primer to the first sequencing primer binding sequence and generating a first sequencing read; ii) hybridizing a second sequencing primer to the second sequencing primer binding sequence and generating a second sequencing read; iii) hybridizing a third sequencing primer to the third sequencing primer binding sequence and generating a third sequencing read; iv) hybridizing a fourth sequencing primer to the fourth sequencing primer binding sequence and generating a fourth sequencing read; v) hybridizing a fifth sequencing primer to the fifth sequencing primer binding sequence and generating a fifth sequencing read; vi) hybridizing a sixth sequencing primer to the sixth sequencing primer binding sequence and generating a sixth sequencing read; vii) hybridizing a seventh sequencing primer to the seventh sequencing primer binding sequence and generating a seventh sequencing read; and viii) hybridizing an eighth sequencing primer to the eighth sequencing primer binding sequence and generating an eighth sequencing read.

In embodiments, sequentially sequencing the overlapping amplification clusters includes: i) hybridizing a first sequencing primer to the first sequencing primer binding sequence and generating a first sequencing read; ii) hybridizing a second sequencing primer to the third sequencing primer binding sequence and generating a second sequencing read; iii) hybridizing a third sequencing primer to the fifth sequencing primer binding sequence and generating a third sequencing read; and iv) hybridizing a fourth sequencing primer to the seventh sequencing primer binding sequence and generating a fourth sequencing read. In embodiments, sequentially sequencing the overlapping amplification clusters includes: i) hybridizing a first sequencing primer to the second sequencing primer binding sequence and generating a first sequencing read; ii) hybridizing a second sequencing primer to the fourth sequencing primer binding sequence and generating a second sequencing read; iii) hybridizing a third sequencing primer to the sixth sequencing primer binding sequence and generating a third sequencing read; and iv) hybridizing a fourth sequencing primer to the eighth sequencing primer binding sequence and generating a fourth sequencing read.

In an aspect is provided a method of sequencing a plurality of template polynucleotides on a solid support, the method including: (a) amplifying a first template polynucleotide including a first adapter sequence and a second adapter sequence, amplifying a second template polynucleotide including a third adapter sequence and a fourth adapter sequence, amplifying a third template polynucleotide including a fifth adapter sequence and a sixth adapter sequence, amplifying a fourth template polynucleotide including a seventh adapter sequence and an eighth adapter sequence, amplifying a fifth template polynucleotide including a ninth adapter sequence and a tenth adapter sequence, and amplifying a sixth template polynucleotide including an eleventh adapter sequence and a twelfth adapter sequence to generate a plurality of overlapping amplification clusters on the solid support, wherein the first adapter sequence includes a first platform primer binding sequence and a first sequencing primer binding sequence; the second adapter sequence includes a second platform primer binding sequence and a second sequencing primer binding sequence; the third adapter sequence includes the first platform primer binding sequence and a third sequencing primer binding sequence; the fourth adapter sequence includes the second platform primer binding sequence and a fourth sequencing primer binding sequence; the fifth adapter sequence includes a third platform primer binding sequence and a fifth sequencing primer binding sequence; the sixth adapter sequence includes a fourth platform primer binding sequence and a sixth sequencing primer binding sequence; the seventh adapter sequence includes the third platform primer binding sequence and a seventh sequencing primer binding sequence; the eighth adapter sequence includes the fourth platform primer binding sequence and an eighth sequencing primer binding sequence; the ninth adapter sequence includes a fifth platform primer binding sequence and a ninth sequencing primer binding sequence; the tenth adapter sequence includes a sixth platform primer binding sequence and a tenth sequencing primer binding sequence; the eleventh adapter sequence includes the fifth platform primer binding sequence and an eleventh sequencing primer binding sequence; and the twelfth adapter sequence includes the sixth platform primer binding sequence and a twelfth sequencing primer binding sequence (b) sequentially sequencing the overlapping amplification clusters by i) hybridizing a first sequencing primer to the first sequencing primer binding sequence and generating a first sequencing read; ii) hybridizing a second sequencing primer to the second sequencing primer binding sequence and generating a second sequencing read; iii) hybridizing a third sequencing primer to the third sequencing primer binding sequence and generating a third sequencing read; iv) hybridizing a fourth sequencing primer to the fourth sequencing primer binding sequence and generating a fourth sequencing read; v) hybridizing a fifth sequencing primer to the fifth sequencing primer binding sequence and generating a fifth sequencing read; vi) hybridizing a sixth sequencing primer to the sixth sequencing primer binding sequence and generating a sixth sequencing read; vii) hybridizing a seventh sequencing primer to the seventh sequencing primer binding sequence and generating a seventh sequencing read; viii) hybridizing an eighth sequencing primer to the eighth sequencing primer binding sequence and generating an eighth sequencing read; ix) hybridizing a ninth sequencing primer to the ninth sequencing primer binding sequence and generating a ninth sequencing read; x) hybridizing a tenth sequencing primer to the tenth sequencing primer binding sequence and generating a tenth sequencing read; xi) hybridizing an eleventh sequencing primer to the eleventh sequencing primer binding sequence and generating an eleventh sequencing read; and xii) hybridizing a twelfth sequencing primer to the twelfth sequencing primer binding sequence and generating a twelfth sequencing read.

In embodiments, sequentially sequencing the overlapping amplification clusters includes: i) hybridizing a first sequencing primer to the first sequencing primer binding sequence and generating a first sequencing read; ii) hybridizing a second sequencing primer to the third sequencing primer binding sequence and generating a second sequencing read; iii) hybridizing a third sequencing primer to the fifth sequencing primer binding sequence and generating a third sequencing read; iv) hybridizing a fourth sequencing primer to the seventh sequencing primer binding sequence and generating a fourth sequencing read; v) hybridizing a fifth sequencing primer to the ninth sequencing primer binding sequence and generating a fifth sequencing read; and vi) hybridizing a sixth sequencing primer to the eleventh sequencing primer binding sequence and generating a sixth sequencing read. In embodiments, sequentially sequencing the overlapping amplification clusters includes: i) hybridizing a first sequencing primer to the second sequencing primer binding sequence and generating a first sequencing read; ii) hybridizing a second sequencing primer to the fourth sequencing primer binding sequence and generating a second sequencing read; iii) hybridizing a third sequencing primer to the sixth sequencing primer binding sequence and generating a third sequencing read; iv) hybridizing a fourth sequencing primer to the eighth sequencing primer binding sequence and generating a fourth sequencing read; v) hybridizing a fifth sequencing primer to the tenth sequencing primer binding sequence and generating a fifth sequencing read; and vi) hybridizing a sixth sequencing primer to the twelfth sequencing primer binding sequence and generating a sixth sequencing read.

In embodiments, amplifying the first template polynucleotide and the second template polynucleotide occurs simultaneously. In embodiments, amplifying the first template polynucleotide, the second template polynucleotide, the third template polynucleotide, and the fourth template polynucleotide occurs simultaneously. In embodiments, amplifying the first template polynucleotide, the second template polynucleotide, the third template polynucleotide, the fourth template polynucleotide, the fifth template polynucleotide, and the sixth template polynucleotide occurs simultaneously.

In an aspect is provided a method of amplifying a plurality of template polynucleotides, the method including: (a) contacting a solid support with a first template polynucleotide including a first adapter sequence thereby forming a first complex attached to the solid support and contacting the solid support with a second template polynucleotide including a second adapter sequence thereby forming a second complex attached to the solid support, wherein: the first adapter sequence includes a first platform primer binding sequence complementary to a first amplification primer (e.g., a platform primer), and a first sequencing primer binding sequence, and the second adapter sequence includes the first platform primer binding sequence and a second sequencing primer binding sequence; the first complex includes a first amplification primer attached to the solid support hybridized to the first adapter sequence; and the second complex includes a second amplification primer attached to the solid support hybridized to the second adapter sequence, wherein the first and second amplification primer comprise the same sequence; and the first sequencing primer binding sequence is different from the second sequencing primer binding sequence; (b) amplifying the first template polynucleotide and the second template polynucleotide to form a plurality of first amplification products and plurality of second amplification products that form overlapping amplification clusters on the solid support.

In an aspect is provided a method of amplifying a plurality of template polynucleotides, the method including: (a) contacting a solid support with a first template polynucleotide including a first adapter sequence thereby forming a first complex attached to the solid support and contacting the solid support with a second template polynucleotide including a second adapter sequence thereby forming a second complex attached to the solid support, wherein: the first adapter sequence includes a first platform primer binding sequence complementary to a first amplification primer, and a first sequencing primer binding sequence, and the second adapter sequence includes the first platform primer binding sequence and a second sequencing primer binding sequence; the first complex includes a first amplification primer attached to the solid support hybridized to the first adapter sequence; and the second complex includes a second amplification primer attached to the solid support hybridized to the second adapter sequence, wherein the first and second amplification primer include the same sequence; and the first sequencing primer binding sequence is different from the second sequencing primer binding sequence; (b) amplifying the first template polynucleotide and the second template polynucleotide to form a plurality of first amplification products and plurality of second amplification products that form overlapping amplification clusters on the solid support.

In an aspect is provided a method of amplifying a plurality of template polynucleotides, the method including: (a) contacting a solid support with a first template polynucleotide including a first adapter sequence thereby forming a first complex attached to the solid support, contacting the solid support with a second template polynucleotide including a second adapter sequence thereby forming a second complex attached to the solid support, contacting the solid support with a third template polynucleotide including a third adapter sequence thereby forming a third complex attached to the solid support, contacting the solid support with a fourth template polynucleotide including a fourth adapter sequence thereby forming a fourth complex attached to the solid support, wherein: the first adapter sequence includes a first platform primer binding sequence complementary to a first amplification primer, and a first sequencing primer binding sequence, the second adapter sequence includes the first platform primer binding sequence and a second sequencing primer binding sequence, the third adapter sequence includes a second platform primer binding sequence complementary to a second amplification primer, and a third sequencing primer binding sequence, and the fourth adapter sequence includes the second platform primer binding sequence and a fourth sequencing primer binding sequence; the first complex includes a first amplification primer attached to the solid support hybridized to the first adapter sequence; the second complex includes a second amplification primer attached to the solid support hybridized to the second adapter sequence, wherein the first and second amplification primer include the same sequence; the third complex includes a third amplification primer attached to the solid support hybridized to the third adapter sequence; the fourth complex includes a fourth amplification primer attached to the solid support hybridized to the fourth adapter sequence, wherein the third and fourth amplification primer include the same sequence; and the first sequencing primer binding sequence, second sequencing primer binding sequence, third sequencing primer binding sequence, and fourth sequencing primer binding sequence are different from each other; (b) amplifying the first template polynucleotide, the second template polynucleotide, the third template polynucleotide, and the fourth template polynucleotide to form a plurality of first amplification products, plurality of second amplification products, plurality of third amplification products, and plurality of fourth amplification products that form overlapping amplification clusters on the solid support.

In an aspect is provided a method of amplifying a plurality of template polynucleotides, the method including: (a) contacting a solid support with a first template polynucleotide including a first adapter sequence thereby forming a first complex attached to the solid support, contacting the solid support with a second template polynucleotide including a second adapter sequence thereby forming a second complex attached to the solid support, contacting the solid support with a third template polynucleotide including a third adapter sequence thereby forming a third complex attached to the solid support, contacting the solid support with a fourth template polynucleotide including a fourth adapter sequence thereby forming a fourth complex attached to the solid support, contacting the solid support with a fifth template polynucleotide including a fifth adapter sequence thereby forming a fifth complex attached to the solid support, contacting the solid support with a sixth template polynucleotide including a sixth adapter sequence thereby forming a sixth complex attached to the solid support, contacting the solid support with a seventh template polynucleotide including a seventh adapter sequence thereby forming a seventh complex attached to the solid support, contacting the solid support with an eighth template polynucleotide including an eighth adapter sequence thereby forming an eighth complex attached to the solid support, wherein: the first adapter sequence includes a first platform primer binding sequence complementary to a first amplification primer, and a first sequencing primer binding sequence, the second adapter sequence includes the first platform primer binding sequence and a second sequencing primer binding sequence, the third adapter sequence includes a second platform primer binding sequence complementary to a second amplification primer, and a third sequencing primer binding sequence, the fourth adapter sequence includes the second platform primer binding sequence and a fourth sequencing primer binding sequence, the fifth adapter sequence includes a third platform primer binding sequence complementary to a third amplification primer, and a fifth sequencing primer binding sequence, the sixth adapter sequence includes the third platform primer binding sequence and a sixth sequencing primer binding sequence, the seventh adapter sequence includes a fourth platform primer binding sequence complementary to a fourth amplification primer, and a seventh sequencing primer binding sequence, and the eighth adapter sequence includes the fourth platform primer binding sequence and an eighth sequencing primer binding sequence; the first complex includes a first amplification primer attached to the solid support hybridized to the first adapter sequence; the second complex includes a second amplification primer attached to the solid support hybridized to the second adapter sequence, wherein the first and second amplification primer include the same sequence; the third complex includes a third amplification primer attached to the solid support hybridized to the third adapter sequence; the fourth complex includes a fourth amplification primer attached to the solid support hybridized to the fourth adapter sequence, wherein the third and fourth amplification primer include the same sequence; the fifth complex includes a fifth amplification primer attached to the solid support hybridized to the fifth adapter sequence; the sixth complex includes a sixth amplification primer attached to the solid support hybridized to the sixth adapter sequence, wherein the fifth and sixth amplification primer include the same sequence; the seventh complex includes a seventh amplification primer attached to the solid support hybridized to the seventh adapter sequence; the eighth complex includes an eighth amplification primer attached to the solid support hybridized to the eighth adapter sequence, wherein the seventh and eighth amplification primer include the same sequence; and the first sequencing primer binding sequence, second sequencing primer binding sequence, third sequencing primer binding sequence, fourth sequencing primer binding sequence, fifth sequencing primer binding sequence, sixth sequencing primer binding sequence, seventh sequencing primer binding sequence, and eighth sequencing primer binding sequence are different from each other; (b) amplifying the first template polynucleotide, the second template polynucleotide, the third template polynucleotide, the fourth template polynucleotide, the fifth template polynucleotide, the sixth template polynucleotide, the seventh template polynucleotide, and the eighth template polynucleotide to form a plurality of first amplification products, plurality of second amplification products, plurality of third amplification products, plurality of fourth amplification products, plurality of fifth amplification products, plurality of sixth amplification products, plurality of seventh amplification products, and plurality of eighth amplification products that form overlapping amplification clusters on the solid support.

In an aspect is provided a method of amplifying a plurality of template polynucleotides, the method including: (a) contacting a solid support with a first template polynucleotide including a first adapter sequence thereby forming a first complex attached to the solid support, contacting the solid support with a second template polynucleotide including a second adapter sequence thereby forming a second complex attached to the solid support, contacting the solid support with a third template polynucleotide including a third adapter sequence thereby forming a third complex attached to the solid support, contacting the solid support with a fourth template polynucleotide including a fourth adapter sequence thereby forming a fourth complex attached to the solid support, contacting the solid support with a fifth template polynucleotide including a fifth adapter sequence thereby forming a fifth complex attached to the solid support, contacting the solid support with a sixth template polynucleotide including a sixth adapter sequence thereby forming a sixth complex attached to the solid support, contacting the solid support with a seventh template polynucleotide including a seventh adapter sequence thereby forming a seventh complex attached to the solid support, contacting the solid support with an eighth template polynucleotide including an eighth adapter sequence thereby forming an eighth complex attached to the solid support, contacting the solid support with a ninth template polynucleotide including a ninth adapter sequence thereby forming a ninth complex attached to the solid support, contacting the solid support with a tenth template polynucleotide including a tenth adapter sequence thereby forming a tenth complex attached to the solid support, contacting the solid support with an eleventh template polynucleotide including an eleventh adapter sequence thereby forming an eleventh complex attached to the solid support, contacting the solid support with a twelfth template polynucleotide including a twelfth adapter sequence thereby forming a twelfth complex attached to the solid support, wherein: the first adapter sequence includes a first platform primer binding sequence complementary to a first amplification primer, and a first sequencing primer binding sequence, the second adapter sequence includes the first platform primer binding sequence and a second sequencing primer binding sequence, the third adapter sequence includes a second platform primer binding sequence complementary to a second amplification primer, and a third sequencing primer binding sequence, the fourth adapter sequence includes the second platform primer binding sequence and a fourth sequencing primer binding sequence, the fifth adapter sequence includes a third platform primer binding sequence complementary to a third amplification primer, and a fifth sequencing primer binding sequence, the sixth adapter sequence includes the third platform primer binding sequence and a sixth sequencing primer binding sequence, the seventh adapter sequence includes a fourth platform primer binding sequence complementary to a fourth amplification primer, and a seventh sequencing primer binding sequence, the eighth adapter sequence includes the fourth platform primer binding sequence and an eighth sequencing primer binding sequence, the ninth adapter sequence includes a fifth platform primer binding sequence complementary to a fifth amplification primer, and a ninth sequencing primer binding sequence, the tenth adapter sequence includes the fifth platform primer binding sequence and a ninth sequencing primer binding sequence; the eleventh adapter sequence includes a sixth platform primer binding sequence complementary to a sixth amplification primer, and an eleventh sequencing primer binding sequence, and the twelfth adapter sequence includes the sixth platform primer binding sequence and a twelfth sequencing primer binding sequence; the first complex includes a first amplification primer attached to the solid support hybridized to the first adapter sequence; the second complex includes a second amplification primer attached to the solid support hybridized to the second adapter sequence, wherein the first and second amplification primer include the same sequence; the third complex includes a third amplification primer attached to the solid support hybridized to the third adapter sequence; the fourth complex includes a fourth amplification primer attached to the solid support hybridized to the fourth adapter sequence, wherein the third and fourth amplification primer include the same sequence; the fifth complex includes a fifth amplification primer attached to the solid support hybridized to the fifth adapter sequence; the sixth complex includes a sixth amplification primer attached to the solid support hybridized to the sixth adapter sequence, wherein the fifth and sixth amplification primer include the same sequence; the seventh complex includes a seventh amplification primer attached to the solid support hybridized to the seventh adapter sequence; the eighth complex includes an eighth amplification primer attached to the solid support hybridized to the eighth adapter sequence, wherein the seventh and eighth amplification primer include the same sequence; the ninth complex includes a ninth amplification primer attached to the solid support hybridized to the ninth adapter sequence; the tenth complex includes a tenth amplification primer attached to the solid support hybridized to the tenth adapter sequence, wherein the ninth and tenth amplification primer include the same sequence; the eleventh complex includes an eleventh amplification primer attached to the solid support hybridized to the eleventh adapter sequence; and the twelfth complex includes a twelfth amplification primer attached to the solid support hybridized to the twelfth adapter sequence, wherein the eleventh and twelfth amplification primer include the same sequence; and the first sequencing primer binding sequence, second sequencing primer binding sequence, third sequencing primer binding sequence, fourth sequencing primer binding sequence, fifth sequencing primer binding sequence, sixth sequencing primer binding sequence, seventh sequencing primer binding sequence, eighth sequencing primer binding sequence, ninth sequencing primer binding sequence, tenth sequencing primer binding sequence, eleventh sequencing primer binding sequence, and twelfth sequencing primer binding sequence are different from each other; (b) amplifying the first template polynucleotide, the second template polynucleotide, the third template polynucleotide, the fourth template polynucleotide, the fifth template polynucleotide, the sixth template polynucleotide, the seventh template polynucleotide, the eighth template polynucleotide, the ninth template polynucleotide, the tenth template polynucleotide, the eleventh template polynucleotide, and the twelfth template polynucleotide to form a plurality of first amplification products, plurality of second amplification products, plurality of third amplification products, plurality of fourth amplification products, plurality of fifth amplification products, plurality of sixth amplification products, plurality of seventh amplification products, plurality of eighth amplification products, plurality of ninth amplification products, plurality of tenth amplification products, plurality of eleventh amplification products, and plurality of twelfth amplification products that form overlapping amplification clusters on the solid support.

In embodiments, the method further includes sequentially sequencing the first and second amplification products, the sequencing including: (i) hybridizing and extending a first sequencing primer to the first amplification product, incorporating one or more modified nucleotides into the sequencing primer with a polymerase to create an extension strand, and detecting the one or more incorporated nucleotides so as to identify each incorporated nucleotide in the extension strand, thereby generating a first sequencing read; and (ii) hybridizing and extending a second sequencing primer to the second amplification product, incorporating one or more modified nucleotides into the sequencing primer with a polymerase to create an extension strand, and detecting the one or more incorporated nucleotides so as to identify each incorporated nucleotide in the extension strand, thereby generating a second sequencing read.

In embodiments, the method further includes sequentially sequencing the first and second amplification products, the sequencing including: (i) hybridizing and extending a first sequencing primer to the first amplification product, incorporating one or more modified nucleotides into the sequencing primer with a polymerase to create an extension strand, and detecting the one or more incorporated nucleotides so as to identify each incorporated nucleotide in the extension strand, thereby generating a first sequencing read; and (ii) hybridizing and extending a second sequencing primer to the second amplification product, incorporating one or more modified nucleotides into the sequencing primer with a polymerase to create an extension strand, and detecting the one or more incorporated nucleotides so as to identify each incorporated nucleotide in the extension strand, thereby generating a second sequencing read.

In embodiments, the method further includes sequentially sequencing the first and second amplification products, the sequencing including: hybridizing a first sequencing primer to the first amplification product and contacting the sequencing primer with a sequencing solution including one or more modified nucleotides including a reversible terminator, and monitoring the sequential incorporation of complementary nucleotides in a first optically resolvable feature, wherein the reversible terminator is removed prior to the introduction of the next complementary nucleotide; and hybridizing a second sequencing primer to the second amplification product and contacting the sequencing primer with a sequencing solution including one or more modified nucleotides including a reversible terminator, and monitoring the sequential incorporation of complementary nucleotides in a second optically resolvable feature, wherein the reversible terminator is removed prior to the introduction of the next complementary nucleotide; wherein the first and second optically resolvable features overlap.

In embodiments, the method further includes contacting the solid support with a third template polynucleotide including a third adapter sequence thereby forming a third complex attached to the solid support and contacting the solid support with a fourth template polynucleotide including a fourth adapter sequence thereby forming a fourth complex attached to the solid support, wherein (i) the third adapter sequence includes the first platform primer binding sequence and a third sequencing primer binding sequence; (ii) the fourth adapter sequence includes the second platform primer binding sequence and a fourth sequencing primer binding sequence; and amplifying the third template polynucleotide and the fourth template polynucleotide to form a plurality of third amplification products and plurality of fourth amplification products that form overlapping amplification clusters on the solid support.

In embodiments, the method further includes sequentially sequencing the third and fourth amplification products, the sequencing including: (i) hybridizing and extending a third sequencing primer to the third amplification product, incorporating one or more modified nucleotides into the sequencing primer with a polymerase to create an extension strand, and detecting the one or more incorporated nucleotides so as to identify each incorporated nucleotide in the extension strand, thereby generating a third sequencing read; and (ii) hybridizing and extending a fourth sequencing primer to the fourth amplification product, incorporating one or more modified nucleotides into the sequencing primer with a polymerase to create an extension strand, and detecting the one or more incorporated nucleotides so as to identify each incorporated nucleotide in the extension strand, thereby generating a fourth sequencing read.

In embodiments, the method further includes sequentially sequencing the third and fourth amplification products, the sequencing including: hybridizing a third sequencing primer to the third amplification product and contacting the sequencing primer with a sequencing solution comprising one or more modified nucleotides including a reversible terminator, and monitoring the sequential incorporation of complementary nucleotides in a third optically resolvable feature wherein the reversible terminator is removed prior to the introduction of the next complementary nucleotide; and hybridizing a fourth sequencing primer to the fourth amplification product and contacting the sequencing primer with a sequencing solution including one or more modified nucleotides including a reversible terminator, and monitoring the sequential incorporation of complementary nucleotides in a fourth optically resolvable feature, wherein the reversible terminator is removed prior to the introduction of the next complementary nucleotide; wherein the third and fourth optically resolvable features overlap. In embodiments, the first, second, third, and fourth optically resolvable features overlap.

In an aspect is provided a method of sequencing a plurality of template polynucleotides on a solid support, the method including: (a) amplifying a first template polynucleotide including a first adapter sequence and a second adapter sequence and a second template polynucleotide including a third adapter sequence and a fourth adapter sequence to generate a plurality of amplification clusters on a solid support, wherein the first adapter sequence includes a first platform primer binding sequence and a first sequencing primer binding sequence; the second adapter sequence includes a second platform primer binding sequence and a second sequencing primer binding sequence; the third adapter sequence includes the first platform primer binding sequence and a third sequencing primer binding sequence; the fourth adapter sequence includes the second platform primer binding sequence and a fourth sequencing primer binding sequence; (b) sequentially sequencing the amplification clusters by i) hybridizing a first sequencing primer to the first sequencing primer binding sequence and generating a first sequencing read; ii) hybridizing a second sequencing primer to the second sequencing primer binding sequence and generating a second sequencing read; iii) hybridizing a third sequencing primer to the third sequencing primer binding sequence and generating a third sequencing read; iv) hybridizing a fourth sequencing primer to the fourth sequencing primer binding sequence and generating a fourth sequencing read.

In an aspect is provided a method for amplifying polynucleotides, the method including: contacting a solid support with a first population of polynucleotides including a first sequencing primer binding sequence thereby forming a first complex, and contacting the solid support with a second population of polynucleotides including a second sequencing primer binding sequence thereby forming a second complex, wherein the first complex including a first polynucleotide including the first sequencing primer binding sequence hybridized to a first oligonucleotide attached to the solid support and wherein the second complex includes a second polynucleotide including the second sequencing primer binding sequence hybridized to a second oligonucleotide attached to the solid support; and contacting the first complex with a polymerase and extending the first oligonucleotide thereby forming a plurality of first amplification products and contacting the second complex with the polymerase and extending the second oligonucleotide thereby forming a plurality of second amplification products.

In embodiments, the first population of polynucleotides includes the same sequencing primer binding sequence but different sequences overall. In embodiments, the first population of polynucleotides includes the same sequencing primer binding sequence and the same sequences overall. In embodiments, the second population of polynucleotides includes the same sequencing primer binding sequence but different sequences overall. In embodiments, the second population of polynucleotides includes the same sequencing primer binding sequence and the same sequences overall.

In embodiments, the first and second oligonucleotides are different.

In embodiments, the solid support further includes a first plurality of oligonucleotides including the first oligonucleotide attached to the solid support and a second plurality of oligonucleotides including the second oligonucleotide attached to the solid support. In embodiments, the first plurality of oligonucleotides includes the same sequence.

In embodiments, the second plurality of oligonucleotides includes the same sequence.

In embodiments, the first population of polynucleotides and the second population of polynucleotides are each single-stranded prior to forming the first complex and second complex.

In embodiments, the method includes contacting a solid support with 3, 4, 5, 6, 7, 8, 9, 10, 11, or 12 different populations of polynucleotides wherein each of the different populations have a different sequencing primer binding sequence relative to each different population, and each of the different populations have a common sequencing primer binding sequence within each population.

In embodiments, the first population of polynucleotides each further include a first platform primer binding sequence complementary to the first plurality of oligonucleotides attached to the solid support and the second population of polynucleotides each further include the second platform primer binding sequence complementary to the second plurality of oligonucleotides attached to the solid support.

In embodiments, the polynucleotides of the first population of polynucleotides each include a first sequencing primer binding sequence and a third sequencing primer binding sequence. In embodiments, the polynucleotides of the second population of polynucleotides each include a second sequencing primer binding sequence and a fourth sequencing primer binding sequence.

In embodiments, contacting the first complex and the second complex with the polymerase includes bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, emulsion PCR, or combinations thereof. In embodiments, contacting the first complex and the second complex with the polymerase includes bridge polymerase chain reaction (bPCR) amplification, solid-phase rolling circle amplification (RCA), or solid-phase exponential rolling circle amplification (eRCA).

In embodiments, the method further includes sequencing the plurality of first amplification products or complements thereof and sequencing the plurality of second amplification products or complements thereof. In embodiments, sequencing includes a sequencing-by-synthesis or sequencing-by-binding process. In embodiments, sequencing includes hybridizing a first sequencing primer to the plurality of first amplification products and a second sequencing primer to the plurality of second amplification products, or complements thereof, and contacting the first sequencing primer and the second sequencing primer with a sequencing solution including one or more modified nucleotides including a reversible terminator, and monitoring the sequential incorporation of complementary nucleotides to generate one or more sequencing reads, wherein the reversible terminator is removed prior to the introduction of the next complementary nucleotide. In embodiments, sequencing includes hybridizing a first sequencing primer to the plurality of first amplification products and a second sequencing primer to the plurality of second amplification products, or complements thereof, incorporating one or more modified nucleotides including a reversible terminator into the first sequencing primer with the polymerase to create a first extension strand and incorporating one or more modified nucleotides including a reversible terminator into the second sequencing primer with the polymerase to create a second extension strand, and detecting the one or more incorporated nucleotides so as to identify each incorporated nucleotide in the extension strand, thereby generating one or more sequencing reads, wherein the reversible terminator is removed prior to the introduction of the next complementary nucleotide.

In embodiments, the reversible terminators are removed sequentially. In embodiments, the reversible terminators are removed in parallel.

In embodiments, sequencing includes hybridizing a first sequencing primer to the plurality of first amplification products and a second sequencing primer to the plurality of second amplification products, or complements thereof, incorporating one or more modified nucleotides into the first sequencing primer with the polymerase to create a first extension strand and detecting the one or more incorporated nucleotides in a first optically resolvable feature; and incorporating one or more modified nucleotides into the second sequencing primer with the polymerase to create a second extension strand, and detecting the one or more incorporated nucleotides in a second optically resolvable feature; wherein the first and second optically resolvable features overlap. In embodiments, the method further includes incorporating a dideoxy nucleotide triphosphate (ddNTP) into the first extension strand prior to hybridizing the second sequencing primer. In embodiments, the method further includes incorporating a dideoxy nucleotide triphosphate (ddNTP) into the second extension strand. In embodiments, the method further includes incorporating a dideoxy nucleotide triphosphate (ddNTP) into the first extension strand, the second extension strand, or both the first and second extension strand. In embodiments, the method further includes incorporating a dideoxy nucleotide triphosphate (ddNTP) into the first extension strand prior to detecting the incorporated nucleotides. In embodiments, the method further includes incorporating a dideoxy nucleotide triphosphate (ddNTP) into the second extension strand prior to detecting the incorporated nucleotides.

In embodiments, amplifying includes hybridizing the first template polynucleotide to a first immobilized oligonucleotide and hybridizing the second template polynucleotide to a second immobilized oligonucleotide and extending the first and second immobilized oligonucleotide to form a plurality of first amplification products and plurality of second amplification products. In embodiments, amplifying includes a bridge amplification method (e.g., t-bPCR or c-bPCR). In embodiments, amplifying includes hybridizing the first template polynucleotide to a first immobilized oligonucleotide and extending the first immobilized oligonucleotide to form a plurality of first amplification products. In embodiments, amplifying includes a rolling circle amplification method (e.g., RCA or eRCA).

In embodiments, the solid support is a multiwell container or an unpatterned solid support (e.g., an unpatterned surface). In embodiments, the solid support is a multiwell container. In embodiments, the solid support is an unpatterned solid support. In embodiments, the solid support includes a photoresist. A photoresist is a light-sensitive polymer material used to form a patterned coating on a surface. The process begins by coating a substrate (e.g., a glass substrate) with a light-sensitive organic material. A mask with the desired pattern is used to block light so that only unmasked regions of the material will be exposed to light. In the case of a positive photoresist, the photosensitive material is degraded by light and a suitable solvent will dissolve away the regions that were exposed to light, leaving behind a coating where the mask was placed. In the case of a negative photoresist, the photosensitive material is strengthened (either polymerized or cross-linked) by light, and a suitable solvent will dissolve away only the regions that were not exposed to light, leaving behind a coating in areas where the mask was not placed. In embodiments, the solid support includes an epoxy-based photoresist (e.g., SU-8, SU-8 2000, SU-8 3000, SU-8 GLM2060). In embodiments, the solid support includes a negative photoresist. Negative refers to a photoresist whereby the parts exposed to UV become cross-linked (i.e., immobilized), while the remainder of the polymer remains soluble and can be washed away during development. In embodiments, the solid support includes an Off-stoichiometry thiol-enes (OSTE) polymer (e.g., an OSTE resist). In embodiments, the solid support includes an Hydrogen Silsesquioxane (HSQ) polymer (e.g., HSQ resist). In embodiments, the solid support includes a crosslinked polymer matrix on the surface of the wells and the interstitial regions.

In embodiments, the solid support includes a nanoimprint resist. In embodiments, the solid support includes a photoresist and polymer layer, wherein the photoresist is between the solid support and the polymer layer. In embodiments the photoresist is on the interstitial areas and not the surface of the wells. Suitable photoresist compositions are known in the art, such as, for example the compositions and resins described in U.S. Pat. No. 6,897,012; U.S. 6,991,888; U.S. Pat. Nos. 4,882,245; 7,467,632; 4,970,276, each of which is incorporated herein by reference in their entirety. In embodiments, the solid support includes a photoresist and polymer layer, wherein the photoresist is covalently attached to the solid support and covalently attached to the polymer layer. In embodiments, the resist is an amorphous (non-crystalline) fluoropolymer (e.g., CYTOP® from Bellex), a crystalline fluoropolymer, or a fluoropolymer having both amorphous and crystalline domains. In embodiments, the resist is a suitable polysiloxane, such as polydimethylsiloxane (PDMS). In embodiments, the solid support includes a resist (e.g., a nanoimprint lithography (NIL) resist). Nanoimprint resists can include thermal curable materials (e.g., thermoplastic polymers), and/or UV-curable polymers. In embodiments, the solid support is generated by pressing a transparent mold possessing the pattern of interest (e.g., the pattern of wells) into photo-curable liquid film, followed by solidifying the liquid materials via a UV light irradiation. Typical UV-curable resists have low viscosity, low surface tension, and suitable adhesion to the glass substrate. For example, the solid support surface, but not the surface of the wells, is coated in an organically modified ceramic polymer (ORMOCER®, registered trademark of Fraunhofer-Gesellschaft zur Förderung der angewandten Forschung e. V. in Germany). Organically modified ceramics contain organic side chains attached to an inorganic siloxane backbone. Several ORMOCER® polymers are now provided under names such as "Ormocore", "Ormoclad" and "Ormocomp" by Micro Resist Technology GmbH. In embodiments, the solid support includes a resist as described in Haas et al Volume 351, Issues 1-2, 30 Aug. 1999, Pages 198-203, US 2015/0079351A1, US 2008/0000373, or US 2010/0160478, each of which is incorporated herein by reference. In embodiments, the solid support surface, and the surface of the wells, is coated in an organically modified ceramic polymer (ORMOCER®, registered trademark of Fraunhofer-Gesellschaft zur Förderung der angewandten Forschung e. V. in Germany). In embodiments, the resist (e.g., the organically modified ceramic polymer) is not removed prior to particle deposition. In embodiments, the wells are within the resist polymer and not the solid support.

In embodiments, the solid support includes a plurality of immobilized oligonucleotides. In embodiments, the solid support includes a plurality of oligonucleotides immobilized to a polymer. In embodiments, the solid support includes a plurality of particles. In embodiments, the particles are non-covalently attached to the wells. In embodiments, the particles are physiosorbed to the wells. In embodiments, the particles are covalently attached to the wells. In embodiments, each particle attaches to the polymer layer of the surface (e.g., non-covalently attach to the polymer layer). In embodiments, the particles contact the well and remain attached without any additional means for attachment (e.g., without the hybridization of complementary oligonucleotides immobilized on the solid support).

In embodiments, the plurality of oligonucleotides is present at a density of about 100 oligonucleotides per $\mu m^2$ to about 1,000,000 oligonucleotides per $\mu m^2$. In embodiments, the plurality of oligonucleotides is present at a density of about 100 oligonucleotides per $\mu m^2$ to about 1,000 oligonucleotides per $\mu m^2$. In embodiments, the plurality of oligonucleotides is present at a density of about 100 oligonucleotides per $\mu m^2$ to about 10,000 oligonucleotides per $\mu m^2$. In embodiments, the plurality of oligonucleotides is present at a density of about 100 oligonucleotides per $\mu m^2$ to about 100,000 oligonucleotides per $\mu m^2$. In embodiments, the plurality of oligonucleotides is present at a density of about 100 oligonucleotides per $\mu m^2$ to about 500,000 oligonucleotides per $\mu m^2$. In embodiments, the plurality of oligonucleotides is present at a density of about 100, 1,000, 10,000, 50,000, 100,000, 250,000, 500,000, 750,000, or 1,000,000 oligonucleotides per $\mu m^2$.

In embodiments, the first template polynucleotide and second template polynucleotide are double-stranded DNA. In embodiments, the first template polynucleotide and second template polynucleotide are single-stranded DNA. In embodiments, the polynucleotides of each population are double-stranded DNA. In embodiments, the polynucleotides of each population are partially single-stranded DNA (e.g., include a single stranded region of DNA). In embodiments, the polynucleotides of each population are single-stranded DNA.

In embodiments, a subset of the amplification clusters include: i) amplification products including the first template polynucleotide sequence; and ii) complementary amplification products including a complement of the first template polynucleotide sequence. In embodiments, the method further includes hybridizing a sequencing primer to the complementary amplification products and generating a complementary sequencing read.

In an aspect is provided a method of amplifying a plurality of template polynucleotides, the method including: (a) contacting a surface with a first template polynucleotide including a first adapter sequence thereby forming a first complex attached to the surface and contacting the surface with a second template polynucleotide including a second adapter sequence thereby forming a second complex attached to the surface, wherein: (i) the first adapter sequence includes a first platform primer binding sequence and a first sequencing primer binding sequence; (ii) the second adapter sequence includes a second platform primer binding sequence and a second sequencing primer binding sequence; (iii) the first complex includes a first amplification primer attached to the surface hybridized to the first adapter sequence; (iv) the second complex includes a second amplification primer attached to the surface hybridized to the second adapter sequence; and (v) the first platform primer binding sequence is different from the second platform primer binding sequence, said first sequencing primer binding sequence is different from the second sequencing primer binding sequence and the first amplification primer is different from the second amplification primer; (b) amplifying the first template polynucleotide and the second template polynucleotide to form a plurality of first amplification products and plurality of second amplification products that form amplification clusters on the surface.

In an aspect is provided a method of amplifying a plurality of template polynucleotides, the method including: (a) contacting a surface with a first template polynucleotide including a first adapter sequence thereby forming a first hybridized complex attached to the surface and a second template polynucleotide including a second adapter sequence thereby forming a second hybridized complex attached to the surface, wherein: (i) the first adapter sequence includes a first platform primer binding sequence and a first sequencing primer binding sequence; (ii) the second adapter sequence includes a second platform primer binding sequence and a second sequencing primer binding sequence; (iii) the first hybridized complex includes a first amplification primer attached to the surface hybridized to the first adapter sequence; (iv) the second hybridized complex includes a second amplification primer attached to the surface hybridized to the second adapter sequence; and (v) the first platform primer binding sequence is different from the second platform primer binding sequence, the first sequencing primer binding sequence is different from the second sequencing primer binding sequence and the first amplification primer is different from the second amplification primer; (b) amplifying the first template polynucleotide and the second template polynucleotide to form a plurality of first template amplicons and plurality of second template amplicons that form overlapping amplification clusters on the surface.

In embodiments, the first complex is hybridized to the first platform primer binding sequence. In embodiments, the second complex is hybridized to the second platform primer binding sequence.

In embodiments, the method further includes: (i) hybridizing and extending a first sequencing primer in a first sequencing cycle and detecting one or more labels in a first detection region to generate a sequencing read for the first template polynucleotide, wherein the first sequencing primer is complementary to the first sequencing primer binding sequence, and (ii) hybridizing and extending a second sequencing primer in a second sequencing cycle and detecting one or more labels in a second detection region to generate a sequencing read for the second template polynucleotide, wherein the second sequencing primer is complementary to the second sequencing primer binding sequence. In embodiments, the first and second detection regions are overlapping.

In embodiments, the method further includes (i) hybridizing and extending a first sequencing primer in a first sequencing cycle and detecting one or more labels in a first detection region to generate a sequencing read for the first template polynucleotide, wherein the first sequencing primer is complementary to the first sequencing primer binding sequence, and (ii) hybridizing and extending a second sequencing primer in a second sequencing cycle and detecting one or more labels in a second detection region to generate a sequencing read for the second template polynucleotide, wherein the second sequencing primer is complementary to the second sequencing primer binding sequence, and wherein the first and second detection regions are overlapping.

In embodiments, the method further includes contacting the surface with a third template polynucleotide including a third adapter sequence thereby forming a third complex attached to the surface and a fourth template polynucleotide including a fourth adapter sequence thereby forming a fourth complex attached to the surface, wherein (i) the third adapter sequence includes the first platform primer binding sequence and a third sequencing primer binding sequence; (ii) the fourth adapter sequence includes the second platform primer binding sequence and a fourth sequencing primer binding sequence.

In embodiments, the third complex is hybridized to the third platform primer binding sequence. In embodiments, the fourth complex is hybridized to the fourth platform primer binding sequence.

In embodiments, the method further includes contacting the surface with a third template polynucleotide including a third adapter sequence thereby forming a third hybridized complex attached to the surface and a fourth template polynucleotide including a fourth adapter sequence thereby forming a fourth hybridized complex attached to the surface, wherein (i) the third adapter sequence includes the first platform primer binding sequence and a third sequencing primer binding sequence; (ii) the fourth adapter sequence includes the second platform primer binding sequence and a fourth sequencing primer binding sequence.

In embodiments, the method further includes (i) hybridizing and extending a third sequencing primer in a first sequencing cycle and detecting one or more labels in a first detection region to generate a sequencing read for the third template polynucleotide, wherein the third sequencing primer is complementary to the third sequencing primer binding sequence, and (ii) hybridizing and extending a fourth sequencing primer in a second sequencing cycle and detecting one or more labels in a second detection region to generate a sequencing read for the fourth template polynucleotide, wherein the fourth sequencing primer is complementary to the fourth sequencing primer. In embodiments, the first and second detection regions are overlapping.

In embodiments, the method further includes (i) hybridizing and extending a third sequencing primer in a first sequencing cycle and detecting one or more labels in a first detection region to generate a sequencing read for the third template polynucleotide, wherein the third sequencing primer is complementary to the third sequencing primer binding sequence, and (ii) hybridizing and extending a fourth sequencing primer in a second sequencing cycle and detecting one or more labels in a second detection region to generate a sequencing read for the fourth template polynucleotide, wherein the fourth sequencing primer is complementary to the fourth sequencing primer, and wherein the first and second detection regions are overlapping.

In an aspect is provided a method for sequencing populations of a plurality of template polynucleotides. In embodiments, each population of template polynucleotides includes a unique initiation point for sequencing (i.e., each population of template polynucleotides includes a unique adapter sequence including a sequence complementary to a sequencing primer for that population of template polynucleotides). For example, the array may contain four distinct populations of template polynucleotides that are interspersed within a plurality of features (e.g., see the illustrations provided in FIGS. 5A-5B). The first population may be sequenced by hybridizing a first sequencing primer to the template polynucleotides that include the complementary sequence for the first sequencing primer. Following sequencing to generate a sequencing read of sufficient length, the first population of template polynucleotides are terminated, cleaved, or extended with native nucleotides to prevent any additional sequencing from that population. The subsequent populations of polynucleotides may be successively sequenced in a similar manner until all populations of template polynucleotides are sequenced.

In an aspect is provided a method of sequencing a plurality of template polynucleotides on a surface. In embodiments, the method includes (a) amplifying the plurality of template polynucleotides to generate a plurality of overlapping amplification clusters on a surface, wherein: (i) an overlapping amplification cluster includes amplicons of a first template polynucleotide including a first adapter sequence, and amplicons of a second template polynucleotide including a second adapter sequence; (ii) the first adapter sequence and second adapter sequence include a sequence complementary to an amplification primer attached to the surface; (iii) the first adapter sequence includes a sequence complementary to a first sequencing primer; and (iv) the second adapter sequence includes a sequence complementary to a second sequencing primer that is different from the first sequencing primer; (b) for each of a plurality of the overlapping amplification clusters: (i) extending the first sequencing primer hybridized to the first adapter sequence in a sequencing cycle and detecting one or more labels in a first detection region to generate a sequencing read for the first template, and (ii) extending the second sequencing primer hybridized to the second adapter sequence in a sequencing cycle and detecting one or more labels in a second detection region to generate a sequencing read for the second template, wherein the first and second detection regions are overlapping. In embodiments, the first and second template polynucleotides are not substantially complementary to each other.

In an aspect is provided a method of sequencing a plurality of template polynucleotides, the method including: (a) amplifying the plurality of template polynucleotides to generate a plurality of overlapping amplification clusters on a surface, wherein: (i) an overlapping amplification cluster includes double-stranded amplicons of a first template polynucleotide including a first adapter sequence, and double-stranded amplicons of a second template polynucleotide including a second adapter sequence; (ii) the first adapter sequence and second adapter sequence include a sequence complementary to an amplification primer attached to the surface; (iii) the first adapter sequence includes a sequence complementary to a first sequencing primer; and (iv) the second adapter sequence includes a sequence complementary to a second sequencing primer that is different from the first sequencing primer; (b) for each of a plurality of the overlapping amplification clusters: (i) extending the first sequencing primer hybridized to the first adapter sequence in a sequencing cycle and detecting one or more labels in a first detection region to generate a sequencing read for the first template, and (ii) extending the second sequencing primer hybridized to the second adapter sequence in a sequencing cycle and detecting one or more labels in a second detection region to generate a sequencing read for the second template, wherein the first and second detection regions are overlapping. In embodiments, the first and second template polynucleotides are not substantially complementary to each other.

In some embodiments, the first template polynucleotide further includes a third adapter sequence, wherein the third adapter sequence includes i) a sequence complementary to an amplification primer attached to the surface, and ii) a sequence complementary to a third sequencing primer; and wherein the second template polynucleotide further includes a fourth adapter sequence, wherein the fourth adapter sequence includes i) a sequence complementary to an amplification primer attached to the surface, and ii) a sequence complementary to a fourth sequencing primer. In embodiments, the first adapter sequence and third adapter sequence each include a sequence complementary to the same amplification primer attached to the surface (e.g., pp1). In embodiments, the second adapter sequence and fourth adapter sequence each include a sequence complementary to the same amplification primer attached to the surface (e.g., pp2). In embodiments, the method further includes hybridizing a third sequencing primer to the third adapter sequence and a fourth sequencing primer to the fourth adapter sequence, extending the third and fourth sequencing primers and detecting one or more labels in the first and second detection regions to generate second sequencing reads for the first and second template polynucleotides. It is understood that first, second, third, fourth, fifth, sixth, etc. may be interchanged when in reference to each other depending on the context.

In embodiments, prior to step (a), the method further includes ligating a first adapter to a first end of the first template polynucleotide and ligating a second adapter to a first end of the second template polynucleotide. In embodiments, prior to step (a), the method further includes ligating a first adapter to a first end of the first template polynucleotide, ligating a third adapter to a second end of the first template polynucleotide, ligating a second adapter to a first end of the second template polynucleotide, and ligating a fourth adapter to a second end of the second template polynucleotide.

In embodiments, the double-stranded amplification product includes common sequences at their 5' and 3' ends (e.g., an amplification primer binding site). In this context the term "common" is interpreted as meaning common to all of the template polynucleotides of a particular population in the library that include a substantially identical sequence. For example, the double-stranded amplification product may include a first adapter sequence at the 5' end and a second adapter sequence at the 3' end. Typically, the first adapter sequence and the second adapter sequence will consist of no more than 100, or no more than 50, or no more than 40 consecutive nucleotides at the 5' and 3' ends, respectively, of each strand of each template polynucleotide. The precise length of the two sequences may or may not be identical. The precise sequences of the common regions are generally not material to the invention and may be selected by the user. The common sequences will typically include primer-binding sequences (i.e., regions of complementarity for a primer) which enable specific annealing of primers when the template polynucleotides are in used in a solid-phase amplification reaction. The primer-binding sequences are thus determined by the sequence of the primers to be ultimately used for solid-phase amplification.

In some embodiments, the first and second detection regions overlap by at least 25%. In embodiments, the first and second detection regions overlap by at least 50%. In other embodiments, the first and second detection regions overlap by at least 75%. In embodiments, the first and second detection regions overlap by at least 25%, at least 50%, or at least 75%. In some embodiments, the first and second detection regions overlap by between at least 25% to 100%. In some embodiments, the first and second detection regions overlap by between at least 50% to 100%. In some embodiments, the first and second detection regions overlap by between at least 75% to 100%. In some embodiments, the first and second detection regions overlap by about 25%. In embodiments, the first and second detection regions overlap by about 50%. In other embodiments, the first and second detection regions overlap by about 75%. In embodiments, the first and second detection regions overlap by about 25%, about 50%, or about 75%. In some embodiments, the first and second detection regions overlap by between about 25% to 100%. In some embodiments, the first and second detection regions overlap by between about 50% to 100%. In some embodiments, the first and second detection regions overlap by between about 75% to 100%. In embodiments, a detection region is a feature. In embodiments, a detection region is a cluster. In embodiments, the first and second detection regions are the same feature.

In embodiments, the plurality of amplifications clusters include overlapping amplification clusters (e.g., overlapping amplification clusters on a patterned array or multiwell solid support). In embodiments, solid support includes both overlapping and non-overlapping amplification clusters.

In some embodiments, the overlapping amplification cluster includes a total cluster density per unit area of about 100,000 to about 2,000,000 amplicons per $mm^2$. In embodiments, the overlapping amplification cluster includes a total cluster density per unit area of about 200,000 to about 1,750,000 amplicons per $mm^2$. In embodiments, the overlapping amplification cluster includes a total cluster density per unit area of about 300,000 to about 1,500,000 amplicons per $mm^2$. In embodiments, the overlapping amplification cluster includes a total cluster density per unit area of about 400,000 to about 1,250,000 amplicons per $mm^2$. In embodiments, the overlapping amplification cluster includes a total cluster density per unit area of about 500,000 to about 1,000,000 amplicons per $mm^2$. In embodiments, the overlapping amplification cluster includes a total cluster density per unit area of about 100,000 to about 750,000 amplicons per $mm^2$. In embodiments, the overlapping amplification cluster includes a total cluster density per unit area of about 50,000 to about 500,000 amplicons per $mm^2$. In some embodiments, the solid support includes an amplification cluster density per unit area of about 100,000 to about 2,000,000 amplicons per $mm^2$. In embodiments, the solid support includes an amplification cluster density per unit area of about 200,000 to about 1,750,000 amplicons per $mm^2$. In embodiments, the solid support includes an amplification cluster density per unit area of about 300,000 to about 1,500,000 amplicons per $mm^2$. In embodiments, the solid support includes an amplification cluster density per unit area of about 400,000 to about 1,250,000 amplicons per $mm^2$. In embodiments, the solid support includes an amplification cluster density per unit area of about 500,000 to about 1,000,000 amplicons per $mm^2$. In embodiments, the solid support includes an amplification cluster density per unit area of about 100,000 to about 750,000 amplicons per $mm^2$. In embodiments, the solid support includes an amplification cluster density per unit area of about 50,000 to about 500,000 amplicons per $mm^2$.

In embodiments, the cluster is monoclonal (i.e., one template polynucleotide (e.g., a first template polynucleotide) binds and is amplified within the feature). In embodiments, the cluster is polyclonal (i.e., more than one template polynucleotide type (e.g., a first template polynucleotide and a second template polynucleotide) binds and is amplified within the feature). In embodiments, the array contains a ratio of monoclonal (e.g., one template polynucleotide (e.g., a first template polynucleotide)), diclonal (e.g., two template polynucleotides (e.g., a first and a second template polynucleotide)), triclonal (e.g., three template polynucleotides (e.g., a first, second, and a third template polynucleotide)), quadraclonal (e.g., four template polynucleotides (e.g., a first, second, third, and fourth template polynucleotide)), etc. clusters. In embodiments, multiple different template polynucleotides seed one spot (i.e., a feature) of a patterned array, and is referred to herein as a polyclonal feature. In embodiments, a fraction of the surface area within the feature is occupied by copies of one template type, and another fraction of the patterned spot can be occupied by copies of another template type (e.g., a first template polynucleotide and a second template polynucleotide, wherein each template polynucleotide is different). The fractions of the template polynucleotides within the feature are inherently stochastic and governed by Poisson statistics, however the ratios may be influenced by underseeing or overseeding (i.e., providing less or more template polynucleotides relative to the number of available sites on the array). In some embodiments, the ratio of overlapping amplification clusters to monoclonal amplification clusters is at least about 1:1. In some embodiments, the ratio of overlapping amplification clusters to monoclonal amplification clusters is at least about 2:1. In embodiments, the ratio of overlapping amplification clusters to monoclonal amplification clusters is at least about 2.5:1. In embodiments, the ratio of overlapping amplification clusters to monoclonal amplification clusters is at least about 3:1. In some embodiments, the ratio of overlapping amplification clusters to monoclonal amplification clusters is about 1:1. In some embodiments, the ratio of overlapping amplification clusters to monoclonal amplification clusters is about 2:1. In embodiments, the ratio of overlapping amplification clusters to monoclonal amplification clusters is about 2.5:1. In embodiments, the ratio of overlapping amplification clusters to monoclonal amplification clusters is about 3:1.

In embodiments, the different populations of polynucleotides are single-stranded, or include single-stranded regions, prior to contacting the solid support and/or forming the complexes. In embodiments, the different populations of double-stranded polynucleotides are denatured (e.g., by chemical denaturation and/or heat denaturation) into single-stranded polynucleotides prior to forming the complexes. In embodiments, the different populations of polynucleotides are circular templates.

In embodiments, the method includes contacting a solid support with 3, 4, 5, 6, 7, 8, 9, 10, 11, or 12 populations of polynucleotides. In embodiments, the method includes contacting a solid support with 3 populations of polynucleotides. In embodiments, the method includes contacting a solid support with 4 populations of polynucleotides. In embodiments, the method includes contacting a solid support with 5 populations of polynucleotides. In embodiments, the method includes contacting a solid support with 6 populations of polynucleotides. In embodiments, the method includes contacting a solid support with 7 populations of polynucleotides. In embodiments, the method includes contacting a solid support with 8 populations of polynucleotides. In embodiments, the method includes contacting a solid support with 9 populations of polynucleotides. In embodiments, the method includes contacting a solid support with 10 populations of polynucleotides. In embodiments, the method includes contacting a solid support with 11 populations of polynucleotides. In embodiments, the method includes contacting a solid support with 12 populations of polynucleotides. In embodiments, the method includes contacting a solid support with more than 12 populations of polynucleotides.

In some embodiments, the plurality of template polynucleotides are double-stranded template polynucleotides. In some embodiments, the plurality of template polynucleotides are single-stranded template polynucleotides. In embodiments, the plurality of template polynucleotides are circular template polynucleotides.

In embodiments, prior to step (a), the method further includes ligating a first adapter to a first end of the first template polynucleotide and ligating a second adapter to a first end of the second template polynucleotide. In embodiments, prior to step (a), the method further includes ligating a first adapter to a first end of the first template polynucleotide, ligating a third adapter to a second end of the first template polynucleotide, ligating a second adapter to a first end of the second template polynucleotide, and ligating a fourth adapter to a second end of the second template polynucleotide.

In some embodiments, the method further includes ligating a first adapter to a first end of the first template polynucleotide and ligating a second adapter to a first end of the second template polynucleotide. In embodiments, the method further includes ligating a first adapter to a first end of the first template polynucleotide, ligating a third adapter to a second end of the first template polynucleotide, ligating a second adapter to a first end of the second template polynucleotide, and ligating a fourth adapter to a second end of the second template polynucleotide.

In some embodiments, the first and second template polynucleotides include substantially identical template sequences, i.e., the first template polynucleotide and the second template polynucleotide include the same template sequence and are each ligated to distinct combinations of first and second adapter sequences, or first, second, third, and fourth adapter sequences. For example, a first template polynucleotide includes a template polynucleotide sequence and a first adapter sequence, and a second template polynucleotide includes the same template polynucleotide sequence as the first template polynucleotide, and further includes a second adapter sequence. In embodiments, the first adapter sequence and the second adapter sequence include different sequencing primer binding regions (i.e., a polynucleotide sequence complementary to a first sequencing primer and a polynucleotide sequence complementary to a second sequencing primer, respectively).

In some embodiments, the first and second template polynucleotides include different template sequences, i.e., the first template polynucleotide and the second template polynucleotide include different template sequences and are each ligated to distinct combinations of first and second adapter sequences, or first, second, third, and fourth adapter sequences. For example, a first template polynucleotide includes a template polynucleotide sequence and a first adapter sequence, and a second template polynucleotide includes a different template polynucleotide sequence, and further includes a second adapter sequence. In embodiments, the first template polynucleotide and the second template polynucleotide are less than 1% homologous (i.e., the first and second template polynucleotides include different template sequences). In embodiments, the first template polynucleotide and the second template polynucleotide are less than 1%, 2%, 3%, 4%, or 5% homologous. In embodiments, the first adapter sequence and the second adapter sequence include different sequencing primer binding regions (i.e., a polynucleotide sequence complementary to a first sequencing primer and a polynucleotide sequence complementary to a second sequencing primer, respectively).

In some embodiments, the first and second adapter sequences further include a barcode sequence. In embodiments, the first and second adapter sequences further include a barcode sequence alone or in combination with a sequence of one or both of (a) the sample polynucleotide, or (b) one or more additional barcode sequences, uniquely distinguishing the template polynucleotide from other template polynucleotides in the plurality. In embodiments, each barcode sequence is selected from a set of barcode sequences represented by a random or partially random sequence. In other embodiments, each barcode sequence is selected from a set of barcode sequences represented by a random sequence. In other embodiments, each barcode sequence differs from every other barcode sequence by at least two nucleotide positions. In embodiments, each barcode sequence includes about 5 to about 20 nucleotides, or about 10 to about 20 nucleotides.

In embodiments, the template polynucleotide includes a first adapter and a second adapter, wherein the first adapter is a Y-adapter, a hairpin adapter, a blunt-ended adapter, or an adapter including a single-strand overhang and the second adapter is a Y-adapter, a hairpin adapter, a blunt-ended adapter, or an adapter including a single-strand overhang. In embodiments, the template polynucleotide includes a first adapter and a second adapter, wherein the first adapter is a Y-adapter and the second adapter is a Y-adapter. In embodiments, the template polynucleotide includes a first adapter and a second adapter, wherein the first adapter is a Y-adapter and the second adapter is a hairpin adapter. In embodiments, the template polynucleotide includes a first adapter and a second adapter, wherein the first adapter is a hairpin adapter and the second adapter is a Y-adapter. In embodiments, the template polynucleotide includes a first adapter and a second adapter, wherein the first adapter is a hairpin adapter and the second adapter is a hairpin adapter.

In embodiments, ligating includes ligating both the 3' end and the 5' end of the duplex region of the first adapter to a double stranded nucleic acid. In embodiments, ligating includes ligating either the 3' end or the 5' end of the duplex region of the first adapter to a double stranded nucleic acid. In embodiments, ligating includes ligating the 5' end of the duplex region of the first adapter to the double stranded nucleic acid and not the 3' end of the duplex region. In embodiments, the method includes ligating a first adapter to a first end of the double stranded nucleic acid wherein both strands of the double stranded nucleic acid are ligated to the first adapter. In embodiments, the method includes ligating a first adapter to a first end of the double stranded nucleic acid wherein one strand of the double stranded nucleic acid is ligated to the first adapter.

In embodiments, the first adapter and/or second adapter is a Y-adapter. In embodiments, a Y-adapter includes a first strand and a second strand where a portion of the first strand (e.g., 3'-portion) is complementary, or substantially complementary, to a portion (e.g., 5'-portion) of the second strand. In embodiments, a Y-adapter includes a first strand and a second strand where a 3'-portion of the first strand is hybridized to a 5'-portion of the second strand. In embodiments, the 3'-portion of the first strand that is substantially complementary to the 5'-portion of the second strand forms a duplex including double stranded nucleic acid. Accordingly, a Y-adapter often includes a first end including a duplex region including a double stranded nucleic acid, and a second end including a forked region including a 5'-arm and a 3'-arm. In some embodiments, a 5'-portion of the first stand (e.g., 5'-arm) and a 3'-portion of the second strand (3'-arm) are not complementary. In embodiments, the first and second strands of a Y-adapter are not covalently attached to each other. In embodiments, the Y-adapter includes (i) a first strand having a 5'-arm and a 3'-portion, and (ii) a second strand having a 3'-arm and a 5'-portion, wherein the 3'-portion of the first strand is substantially complementary to the 5'-portion of the second strand, and the 5'-arm of the first strand is not substantially complementary to the 3'-arm of the second strand. In some embodiments, the first adapter includes a sample barcode sequence, a molecular identifier sequence, or both a sample barcode sequence and a molecular identifier sequence. In some embodiments, the first adapter includes a sample barcode sequence (e.g., a 6-10 nucleotide sequence).

In some embodiments, each strand of a Y-adapter, each of the non-complementary arms of a Y-adapter, or a duplex portion of a Y-adapter has a length independently selected from at least 5, at least 10, at least 15, at least 25, and at least 40 nucleotides. In some embodiments, each strand of a Y-adapter, each of the non-complementary arms of a Y-adapter, or a duplex portion of a Y-adapter has a length in a range independently selected from 15 to 500 nucleotides, 15-250 nucleotides, 15 to 200 nucleotides, 15 to 150 nucleotides, 20 to 100 nucleotides, 20 to 50 nucleotides and 10-50 nucleotides. In embodiments, one or both non-complementary arms of the Y-adapter is about or at least about 10, 15, 20, 25, 30, 35, 40, 45, 50, or more nucleotides in length. In embodiments, one or both non-complementary arms of the Y-adapter is about or at least about 20 nucleotides in length. In embodiments, one or both non-complementary arms of the Y-adapter is about or at least about 30 nucleotides in length. In embodiments, one or both non-complementary arms of the Y-adapter is about or at least about 40 nucleotides in length. In embodiments, the duplex portion of a Y-adapter is about or at least about 5, 10, 15, 20, 25, 30, or more nucleotides in length. In embodiments, the duplex portion of a Y-adapter is about 5-50, 5-25, or 10-15 nucleotides in length. In embodiments, the duplex portion of a Y-adapter is about or at least about 10 nucleotides in length. In embodiments, the duplex portion of a Y-adapter is about or at least about 15 nucleotides in length. In embodiments, the duplex portion of a Y-adapter is about or at least about 12 nucleotides in length. In embodiments, the duplex portion of a Y-adapter is about or at least about 20 nucleotides in length.

In some embodiments, a Y-adapter includes a first end including a duplex region including a double stranded nucleic acid, and a second end including a forked region, where the first end is configured for ligation to an end of a double stranded nucleic acid (e.g., a nucleic acid fragment, e.g., a library insert). In embodiments, a duplex end of a Y-adapter includes a 5'-overhang or a 3'-overhang that is complementary to a 3'-overhang or a 5'-overhang of an end of a double stranded nucleic acid. In some embodiments, a duplex end of a Y-adapter includes a blunt end that can be ligated to a blunt end of a double stranded nucleic acid. In certain embodiment, a duplex end of a Y-adapter includes a 5'-end that is phosphorylated.

In some embodiments, the first and/or second adapter (e.g., one or both strands of a Y-adapter) include one or more of a primer binding site, a capture nucleic acid binding site (e.g., a nucleic acid sequence complementary to a capture nucleic acid), a UMI, a sample barcode, a sequencing adapter, a label, a binding motif, the like or combinations thereof. In some embodiments, a non-complementary portion (e.g., 5'-arm and/or 3'-arm) of a Y-adapter includes one or more of a primer binding site, a capture nucleic acid binding site (e.g., a nucleic acid sequence complementary to a capture nucleic acid), a UMI, a sample barcode, a sequencing adapter, a label, a binding motif, the like or combinations thereof. In certain embodiments, a non-complementary portion of a Y-adapter includes a primer binding site. In certain embodiments, a non-complementary portion of a Y-adapter includes a binding site for a capture nucleic acid. In certain embodiments, a non-complementary portion of a Y-adapter includes a primer binding site and a UMI. In certain embodiments, a non-complementary portion of a Y-adapter includes a binding motif. In embodiments, the first and/or second adapter (e.g., one or both strands of a Y-adapter) does not include a UMI or sample barcode.

In embodiments, a complementary strand (e.g., a 3'-portion or 5'-portion) of a Y-adapter includes a primer binding site. In certain embodiments, a complementary strand (e.g., a 3'-portion or 5'-portion) of a Y-adapter includes a binding site for a capture nucleic acid. In certain embodiments, a complementary strand (e.g., a 3'-portion or 5'-portion) of a Y-adapter includes a primer binding site and a UMI. In certain embodiments, a complementary strand (e.g., a 3'-portion or 5'-portion) of a Y-adapter includes a binding motif.

In some embodiments, each of the non-complementary portions (i.e., arms) of a Y-adapter independently have a predicted, calculated, mean, average or absolute melting temperature (Tm) that is greater than 50° C., greater than 55° C., greater than 60° C., greater than 65° C., greater than 70° C. or greater than 75° C. In some embodiments, each of the non-complementary portions of a Y-adapter independently have a predicted, estimated, calculated, mean, average or absolute melting temperature (Tm) that is in a range of 50-100° C., 55-100° C., 60-100° C., 65-100° C., 70-100° C., 55-95° C., 65-95° C., 70-95° C., 55-90° C., 65-90° C., 70-90° C., or 60-85° C. In embodiments, the Tm is about or at least about 70° C. In embodiments, the Tm is about or at least about 75° C. In embodiments, the Tm is about or at least about 80° C. In embodiments, the Tm is a calculated Tm. Tm's are routinely calculated by those skilled in the art, such as by commercial providers of custom oligonucleotides. In embodiments, the Tm for a given sequence is determined based on that sequence as an independent oligo. In embodiments, Tm is calculated using web-based algorithms, such as Primer3 and Primer3Plus (www.bioinformatics.nl/cgi-bin/primer3plus/primer3plus.cgi) using default parameters. The Tm of a non-complementary portion of a Y-adapter can be changed (e.g., increased) to a desired Tm using a suitable method, for example by changing (e.g., increasing) GC content, changing (e.g., increasing) length and/or by the inclusion of modified nucleotides, nucleotide analogues and/or modified nucleotides bonds, non-limiting examples of which include locked nucleic acids (LNAs, e.g., bicyclic nucleic acids), bridged nucleic acids (BNAs, e.g., constrained nucleic acids), C5-modified pyrimidine bases (for example, 5-methyl-dC, propynyl pyrimidines, among others) and alternate backbone chemistries, for example peptide nucleic acids (PNAs), morpholinos, the like or combinations thereof. Accordingly, in some embodiments, each of the non-complementary portion of a Y-adapter independently includes one or more modified nucleotides, nucleotide analogues and/or modified nucleotides bonds.

In some embodiments, each of the non-complementary portions of a Y-adapter independently includes a GC content of greater than 40%, greater than 50%, greater than 55%, greater than 60% greater than 65% or greater than 70%. In certain embodiments, each of the non-complementary portions of a Y-adapter independently includes a GC content in a range of 40-100%, 50-100%, 60-100% or 70-100%. In embodiments, one or both non-complementary portions of a Y-adapter have a GC content of about or more than about 40%. In embodiments, one or both non-complementary portions of a Y-adapter have a GC content of about or more than about 50%. In embodiments, one or both non-complementary portions of a Y-adapter have a GC content of about or more than about 60%. Non-base modifiers can also be incorporated into a non-complementary portion of a Y-adapter to increase Tm, non-limiting examples of which include a minor grove binder (MGB), spermine, G-clamp, a Uaq anthraquinone cap, the like or combinations thereof.

In certain embodiments, a duplex region of a Y-adapter includes a predicted, estimated, calculated, mean, average or absolute Tm in a range of 30-70° C., 35-65° C., 35-60° C., 40-65° C., 40-60° C., 35-55° C., 40-55° C., 45-50° C. or 40-50° C. In embodiments, the Tm of a duplex region of the Y-adapter is about or more than about 30° C. In embodiments, the Tm of a duplex region of the Y-adapter is about or more than about 35° C. In embodiments, the Tm of a duplex region of the Y-adapter is about or more than about 40° C. In embodiments, the Tm of a duplex region of the Y-adapter is about or more than about 45° C. In embodiments, the Tm of a duplex region of the Y-adapter is about or more than about 50° C.

In some embodiments, the first adapter and/or second adapter is a hairpin adapter. In some embodiments, the first adapter and/or second adapter is a hairpin adapter wherein the hairpin adapter includes a cleavable site. In embodiments, the cleavable site includes a diol linker, disulfide linker, photocleavable linker, abasic site, deoxyuracil triphosphate (dUTP), deoxy-8-oxo-guanine triphosphate (d-8-oxoG), methylated nucleotide, ribonucleotide, or a sequence containing a modified or unmodified nucleotide that is specifically recognized by a cleaving agent.

In embodiments, a hairpin adapter includes a single nucleic acid strand including a stem-loop structure. A hairpin adapter can be any suitable length. In some embodiments, a hairpin adapter is at least 40, at least 50, or at least 100 nucleotides in length. In some embodiments, a hairpin adapter has a length in a range of 45 to 500 nucleotides, 75-500 nucleotides, 45 to 250 nucleotides, 60 to 250 nucleotides or 45 to 150 nucleotides. In some embodiments, a hairpin adapter comprises a nucleic acid having a 5'-end, a 5'-portion, a loop, a 3'-portion and a 3'-end (e.g., arranged in a 5' to 3' orientation). In some embodiments, the 5' portion of a hairpin adapter is annealed and/or hybridized to the 3' portion of the hairpin adapter, thereby forming a stem portion of the hairpin adapter. In some embodiments, the 5' portion of a hairpin adapter is substantially complementary to the 3' portion of the hairpin adapter. In certain embodiments, a hairpin adapter comprises a stem portion (i.e., stem) and a loop, wherein the stem portion is substantially double stranded thereby forming a duplex. In some embodiments, the loop of a hairpin adapter comprises a nucleic acid strand that is not complementary (e.g., not substantially complementary) to itself or to any other portion of the hairpin adapter. In some embodiments, the second adapter includes a sample barcode sequence, a molecular identifier sequence, or both a sample barcode sequence and a molecular identifier sequence. In some embodiments, the second adapter includes a sample barcode sequence.

In some embodiments, a duplex region or stem portion of a hairpin adapter includes an end that is configured for ligation to an end of double stranded nucleic acid (e.g., a nucleic acid fragment, e.g., a library insert). In embodiments, an end of a duplex region or stem portion of a hairpin adapter includes a 5'-overhang or a 3'-overhang that is complementary to a 3'-overhang or a 5'-overhang of one end of a double stranded nucleic acid. In some embodiments, an end of a duplex region or stem portion of a hairpin adapter includes a blunt end that can be ligated to a blunt end of a double stranded nucleic acid. In certain embodiment, an end of a duplex region or stem portion of a hairpin adapter includes a 5'-end that is phosphorylated. In some embodiments, a stem portion of a hairpin adapter is at least 15, at least 25, or at least 40 nucleotides in length. In some embodiments, a stem portion of a hairpin adapter has a length in a range of 15 to 500 nucleotides, 15-250 nucleotides, 15 to 200 nucleotides, 15 to 150 nucleotides, 20 to 100 nucleotides or 20 to 50 nucleotides.

In some embodiments, the loop of a hairpin adapter includes one or more of a primer binding site, a capture nucleic acid binding site (e.g., a nucleic acid sequence complementary to a capture nucleic acid), a UMI, a sample barcode, a sequencing adapter, a label, the like or combinations thereof. In certain embodiments, a loop of a hairpin adapter includes a primer binding site. In certain embodiments, a loop of a hairpin adapter includes a primer binding site and a UMI. In certain embodiments, a loop of a hairpin adapter includes a binding motif.

In some embodiments, the loop of a hairpin adapter has a predicted, calculated, mean, average or absolute melting temperature (Tm) that is greater than 50° C., greater than 55° C., greater than 60° C., greater than 65° C., greater than 70° C. or greater than 75° C. In some embodiments, a loop of a hairpin adapter has a predicted, estimated, calculated, mean, average or absolute melting temperature (Tm) that is in a range of 50-100° C., 55-100° C., 60-100° C., 65-100° C., 70-100° C., 55-95° C., 65-95° C., 70-95° C., 55-90° C., 65-90° C., 70-90° C., or 60-85° C. In embodiments, the Tm of the loop is about 65° C. In embodiments, the Tm of the loop is about 75° C. In embodiments, the Tm of the loop is about 85° C. The Tm of a loop of a hairpin adapter can be changed (e.g., increased) to a desired Tm using a suitable method, for example by changing (e.g., increasing GC content), changing (e.g., increasing) length and/or by the inclusion of modified nucleotides, nucleotide analogues and/or modified nucleotides bonds, non-limiting examples of which include locked nucleic acids (LNAs, e.g., bicyclic nucleic acids), bridged nucleic acids (BNAs, e.g., constrained nucleic acids), CS-modified pyrimidine bases (for example, 5-methyl-dC, propynyl pyrimidines, among others) and alternate backbone chemistries, for example peptide nucleic acids (PNAs), morpholinos, the like or combinations thereof. Accordingly, in some embodiments, a loop of a hairpin adapter comprises one or more modified nucleotides, nucleotide analogues and/or modified nucleotides bonds.

In some embodiments, the loop of a hairpin adapter independently includes a GC content of greater than 40%, greater than 50%, greater than 55%, greater than 60% greater than 65% or greater than 70%. In certain embodiments, a loop of a hairpin adapter independently includes a GC content in a range of 40-100%, 50-100%, 60-100% or 70-100%. In embodiments, the loop has a GC content of about or more than about 40%. In embodiments, the loop has a GC content of about or more than about 50%. In embodiments, the loop has a GC content of about or more than about 60%. Non-base modifiers can also be incorporated into a loop of a hairpin adapter to increase Tm, non-limiting examples of which include a minor grove binder (MGB), spermine, G-clamp, a Uaq anthraquinone cap, the like or combinations thereof. A loop of a hairpin adapter can be any suitable length. In some embodiments, a loop of a hairpin adapter is at least 15, at least 25, or at least 40 nucleotides in length. In some embodiments, a hairpin adapter has a length in a range of 15 to 500 nucleotides, 15-250 nucleotides, 20 to 200 nucleotides, 30 to 150 nucleotides or 50 to 100 nucleotides.

In certain embodiments, a duplex region or stem region of a hairpin adapter includes a predicted, estimated, calculated, mean, average or absolute Tm in a range of 30-70° C., 35-65° C., 35-60° C., 40-65° C., 40-60° C., 35-55° C., 40-55° C., 45-50° C. or 40-50° C. In embodiments, the Tm of the stem region is about or more than about 35° C. In embodiments, the Tm of the stem region is about or more than about 40° C. In embodiments, the Tm of the stem region is about or more than about 45° C. In embodiments, the Tm of the stem region is about or more than about 50° C.

In embodiments, the method further includes hybridizing (a) the first template polynucleotide including the first adapter sequence and (b) the second template polynucleotide including the second adapter sequence to a plurality of amplification primers attached on the surface.

In some embodiments, fewer than 35% of all of the clusters are monoclonal amplification clusters. In some embodiments, fewer than 30% of all of the clusters are monoclonal amplification clusters. In some embodiments, fewer than 25% of all of the clusters are monoclonal amplification clusters. In some embodiments, fewer than 20% of all of the clusters are monoclonal amplification clusters. In some embodiments, fewer than 15% of all of the clusters are monoclonal amplification clusters. In some embodiments, fewer than 10% of all of the clusters are monoclonal amplification clusters. In some embodiments, fewer than 5% of all of the clusters are monoclonal amplification clusters. In some embodiments, fewer than 1% of all of the clusters are monoclonal amplification clusters.

In some embodiments, at least 30% of all of the clusters are overlapping amplification clusters. In some embodiments, at least 35% of all of the clusters are overlapping amplification clusters. In some embodiments, at least 40% of all of the clusters are overlapping amplification clusters. In some embodiments, at least 45% of all of the clusters are overlapping amplification clusters. In some embodiments, at least 50% of all of the clusters are overlapping amplification clusters. In some embodiments, at least 55% of all of the clusters are overlapping amplification clusters. In some embodiments, at least 60% of all of the clusters are overlapping amplification clusters. In some embodiments, at least 65% of all of the clusters are overlapping amplification clusters. In some embodiments, at least 70% of all of the clusters are overlapping amplification clusters. In some embodiments, at least 75% of all of the clusters are overlapping amplification clusters. In some embodiments, at least 80% of all of the clusters are overlapping amplification clusters. In some embodiments, at least 85% of all of the clusters are overlapping amplification clusters. In some embodiments, at least 90% of all of the clusters are overlapping amplification clusters. In some embodiments, at least 95% of all of the clusters are overlapping amplification clusters. In some embodiments, 100% of all of the clusters are overlapping amplification clusters.

In embodiments, the amplicons of a first template polynucleotide include at least one cleavable site. In embodiments, the method further includes removing the amplicons of a first template polynucleotide by cleaving the amplicons at a cleavable site. In some embodiments, cleaving includes enzymatically or chemically cleaving the at least one cleavable site. In embodiments, the cleavable site includes a diol linker, disulfide linker, photocleavable linker, abasic site, deoxyuracil triphosphate (dUTP), deoxy-8-oxo-guanine triphosphate (d-8-oxoG), methylated nucleotide, ribonucleotide, or a sequence containing a modified or unmodified nucleotide that is specifically recognized by a cleaving agent. In embodiments, cleaving the amplicons of a first template polynucleotide includes contacting the cleavable site with a cleaving agent, wherein the cleaving agent includes a reducing agent, sodium periodate, RNase, formamidopyrimidine DNA glycosylase (Fpg), endonuclease, or uracil DNA glycosylase (UDG). In embodiments, the cleaving agent is an endonuclease enzyme such as nuclease P1, AP endonuclease, T7 endonuclease, T4 endonuclease IV, Bal 31 endonuclease, Endonuclease I (endo I), Micrococcal nuclease, Endonuclease II (endo VI, exo III), nuclease BAL-31 or mung bean nuclease. In embodiments, the cleaving agent includes a restriction endonuclease, including, for example a type IIS restriction endonuclease. In embodiments, the cleaving agent is an exonuclease (e.g., RecBCD), restriction nuclease, endoribonuclease, exoribonuclease, or RNAse (e.g., RNAse I, II, or III). In embodiments, the cleaving agent is a restriction enzyme. In embodiments, the cleaving agent includes a glycosylase and one or more suitable endonucleases. In embodiments, cleavage is performed under alkaline (e.g., pH greater than 8) buffer conditions at between 40° C. to 80° C.

In embodiments, both strands of the double-stranded polynucleotide (e.g., the template polynucleotide and the complement thereof) are sequenced. For example, in embodiments, a first invasion strand is generated by hybridizing an invasion primer to the second strand of the double-stranded amplification product, and extending the invasion primer, wherein the invasion primer is not covalently attached to the solid support; and generating a first sequencing read by hybridizing one or more sequencing primers to the first strand, and extending the one or more first sequencing primers. In embodiments, the method further includes removing the first invasion strand; generating a second invasion strand hybridized to the first strand by hybridizing a second invasion primer to the first strand, and extending the second invasion primer, wherein the second invasion primer is not covalently attached to the solid support; and generating a second sequencing read by hybridizing one or more second sequencing primers to the second strand, and extending the one or more second sequencing primers. In embodiments, additional invasion strands may be generated (e.g., a third invasion strand, a fourth invasion strand, etc.) by hybridizing an invasion primer to the first or second strand of additional double-stranded amplification products of the overlapping amplification clusters, and further generating additional sequencing reads (e.g., generating a third sequencing read, generating a fourth sequencing read, etc.). Additional methods of invasion strand synthesis and methods thereof are described in U.S. patent application Ser. No. 17/666,458, which is incorporated herein by reference in its entirety. Alternatively, paired-read methods known in the art include hybridizing a first sequencing primer and sequencing a first strand, removing the first sequencing primer and the extension product generated during sequencing, hybridizing a second sequencing primer to the complementary strand (i.e., the second strand) and sequencing the second strand. Optionally, the first strand may be cleaved and removed prior to sequencing the complementary strand.

In embodiments, prior to generating a first invasion strand, the method includes removing immobilized primers that do not contain a first or second strand (i.e., unused primers).

Methods of removing immobilized primers can include digestion using an enzyme with exonuclease activity. Removing unused primers may serve to increase the free volume and allow for greater accessibility of the invasion primer. Removal of unused primers may also prevent opportunities for the newly released first strand to rehybridize to an available surface primer, producing a priming site off the available surface primer, thereby facilitating the "reblocking" of the released first strand.

In embodiments, prior to generating a first invasion strand, the method includes blocking the immobilized primers that do not include a first or second strand. In embodiments, the immobilized oligonucleotides include blocking groups at their 3' ends that prevent polymerase extension. A blocking moiety prevents formation of a covalent bond between the 3' hydroxyl moiety of the nucleotide and the 5' phosphate of another nucleotide. In embodiments, prior to generating a first invasion strand the method includes incubating the amplification products with dideoxynucleotide triphosphates (ddNTPs) to block the 3'-OH of the immobilized oligonucleotides from future extension.

In embodiments, the invasion primer includes a cleavable site. In embodiments, the cleavable site is located at the 3' end of the invasion primer. In embodiments, the method further includes cleaving the cleavable site in the invasion primer to generate a free 3' end within the invasion primer, removing the invasion strand, and generating a second sequencing read by extending the invasion primer.

Any suitable enzymatic, chemical, or photochemical cleavage reaction may be used to cleave the cleavable site. The cleavage reaction may result in removal of a part or the whole of the template polynucleotide being cleaved. Suitable cleavage means include, for example, restriction enzyme digestion, in which case the cleavable site is an appropriate restriction site for the enzyme which directs cleavage of one or both strands of a duplex template; RNase digestion or chemical cleavage of a bond between a deoxyribonucleotide and a ribonucleotide, in which case the cleavable site may include one or more ribonucleotides; chemical reduction of a disulfide linkage with a reducing agent (e.g., THPP or TCEP), in which case the cleavable site should include an appropriate disulfide linkage; chemical cleavage of a diol linkage with periodate, in which case the cleavable site should include a diol linkage; generation of an abasic site and subsequent hydrolysis, etc. In embodiments, the cleavable site is included in the surface immobilized primer (e.g., within the polynucleotide sequence of the primer). In embodiments, one strand of the double-stranded amplification product (or the surface immobilized primer) may include a diol linkage which permits cleavage by treatment with periodate (e.g., sodium periodate). It will be appreciated that more than one diol can be included at the cleavable site. One or more diol units may be incorporated into a polynucleotide using standard methods for automated chemical DNA synthesis. Polynucleotide primers including one or more diol linkers can be conveniently prepared by chemical synthesis. The diol linker is cleaved by treatment with any substance which promotes cleavage of the diol (e.g., a diol-cleaving agent). In embodiments, the diol-cleaving agent is periodate, e.g., aqueous sodium periodate ($NaIO_4$). Following treatment with the diol-cleaving agent (e.g., periodate) to cleave the diol, the cleaved product may be treated with a "capping agent" in order to neutralize reactive species generated in the cleavage reaction. Suitable capping agents for this purpose include amines, e.g., ethanolamine or propanolamine.

In embodiments, the cleavable site is not in the immobilized primer sequence (e.g., within the polynucleotide sequence of the primer). In embodiments, the cleavable site is included in the linking moiety responsible for tethering the primer to the substrate. In embodiments, the cleavable site is a cleavable linker (e.g., a disulfide containing linker that cleaves when exposed to a reducing agent).

In embodiments, the cleavable site includes one or more ribonucleotides. In embodiments, the cleavable site includes 2 to 5 ribonucleotides. In embodiments, the cleavable site includes one ribonucleotide. In embodiments, the cleavable site includes more than one ribonucleotide. In embodiments, the cleavable site includes deoxyuracil triphosphate (dUTP) or deoxy-8-oxo-guanine triphosphate (d-8-oxoG).

In some embodiments, the method includes about 5 to about 200 sequencing cycles (e.g., about 5 to about 200 sequencing cycles per sequencing primer). In some embodiments, the method includes about 8 to about 200 sequencing cycles. In some embodiments, the method includes about 10 to about 200 sequencing cycles. In some embodiments, the method includes about 15 to about 200 sequencing cycles. In some embodiments, the method includes about 20 to about 200 sequencing cycles. In some embodiments, the method includes about 30 to about 200 sequencing cycles. In some embodiments, the method includes about 40 to about 200 sequencing cycles. In some embodiments, the method includes about 50 to about 200 sequencing cycles. In embodiments, the method includes about 5 sequencing cycles. In embodiments, the method includes about 8 sequencing cycles. In embodiments, the method includes about 10 sequencing cycles. In embodiments, the method includes about 15 sequencing cycles. In embodiments, the method includes about 20 sequencing cycles. In embodiments, the method includes about 30 sequencing cycles. In embodiments, the method includes about 40 sequencing cycles. In embodiments, the method includes about 50 sequencing cycles. In embodiments, the method includes about 75 sequencing cycles. In embodiments, the method includes about 100 sequencing cycles. In embodiments, the method includes about 125 sequencing cycles. In embodiments, the method includes about 150 sequencing cycles. In embodiments, the method includes about 175 sequencing cycles. In embodiments, the method includes about 200 sequencing cycles. In some embodiments, the method includes about 5 to about 200 sequencing cycles per sequencing primer. Thus, depending on the number of sequencing primers used, multiple sets of sequencing cycles may be employed (e.g., a first set of 200 cycles, a second set of 200 cycles, a third set of 200 cycles) resulting in a cumulative total of sequencing cycles that is the sum of each set of sequencing cycles.

In some embodiments, the method includes a sequencing reaction mixture including a different sequencing primer every about 5 to about 50 sequencing cycles. In some embodiments, the method includes a sequencing reaction mixture including a different sequencing primer every about 5, 10, 15, 20, 30, 40, or 50 sequencing cycles. In some embodiments, the method includes a sequencing reaction mixture including a different sequencing primer every about 25 to about 75 sequencing cycles. In some embodiments, the method includes a sequencing reaction mixture including a different sequencing primer every about 25, 30, 35, 40, 45, 50, 55, 60, 65, 70, or 75 sequencing cycles. In embodiments, the method includes a sequencing reaction mixture including a different sequencing primer every about 5 to about 50 sequencing cycles, wherein each sequencing primer is not used more than once during the entire sequencing run. In embodiments, the method includes a sequencing reaction mixture including a different sequencing primer every about 25 to about 75 sequencing cycles, wherein each sequencing primer is not used more than once during the entire sequencing run. In embodiments, the method includes a sequencing reaction mixture including a different sequencing primer every about 5, 10, 15, 20, 30, 40, or 50 sequencing cycles, wherein each sequencing primer is not used more than once during the entire sequencing run. In embodiments, the method includes a sequencing reaction mixture including a different sequencing primer every about 25, 30, 35, 40, 45, 50, 55, 60, 65, 70, or 75 sequencing cycles, wherein each sequencing primer is not used more than once during the entire sequencing run. In embodiments, the method includes a sequencing reaction mixture including one or more different sequencing primers every about 5 to about 50 sequencing cycles. In embodiments, the method includes a sequencing reaction mixture including one or more different sequencing primers every about 25 to about 75 sequencing cycles. In embodiments, the method includes a sequencing reaction mixture including one or more different sequencing primers every about 5, 10, 15, 20, 30, 40, or 50 sequencing cycles. In embodiments, the method includes a sequencing reaction mixture including one or more different sequencing primers every about 25, 30, 35, 40, 45, 50, 55, 60, 65, 70, or 75 sequencing cycles.

In embodiments, the method further includes incorporating with a polymerase a plurality of native deoxy nucleotide triphosphates (dNTPs) prior to hybridizing the next sequencing primer. In embodiments, the method further includes incorporating with a polymerase a plurality of native deoxy nucleotide triphosphates (dNTPs) prior to hybridizing the next sequencing primer into a 3' end of the extended sequencing primer. In some embodiments, the method includes incorporating a plurality of native deoxy nucleotide triphosphates (dNTPs) into the 3' end of the extended sequencing primer. In some embodiments, the method includes incorporating a plurality of native deoxy nucleotide triphosphates (dNTPs) into the 3' end of the extended sequencing primer until the entire template has been copied. In embodiments, the method includes incorporating a plurality of native dNTPs into the 3' end of the extended sequencing primer until the entire template has been copied, wherein the plurality of native dNTPs is introduced every about 25 to about 75 sequencing cycles.

In embodiments, the method further includes incorporating a non-extendable nucleotide (e.g., a dideoxy nucleotide triphosphate (ddNTP)) prior to hybridizing the next sequencing primer. In embodiments, the method further includes incorporating a dideoxy nucleotide triphosphate (ddNTP) prior to hybridizing the next sequencing primer. In embodiments, the method further includes incorporating a dideoxy nucleotide triphosphate (ddNTP) prior to hybridizing the next sequencing primer into a 3' end of each of a plurality of extended sequencing primers. In some embodiments, the method includes incorporating one or more dideoxy nucleotide triphosphates (ddNTPs) into the 3' end of each extended sequencing primer. In embodiments, one or more ddNTPs are incorporated into the 3' end of each extended sequencing primer every about 25 to about 75 sequencing cycles.

In some embodiments, the method includes a sequencing reaction mixture including a plurality of different sequencing primer species, wherein all but one of the sequencing primer species is terminated with one or more irreversibly terminated nucleotide at the 3' end. In some embodiments, the method includes a sequencing reaction mixture including a plurality of different sequencing primer species, wherein all but one of the sequencing primer species is terminated with one or more ddNTPs (e.g., ddCTP, ddATP, ddGTP, or ddTTP) at the 3' end. In embodiments, a cleavable site is present next to the one or more ddNTPs on the 3' end, wherein the cleavable site precedes the ddNTPs. In embodiments, the number of different sequencing primer species corresponds to the number of unique adapter sequences and sequencing primer regions present on the template polynucleotides on the surface. For example, if 4 unique sequencing primer binding sites are present on the template polynucleotides, then the sequencing reaction mixture would contain 1 sequencing primer with an extendable 3' end (e.g., a 3'-OH), and 3 sequencing primers with a cleavable site and one or more ddNTPs at the 3' end. All sequencing primers would hybridize to the complementary adapter sequences simultaneously. In embodiments, each cleavable site present in each terminated sequencing primer species is different from the other cleavable sites of the other terminated sequencing primer species. After sufficient sequencing reads have been generated from the first sequencing primer, extension may be terminated, for example, by incorporation of a ddNTP. Subsequently, a cleaving agent as described herein is introduced to generate an extendable 3' end on a subsequent sequencing primer. In some embodiments, after about 25 to about 75 sequencing cycles, the extended sequencing primer is terminated with a ddNTP, a new cleavable site is cleaved, and sequencing of with a new sequencing primer is initiated.

In some embodiments, the template polynucleotide includes genomic DNA, complementary DNA (cDNA), cell-free DNA (cfDNA), messenger RNA (mRNA), transfer RNA (tRNA), ribosomal RNA (rRNA), cell-free RNA (cfRNA), or noncoding RNA (ncRNA).

In embodiments, the template polynucleotide is about 20 to 100 nucleotides in length. In embodiments, the template polynucleotide is about 30 to 100 nucleotides in length. In embodiments, the template polynucleotide is about 40 to 100 nucleotides in length. In embodiments, the template polynucleotide is about 50 to 100 nucleotides in length. In embodiments, the template polynucleotide is about 60 to 100 nucleotides in length. In embodiments, the template polynucleotide is about 70 to 100 nucleotides in length. In embodiments, the template polynucleotide is about 80 to 100 nucleotides in length. In embodiments, the template polynucleotide is about 90 to 100 nucleotides in length. In embodiments, the template polynucleotide is about 20 to 200 nucleotides in length. In embodiments, the template polynucleotide is about 30 to 200 nucleotides in length. In embodiments, the template polynucleotide is about 40 to 200 nucleotides in length. In embodiments, the template polynucleotide is about 50 to 200 nucleotides in length. In embodiments, the template polynucleotide is about 60 to 200 nucleotides in length. In embodiments, the template polynucleotide is about 70 to 200 nucleotides in length. In embodiments, the template polynucleotide is about 80 to 200 nucleotides in length. In embodiments, the template polynucleotide is about 90 to 200 nucleotides in length. In embodiments, the template polynucleotide is about 100 to 200 nucleotides in length. In embodiments, the template polynucleotide is less than about 50 nucleotides in length. In embodiments, the template polynucleotide is less than about 75 nucleotides in length. In embodiments, the template polynucleotide is less than about 100 nucleotides in length. In embodiments, the template polynucleotide is less than about 125 nucleotides in length. In embodiments, the template polynucleotide is less than about 150 nucleotides in length. In embodiments, the template polynucleotide is less than about 175 nucleotides in length. In embodiments, the template polynucleotide is less than about 200 nucleotides in length.

In embodiments, amplifying includes bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, emulsion PCR, or combinations thereof. In embodiments, amplifying includes bridge polymerase chain reaction (bPCR) amplification, solid-phase rolling circle amplification (RCA), or solid-phase exponential rolling circle amplification (eRCA).

In some embodiments, amplifying includes bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, or emulsion PCR on particles, or combinations thereof. In embodiments, amplifying includes a bridge polymerase chain reaction (bPCR) amplification. In embodiments, amplifying includes a thermal bridge polymerase chain reaction (t-bPCR) amplification. In embodiments, amplifying includes a chemical bridge polymerase chain reaction (c-bPCR) amplification. Chemical bridge polymerase chain reactions include fluidically cycling a denaturant (e.g., formamide) and maintaining the temperature within a narrow temperature range (e.g., +/−5° C.). In contrast, thermal bridge polymerase chain reactions include thermally cycling between high temperatures (e.g., 85° C.-95° C.) and low temperatures (e.g., 60° C.-70° C.). Thermal bridge polymerase chain reactions may also include a denaturant, typically at a much lower concentration than traditional chemical bridge polymerase chain reactions.

In embodiments, the amplifying is at discrete locations in an ordered array of amplification sites on the surface. In some embodiments, the surface does not include an ordered array of amplification sites. For example, the surface may be uniformly coated with amplification primers, rather than coating some areas (amplification sites) and not others (interstitial regions).

In embodiments, the sequencing includes sequencing-by-synthesis, sequencing by ligation, or pyrosequencing. In embodiments, generating a first sequencing read or a second sequencing read includes a sequencing by synthesis process.

In embodiments, sequentially sequencing the amplification clusters includes generating a plurality of sequencing reads. In embodiments, sequentially sequencing the amplification clusters produces one or more sequencing reads.

In embodiments, monitoring the sequential incorporation of complementary nucleotides includes a sequencing-by-synthesis, sequencing-by-ligation, or sequencing-by-binding process.

In embodiments, monitoring the sequential incorporation of complementary nucleotides includes incorporating one or more modified nucleotides into the sequencing primer with a polymerase to create an extension strand, and detecting the one or more incorporated nucleotides so as to identify each incorporated nucleotide in said extension strand, thereby generating one or more sequencing reads.

In embodiments, monitoring the sequential incorporation of complementary nucleotides includes incorporating one or more modified nucleotides into the first sequencing primer with a polymerase to create an extension strand, and detecting the one or more incorporated nucleotides in a first optically resolvable feature; incorporating one or more modified nucleotides into the second sequencing primer with a polymerase to create an extension strand, and detecting the one or more incorporated nucleotides in a second optically resolvable feature; incorporating one or more modified nucleotides into the third sequencing primer with a polymerase to create an extension strand, and detecting the one or more incorporated nucleotides in a third optically resolvable feature; and incorporating one or more modified nucleotides into the fourth sequencing primer with a polymerase to create an extension strand, and detecting the one or more incorporated nucleotides in a fourth optically resolvable feature; wherein the optically resolvable features overlap.

In embodiments, sequentially sequencing the amplification clusters includes a sequencing-by-synthesis or sequencing-by-binding process.

In embodiments, sequentially sequencing the amplification clusters includes extending the sequencing primer with a labeled modified nucleotide and detecting the incorporated labeled modified nucleotide.

In embodiments, sequentially sequencing the amplification clusters includes specifically contacting the sequencing primer with a polymerase and a labeled modified nucleotide and detecting the specific contacting.

In embodiments, generating a sequencing read includes executing a plurality of sequencing cycles, each cycle including extending the sequencing primer by incorporating a nucleotide or nucleotide analogue using a polymerase and detecting a characteristic signature indicating that the nucleotide or nucleotide analogue has been incorporated.

In embodiments, the method includes sequencing the first and/or the second strand of a double-stranded amplification product by extending a sequencing primer hybridized thereto. A variety of sequencing methodologies can be used such as sequencing-by-synthesis (SBS), pyrosequencing, sequencing by ligation (SBL), or sequencing by hybridization (SBH). Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210,891; 6,258,568; and. 6,274,320, each of which is incorporated herein by reference in its entirety). In pyrosequencing, released PPi can be detected by being converted to adenosine triphosphate (ATP) by ATP sulfurylase, and the level of ATP generated can be detected via light produced by luciferase. In this manner, the sequencing reaction can be monitored via a luminescence detection system. In both SBL and SBH methods, target nucleic acids, and amplicons thereof, that are present at features of an array are subjected to repeated cycles of oligonucleotide delivery and detection. SBL methods, include those described in Shendure et al. Science 309:1728-1732 (2005); U.S. Pat. Nos. 5,599,675; and 5,750,341, each of which is incorporated herein by reference in its entirety; and the SBH methodologies are as described in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977, each of which is incorporated herein by reference in its entirety.

In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. A plurality of different nucleic acid fragments that have been attached at different locations of an array can be subjected to an SBS technique under conditions where events occurring for different templates can be distinguished due to their location in the array. In embodiments, the sequencing step includes annealing and extending a sequencing primer to incorporate a detectable label that indicates the identity of a nucleotide in the target polynucleotide, detecting the detectable label, and repeating the extending and detecting steps. In embodiments, the methods include sequencing one or more bases of a target nucleic acid by extending a sequencing primer hybridized to a target nucleic acid (e.g., an amplification product produced by the amplification methods described herein). In embodiments, the sequencing step may be accomplished by a sequencing-by-synthesis (SBS) process. In embodiments, sequencing comprises a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 10,738,072, 7,541,444 and 7,057,026. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template. Non-limiting examples of suitable labels are described in U.S. Pat. Nos. 8,178,360, 5,188,934 (4,7-dichlorofluorscein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthene dyes): U.S. Pat. No. 5,688,648 (energy transfer dyes); and the like.

In embodiments, sequencing is performed according to a "sequencing-by-binding" method (see, e.g., U.S. Pat. Pubs. US2017/0022553 and US2019/0048404, each of which is incorporated herein by reference in its entirety), which refers to a sequencing technique wherein specific binding of a polymerase and cognate nucleotide to a primed template nucleic acid molecule (e.g., blocked primed template nucleic acid molecule) is used for identifying the next correct nucleotide to be incorporated into the primer strand of the primed template nucleic acid molecule. The specific binding interaction need not result in chemical incorporation of the nucleotide into the primer. In some embodiments, the specific binding interaction can precede chemical incorporation of the nucleotide into the primer strand or can precede chemical incorporation of an analogous, next correct nucleotide into the primer. Thus, detection of the next correct nucleotide can take place without incorporation of the next correct nucleotide.

In embodiments, the first sequencing primer and the second sequencing primer are hybridized simultaneously to the first template polynucleotide and the second template polynucleotide. In embodiments, the first sequencing primer and the second sequencing primer are hybridized sequentially to the first template polynucleotide and the second template polynucleotide. In embodiments, the second sequencing primer is hybridized to the second template polynucleotide after the sequencing read for the first template polynucleotide has been generated. In embodiments, the second sequencing primer is hybridized to the second template polynucleotide before the sequencing read for the first template polynucleotide has been generated. In embodiments, the second sequencing primer is hybridized to the second template polynucleotide while the sequencing read for the first template polynucleotide is being generated. In embodiments, the third sequencing primer and the fourth sequencing primer are hybridized simultaneously to the third template polynucleotide and the fourth template polynucleotide. In embodiments, the third sequencing primer and the fourth sequencing primer are hybridized sequentially to the third template polynucleotide and the fourth template polynucleotide. In embodiments, the fourth sequencing primer is hybridized to the fourth template polynucleotide after the sequencing read for the third template polynucleotide has been generated. In embodiments, the fourth sequencing primer is hybridized to the fourth template polynucleotide before the sequencing read for the third template polynucleotide has been generated. In embodiments, the fourth sequencing primer is hybridized to the fourth template polynucleotide while the sequencing read for the third template polynucleotide is being generated.

In embodiments, the first sequencing primer and the second sequencing primer are hybridized simultaneously to the first template polynucleotide and the second template polynucleotide, wherein one of the first sequencing primer or the second sequencing primer further includes a blocking element (e.g., a blocking element that prevents nucleotide incorporation with a polymerase). In embodiments, the blocking element is reversible. In embodiments, the blocking element is a ddNTP, a uracil, or a combination thereof (e.g., a ddNTP and a uracil). In embodiments the blocking element is a reversible terminator. In embodiments, once the sequencing read for the first template polynucleotide is generated, the blocking element of the second sequencing primer is removed and the sequencing read for the second template polynucleotide is generated (e.g., a uracil 5' of a ddNTP in the second sequencing primer is cleaved, the free 3' end is dephosphorylated with calf intestinal alkaline phosphatase (CIP) or T4 polynucleotide kinase (PNK), and a second sequencing process is initiated). In embodiments, once the sequencing read for the second template polynucleotide is generated, the blocking element of the first sequencing primer is removed and the sequencing read for the first template polynucleotide is generated (e.g., a uracil 5' of a ddNTP in the first sequencing primer is cleaved, the free 3' end is dephosphorylated with calf intestinal alkaline phosphatase (CIP) or T4 polynucleotide kinase (PNK), and a second sequencing process is initiated).

In embodiments, the third sequencing primer and the fourth sequencing primer are hybridized simultaneously to the third template polynucleotide and the fourth template polynucleotide, wherein one of the third sequencing primer or the fourth sequencing primer further includes a blocking element (e.g., a blocking element that prevents nucleotide incorporation with a polymerase). In embodiments, the blocking element is reversible. In embodiments, the blocking element is a ddNTP, a uracil, or a combination thereof (e.g., a ddNTP and a uracil). In embodiments the blocking element is a reversible terminator. In embodiments, once the sequencing read for the third template polynucleotide is generated, the blocking element of the fourth sequencing primer is removed and the sequencing read for the fourth template polynucleotide is generated (e.g., a uracil 5' of a ddNTP in the fourth sequencing primer is cleaved, the free 3' end is dephosphorylated with calf intestinal alkaline phosphatase (CIP) or T4 polynucleotide kinase (PNK), and a second sequencing process is initiated). In embodiments, once the sequencing read for the fourth template polynucleotide is generated, the blocking element of the third sequencing primer is removed and the sequencing read for the third template polynucleotide is generated (e.g., a uracil 5' of a ddNTP in the third sequencing primer is cleaved, the free 3' end is dephosphorylated with calf intestinal alkaline phosphatase (CIP) or T4 polynucleotide kinase (PNK), and a second sequencing process is initiated).

In embodiments, the blocking element includes an oligo, a protein, or a combination thereof. In embodiments, the blocking element includes an oligo. In embodiments, the blocking element is an oligo. In embodiments, the blocking element is an oligonucleotide having 5-25 nucleotides. In embodiments, the blocking element is an oligonucleotide having 10-50 nucleotides. In embodiments, the blocking element is an oligonucleotide having 20-75 nucleotides. In embodiments, the blocking element is an oligonucleotide having about 5, about 10, about 20, about 25, about 50, or about 75 nucleotides. In embodiments, the blocking element is a non-extendable oligomer. In embodiments, the blocking element includes two or more tandemly arranged oligos. In embodiments, the blocking element is a single-stranded oligonucleotide having a 5' end and a 3' end. In embodiments, the blocking element includes a 3'-blocked oligo. In embodiments, the blocking element includes a blocking moiety on the 3' nucleotide. A blocking moiety on a nucleotide can be reversible, whereby the blocking moiety can be removed or modified to allow the 3' hydroxyl to form a covalent bond with the 5' phosphate of another nucleotide. For example, a reversible terminator may refer to a blocking moiety located, for example, at the 3' position of the nucleotide and may be a chemically cleavable moiety such as an allyl group, an azidomethyl group or a methoxymethyl group, or may be an enzymatically cleavable group such as a phosphate ester. In embodiments the blocking moiety is not reversible (e.g., the blocking element including a blocking moiety irreversibly prevents extension).

In embodiments, the blocking element includes an oligo having a 3' dideoxynucleotide or similar modification to prevent extension by a polymerase and is used in conjunction with a non-strand displacing polymerase. In some embodiments, the blocking oligomer contains one or more non-natural bases that facilitate hybridization of the blocker to the target sequence (e.g., LNA bases). In some embodiments, the blocking oligomer contains other modified bases to increase resistance to exonuclease digestion (e.g., one or more phosphorothioate bonds). In embodiments, the blocking element is an oligonucleotide including one or more modified nucleotides, such as iso dGTP or iso dCTP, which are complementary to each other. In a reaction of polymerization lacking the complementary modified nucleotides, extension is blocked. In another embodiment, the blocking element is an oligonucleotide including a 3' cleavable linker containing PEG, thereby blocking extension. In another embodiment, the blocking element is an oligonucleotide including one or more sequences which are recognized and bound by one or more short RNA or PNA oligos, thereby blocking the extension by a strand displacing DNA polymerase that cannot strand displace RNA or PNA. In embodiments, the blocking element is a modified nucleotide (e.g., a nucleotide including a reversible terminator, such as a 3'-reversible terminating moiety).

In embodiments, the blocking element includes an oligo, a protein, or a combination thereof. In embodiments, the blocking element includes a protein. In embodiments, the blocking element includes one or more proteins. The blocking element need not be an oligomer; in some embodiments, for example, the blocking element is a protein that selectively binds to the target sequence and prevents polymerase extension. In embodiments, the blocking element is an oligonucleotide including one or more modified nucleotides. In embodiments, the blocking element is an oligonucleotide including one or more modified nucleotides, wherein one or more modified nucleotides is linked to biotin, to which a protein (e.g., streptavidin) can be bound, thereby blocking polymerase extension. In embodiments, the blocking element includes one or more sequences which is recognized and bound by one or more single-stranded DNA-binding proteins, thereby blocking polymerase extension at the bound site.

In embodiments, sequencing includes hybridizing a first sequencing primer to a first amplification product or complement thereof, incorporating one or more modified nucleotides into the sequencing primer with a polymerase to create an extension strand, and detecting the one or more incorporated nucleotides in a first optically resolvable feature; and hybridizing a second sequencing primer to a second amplification product or complement thereof, incorporating one or more modified nucleotides into the sequencing primer with a polymerase to create an extension strand, and detecting the one or more incorporated nucleotides in a second optically resolvable feature; wherein the first and second optically resolvable features overlap. In embodiments, the method further includes incorporating a dideoxy nucleotide triphosphate (ddNTP) into the extension strand prior to hybridizing the second sequencing primer.

In embodiments, the overlapping optically resolvable features overlap by at least 25%, at least 50%, or at least 75%. In embodiments, the overlapping optically resolvable features overlap by greater than 75%. In embodiments, the overlapping optically resolvable features overlap by about 25%, about 50%, or about 75%. In embodiments, the overlapping optically resolvable features overlap by about 25%. In embodiments, the overlapping optically resolvable features overlap by about 50%. In embodiments, the overlapping optically resolvable features overlap by 75%. In embodiments, the overlapping optically resolvable features overlap by 10%, 20%, 30%, 40%, 50% or more.

In embodiments, the optically resolvable feature includes an area of about 0.5 µm² to about 1.5 µm². In embodiments, the optically resolvable feature includes an area of about 0.5 µm², about 0.6 µm², about 0.7 µm², about 0.8 µm², about 0.9 µm², about 1.0 µm², about 1.1 µm², about 1.2 µm², about 1.3 µm², about 1.4 µm², or about 1.5 µm².

In embodiments, the optically resolvable features overlap by at least 25%, at least 50%, or at least 75%. In embodiments, the optically resolvable features overlap by greater than 75%.

In embodiments, the sequencing primer is a sequence selected from the group consisting of SEQ ID NO:1 to SEQ ID NO:96, or a complement thereof.

Sequencing includes, for example, detecting a sequence of signals. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the nucleotides are labeled with at least two unique fluorescent dyes. In embodiments, the readout is accomplished by epifluorescence imaging. A variety of sequencing chemistries are available, non-limiting examples of which are described herein.

Flow cells provide a convenient format for housing an array of clusters produced by the methods described herein, in particular when subjected to an SBS or other detection technique that involves repeated delivery of reagents in cycles. For example, to initiate a first SBS cycle, one or more labeled nucleotides and a DNA polymerase in a buffer, can be flowed into/through a flow cell that houses an array of clusters. The clusters of an array where primer extension causes a labeled nucleotide to be incorporated can then be detected. Optionally, the nucleotides can further include a reversible termination moiety that temporarily halts further primer extension once a nucleotide has been added to a primer. For example, a nucleotide analog having a reversible terminator moiety can be added to a primer such that subsequent extension cannot occur until a deblocking agent (e.g., a reducing agent) is delivered to remove the moiety. Thus, for embodiments that use reversible termination, a deblocking reagent (e.g., a reducing agent) can be delivered to the flow cell (before, during, or after detection occurs). Washes can be carried out between the various delivery steps as needed. The cycle can then be repeated N times to extend the primer by N nucleotides, thereby detecting a sequence of length N. Example SBS procedures, fluidic systems and detection platforms that can be readily adapted for use with an array produced by the methods of the present disclosure are described, for example, in Bentley et al., Nature 456: 53-59 (2008), US Patent Publication 2018/0274024, WO 2017/205336, US Patent Publication 2018/0258472, each of which are incorporated herein in their entirety for all purposes.

Use of the sequencing method outlined above is a non-limiting example, as essentially any sequencing methodology which relies on successive incorporation of nucleotides into a polynucleotide chain can be used. Suitable alternative techniques include, for example, pyrosequencing methods, FISSEQ (fluorescent in situ sequencing), MPSS (massively parallel signature sequencing), or sequencing by ligation-based methods.

In embodiments, generating a sequencing read includes determining the identity of the nucleotides in the template polynucleotide (or complement thereof). In embodiments, a sequencing read, e.g., a first sequencing read or a second sequencing read, includes determining the identity of a portion (e.g., 1, 2, 5, 10, 20, 50 nucleotides) of the total template polynucleotide. In embodiments the first sequencing read determines the identity of 5-10 nucleotides and the second sequencing read determines the identity of more than 5-10 nucleotides (e.g., 11 to 200 nucleotides). In embodiments the first sequencing read determines the identity of more than 5-10 nucleotides (e.g., 11 to 200 nucleotides) and the second sequencing read determines the identity of 5-10 nucleotides. In embodiments, following the generation of a sequencing read, subsequent extension is performed using a plurality of standard (e.g., non-modified) dNTPs until the complementary strand is copied. In other embodiments, following the generation of a sequencing read, subsequent extension is performed using a plurality of dideoxy nucleotide triphosphates (ddNTPs) to prevent further extension of the first sequencing read product during a second sequencing read. In embodiments, following the identification of at least 5-10 (e.g., 11 to 200 nucleotides, or up to 1000 nucleotides), subsequent extension is performed using a plurality of standard (e.g., non-modified) dNTPs until the complementary strand is copied. In embodiments, following the identification of at least 5-10 (e.g., 11 to 200 nucleotides, or up to 1000 nucleotides), subsequent extension is performed using a plurality of dideoxy nucleotide triphosphates (ddNTPs) to prevent further extension of the sequencing read product.

In embodiments, the method includes generating about 500 million (M) to about $3 \times 10^{11}$ sequencing reads. In embodiments, the method includes generating about 500 million, about 750 million, about $1 \times 10^9$, about $2 \times 10^9$, about $3 \times 10^9$, about $4 \times 10^9$, about $5 \times 10^9$, about $6 \times 10^9$, about $7 \times 10^9$, about $8 \times 10^9$, about $9 \times 10^9$, about $1 \times 10^{10}$, about $2 \times 10^{10}$, about $3 \times 10^{10}$, about $4 \times 10^{10}$, about $5 \times 10^{10}$, about $6 \times 10^{10}$, about $7 \times 10^{10}$, about $8 \times 10^{10}$, about $9 \times 10^{10}$, about $1 \times 10^{11}$, about $2 \times 10^{11}$, or about $3 \times 10^{11}$ sequencing reads.

In embodiments, the method produces about 300 million sequencing reads, with greater than 99.9% accuracy. In embodiments, the method produces about 450 million sequencing reads, with greater than 99.9% accuracy. In embodiments, the method produces about 500 million sequencing reads, with greater than 99.9% accuracy. In embodiments, the method produces about 600 million sequencing reads, with greater than 99.9% accuracy. In embodiments the method produces about 750 million sequencing reads, with greater than 99.9% accuracy. In embodiments, the method produces about 1 billion sequencing reads, with greater than 99.9% accuracy. In embodiments, the method produces about 1, with greater than 99.9% accuracy. 2 billion sequencing reads, with greater than 99.9% accuracy. In embodiments, the method produces between about 300 million and 600 million sequencing reads, with greater than 99.9% accuracy. In embodiments, the method produces between about 600 million and 1 billion sequencing reads, with greater than 99.9% accuracy. In embodiments the method produces between about 1 billion and 1, with greater than 99.9% accuracy. 2 billion sequencing reads, with greater than 99.9% accuracy. In embodiments, the method produces more than 1, with greater than 99.9% accuracy. 2 billion sequencing reads, with greater than 99.9% accuracy. Base calling accuracy, measured by the Phred quality score (Q score), is the most common metric used to assess the accuracy of a sequencing platform. It indicates the probability that a given base is called incorrectly by the sequencer. For example, if the base calling algorithm assigns a Q score of 30 (Q30) to a base, this is equivalent to the probability of an incorrect base call 1 in 1000 times. This means that the base call accuracy (i.e., the probability of a correct base call) is 99.9%. In embodiments, the accuracy is 99.99%. In embodiments, the accuracy is 99.999%. In embodiments, the accuracy is 99.9999%. In embodiments, the accuracy is between about 99.9999% to 100%. In embodiments, the accuracy is between about 99.999% to 100%. In embodiments, the accuracy is between about 99.99% to 100%.

In embodiments, the method produces about 500 million sequencing reads. In embodiments, the method produces about 600 million sequencing reads. In embodiments, the method produces about 750 million sequencing reads. In embodiments, the method produces about 900 million sequencing reads. In embodiments, the method produces about 1 billion sequencing reads. In embodiments, the method produces about 1.2 billion sequencing reads. In embodiments, the method produces about 1.5 billion sequencing reads. In embodiments, the method produces about 1.8 billion sequencing reads. In embodiments, the method produces about 2 billion sequencing reads. In embodiments, the method produces about 2.2 billion sequencing reads. In embodiments, the method produces about 2.4 billion sequencing reads. In embodiments, the method produces between about 500 million and 750 million sequencing reads. In embodiments, the method produces between about 750 million and 1.2 billion sequencing reads. In embodiments, the method produces between about 1.2 billion and 2.4 billion sequencing reads. In embodiments, the method produces more than about 2.4 billion sequencing reads.

In embodiments, each template polynucleotide is not reseeded, reamplified, or both reseeded and reamplified after generating each sequencing read. In embodiments, each template polynucleotide is not reseeded after generating each sequencing read. In embodiments, each template polynucleotide is not reamplified after generating each sequencing read. In embodiments, each template polynucleotide is not reseeded and reamplified after generating each sequencing read.

In embodiments, the method generates a total number of sequencing reads greater than the number of features (i.e., the number of detectable features) on the solid support. In embodiments, the method generates a total number of sequencing reads greater than the number of optically resolvable features on the solid support. In embodiments, wherein the method generates a total number of sequencing reads greater than 100% of the optically resolvable features on the solid support.

In embodiments, the sequencing method relies on the use of modified nucleotides that can act as reversible reaction terminators. Once the modified nucleotide has been incorporated into the growing polynucleotide chain complementary to the region of the template being sequenced there is no free 3'-OH group available to direct further sequence extension and therefore the polymerase cannot add further nucleotides. Once the identity of the base incorporated into the growing chain has been determined, the 3' reversible terminator may be removed to allow addition of the next successive nucleotide. These such reactions can be done in a single experiment if each of the modified nucleotides has attached a different label, known to correspond to the particular base, to facilitate discrimination between the bases added at each incorporation step. Alternatively, a separate reaction may be carried out containing each of the modified nucleotides separately.

The modified nucleotides may carry a label (e.g., a fluorescent label) to facilitate their detection. Each nucleotide type may carry a different fluorescent label. However, the detectable label need not be a fluorescent label. Any label can be used which allows the detection of an incorporated nucleotide. One method for detecting fluorescently labeled nucleotides includes using laser light of a wavelength specific for the labeled nucleotides, or the use of other suitable sources of illumination. The fluorescence from the label on the nucleotide may be detected (e.g., by a CCD camera or other suitable detection means).

In embodiments, the methods of sequencing a nucleic acid include extending a complementary polynucleotide (e.g., a primer) that is hybridized to the nucleic acid by incorporating a first nucleotide. In embodiments, the method includes a buffer exchange or wash step. In embodiments, the methods of sequencing a nucleic acid include a sequencing solution. The sequencing solution includes (a) an adenine nucleotide, or analog thereof; (b) (i) a thymine nucleotide, or analog thereof, or (ii) a uracil nucleotide, or analog thereof; (c) a cytosine nucleotide, or analog thereof and (d) a guanine nucleotide, or analog thereof.

In certain embodiments, the sequencing methods provided herein comprises sequencing both strands of a double-stranded nucleic acid with an error rate of $5\times10^{-5}$ or less, $1\times10^{-5}$ or less, $5\times10^{-6}$ or less, $1\times10^{-6}$ or less, $5\times10^{-7}$ or less, $1\times10^{-7}$ or less, $5\times10^{-8}$ or less, or $1\times10^{-8}$ or less. In certain embodiments, the sequencing methods provided herein comprises sequencing both strands of a double-stranded nucleic acid with an error rate of $5\times10^{-5}$ to $1\times10^{-8}$, $1\times10^{-5}$ to $1\times10^{-8}$, $5\times10^{-5}$ to $1\times10^{-7}$, $1\times10^{-5}$ to $1\times10^{-7}$, $5\times10^{-6}$ to $1\times10^{-8}$, or $1\times10^{-6}$ to $1\times10^{-8}$. In certain embodiments, the sequencing methods provided herein comprises sequencing both strands of a double-stranded nucleic acid with an error rate of $1\times10^{-7}$ to $1\times10^{-8}$.

In an aspect is provided a method of making different populations of polynucleotides. In embodiments, the method includes making different populations of polynucleotides in a single reaction vessel. In embodiments, each population of polynucleotides include a different sequencing primer binding sequence. In embodiments, each population of polynucleotides include a different pair of sequencing primer binding sequences. In embodiments, the method includes fragmenting a nucleic acid molecule to form nucleic acid fragments. Three approaches available to fragment nucleic acid chains include: physical, enzymatic, and chemical. DNA fragmentation is typically done by physical methods (i.e., nebulization, acoustic shearing, and sonication) or enzymatic methods (i.e., non-specific endonuclease cocktails and transposase tagmentation reactions). Following fragmentation, the DNA fragments are end repaired or end polished. Typical polishing mixtures contain T4 DNA polymerase and T4 polynucleotide kinase. These enzymes excise 3' overhangs, fill in 3' recessed ends, and remove any potentially damaged nucleotides thereby generating blunt ends on the nucleic acid fragments. The T4 polynucleotide kinase used in the polishing mix adds a phosphate to the 5' ends of DNA fragments that can be lacking such, thus making them ligation-compatible to NGS adapters. Generally, a single adenine base is added to form an overhang via an A-tailing reaction. This "A" overhang allows adapters containing a single thymine overhanging base to base pair with the fragments.

In embodiments, the method includes ligating an adapter to each end of the nucleic acid fragment (alternatively referred to as a library insert). Ligation of double-stranded DNA adapters may be accomplished by use of T4 DNA ligase. Depending on the adapter, some double-stranded adapters may not have 5' phosphates and contain a 5' overhang on one end to prevent ligation in the incorrect orientation. In embodiments, the method includes ligating a first adapter to the end of the nucleic acid fragment and ligating a second adapter to the end of the nucleic acid fragment. In embodiments, the method includes ligating a first adapter to a 5' end of the nucleic acid fragment and ligating a second adapter to the 3' end of the nucleic acid fragment. In embodiments, the first adapter sequence includes a first platform primer binding sequence and a first sequencing primer binding sequence and said second adapter sequence includes a second platform primer binding sequence and a second sequencing primer binding sequence. In embodiments, the first platform primer binding sequence is different from the second platform primer binding sequence. In embodiments, the first sequencing primer binding sequence is different from the second sequencing primer binding sequence. In embodiments, the method includes ligating a third adapter to the end of a different nucleic acid fragment and ligating a fourth adapter to the end of the nucleic acid fragment. In embodiments, the method includes ligating a third adapter to a 5' end of the nucleic acid fragment and ligating a fourth adapter to the 3' end of the nucleic acid fragment. In embodiments, the third adapter sequence includes the first platform primer binding sequence and a third sequencing primer binding sequence and said fourth adapter sequence includes the second platform primer binding sequence and a fourth sequencing primer binding sequence. In embodiments, the third sequencing primer binding sequence is different from the fourth sequencing primer binding sequence.

In embodiments, the method includes contacting a plurality of nucleic acid fragments with an adapter composition, wherein the adapter composition includes a first adapter including a first platform primer binding sequence and a first sequencing primer binding sequence; a second adapter including a second platform primer binding sequence and a second sequencing primer binding sequence; a third adapter including the third platform primer binding sequence and a third sequencing primer binding sequence. In embodiments the adapter composition includes a fourth adapter, including the second platform primer binding sequence and a fourth sequencing primer binding sequence. In embodiments, the first sequencing primer binding sequence, second sequencing primer binding sequence, third sequencing primer binding sequence, and fourth sequencing primer binding sequence are different.

In embodiments, the method further includes size-selecting and/or purification. By doing this, unligated adapters and adapter dimers are removed, and the optimal size-range for subsequent PCR and sequencing is selected. Adapter dimers are the result of self-ligation of the adapters without an insert sequence. These dimers form clusters very efficiently and consume valuable space on the flow cell without generating any useful data. Thus, known cleanup methods may be used, such as magnetic bead-based clean up, or purification on agarose gels.

EXAMPLES

Example 1. Multiplexed Short Read RNA-Seq

Sequencing RNA (e.g., mRNA, rRNA, and tRNA) allows for transcriptome investigation and discovery, and provides useful insight informing scientists which genes are turned on in a cell, what their level of expression is, and at what times they are activated or shut off. Methods for sequencing of RNA are known in the art. RNA sequencing (RNA-seq) uses massively parallel sequencing to allow, for example, transcriptome analyses of genomes at a far higher resolution than is available with Sanger sequencing- and microarray-based methods. In RNA-seq methods, complementary DNAs (cDNAs) and copies of cDNAs generated from the RNA of interest are directly sequenced using next-generation sequencing technologies. RNA-seq has been used successfully to precisely quantify transcript levels, confirm, or revise previously annotated 5' and 3' ends of genes, and map exon/intron boundaries (Eminaga S et al., Curr. Protoc. in Mol. Biol., 2013, 103:4.17.1-4.17.14). RNA-seq has been widely applied to both well-studied model organisms and non-model organisms, to provide information on transcript profile of organisms, and to give important insights into biological processes. For organisms with known reference genomes, researchers usually take advantage of a mapping-first strategy to analyze transcriptome data. However, a mapping-first strategy is not suitable when reference sequence is not available or incomplete. Thus, for organisms with un-sequenced genome or cancer cells with widespread chimeric RNAs (Kannan K et al. Proc. Natl. Acad. Sci. U.S.A., 2011, 108(22):9172-77, and Maher C A et al. Nature, 2009, 458(7234):97-101), de novo assembly is essential to provide a workable solution for transcriptome analysis. With optimized transcriptome assembly methods, de novo assembly of short sequence reads into transcripts allows researchers to reconstruct the sequences of a full transcriptome, identify and catalog all expressed genes, separate isoforms, and capture the expression levels of transcripts (Zhao Q Y et al. BMC Bioinformatics, 2011, 12:S2).

Current short read RNA-seq techniques typically sequence between 50 to 100 base pairs in a single run, facilitating higher coverage than long read techniques (Kukurba K R and Montgomery S B, Cold Spring Harb. Protoc. 2015, 2015(11): 951-969). For single-cell RNA-seq applications, paired-end sequencing is advantageous to gain greater sequencing depth. In one read, a UMI and cell barcode is read (typically 15-40 bp), whereas the second read serves to sequence the actual transcript. In the context of paired-end sequencing, it becomes important to have distinct sequencing primers for both reads of the paired-end workflow. Furthermore, 30 base pair short reads from RNA-seq are reported as sufficient in certain contexts, for example, to give information about how two exons are connected, diagnose the presence of an infectious disease, or quantify chromosomes (Wang Z et al. Nat. Rev. Genet. 2009, 10(1): 57-63). This translates to, for example, a 30-cycle run consuming an entire lane of a flow cell and associated reagents only to sequence a single RNA sample, drastically underutilizing the available sequencing space and resources. Described herein is a method of sequencing nucleic acids that increases that number of reads that may be sequenced on a single flow cell lane. By utilizing multiple different sequencing primers in combination with corresponding adapters, significantly more reads may be sequenced in each flow cell lane during a single run. For example, an RNA sample may be prepared with 4 unique adapters that can each hybridize to a unique sequencing primer. If a particular region on the flow cell is seeded by a template with sequencing primer #1, and also by templates with sequencing primers #2 and #4, for example, they can be sequenced independently thereafter, assuming there is sufficient signal-to-background for each template. In some embodiments, one template may amplify more efficiently than the other seeded templates, leading to one template outcompeting others. When enough copies of a template are made to have sufficient signal-to-background to be detected, that specific template can be sequenced and detected. Initially, 30 sequencing cycles would be performed with sequencing primer #1, followed by another 30 sequencing cycles with sequencing primer #2, and then another 30 cycles with sequencing primer #4, until all of the seeded templates in a region have been identified. In some embodiments, more than 3, 4, or 5 sequencing primers may be used to identify all of the seeded templates in a region. In some embodiments, 10 or more sequencing primers may be used to identify all of the seeded templates in a region.

This method greatly increases the number of reads that may be obtained for those users with limited sequencing resources, for example, those limited to a single flow cell and associated reagent mixture. Additionally, this method could allow for 4 independent samples to be sequenced without having to read 4 barcodes (unique sample indices), as each independent sample would have its own unique adapter and associated sequencing primer. For paired-end applications, the adapters of the invention would be coupled (e.g., one sample would receive two unique adapters in a single solution), such that each sample would use a predetermined matched pair of sequencing primers. Flow cell and clustering reagents would be shared for all libraries that are prepared, reducing reagent costs and protocol time. A single 2×50 bp sequencing run of a two-lane Illumina NovaSeq 6000 S2 flow cell is priced at approximately $10,000 (see, for example, www.research.ncsu.edu/gsl/pricing/); the methods described herein would enable, for example, 4 times the data to be acquired for the same $10,000 price. In embodiments, depending on the target read length, even greater economic value can be achieved through the use of the methods and compositions disclosed herein, dramatically expanding both the throughput of sequencing data that may be collected and public access to such resources.

The nucleic acid sample used for this experiment contains total RNA or mRNA, preferably purified RNA or mRNA, from an organism (e.g., human). Total RNA includes, but is not limited to, protein coding RNA also called coding RNA such as messenger RNA (mRNA) and non-protein coding RNA (non-coding RNA or ncRNA), such as ribosomal RNA (rRNA), transfer RNA (tRNA), micro RNA (miRNA), small interfering RNA (siRNA), piwi-interacting RNA (piRNA), small nuclear RNA (snRNA) and small nucleolar RNA (snoRNA). Each one of these RNA types may be used as input. Optionally, and preferably, the RNA will include a poly(A) tail, however the RNA molecule may not have a poly(A) tail (e.g., non-protein coding RNAs (ncRNA) such as ribosomal RNA (rRNA), transfer RNA (tRNA), micro RNA (miRNA), small interfering RNA (siRNA), piwi-interacting RNA (piRNA) and small nuclear RNA (snRNA)). For example, prokaryotic mRNA does not have a poly(A) tail. In RNA molecules that do not have a poly A tail, a poly(A) tail may be added synthetically (e.g. enzymatically) to validate these studies. In embodiments, a poly(A) tail is enzymatically added to the RNA molecule using known techniques in the art.

RNA library preparation is performed according to known methods in the art, e.g., described elsewhere and briefly below. An isolated RNA molecule (e.g., mRNA), may be further purified and selected for polyadenylation utilizing known techniques in the art (e.g., by mixing RNA with poly(T) oligomers covalently attached to a substrate, such as magnetic beads). The RNA may be reverse transcribed (e.g., reverse transcription with a non-strand displacing RT) to cDNA, followed by a DNA polymerase-mediated second strand synthesis to yield an input DNA molecule. In an alternative option, a surface immobilized poly(T) (e.g., a bead containing a poly(T) sequence) hybridizes with the poly(A) portion of the input RNA. Also present, either before or after the poly(T) sequence, is a priming region for a reverse transcriptase. In the presence of a reverse transcriptase, complementary DNA (cDNA) is generated. The RNA is then removed.

Prior to ligation, adenylation of repaired nucleic acids using a polymerase which lacks 3'-5' exonuclease activity is often performed in order to minimize chimera formation and adapter-adapter (dimer) ligation products. In these methods, single 3' A-overhang DNA fragments are ligated to single 5' T-overhang adapters, whereas A-overhang fragments and T-overhang adapters have incompatible cohesive ends for self-ligation. During size selection, fragments of undesired size are eliminated from the library using gel or bead-based selection in order to optimize the library insert size for the desired sequencing read length. This often maximizes sequence data output by minimizing overlap of paired end sequencing that occurs from short DNA library inserts. Amplifying libraries prior to NGS analysis is typically a beneficial step to ensure there is a sufficient quantity of material to be sequenced.

Embodiments of the adapter oligonucleotide sequences contemplated herein include those shown in FIG. 1, referred to as P1, P2, P3, and P4 adapters, respectively. The illustrations depict embodiments of the oligo sequences wherein there are two different platform primer binding sequences, pp1 and pp2, in combination with four different sequencing primer binding sites: SP1, SP2, SP3, and SP4. Any P1 adapter, or the complement thereof, may be combined with any P2 or P4 adapter, or complement thereof, when preparing the template nucleic acid sequence. Any P3 adapter, or the complement thereof, may be combined with any P2 or P4 adapter, or complement thereof, when preparing the template nucleic acid sequence. The 5' end of any of the adapters shown in FIG. 1 may be covalently attached to a solid surface via a linker (not shown).

In some aspects of a method herein, an adapter-target-adapter nucleic acid template (FIGS. 2A-2B) is provided where two adapters are ligated to each respective end of a polynucleotide duplex. A polynucleotide duplex refers to a double-stranded portion of a polynucleotide, for example, a cDNA polynucleotide desired to be sequenced. Each adapter is a Y adapter (alternatively, this may be referred to as a mismatched adapter or a forked adapter) that is ligated to one end of a polynucleotide duplex. The adapter is formed by annealing two single-stranded oligonucleotides, such as P1 and P2'. FIG. 2A shows a DNA template with P1 and P2' adapters ligated to the ends. P1 and P2' may be prepared by a suitable automated oligonucleotide synthesis technique. The oligonucleotides are partially complementary such that a 3' end and/or a 3' portion of P1 is complementary to the 5' end and/or a 5' portion of P2'. A 5' end and/or a 5' portion of P1 and a 3' end and/or a 3' portion of P2' are not complementary to each other, in certain embodiments. When the two strands are annealed, the resulting Y adapter is double-stranded at one end (the double-stranded region) and single-stranded at the other end (the unmatched region), and resembles a 'Y' shape.

The single-stranded portions (the unmatched regions) of both P1 and P2' have an elevated melting temperature (Tm) (e.g., about 75° C.) relative to their respective complements to enable efficient binding of surface primers and stable binding of sequencing primers. In contrast to the single-stranded portions, a double-stranded region, in certain embodiments, has a moderate Tm (e.g., 40-45° C.) so that it is stable during ligation. In embodiments, a double-stranded region has an elevated Tm (e.g., 60-70° C.). In embodiments, the GC content of the double-stranded region is >50% (e.g., approximately 60-75% GC content). The unmatched region of P1 and P2', in certain embodiments, are about 25-35 nucleotides (e.g., 30 nucleotides), whereas the double-stranded region is shorter, ranging about 10-20 nucleotides (e.g., 13 nucleotides) in total. In embodiments, the unmatched region of P1 and P2' are about 35-60 nucleotides (e.g. 60 nucleotides).

A ligation reaction between the Y adapters and the cDNA fragments is then performed using a suitable ligase enzyme (e.g. T4 DNA ligase) which joins two Y adapters to each DNA fragment, one at either end, to form adapter-target-adapter constructs. A mixture of adapter sequences are utilized (as depicted in FIG. 1) during the target-adapter ligation step, such that a defined number of unique adapters are present. The products of this reaction can be purified from leftover unligated adapters by a number of means (e.g., NucleoMag NGS Clean-up and Size Select kit, Solid Phase Reversible Immobilization (SPRI) bead methods such as AMPureXP beads, PCRclean-dx kit, Axygen AxyPrep FragmentSelect-I Kit), including size-inclusion chromatography, preferably by electrophoresis through an agarose gel slab followed by excision of a portion of the agarose that contains the DNA greater in size that the size of the adapter.

Figure 7A:
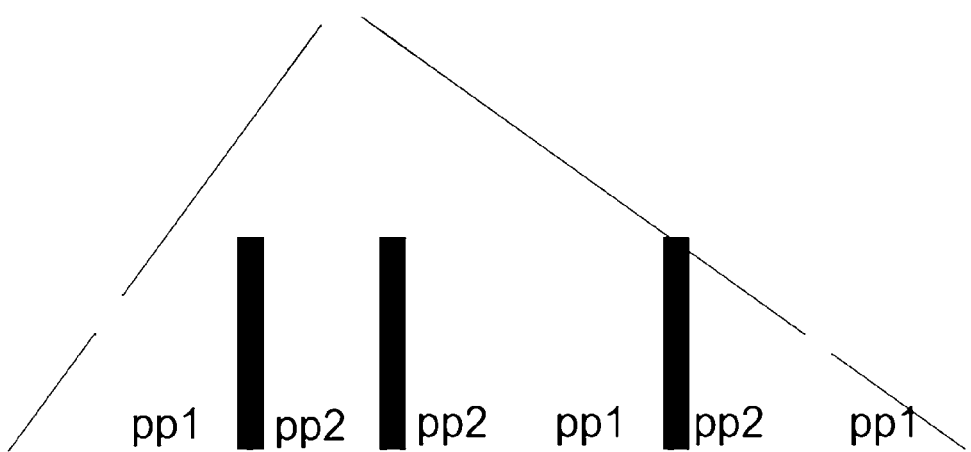
FIGS. 7A-7B. Solid supports including immobilized oligonucleotides. Illustrated in FIG. 7A is a pattered solid support containing a plurality of wells separated by interstitial regions, alternatively referred to herein as a multiwell container. Each feature includes a plurality of immobilized oligonucleotides, referred to as platform primer oligonucleotides. Each well optionally includes a polymer and/or a particle, wherein the platform primer oligonucleotides are covalently attached to the particle and/or the polymer at the 5' end of each oligonucleotide. Within each feature, as depicted in FIG. 7A and FIG. 7B, the plurality of immobilized oligonucleotides include a first platform primer oligonucleotide (pp1) having complementarity to all or a portion of the adapter P1 and P3, and a second platform primer oligonucleotide (pp2) having complementarity to all or a portion of the adapter P2 or P4.
Figure 7B:
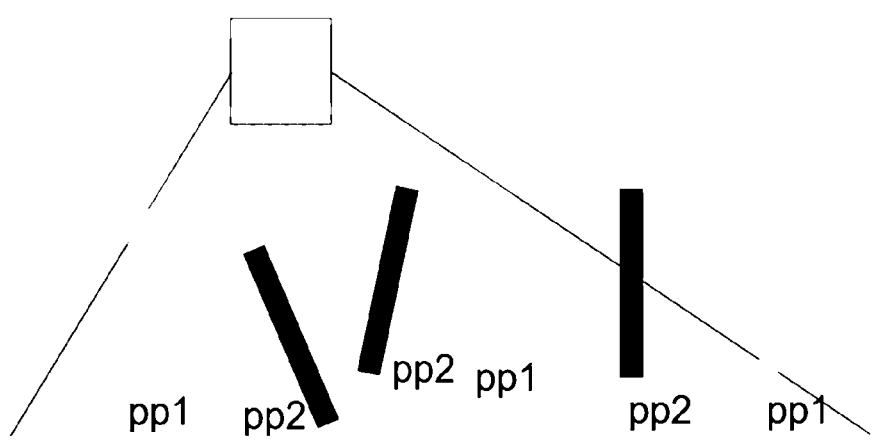

Once formed, the library of adapter-target-adapter templates prepared according to the methods described above can be used for solid-phase nucleic acid amplification. Examples of seeding and amplification are provided in FIGS. 7A-7B; FIGS. FIGS. 8A-8B; and/or FIGS. 9A-9C. For example, each feature includes a plurality of immobilized oligonucleotides, referred to as platform primer oligonucleotides. Within each feature, as depicted in FIG. 7A and FIG. 7B, the plurality of immobilized oligonucleotides include a first platform primer oligonucleotide (pp1) having complementarity to all or a portion of the adapter P1 and P3, and a second platform primer oligonucleotide (pp2) having complementarity to all or a portion of the adapter P2 or P4. The prepared library molecules (i.e., nucleic acids having the appropriate adapters on each end) are allowed to contact the solid support and may contact a single feature. For example, if one molecule seeds (i.e., hybridizes to the surface-immobilized oligonucleotide) a single feature and is amplified it is referred to as a monoclonal colony. Colony formation, alternatively referred to as a cluster, for a P1'-template-P2 molecule and a P3'-template-P4 molecule is illustrated in FIGS. 8A-8B, where an initial molecule anneals to a first immobilized oligonucleotide and is extended to form an immobilized extension product (FIG. 8A). The initial seeding molecule is removed and the immobilized extension product hybridizes to a second immobilized oligonucleotide, and with a polymerase is extended to form a second immobilized extension product (FIG. 8B). Under suitable amplification conditions, the process is repeated to form a plurality of immobilized extension products, as illustrated in FIG. 8C, wherein each extension product is capable of being sequenced by hybridizing the appropriate sequencing primer: SP1, SP2, SP3, or SP4. A similar process occurs on unpatterned solid supports, as illustrated in FIGS. 8D-8F. Alternatively, seeding and amplification of different circularized libraries is described herein. The prepared library molecules may be circularized in solution and annealed to a complementary immobilized oligonucleotide as illustrated in FIG. 9A, or a linear nucleic acid molecule may be circularized on the solid support, as illustrated in FIG. 9B. As illustrated in FIG. 9B, a splint oligonucleotide hybridizes to both ends of the library molecule, and following ligation, a circular template molecule is annealed to the primer. A nucleic acid polymerase (e.g., a strand-displacing polymerase, depicted as a cloud) then extends the primer that is hybridized to the circular nucleic acid template by continuously progressing around the circular nucleic acid template to replicate the sequence of the nucleic acid template over and over again (rolling circle mechanism). The rolling circle amplification typically produces concatemers comprising tandem repeat units of the circular nucleic acid template sequence, as illustrated in FIG. 9C. The solid support optionally may include a second immobilized oligonucleotide as illustrated in FIG. 9A and FIG. 9B to faciliatate non-linear circular amplification modalities such as exponential rolling circle amplification (eRCA).

Figure 3A:
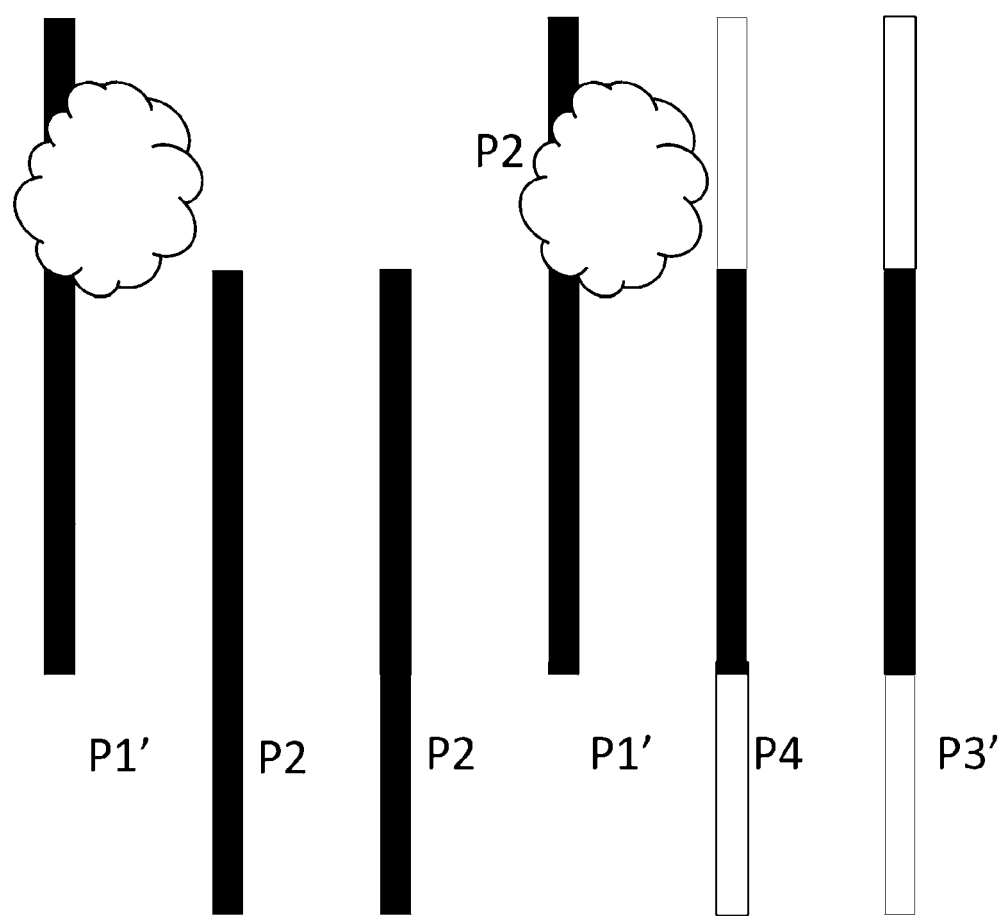
FIGS. 3A-3B shows an illustration depicting an embodiment of sequencing a multiplexed array. A substrate, depicted as dashed box at the bottom, includes immobilized primers, pp1 and pp2, or complements thereof. The library molecules, e.g., library molecules as depicted in FIGS. 2A-2B, are allowed to contact and hybridize with the immobilized primers, or complements thereof, and in the presence of a polymerase (illustrated as a cloud) the immobilized primers are extended to generate a copy of the initial library molecule. Subsequent amplification of the initial library may then occur to generate clusters of template nucleic acids, each template nucleic acid comprising two of four different sequencing primer binding sites SP1, SP2, SP3, and SP4, or a complement thereof.
Figure 3B:
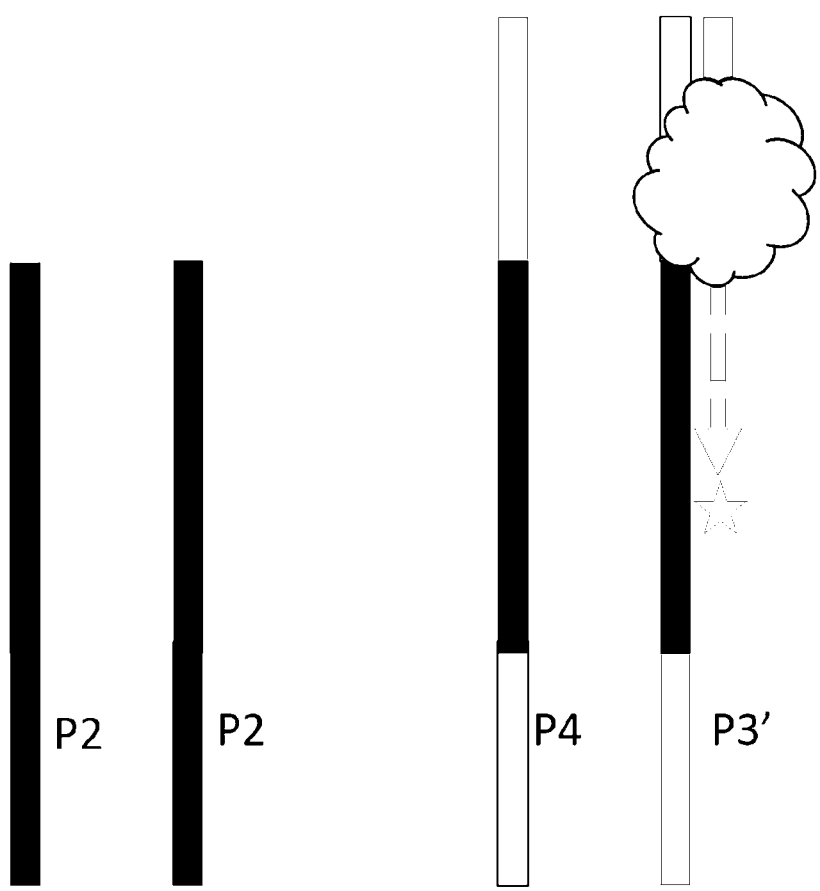

FIGS. 3A-3B shows an illustration depicting an embodiment of sequencing a multiplexed array, for example a cDNA array. A substrate (e.g., a flow cell), depicted as dashed lines, includes immobilized primers, pp1 and pp2, or complements thereof. The library molecules, e.g., library molecules as depicted in FIGS. 2A-2B, are optionally denatured (e.g., chemical or thermal denaturation, or both), and brought into contact and hybridized with the immobilized primers, or complements thereof, and in the presence of a polymerase the immobilized primers are extended to generate a copy of the initial library molecule. Subsequent amplification of the initial library may then occur to generate clusters of template nucleic acids, each template nucleic acid comprising two of four different sequencing primer binding sites SP1, SP2, SP3, and SP4, or a complement thereof. FIG. 3A shows an example of a cluster of immobilized nucleic acids, each nucleic acid comprising a first and a second sequencing primer binding site. A first sequencing primer complementary to SP2 hybridizes to the template and is extended in the presence of a polymerase and detectable nucleotides, illustrated as a dashed line and star. Following a first plurality of sequencing cycles, the immobilized strands are optionally removed, and a second plurality of sequencing cycles on the same cluster may commence in a similar fashion. FIG. 3B shows a second sequencing primer complementary to SP3 hybridizes to the template and is extended in the presence of a polymerase and detectable nucleotides, illustrated as a dashed line and star. The remaining templates may be sequenced as outlined above, e.g., by hybridizing a third and fourth sequencing primer to the respective template and sequencing.

Figure 4:
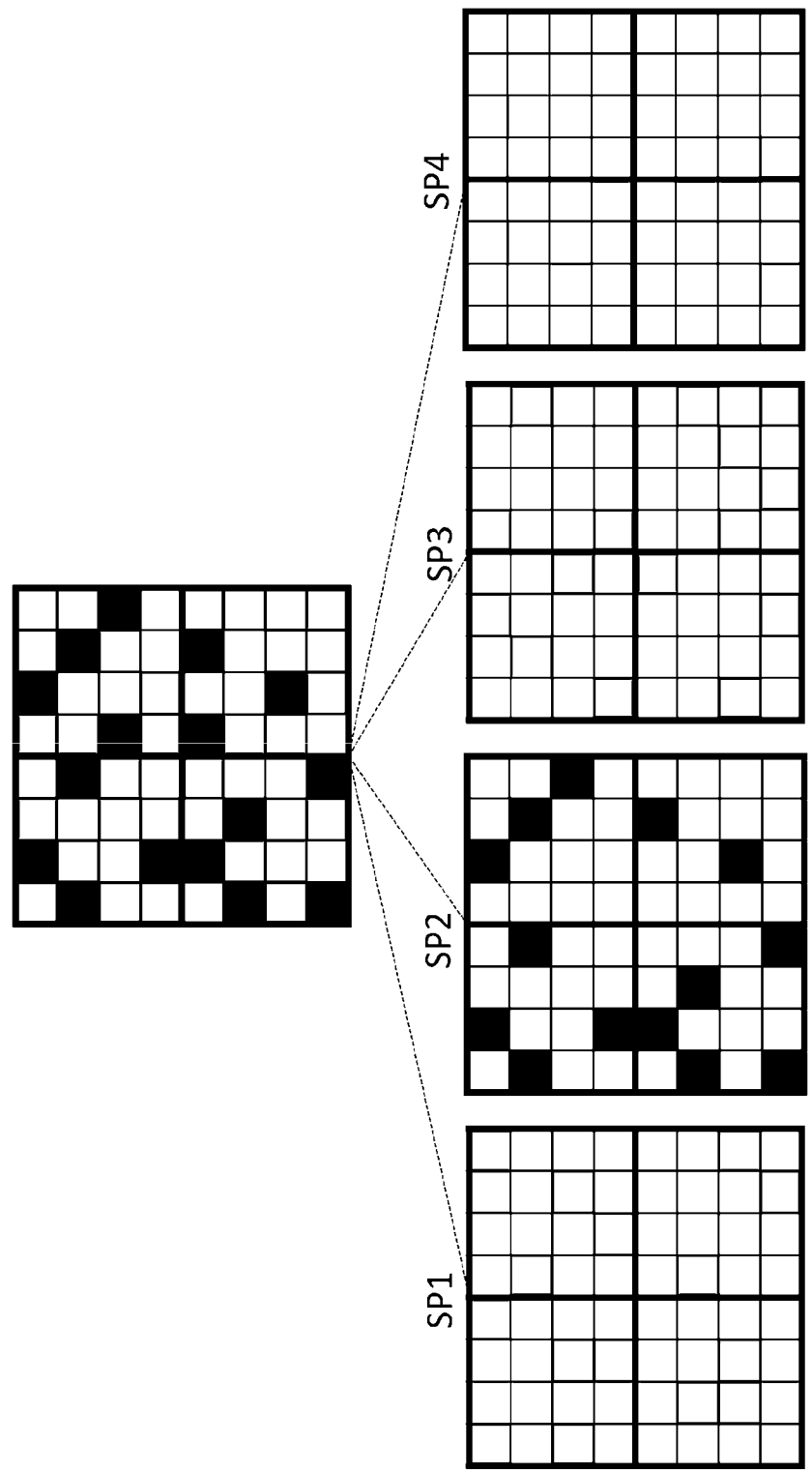
FIG. 4 shows an illustration of a single, polyclonal cluster of a multiplexed array (e.g., a polyclonal feature of a patterned array or a polyclonal feature of an unpatterned solid support) of template nucleic acids. In embodiments, the polyclonal cluster contains a plurality of template nucleic acids, each template containing one of four different sequencing primer binding sites. In embodiments, sequencing is initiated by hybridizing a sequencing primer to one of four different sequencing primer binding sites SP1, SP2, SP3, and SP4, or a complement thereof. A plurality of sequencing cycles then occurs, wherein each cycle comprises extension and detection of the incorporated nucleotide. Illustrated in FIG. 4 is a multiplexed, polyclonal cluster, wherein each template (depicted as a shaded square when active) is active when the appropriate sequencing primer hybridizes and is extended, allowing for selective sequencing of an entire array. For example, when a first sequencing primer SP1 hybridizes to each of the complementary templates in the array and is subjected to a sequencing technique for a plurality of cycles, only a subset of the cluster is detected during that plurality of sequencing cycles. A second round (i.e., a second plurality of sequencing cycles) of sequencing then occurs by hybridizing a second sequencing primer, SP2, to each of the complementary templates in the array and is subjected to a sequencing technique. A third round of sequencing then occurs by hybridizing a third sequencing primer, SP3, to each of the complementary templates in the array and is subjected to a sequencing technique. This is followed by a fourth round of sequencing that occurs by hybridizing a fourth sequencing primer, SP4, to each of the complementary templates in the array and is subjected to a sequencing technique. The entire array may be selectively sequenced by choosing the appropriate initiator, i.e., the appropriate sequencing primer, wherein each sequencing read is thereby generated at different times.

A plurality of sequencing cycles then occur, wherein each cycle comprises extension and detection of the incorporated nucleotide. Illustrated in FIG. 4 is a single, polyclonal cluster comprising a plurality of templates, wherein each template (depicted as a shaded square when active) is active when the appropriate sequencing primer hybridizes and is extended, allowing for selective sequencing of an entire array. For example, when a first sequencing primer SP1 hybridizes to each of the complementary templates in the cluster and is subjected to a sequencing technique for a plurality of cycles, only a subset of the cluster is detected during that plurality of sequencing cycles. A second round (i.e., a second plurality) of sequencing then occurs by hybridizing a second sequencing primer, SP2, to each of the complementary templates in the array and is subjected to a sequencing technique. A third round of sequencing then occurs by hybridizing a third sequencing primer, SP3, to each of the complementary templates in the array and is subjected to a sequencing technique. This is followed by a fourth round of sequencing that occurs by hybridizing a fourth sequencing primer, SP4, to each of the complementary templates in the array and is subjected to a sequencing technique. The entire array may be selectively sequenced by choosing the appropriate initiator, i.e., the appropriate sequencing primer.

Figures 5A, 5B:
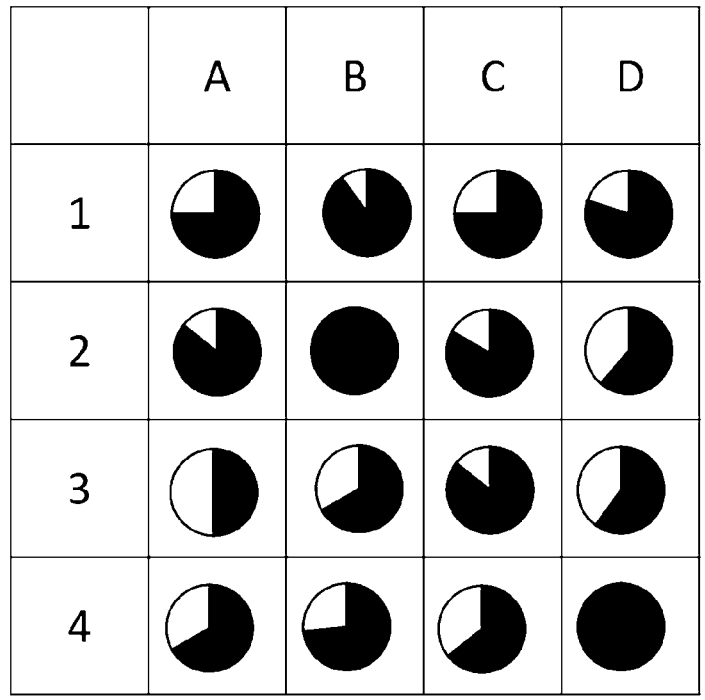
FIGS. 5A-5B shows an illustration of sequencing a multiplexed array of template nucleic acids.

In embodiments, each polyclonal cluster contains a plurality of templates having more than two (e.g., four) different primer binding sites. In some embodiments, the clusters present in a detection region contain monoclonal (e.g., substantially identical) template polynucleotide sequences. In other embodiments, the clusters present in a detection region contain polyclonal (e.g., different) template polynucleotide sequences, and/or different adapter sequences. Sequencing is initiated by hybridizing a sequencing primer to one of four different sequencing primer binding sites SP1, SP2, SP3, and SP4, or a complement thereof. A plurality of sequencing cycles then occurs, each cycle comprising extension and detection of the incorporated nucleotide. Illustrated in FIGS. 5A-5B is sequencing of a multiplexed array of template nucleic acids. FIG. 5A depicts a 4×4 patterned array, wherein each polyclonal cluster (alternatively referred to herein as a feature) includes template nucleic acids that include two to four different sequencing primer complements, depicted as four different colors. Sequencing is initiated by hybridizing a sequencing primer to one of four different sequencing primer binding sites SP1, SP2, SP3, and SP4, or a complement thereof. A plurality of sequencing cycles then occurs, each cycle comprising extension and detection of the incorporated nucleotide. Illustrated in FIG. 5B is the multiplexed array wherein each cluster (depicted as a shaded circle) is active when the appropriate sequencing primer hybridizes and is extended, allowing for selective sequencing of an entire array. Depicted in FIG. 5B, when the cluster contains a plurality of templates having different primer binding sites, e.g., regions complementary to SP1, SP2, and SP3, only the clusters containing complementarity to the appropriate sequencing primer is active during each plurality of sequencing cycles. For example, when a first sequencing primer SP1 hybridizes to each of the complementary templates in the array, only a subset of the array is detected during that round of sequencing. A second round of sequencing then occurs by hybridizing a second sequencing primer, SP2, to each of the complementary templates in the array, and so on. The same clusters may be active and detectable during each round of sequencing if the cluster includes templates with two or more different sequencing primer binding sites.

Using the methods described herein, we prepared human universal reference RNA-seq libraries, including adapter sequences corresponding to the SP and M1 to M12 sequences described herein and in Table 1. Two libraries (SP and MD were seeded onto a flow cell at a concentration of 10 pM each, for a total of 20 pM template seeded. Following solid phase cluster amplification, paired-read sequencing (2×105 bp) was performed using sequencing primers complementary to each adapter. Approximately 380 million paired reads were generated cumulatively, with between approximately 86% to 88% of called bases having a quality score of Q30. Subsequently, three of the prepared libraries (SP, M1, and M3) were seeded onto a flow cell at a concentration of 10 pM each, for a total of 30 pM template seeded. Following solid phase cluster amplification, paired-read sequencing (2×105 bp) was performed using sequencing primers complementary to each adapter. Approximately 450 million paired reads were generated cumulatively, with between approximately 80% to 88% of called bases having a quality score of Q30. These results indicate that two and three RNAseq libraries can be sequenced consecutively (in paired-read format) on a single flow cell with high throughput and sequencing read quality.

Example 2. NIPT Chromosome Counting

Non-invasive prenatal testing (NIPT), for example, trisomy detection, relies on the accurate representation of genetic material originating on a chromosome compared to genetic material originating from other chromosomes. In prenatal care, cell-free DNA (cfDNA) of fetal origin obtained from maternal blood is used to detect fetal aneuploidies as early as the 10th week of gestation (Norton M E et al. N. Engl. J. Med. 2015; 372:1589-97). Typical single-gene NIPT analyses recover the dosage of pathogenic alleles, the fraction of cfDNA isolated from maternal blood that is of fetal origin, the number of DNA molecules assayed, and paternal inheritance of variants not found in the mother's genotype (Tsao D S et al. Scientific Reports 2019; 9: 14382). Whole-genome sequencing of fetal cfDNA fragments has been demonstrated to be efficacious in detecting fetal aneuploidy for multiple chromosomes across the genome, with high sensitivity and specificity for the detection of trisomies 21, 18, 13, and monosomy X (Bianchi D W et al. Obstetrics & Gynecology 2012; 119(5): 890-901). These non-invasive prenatal tests (NIPT) are routinely used in clinical care and are also covered by health insurance (van Schendel R V et al. BMC Health Services Research 2017; 17:670).

NIPT routinely infers copy number alterations (CNAs) through routine shallow-depth whole-genome sequencing (sWGS) data (0.1× to 1× coverage) (Raman L et al. Nucleic Acids Research 2018; 47(4): 1605-14). Studies into the influence of read counts on CNA prediction accuracy have found that higher number of reads allow for further increasing of accuracy, with some sources recommending the use of approximately 16M-17M reads for analyses (i.e., 0.35× genome coverage for 2×35 bp reads), due to the fact that the detection rate reaches a plateau for a 10% fetal fraction and >3 Mb deletion sizes, which is the average fetal fraction in pregnant women in the most relevant weeks of pregnancy for NIPT (Kucharik M et al. PLoS ONE 2020; 15(8): e0238245). Using more reads may be beneficial, especially for small deletions and in circumstances where there is a low fetal fraction. As described in Example 1, the cost for a typical flow cell can be in the tens of thousands of dollars, especially when higher read counts are desired, limiting the feasibility of broad adoption of ultra-high throughput NIPT for clinical diagnostics.

Described herein is a method of sequencing nucleic acids that increases that number of reads that may be sequenced on a single flow cell lane. By utilizing multiple different sequencing primers in combination with corresponding adapters, significantly more reads may be sequenced in each flow cell lane during a single run. For example, a NIPT fetal fraction sample may be prepared with 2 unique adapters that can each hybridize to a unique sequencing primer. If a particular region on the flow cell is seeded by a template with sequencing primer #1, and also by templates with sequencing primers #2 and #3, they can be sequenced independently thereafter. Initially, 35 sequencing cycles are performed with sequencing primer #1, followed by another 35 sequencing cycles with sequencing primer #2, and then another 35 cycles with sequencing primer #3, until all of the seeded templates in a region have been identified. In some embodiments, more than 3, 4, or 5 sequencing primers may be used to sequence an identical number of unique templates in a single flow cell lane. This method greatly increases the number of short reads that may be obtained from a single flow cell and reagent mixture, decreasing the cost, and increasing the number of detectable chromosomal aberrations in a NIPT.

Using the methods described herein, we prepared human universal reference RNA-seq libraries, including adapter sequences corresponding to the SP and M1 to M12 sequences described herein and in Table 1. Eight libraries (SP and M1 to M7) were seeded onto a first flow cell, and an additional eight libraries (SP and M6 to M12) were seeded onto a second flow cell at a concentration of 4 pM each, for a total of 32 pM template seeded per flow cell. Following solid phase cluster amplification, sequencing (1×75 bp) was performed using sequencing primers complementary to each library. Approximately 1.03 billion reads were generated cumulatively on the first flow cell, and approximately 1.10 billion reads were generated cumulatively on the second flow cell, with between approximately 80% to 85% of called bases having a quality score of Q30. Processing the sequenced data as 50 bp reads increased the throughput to approximate 1.2 billion cumulative reads. These results indicate that eight unique libraries can be sequenced consecutively on a single flow cell with high throughput and sequencing read quality.

We additionally prepared human whole genome reference libraries, including adapter sequences corresponding to the SP and M1 to M12 sequences described herein and in Table 1. Two libraries (SP and M1) were seeded onto a flow cell at a concentration of 8 pM each, for a total of 16 pM template seeded per flow cell. Following solid phase cluster amplification, paired-read sequencing (2×125 bp) was performed using sequencing primers complementary to each library. Approximately 350 million paired reads were generated cumulatively, with between approximately 80% to 82% of called bases having a quality score of Q30. These results indicate that whole genome libraries can be sequenced consecutively on a single flow cell with high throughput and sequencing read quality.

Example 3. Multiplexed Bacterial Genome Sequencing

Using the methods described supra and herein, experiments sequencing several bacterial genomic libraries, either in individual lanes or as multiplexed pools in a single lane were conducted. Each library was prepared with an adapter including a different sequencing primer binding site (i.e., a sequence complementary to different sequencing primers) to selectively initiate sequencing of the respective library. Following seeding and amplification, a plurality of sequencing cycles were performed, wherein each template was actively sequenced when the appropriate sequencing primer hybridized and was extended, allowing for selective sequencing of the overlapping polyclonal cluster.

Template preparation: Bacterial genomic DNA (*Clostridium*, *E. coli*, and *Salmonella* genomic DNA) covering a range of different GC content was purified, fragmented (e.g., fragmented to an average insert size of about 200 bp to about 400 bp), end-repaired, and A-tailed using standard methods for library preparation known in the art. To enable multiplexed sequencing, different adapter sequences were ligated onto each library sample. Templates containing the *Clostridium* genomic DNA were prepared with an adapter including an M1A adapter sequence and M1B adapter sequence listed in Table 1 (e.g., SEQ ID NO: 1 and SEQ ID NO:36); *E. coli* genomic DNA templates were prepared with an adapter including and M5A adapter sequence and M5B adapter sequence listed in Table 1 (e.g., SEQ ID NO: 5 and SEQ ID NO: 40); and *Salmonella* genomic DNA templates were prepared with a SP adapter.

For example, any M1A sequence (e.g., SEQ ID Nos: 1, 11, 21, or 31) that can hybridize to a corresponding complementary M1B sequence (e.g., SEQ ID Nos: 6, 16, 26, or 36) may be used to prepare the adapter (e.g., prepare a Y-shaped adapter as described herein). In general, the adapter sequences were designed to generally have a length of between 30 and 35 nucleotides and an overall GC content of about 50% to about 55%. With respect to the double-stranded region (i.e., the region of the adapter sequence that anneals to a complementary adapter sequence), a length of 12 to 14 nucleotides with a GC content of 52% to 54% was selected. Additionally, adapter sequences were generated to have minimal overlap with each other and known genomic sequences (e.g., a BLAST alignment was performed to determine the % identity against all available sequences in Genbank and primers with any significant matches were removed (e.g., greater than 1% identity to a known sequence)).

A goal of effective primer design is to maximize product yield and minimize off-target amplification, without introducing any biases (e.g., skewing the amplification products to over-or under-represent portions). Prevention of primer-primer interaction artifacts (i.e., primer-dimers) formed by primer-primer binding and subsequent elongation is one way to avoid any deleterious effects. Primer-primer interactions can competitively inhibit binding to target DNA, remove primers from the reaction pool, and exhaust dNTPs, which results in reduced amplification efficiency and suboptimal product yields.

Primer3 allows for the selection of the primer on the basis of melting temperature (Tm), primer length, and 3'-end stability, which was considered when designing each primer set. Calculating the melting temperature and performing thermodynamic modelling for estimating the propensity of primers to hybridize with other primers or to hybridize at unintended sites in the template offer an accurate approach for predicting the energetic stability of DNA structures. For example, because of electronic effects of nucleobase stacking, the stability of 5'-CT-3' hybridized to 3'-GA-5' is different from that of 5'-CA-3' hybridized to 3'-GT-5', despite the base pairings C:G and T:A are the same. It is recommended to perform primer analysis with sophisticated modelling capabilities to capture such electronic effects. Additionally, in silico validation of primer and amplicon sequences was performed. The online software OligoAnalyzer™ Tool provides information on amplicon secondary structure and the possibility of self- or heterodimer formation by the primer sequence itself by calculating the Gibbs free energy ($\Delta G$).

In embodiments, the library sample is double-stranded and an adapter formed by hybridizing two of the sequences described in Table 1 may be ligated to one, or both ends of the double-stranded template. For example, any M1A sequence (e.g., SEQ ID Nos: 1, 11, 21, or 31) that can hybridize to a corresponding complementary M1B sequence (e.g., SEQ ID Nos: 6, 16, 26, or 36) may be used to prepare the adapter (e.g., prepare a Y-shaped adapter as described herein). In embodiments, any M2A sequence (e.g., SEQ ID Nos: 2, 12, 22, or 32) that can hybridize to a corresponding M2B sequence (e.g., SEQ ID Nos: 7, 17, 27, or 37) may be used to prepare the adapter (e.g., prepare a Y-shaped adapter as described herein). In embodiments, any M3A sequence (e.g., SEQ ID Nos: 3, 13, 23, or 33) that can hybridize to a corresponding M3B sequence (e.g., SEQ ID Nos: 8, 18, 28, or 38) may be used to prepare the adapter (e.g., prepare a Y-shaped adapter as described herein). In embodiments, any M4A sequence (e.g., SEQ ID Nos: 4, 14, 24, or 34) that can hybridize to a corresponding M4B sequence (e.g., SEQ ID Nos: 9, 19, 29, or 39) may be used to prepare the adapter (e.g., prepare a Y-shaped adapter as described herein). In embodiments, any M5A sequence (e.g., SEQ ID Nos: 5, 15, 25, or 35) that can hybridize to a corresponding M5B sequence (e.g., SEQ ID Nos: 10, 20, 30, or 40) may be used to prepare the adapter (e.g., prepare a Y-shaped adapter as described herein). In embodiments, any M6A sequence (e.g., SEQ ID Nos: 41, 55, 69, or 83) that can hybridize to a corresponding M6B sequence (e.g., SEQ ID Nos: 48, 62, 76, or 90) may be used to prepare the adapter (e.g., prepare a Y-shaped adapter as described herein). In embodiments, any M7A sequence (e.g., SEQ ID Nos: 42, 56, 70, or 84) that can hybridize to a corresponding M7B sequence (e.g., SEQ ID Nos: 49, 63, 77, or 91) may be used to prepare the adapter (e.g., prepare a Y-shaped adapter as described herein). In embodiments, any M8A sequence (e.g., SEQ ID Nos: 43, 57, 71, or 85) that can hybridize to a corresponding M8B sequence (e.g., SEQ ID Nos: 50, 64, 78, or 92) may be used to prepare the adapter (e.g., prepare a Y-shaped adapter as described herein). In embodiments, any M9A sequence (e.g., SEQ ID Nos: 44, 58, 72, or 86) that can hybridize to a corresponding M9B sequence (e.g., SEQ ID Nos: 51, 65, 79, or 93) may be used to prepare the adapter (e.g., prepare a Y-shaped adapter as described herein). In embodiments, any M10A sequence (e.g., SEQ ID Nos: 45, 59, 73, or 87) that can hybridize to a corresponding M10B sequence (e.g., SEQ ID Nos: 52, 66, 80, or 94) may be used to prepare the adapter (e.g., prepare a Y-shaped adapter as described herein). In embodiments, any M11A sequence (e.g., SEQ ID Nos: 46, 60, 74, or 88) that can hybridize to a corresponding M11B sequence (e.g., SEQ ID Nos: 53, 67, 81, or 95) may be used to prepare the adapter (e.g., prepare a Y-shaped adapter as described herein). In embodiments, any M12A sequence (e.g., SEQ ID Nos: 47, 61, 75, or 89) that can hybridize to a corresponding M12B sequence (e.g., SEQ ID Nos: 54, 68, 82, or 96) may be used to prepare the adapter (e.g., prepare a Y-shaped adapter as described herein). The sequences chosen for adapter formation and subsequent ligation onto the sample will determine which sequencing primer may be used for selective sequencing of the target library.

Table 1: Multiplex Seeding Adapter Primer Sequences

| Internal Ref Name | Sequence (5'→3') | SEQ ID Num. |
|---|---|---|
| M1A | AACGCCAAACCTACGGCTTTACTTCCTGTGGCT | SEQ ID NO: 1 |
| M2A | TCTTGAGTCATTCGCAGGGCATGTGCCAGACCT | SEQ ID NO: 2 |
| M3A | TCGGCGTTGTCTGCTATCGTTCTTGGCACTCCT | SEQ ID NO: 3 |
| M4A | GGAGCAATAACCATAAGGCCGTTGACAAGCCCT | SEQ ID NO: 4 |
| M5A | GGCGTATTGCCTTGGTTCTGGCAGCCTCATTGT | SEQ ID NO: 5 |
| M1B | CAGCAGAGGGAACGATTTCAACTTCCTGTGGCT | SEQ ID NO: 6 |
| M2B | CTACTGCAAGGGTGTCTAGAATGTGCCAGACCT | SEQ ID NO: 7 |
| M3B | GACCGACTCGTGAAACGTAATCTTGGCACTCCT | SEQ ID NO: 8 |
| M4B | ACACATTCTTTGCGCCCAGAGTTGACAAGCCCT | SEQ ID NO: 9 |
| M5B | ATTTCATTCGACACCCGGTCGCAGCCTCATTGT | SEQ ID NO: 10 |
| M1A_R | TCGGTGTCCTTCATTTCGGCATCCAAACCGCAA | SEQ ID NO: 11 |
| M2A_R | TCCAGACCGTGTACGGGACGCTTACTGAGTTCT | SEQ ID NO: 12 |
| M3A_R | TCCTCACGGTTCTTGCTATCGTCTGTTGCGGCT | SEQ ID NO: 13 |
| M4A_R | TCCCGAACAGTTGCCGGAATACCAATAACGAGG | SEQ ID NO: 14 |
| M5A_R | TGTTACTCCGACGGTCTTGGTTCCGTTATGCGG | SEQ ID NO: 15 |
| M1B_R | TCGGTGTCCTTCAACTTTAGCAAGGGAGACGAC | SEQ ID NO: 16 |
| M2B_R | TCCAGACCGTGTAAGATCTGTGGGAACGTCATC | SEQ ID NO: 17 |
| M3B_R | TCCTCACGGTTCTAATGCAAAGTGCTCAGCCAG | SEQ ID NO: 18 |

-continued

| Internal Ref Name | Sequence (5'→3') | SEQ ID Num. |
|---|---|---|
| M4B_R | TCCCGAACAGTTGAGACCCGCGTTTCTTACACA | SEQ ID NO: 19 |
| M5B_R | TGTTACTCCGACGCTGGCCCACAGCTTACTTTA | SEQ ID NO: 20 |
| M1A_C | TTGCGGTTTGGATGCCGAAATGAAGGACACCGA | SEQ ID NO: 21 |
| M2A_C | AGAACTCAGTAAGCGTCCCGTACACGGTCTGGA | SEQ ID NO: 22 |
| M3A_C | AGCCGCAACAGACGATAGCAAGAACCGTGAGGA | SEQ ID NO: 23 |
| M4A_C | CCTCGTTATTGGTATTCCGGCAACTGTTCGGGA | SEQ ID NO: 24 |
| M5A_C | CCGCATAACGGAACCAAGACCGTCGGAGTAACA | SEQ ID NO: 25 |
| M1B_C | GTCGTCTCCCTTGCTAAAGTTGAAGGACACCGA | SEQ ID NO: 26 |
| M2B_C | GATGACGTTCCCACAGATCTTACACGGTCTGGA | SEQ ID NO: 27 |
| M3B_C | CTGGCTGAGCACTTTGCATTAGAACCGTGAGGA | SEQ ID NO: 28 |
| M4B_C | TGTGTAAGAAACGCGGGTCTCAACTGTTCGGGA | SEQ ID NO: 29 |
| M5B_C | TAAAGTAAGCTGTGGGCCAGCGTCGGAGTAACA | SEQ ID NO: 30 |
| M1A_RC | AGCCACAGGAAGTAAAGCCGTAGGTTTGGCGTT | SEQ ID NO: 31 |
| M2A_RC | AGGTCTGGCACATGCCCTGCGAATGACTCAAGA | SEQ ID NO: 32 |
| M3A_RC | AGGAGTGCCAAGAACGATAGCAGACAACGCCGA | SEQ ID NO: 33 |
| M4A_RC | AGGGCTTGTCAACGGCCTTATGGTTATTGCTCC | SEQ ID NO: 34 |
| M5A_RC | ACAATGAGGCTGCCAGAACCAAGGCAATACGCC | SEQ ID NO: 35 |
| M1B_RC | AGCCACAGGAAGTTGAAATCGTTCCCTCTGCTG | SEQ ID NO: 36 |
| M2B_RC | AGGTCTGGCACATTCTAGACACCCTTGCAGTAG | SEQ ID NO: 37 |
| M3B_RC | AGGAGTGCCAAGATTACGTTTCACGAGTCGGTC | SEQ ID NO: 38 |
| M4B_RC | AGGGCTTGTCAACTCTGGGCGCAAAGAATGTGT | SEQ ID NO: 39 |
| M5B_RC | ACAATGAGGCTGCGACCGGGTGTCGAATGAAAT | SEQ ID NO: 40 |
| M6A | TGTTGCATCTCCACCCGGATTGAGCCTTCAGCT | SEQ ID NO: 41 |
| M7A | CACAACGGGAGCTGTGGAATTGGTTCACCTGGT | SEQ ID NO: 42 |
| M8A | TGGACTAAGACTCGTCCTCCAGCGGACCTAAGT | SEQ ID NO: 43 |
| M9A | GTATGATGGTGTTGCGGCTTCTCGCTTAACGCT | SEQ ID NO: 44 |
| M10A | TCTGAGTGCCAGTGACTTCACGCATTCGCTTGT | SEQ ID NO: 45 |
| M11A | TACGACACACTCGGGCTCTATGGGCTTCATGGT | SEQ ID NO: 46 |
| M12A | GTTTGAGTGAAGGCGGTCCAACCCTTAGTGCGT | SEQ ID NO: 47 |
| M6B | CTATAAGTTTGTCGTGCCCGTGAGCCTTCAGCT | SEQ ID NO: 48 |
| M7B | GGAGTGACACTGACTACGTTTGGTTCACCTGGT | SEQ ID NO: 49 |
| M8B | GTCAACGCCCTAGCAGACATAGCGGACCTAAGT | SEQ ID NO: 50 |
| M9B | CCAGAACCTATTGAGCCTGACTCGCTTAACGCT | SEQ ID NO: 51 |
| M10B | AGGTGTTCGTACAATGAGGCCGCATTCGCTTGT | SEQ ID NO: 52 |
| M11B | TGGTCAAGGGCAACTAATCCTGGGCTTCATGGT | SEQ ID NO: 53 |
| M12B | ACAATTACCCGTTTACCGGCACCCTTAGTGCGT | SEQ ID NO: 54 |
| M6A_R | TCGACTTCCGAGTTAGGCCCACCTCTACGTTGT | SEQ ID NO: 55 |

-continued

| Internal Ref Name | Sequence (5'→3') | SEQ ID Num. |
|---|---|---|
| M7A_R | TGGTCCACTTGGTTAAGGTGTCGAGGGCAACAC | SEQ ID NO: 56 |
| M8A_R | TGAATCCAGGCGACCTCCTGCTCAGAATCAGGT | SEQ ID NO: 57 |
| M9A_R | TCGCAATTCGCTCTTCGGCGTTGTGGTAGTATG | SEQ ID NO: 58 |
| M10A_R | TGTTCGCTTACGCACTTCAGTGACCGTGAGTCT | SEQ ID NO: 59 |
| M11A_R | TGGTACTTCGGGTATCTCGGGCTCACACAGCAT | SEQ ID NO: 60 |
| M12A_R | TGCGTGATTCCCAACCTGGCGGAAGTGAGTTTG | SEQ ID NO: 61 |
| M6B_R | TCGACTTCCGAGTGCCCGTGCTGTTTGAATATC | SEQ ID NO: 62 |
| M7B_R | TGGTCCACTTGGTTTGCATCAGTCACAGTGAGG | SEQ ID NO: 63 |
| M8B_R | TGAATCCAGGCGATACAGACGATCCCGCAACTG | SEQ ID NO: 64 |
| M9B_R | TCGCAATTCGCTCAGTCCGAGTTATCCAAGACC | SEQ ID NO: 65 |
| M10B_R | TGTTCGCTTACGCCGGAGTAACATGCTTGTGGA | SEQ ID NO: 66 |
| M11B_R | TGGTACTTCGGGTCCTAATCAACGGGAACTGGT | SEQ ID NO: 67 |
| M12B_R | TGCGTGATTCCCACGGCCATTTGCCCATTAACA | SEQ ID NO: 68 |
| M6A_C | ACAACGTAGAGGTGGGCCTAACTCGGAAGTCGA | SEQ ID NO: 69 |
| M7A_C | GTGTTGCCCTCGACACCTTAACCAAGTGGACCA | SEQ ID NO: 70 |
| M8A_C | ACCTGATTCTGAGCAGGAGGTCGCCTGGATTCA | SEQ ID NO: 71 |
| M9A_C | CATACTACCACAACGCCGAAGAGCGAATTGCGA | SEQ ID NO: 72 |
| M10A_C | AGACTCACGGTCACTGAAGTGCGTAAGCGAACA | SEQ ID NO: 73 |
| M11A_C | ATGCTGTGTGAGCCCGAGATACCCGAAGTACCA | SEQ ID NO: 74 |
| M12A_C | CAAACTCACTTCCGCCAGGTTGGGAATCACGCA | SEQ ID NO: 75 |
| M6B_C | GATATTCAAACAGCACGGGCACTCGGAAGTCGA | SEQ ID NO: 76 |
| M7B_C | CCTCACTGTGACTGATGCAAACCAAGTGGACCA | SEQ ID NO: 77 |
| M8B_C | CAGTTGCGGGATCGTCTGTATCGCCTGGATTCA | SEQ ID NO: 78 |
| M9B_C | GGTCTTGGATAACTCGGACTGAGCGAATTGCGA | SEQ ID NO: 79 |
| M10B_C | TCCACAAGCATGTTACTCCGGCGTAAGCGAACA | SEQ ID NO: 80 |
| M11B_C | ACCAGTTCCCGTTGATTAGGACCCGAAGTACCA | SEQ ID NO: 81 |
| M12B_C | TGTTAATGGGCAAATGGCCGTGGGAATCACGCA | SEQ ID NO: 82 |
| M6AR_C | AGCTGAAGGCTCAATCCGGGTGGAGATGCAACA | SEQ ID NO: 83 |
| M7AR_C | ACCAGGTGAACCAATTCCACAGCTCCCGTTGTG | SEQ ID NO: 84 |
| M8AR_C | ACTTAGGTCCGCTGGAGGACGAGTCTTAGTCCA | SEQ ID NO: 85 |
| M9AR_C | AGCGTTAAGCGAGAAGCCGCAACACCATCATAC | SEQ ID NO: 86 |
| M10A_RC | ACAAGCGAATGCGTGAAGTCACTGGCACTCAGA | SEQ ID NO: 87 |
| M11A_RC | ACCATGAAGCCCATAGAGCCCGAGTGTGTCGTA | SEQ ID NO: 88 |
| M12A_RC | ACGCACTAAGGGTTGGACCGCCTTCACTCAAAC | SEQ ID NO: 89 |
| M6B_RC | AGCTGAAGGCTCACGGGCACGACAAACTTATAG | SEQ ID NO: 90 |
| M7B_RC | ACCAGGTGAACCAAACGTAGTCAGTGTCACTCC | SEQ ID NO: 91 |
| M8B_RC | ACTTAGGTCCGCTATGTCTGCTAGGGCGTTGAC | SEQ ID NO: 92 |
| M9B_RC | AGCGTTAAGCGAGTCAGGCTCAATAGGTTCTGG | SEQ ID NO: 93 |

-continued

| Internal Ref Name | Sequence (5'→3') | SEQ ID Num. |
|---|---|---|
| M10B_RC | ACAAGCGAATGCGGCCTCATTGTACGAACACCT | SEQ ID NO: 94 |
| M11B_RC | ACCATGAAGCCCAGGATTAGTTGCCCTTGACCA | SEQ ID NO: 95 |
| M12B_RC | ACGCACTAAGGGTGCCGGTAAACGGGTAATTGT | SEQ ID NO: 96 |

Library seeding and amplification: The resulting adapter-ligated libraries were then applied to each of two four-lane flow cells in the indicated order of FIG. 6A, with 10 pM of library used per individual genomic library in lanes 1-3, and 30 pM of the mixed library used in lane 4. The libraries were then amplified using solid-phase amplification methods. In embodiments, the polynucleotides include amplicons of a single species (e.g., "monoclonal"), thereby forming a homogenous cluster. However, in preferred embodiments, the polynucleotides at a given site are heterogeneous (e.g., "polyclonal"), such that individual molecules having different library sequences are present at the site or feature. In some embodiments, a polyclonal cluster includes template polynucleotides including the same template sequence but containing different adapter sequences compared to other substantially identical template polynucleotides (e.g., the same target polynucleotide sequence from different samples, prepared with the different adapter sequences). As used herein, the terms "overlapping amplification cluster" and "overlapping cluster" refer to a site (e.g., a discrete site) on a solid support that includes a plurality of polyclonal immobilized polynucleotides, and a plurality of immobilized complementary polynucleotides. For example, in the mixed library lane (i.e., Lane 4 of each flow cell), polyclonal or overlapping amplification clusters could include: 1) *Clostridium* and *E. coli* template DNA; 2) *Clostridium* and *Salmonella* template DNA; 3) *E. coli* and *Salmonella* template DNA; or 4) *Clostridium, E. coli*, and *Salmonella* template DNA. Following amplification, the clusters were quantified by introducing a nucleic acid stain (e.g., SYBR® Gold stain available from Thermo Fisher, Catalog #S11494 or a FAM (6-fluorescein amidite) labeled oligonucleotide) in the presence of a buffer and allowed to incubate with the amplicons for 10 minutes. After a wash, the substrate containing the stained amplicons was imaged and subjected to post-processing analysis to determine cluster size and brightness. The feature count is significantly higher, approximately twice as bright, in the mixed library lane compared to the individual sample lanes, representative of the mixed library lane generating higher cluster density.

Sequencing: Each template was then sequencing using the corresponding sequencing primer based on the adapter used during library preparation. For the individual samples, lane 1 was sequenced using an M1-specific sequencing primer (i.e., a sequencing primer that anneals to the M1 region of the adapter and one or more labeled modified nucleotides are incorporated into the primer and the incorporated nucleotide is detected), lane 2 using an M5-specific sequencing primer, and lane 3 using an SP-specific sequencing primer. Selective sequencing was performed for the mixed library sample, as outlined in FIG. 6B. The *E. coli* library was sequenced first with the M5b sequencing primer for 80 cycles, followed by denaturing (e.g., NaOH stripping of extended and residual primers (flow cell 1 only)). Blocking of extended and residual un-extended primers having free a 3'-OH was then performed with a dideoxynucleotide triphosphate (ddNTP). Following blocking, the next sequencing primer was annealed (e.g., the M1b sequencing primer for *Clostridium* genome sequencing). The primer stripping/blocking and annealing process was subsequently repeated for the SP primer for *Salmonella* genome sequencing.

The multiplexed seeding in the pooled sample (lane 4 in each flow cell) led to an increase in overall throughput compared to the individual sample lanes. For both of the flow cells, the average throughput increased by a factor of 2.2. These results indicate that multiplexed seeding can increase throughput beyond that seen with the standard template seeding, which is limited by Poisson statistics.

TABLE 2

Percent of filtered reads mapped (average of FC1 and FC2)

| | | Alignment | | |
|---|---|---|---|---|
| | Sequencing | E. Coli | Clostridium | Salmonella |
| E. Coli | Individual | 98.7 | 0.6 | 18.1 |
| | Pool | 98.3 | 0.6 | 17.4 |
| Clostridium | Individual | 0.5 | 97.0 | 0.5 |
| | Pool | 0.5 | 96.8 | 0.4 |
| Salmonella | Individual | 18.9 | 0.6 | 99.0 |
| | Pool | 18.4 | 0.6 | 98.7 |

Table 2 summarizes the percent of filtered reads mapped in each flow cell (reported as the average of FC1 and FC2). The percent of reads sequenced in either the individual samples (i.e., Lanes 1-3, indicated as "Individual") or pooled sample (i.e., Lane 4, indicated as "Pool") were then mapped to *E. coli, Clostridium*, or *Salmonella* reference genomes. FC1 indicates flow cell 1, and FC2 indicates flow cell 2. These results indicate that there is no cross-talk between mismatched libraries and sequencing primers, as signal was detected only in the expected lanes for each genomic library. A fraction of each of the *E. coli*-specific and *Salmonella*-specific reads were aligned to the *Salmonella* and *E. coli* references. Such an overlap is expected as *Salmonella* and *E. coli* are both in the family Enterobacteriaceae.

TABLE 3

% Accuracy for samples in FC1 and FC2

| Flow Cell | Library | Sample Name | Accuracy |
|---|---|---|---|
| FC1 | E. coli | Lane 2 - E. coli | 99.6% |
| FC1 | E. coli | Lane 4 - Mixed Library | 99.7% |
| FC2 | E. coli | Lane 2 - E. coli | 99.8% |
| FC2 | E. coli | Lane 4 - Mixed Library | 99.8% |
| FC1 | Clostridium | Lane 1 - Clostridium | 99.8% |
| FC1 | Clostridium | Lane 4 - Mixed Library | 99.8% |
| FC2 | Clostridium | Lane 1 - Clostridium | 99.8% |
| FC2 | Clostridium | Lane 4 - Mixed Library | 99.8% |
| FC1 | Salmonella | Lane 3 - Salmonella | 99.8% |

TABLE 3-continued

% Accuracy for samples in FC1 and FC2

| Flow Cell | Library | Sample Name | Accuracy |
|---|---|---|---|
| FC1 | *Salmonella* | Lane 4 - Mixed Library | 99.7% |
| FC2 | *Salmonella* | Lane 3 - *Salmonella* | 99.8% |
| FC2 | *Salmonella* | Lane 4 - Mixed Library | 99.8% |

For each sample, the % accuracy is reported in Table 3. Results are split into the individual sample or the mixed library sample and reported for each bacterial genomic library sequenced as samples from flow cell 1 (i.e., samples treated with NaOH upon terminating sequencing for each sequencing primer) or samples from flow cell 2 (i.e., no NaOH treatment). No significant differences were observed comparing FC1 conditions to FC2 conditions (i.e., NaOH stripping step included in FC1 did not affect read quality or throughput). Furthermore, the data presenting herein highlights the improved sequencing throughput afforded by multiplex seeding. The compositions and methods described throughout the application result inefficient savings in reagents and time by analyzing multiple libraries in a single flow cell lane.

Example 4. Multiplexed Proteomics

While the measurement of DNA and RNA have some value in the prediction of protein function, these measurements do not always correlate with protein levels and are blind to the factors critical to protein function, such as post-translational modifications. The unbiased identification and quantification of proteins requires their direct measurement with technologies that specifically detect their unique structure, mass, charge, or biochemical composition (see, Maarten Altelaar A F et al. Nature Rev. Genet. 2013; 14: 35-48, which is incorporated herein by reference). Mass-spectroscopy (MS) allows for thousands of proteins to be analyzed in parallel from a single sample, but has limitations in sample multiplexing as well as sensitivity, and is particularly expensive and labor intensive to perform at scale (see, e.g., Cayer D M et al. Hum. Mol. Genet. 2016; 25(R2): R182-R189, which is incorporated herein by reference). Mass-cytometry is a novel technology whereby antibodies are functionalized with transition metal elements, allowed to bind to cellular proteins, and then analyzed on a mass-cytometer where the antibody-protein complexes are counted using the mass of the transition metal as an indicator. Nanopore sequencing, though currently with minimal examples, allows for single proteins to be analyzed as they are unfolded and threaded through a nanopore, using the changes current through the nanopore opening as a protein signature readout. Aptamers are used to detect proteins, whereby upon aptamer binding and isolation of the aptamer-protein complexes, the aptamers are quantified and identified either through qPCR, microarray, or NGS based analysis. ImmunoPCR, the Proximity-Extension-Assay (PEA), or the Proximity-Ligation-Assay (PLA), merges the properties of antibodies and oligonucleotides, such that the detection of proteins is accomplished by the antibody and the analysis of that detection event is accomplished through the PCR amplification of the attached oligonucleotide tag for either qPCR or NGS based analysis.

Aptamers are relatively short oligonucleotides (50-100 nucleotides in length), and are developed through the iterative evolution of a random library of oligonucleotides until an aptamer of sufficient affinity is acquired (e.g., developed through the SELEX process, described further in U.S. Pat. Nos. 5,475,096 and 5,270,163, which are each incorporated by reference herein). There have been numerous developments of these molecules, where the binding of proteins by aptamers is either detected directly through capture and pull-down assays, such as with the SomaScan technology developed by Somalogic, Inc. Aptamers can be evolved directly to operate in a sandwich-type assay, or indirectly through the release of other nucleic acids or fluorophores upon protein binding to the aptamer sequence (termed structure-switching aptamers). The generation of high-affinity aptamers, termed SOMAmers (or Slow-off Rate Modified Aptamers), which are composed of modified hydrophobic uracil residues as well as the normal nucleobases, allow this high degree of multiplexing (see, U.S. Pat. No. 7,947,447, which is incorporated herein by reference).

Multiplexed aptamer assays that provide solution-based target interaction and separation steps designed to remove specific components of an assay mixture have also been described, see U.S. Pat. Nos. 7,855,054 and 7,964,356 and U.S. Pat. Publication Nos. US 2011/0136099 and US 2012/0115752, each of which is incorporated here by reference. The aptamer assay methods described therein use one or more specific capture steps to separate components of a test sample from the target or targets to be detected while isolating the aptamer-target affinity complex. The sensitivity and specificity of many assay formats are limited by the ability of the detection method to resolve true signal from signal that arises due to non-specific associations during the assay and result in a detectable signal. Methods to reduce background in single or multiplexed aptamer assays while maintaining target/aptamer specific interactions include using serial aptamer binding, washing, and elution steps across multiple solid supports, and have been described in, e.g., U.S. Pat. Publication US 2021/0239692, which is incorporated herein by reference.

Any of the methods described herein may be used to conduct a single-analyte test or a multiplexed analysis of a test sample. Any multiplexed analysis can include the use of two, tens, hundreds, or thousands of aptamers to simultaneously assay an equal number of target molecules in a test sample, such as a biological sample, for example. In these embodiments, a plurality of aptamers is introduced to the test sample and any of the above-described assays can be performed. After release of the aptamers, any suitable multiplexed nucleic acid detection methods can be employed to independently measure the different aptamers that have been released. In one embodiment, this can be accomplished by hybridization to complementary probes that are separately arranged on a solid surface. In another embodiment, next-generation sequencing (NGS) methods can be used to detect and optionally quantify each of the different aptamers. In embodiments, NGS is used to do highly parallelized readout of up to 7k-10k (or more) aptamers or barcodes.

The multiplex priming format described supra and herein is well suited for sequencing a plurality of proteomic target barcodes (e.g., barcodes attached to a protein-specific binding moiety, for example, an aptamer), increasing the number of reads that may be sequenced on a single flow cell. In an embodiment, the specific binding moiety (e.g., the aptamer) includes a barcode. The barcode may be used to unique identify the protein target from a proteome. The barcode may be an extra sequence located on a non-targeting end or region (i.e., the non-functional sequence) of the aptamer. In embodiments, the functional sequence (i.e., sequence that interacts with a protein target) of the aptamer can be read directly, serving as the barcode. Following analyte binding by the aptamer library, the barcodes (e.g., functional, or non-functional sequences of the aptamer) are pooled and labeled with adapters corresponding to unique sequencing primers. By utilizing multiple different sequencing primers in combination with corresponding adapters, significantly more reads may be sequenced in each flow cell lane during a single run. For example, a sample (e.g., an aptamer barcode) may be prepared with 2 unique adapters that can each hybridize to a unique sequencing primer. If a particular region on the flow cell is seeded by a template with sequencing primer #1, and also by templates with sequencing primers #2 and #3, they can be sequenced independently thereafter. Initially, 35 sequencing cycles are performed with sequencing primer #1, followed by another 35 sequencing cycles with sequencing primer #2, and then another 35 cycles with sequencing primer #3, until all of the seeded templates in a region have been identified. In embodiments, different samples (or different pools of samples) are attached to different sequencing adapters. In embodiments, the aptamer barcodes are attached to between 1 to 10 different sequencing adapters. Each round of priming in the multiple primed flow cell, for example, would correspond to an individual sample that could contain any of those proteins in a very wide dynamic range of concentrations. In some embodiments, more than 3, 4, or 5 sequencing primers may be used to sequence an identical number of unique templates in a single flow cell lane. In some embodiments, more than 6, 7, 8, 9, or 10 sequencing primers may be used to sequence an identical number of unique templates in a single flow cell lane This method greatly increases the number of short reads that may be obtained from a single flow cell and reagent mixture, decreasing the cost, and increasing the number of detectable protein targets.

P-EMBODIMENTS

The present disclosure provides the following illustrative embodiments.

Embodiment P1. A method of sequencing a plurality of template polynucleotides, the method comprising: (a) amplifying the plurality of template polynucleotides to generate a plurality of overlapping amplification clusters on a surface, wherein: (i) an overlapping amplification cluster comprises amplicons of a first template polynucleotide comprising a first adapter sequence, and amplicons of a second template polynucleotide comprising a second adapter sequence, wherein the first and second template polynucleotides are not substantially complementary to each other; (ii) the first adapter sequence and second adapter sequence comprise a sequence complementary to an amplification primer attached to the surface; (iii) the first adapter sequence comprises a sequence complementary to a first sequencing primer; and (iv) the second adapter sequence comprises a sequence complementary to a second sequencing primer that is different from the first sequencing primer; (b) for each of a plurality of the overlapping amplification clusters: (i) extending the first sequencing primer hybridized to the first adapter sequence in a sequencing cycle and detecting one or more labels in a first detection region to generate a sequencing read for the first template polynucleotide, and (ii) extending the second sequencing primer hybridized to the second adapter sequence in a sequencing cycle and detecting one or more labels in a second detection region to generate a sequencing read for the second template polynucleotide, wherein the first and second detection regions are overlapping.

Embodiment P2. The method of Embodiment P1, wherein the first template polynucleotide further comprises a third adapter sequence, wherein the third adapter sequence comprises i) a sequence complementary to an amplification primer attached to the surface, and ii) a sequence complementary to a third sequencing primer; and wherein the second template polynucleotide further comprises a fourth adapter sequence, wherein the fourth adapter sequence comprises i) a sequence complementary to an amplification primer attached to the surface, and ii) a sequence complementary to a fourth sequencing primer.

Embodiment P3. The method of Embodiment P1 or Embodiment P2, wherein the first and second detection regions overlap by at least 25%.

Embodiment P4. The method of Embodiment P1 or Embodiment P2, wherein the first and second detection regions overlap by at least 50%.

Embodiment P5. The method of Embodiment P1 or Embodiment P2, wherein the first and second detection regions overlap by at least 75%.

Embodiment P6. The method of any one of Embodiment P1 to Embodiment P5, wherein the overlapping amplification cluster comprises a total cluster density per unit area of about 100,000 to about 2,000,000 amplicons per $mm^2$.

Embodiment P7. The method of any one of Embodiment P1 to Embodiment P6, wherein the ratio of overlapping amplification clusters to monoclonal amplification clusters is at least about 2:1.

Embodiment P8. The method of any one of Embodiment P1 to Embodiment P7, wherein the plurality of template polynucleotides are double-stranded template polynucleotides.

Embodiment P9. The method of any one of Embodiment P1 to Embodiment P8, wherein prior to step (a), the method further comprises ligating a first adapter to a first end of the first template polynucleotide and ligating a second adapter to a first end of the second template polynucleotide.

Embodiment P10. The method of any one of Embodiment P1 to Embodiment P8, wherein prior to step (a), the method further comprises ligating a first adapter to a first end of the first template polynucleotide, ligating a third adapter to a second end of the first template polynucleotide, ligating a second adapter to a first end of the second template polynucleotide, and ligating a fourth adapter to a second end of the second template polynucleotide.

Embodiment P11. The method of any one of Embodiment P1 to Embodiment P10, wherein the first and second template polynucleotides comprise substantially identical template sequences.

Embodiment P12. The method of any one of Embodiment P1 to Embodiment P10, wherein the first and second template polynucleotides comprise different template sequences.

Embodiment P13. The method of any one of Embodiment P1 to Embodiment P12, wherein the first and second adapter sequences further comprise a barcode sequence.

Embodiment P14. The method of Embodiment P13, wherein each barcode sequence is selected from a set of barcode sequences represented by a random or partially random sequence.

Embodiment P15. The method of Embodiment P13 or Embodiment P14, wherein each barcode sequence is selected from a set of barcode sequences represented by a random sequence.

Embodiment P16. The method of any one of Embodiment P13 to Embodiment P15, wherein each barcode sequence differs from every other barcode sequence by at least two nucleotide positions.

Embodiment P17. The method of any one of Embodiment P13 to Embodiment P16, wherein each barcode sequence comprises about 5 to about 20 nucleotides, or about 10 to about 20 nucleotides.

Embodiment P18. The method of any one of Embodiment P9 to Embodiment P17, wherein the first adapter and/or second adapter is a Y-adapter.

Embodiment P19. The method of any one of Embodiment P9 to Embodiment P18, wherein the first adapter and/or second adapter is a hairpin adapter, wherein the hairpin adapter comprises a cleavable site.

Embodiment P20. The method of Embodiment P18, wherein the Y-adapter comprises (i) a first strand having a 5'-arm and a 3'-portion, and (ii) a second strand having a 5'-portion and a 3'-arm, wherein the 3'-portion of the first strand is substantially complementary to the 5'-portion of the second strand, and the 5'-arm of the first strand is not substantially complementary to the 3'-arm of the second strand.

Embodiment P21. The method of Embodiment P18 or Embodiment P20, wherein the ligating of the first adapter comprises ligating a 3'-end of the first strand of the Y-adapter to a 5'-end of a forward strand of the first template polynucleotide, and ligating a 5'-end of the second strand of the Y-adapter to a 3'-end of a reverse strand of the first template polynucleotide.

Embodiment P22. The method of any one of Embodiment P1 to Embodiment P21, wherein fewer than 35% of the clusters are monoclonal amplification clusters.

Embodiment P23. The method of any one of Embodiment P1 to Embodiment P21, wherein at least 30% are overlapping amplification clusters.

Embodiment P24. The method of Embodiment P2, further comprising hybridizing a third sequencing primer to the third adapter sequence and a fourth sequencing primer to the fourth adapter sequence, extending the third and fourth sequencing primers and detecting one or more labels in the first and second detection regions to generate second sequencing reads for the first and second template polynucleotides.

Embodiment P25. The method of any one of Embodiment P1 to Embodiment P24, wherein the amplicons of a first template polynucleotide comprise at least one cleavable site.

Embodiment P26. The method of Embodiment P25, further comprising removing the amplicons of a first template polynucleotide by cleaving the amplicons at a cleavable site.

Embodiment P27. The method of Embodiment P25 or Embodiment P26, wherein cleaving comprises enzymatically or chemically cleaving the at least one cleavable site.

Embodiment P28. The method of any one of Embodiment P19 or Embodiment P25 to Embodiment P27, wherein the cleavable site comprises a diol linker, disulfide linker, photocleavable linker, abasic site, deoxyuracil triphosphate (dUTP), deoxy-8-oxo-guanine triphosphate (d-8-oxoG), methylated nucleotide, ribonucleotide, or a sequence containing a modified or unmodified nucleotide that is specifically recognized by a cleaving agent.

Embodiment P29. The method of any one of Embodiment P25 to Embodiment P28, wherein cleaving the amplicons of a first template polynucleotide comprises contacting the cleavable site with a cleaving agent, wherein the cleaving agent comprises a reducing agent, sodium periodate, RNase, formamidopyrimidine DNA glycosylase (Fpg), endonuclease, or uracil DNA glycosylase (UDG).

Embodiment P30. The method of any one of Embodiment P1 to Embodiment P29, wherein the method comprises about 50 to about 200 sequencing cycles.

Embodiment P31. The method of any one of Embodiment P1 to Embodiment P30, wherein the method comprises a sequencing reaction mixture comprising a different sequencing primer every about 25 to about 75 sequencing cycles.

Embodiment P32. The method of any one of Embodiment P1 to Embodiment P31, wherein the method further comprises incorporating a plurality of native deoxy nucleotide triphosphates (dNTPs) into the 3' end of the extended sequencing primer.

Embodiment P33. The method of any one of Embodiment P1 to Embodiment P32, wherein the method further comprises incorporating a dideoxy nucleotide triphosphate (ddNTP) into the 3' end of each of a plurality of extended sequencing primers.

Embodiment P34. The method of Embodiment P33, wherein the ddNTPs are incorporated into the 3' end of each of a plurality of extended sequencing primers every about 25 to about 75 sequencing cycles.

Embodiment P35. The method of any one of Embodiment P1 to Embodiment P34, wherein the template polynucleotide comprises genomic DNA, complementary DNA (cDNA), cell-free DNA (cfDNA), messenger RNA (mRNA), transfer RNA (tRNA), ribosomal RNA (rRNA), cell-free RNA (cfRNA), or noncoding RNA (ncRNA).

Embodiment P36. The method of any one of Embodiment P1 to Embodiment P35, wherein the template polynucleotide is about 20 to 200 nucleotides in length.

Embodiment P37. The method of any one of Embodiment P1 to Embodiment P35, wherein the template polynucleotide is less than about 100 nucleotides in length.

Embodiment P38. The method of any one of Embodiment P1 to Embodiment P37, wherein amplifying comprises bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, or emulsion PCR on particles, or combinations thereof.

Embodiment P39. The method of any one of Embodiment P1 to Embodiment P38, wherein amplifying comprises a bridge polymerase chain reaction (bPCR) amplification.

Embodiment P40. The method of any one of Embodiment P1 to Embodiment P38, wherein amplifying comprises a thermal bridge polymerase chain reaction (t-bPCR) amplification.

Embodiment P41. The method of any one of Embodiment P1 to Embodiment P38, wherein amplifying comprises a chemical bridge polymerase chain reaction (c-bPCR) amplification.

Embodiment P42. The method of any one of Embodiment P1 to Embodiment P41, wherein said amplifying is at discrete locations in an ordered array of amplification sites on the surface.

Embodiment P43. A substrate comprising: (a) a plurality of overlapping amplification clusters on a surface of the substrate, wherein: (i) an overlapping amplification cluster comprises amplicons of a first template polynucleotide comprising a first adapter sequence, and amplicons of a second template polynucleotide comprising a second adapter sequence, wherein the first and second template polynucleotides are not substantially complementary to each other; (ii)

the first adapter sequence and second adapter sequence comprise a sequence complementary to an amplification primer attached to the surface; (iii) the first adapter sequence comprises a sequence complementary to a first sequencing primer; and (iv) the second adapter sequence comprises a sequence complementary to a second sequencing primer that is different from the first sequencing primer; and (b) a plurality of first sequencing primers hybridized to the first adapter sequences of the overlapping amplification clusters.

Embodiment P44. The substrate of Embodiment P43, wherein the first template polynucleotide further comprises a third adapter sequence, wherein the third adapter sequence comprises i) a sequence complementary to an amplification primer attached to the surface, and ii) a sequence complementary to a third sequencing primer; and wherein the second template polynucleotide further comprises a fourth adapter sequence, wherein the fourth adapter sequence comprises i) a sequence complementary to an amplification primer attached to the surface, and ii) a sequence complementary to a fourth sequencing primer.

Embodiment P45. The substrate of Embodiment P43 or Embodiment P44, wherein the first and second detection regions overlap by at least 25%.

Embodiment P46. The substrate of Embodiment P43 or Embodiment P44, wherein the first and second detection regions overlap by at least 50%.

Embodiment P47. The substrate of Embodiment P43 or Embodiment P44, wherein the first and second detection regions overlap by at least 75%.

Embodiment P48. The substrate of any one of Embodiment P43 to Embodiment P47, wherein the overlapping amplification cluster comprises a total cluster density per unit area of about 100,000 to about 2,000,000 amplicons per $mm^2$.

Embodiment P49. The substrate of any one of Embodiment P43 to Embodiment P48, wherein the ratio of overlapping amplification clusters to monoclonal amplification clusters is at least about 2:1.

Embodiment P50. The substrate of any one of Embodiment P43 to Embodiment P49, wherein the plurality of template polynucleotides are double-stranded template polynucleotides.

Embodiment P51. The substrate of any one of Embodiment P43 to Embodiment P50, wherein the first and second template polynucleotides comprise substantially identical template sequences.

Embodiment P52. The substrate of any one of Embodiment P43 to Embodiment P50, wherein the first and second template polynucleotides comprise different template sequences.

Embodiment P53. The substrate of any one of Embodiment P43 to Embodiment P52, wherein the first and second adapter sequences further comprise a barcode sequence.

Embodiment P54. The substrate of Embodiment P53, wherein each barcode sequence is selected from a set of barcode sequences represented by a random or partially random sequence.

Embodiment P55. The substrate of Embodiment P53 or Embodiment P54, wherein each barcode sequence is selected from a set of barcode sequences represented by a random sequence.

Embodiment P56. The substrate of any one of Embodiment P53 to Embodiment P55, wherein each barcode sequence differs from every other barcode sequence by at least two nucleotide positions.

Embodiment P57. The substrate of any one of Embodiment P53 to Embodiment P56, wherein the barcode sequence comprises about 5 to about 20 nucleotides, or about 10 to about 20 nucleotides.

Embodiment P58. The substrate of any one of Embodiment P43 to Embodiment P57, wherein the first adapter sequence and/or second adapter sequence is a sequence of a Y-adapter.

Embodiment P59. The substrate of any one of Embodiment P43 to Embodiment P57, wherein the first adapter sequence and/or second adapter sequence is a sequence of a hairpin adapter, wherein the hairpin adapter comprises a cleavable site.

Embodiment P60. The substrate of Embodiment P58, wherein the Y-adapter comprises (i) a first strand having a 5'-arm and a 3'-portion, and (ii) a second strand having a 5'-portion and a 3'-arm, wherein the 3'-portion of the first strand is substantially complementary to the 5'-portion of the second strand, and the 5'-arm of the first strand is not substantially complementary to the 3'-arm of the second strand.

Embodiment P61. The substrate of any one of Embodiment P43 to Embodiment P60, wherein fewer than 35% of the clusters are monoclonal amplification clusters.

Embodiment P62. The substrate of any one of Embodiment P43 to Embodiment P60, wherein at least 30% are overlapping amplification clusters.

Embodiment P63. The substrate of any one of Embodiment P43 to Embodiment P62, wherein the amplicons of a first template polynucleotide comprise at least one cleavable site.

Embodiment P64. The substrate of Embodiment P59 or Embodiment P63, wherein the cleavable site comprises a diol linker, disulfide linker, photocleavable linker, abasic site, deoxyuracil triphosphate (dUTP), deoxy-8-oxo-guanine triphosphate (d-8-oxoG), methylated nucleotide, ribonucleotide, or a sequence containing a modified or unmodified nucleotide that is specifically recognized by a cleaving agent.

Embodiment P65. The substrate of any one of Embodiment P43 to Embodiment P64, wherein the template polynucleotide comprises genomic DNA, complementary DNA (cDNA), cell-free DNA (cfDNA), messenger RNA (mRNA), transfer RNA (tRNA), ribosomal RNA (rRNA), cell-free RNA (cfRNA), or noncoding RNA (ncRNA).

Embodiment P66. The substrate of any one of Embodiment P43 to Embodiment P65, wherein the template polynucleotide is about 20 to 200 nucleotides in length.

Embodiment P67. The substrate of any one of Embodiment P43 to Embodiment P65, wherein the template polynucleotide is less than about 100 nucleotides in length.

Embodiment P68. The substrate of any one of Embodiment P43 to Embodiment P67, wherein overlapping amplification clusters form an ordered array at discrete locations on the surface.

Embodiment P69. A method of amplifying a plurality of template polynucleotides, the method comprising: (a) contacting a surface with a first template polynucleotide comprising a first adapter sequence thereby forming a first hybridized complex attached to said surface and a second template polynucleotide comprising a second adapter sequence thereby forming a second hybridized complex attached to said surface, wherein: (i) said first adapter sequence comprises a first platform primer sequence and a first sequencing primer sequence; (ii) said second adapter sequence comprises a second platform primer sequence and a second sequencing primer sequence; (iii) said first hybridized complex comprises a first amplification primer attached to the surface hybridized to said first adapter sequence; (iv)

said second hybridized complex comprises a second amplification primer attached to the surface hybridized to said second adapter sequence; and (v) the first platform primer sequence is different from said second platform primer sequence, said first sequencing primer sequence is different from said second sequencing primer sequence and said first amplification primer is different from said second amplification primer; (b) amplifying the first template polynucleotide and the second template polynucleotide to form a plurality of first template amplicons and plurality of second template amplicons that form overlapping amplification clusters on the surface.

Embodiment P70. The method of Embodiment P69, further comprising: (i) hybridizing and extending a first sequencing primer in a first sequencing cycle and detecting one or more labels in a first detection region to generate a sequencing read for the first template polynucleotide, wherein the first sequencing primer is complementary to the first sequencing primer sequence, and (ii) hybridizing and extending a second sequencing primer in a second sequencing cycle and detecting one or more labels in a second detection region to generate a sequencing read for the second template polynucleotide, wherein the second sequencing primer is complementary to the second sequencing primer sequence, and wherein the first and second detection regions are overlapping.

Embodiment P71. The method of Embodiment P69, further comprising contacting the surface with a third template polynucleotide comprising a third adapter sequence thereby forming a third hybridized complex attached to said surface and a fourth template polynucleotide comprising a fourth adapter sequence thereby forming a fourth hybridized complex attached to said surface, wherein (i) said third adapter sequence comprises the first platform primer sequence and a third sequencing primer sequence; (ii) said fourth adapter sequence comprises the second platform primer sequence and a fourth sequencing primer sequence.

Embodiment P72. The method of Embodiment P72, further comprising: (i) hybridizing and extending a third sequencing primer in a first sequencing cycle and detecting one or more labels in a first detection region to generate a sequencing read for the third template polynucleotide, wherein the third sequencing primer is complementary to the third sequencing primer sequence, and (ii) hybridizing and extending a fourth sequencing primer in a second sequencing cycle and detecting one or more labels in a second detection region to generate a sequencing read for the fourth template polynucleotide, wherein the fourth sequencing primer is complementary to the fourth sequencing primer, and wherein the first and second detection regions are overlapping.

Embodiment P73. The method of Embodiment P70 or Embodiment P72, wherein the first and second detection regions overlap by at least 25%, at least 50%, or at least 75%.

Embodiment P74. The method of any one of Embodiment P69 to P73, wherein the overlapping amplification cluster comprises a total cluster density per unit area of about 100,000 to about 2,000,000 amplicons per mm$^2$.

Embodiment P75. The method of any one of Embodiment P69 to P74, wherein the ratio of overlapping amplification clusters to monoclonal amplification clusters is at least about 2:1.

Embodiment P76. The method of any one of Embodiment P69 to P75, wherein the plurality of template polynucleotides are double-stranded template polynucleotides.

Embodiment P77. The method of any one of Embodiment P69 to Embodiment P76, wherein prior to step (a), the method further comprises ligating a first adapter to a first end of the first template polynucleotide and ligating a second adapter to a first end of the second template polynucleotide.

Embodiment P78. The method of any one of Embodiment P69 to Embodiment P76, wherein prior to step (a), the method further comprises ligating a first adapter to a first end of the first template polynucleotide, ligating a third adapter to a second end of the first template polynucleotide, ligating a second adapter to a first end of the second template polynucleotide, and ligating a fourth adapter to a second end of the second template polynucleotide.

Embodiment P79. The method of any one of Embodiment P69 to Embodiment P78, wherein the first and second template polynucleotides comprise substantially identical template sequences.

Embodiment P80. The method of any one of Embodiment P69 to Embodiment P78, wherein the first and second template polynucleotides comprise different template sequences.

Embodiment P81. The method of any one of Embodiment P69 to Embodiment P80, wherein the first and second adapter sequences further comprise a barcode sequence.

Embodiment P82. The method of any one of Embodiment P69 to Embodiment P81, wherein the first adapter and/or second adapter is a Y-adapter.

Embodiment P83. The method of any one of Embodiment P69 to Embodiment P82, wherein the first adapter and/or second adapter is a hairpin adapter, wherein the hairpin adapter comprises a cleavable site.

Embodiment P84. The method of any one of Embodiment P69 to Embodiment P83, wherein the amplicons of a first template polynucleotide comprise at least one cleavable site.

Embodiment P85. The method of any one of Embodiment P69 to Embodiment P84, wherein the method comprises about 50 to about 200 sequencing cycles.

Embodiment P86. The method of any one of Embodiment P69 to Embodiment P85, wherein the method comprises a sequencing reaction mixture comprising a different sequencing primer every about 25 to about 75 sequencing cycles.

Embodiment P87. The method of any one of Embodiment P69 to Embodiment P86, wherein the method further comprises incorporating a plurality of native deoxy nucleotide triphosphates (dNTPs) into the 3' end of the extended sequencing primer.

Embodiment P88. The method of any one of Embodiment P69 to Embodiment P87, wherein the method further comprises incorporating a dideoxy nucleotide triphosphate (ddNTP) into the 3' end of each of a plurality of extended sequencing primers.

Embodiment P89. The method of Embodiment P88, wherein the ddNTPs are incorporated into the 3' end of each of a plurality of extended sequencing primers every about 25 to about 75 sequencing cycles.

Embodiment P90. The method of any one of Embodiment P69 to Embodiment P89, wherein the template polynucleotide comprises genomic DNA, complementary DNA (cDNA), cell-free DNA (cfDNA), messenger RNA (mRNA), transfer RNA (tRNA), ribosomal RNA (rRNA), cell-free RNA (cfRNA), or noncoding RNA (ncRNA).

Embodiment P91. The method of any one of Embodiment P69 to Embodiment P90, wherein said amplifying is at discrete locations in an ordered array of amplification sites on the surface.

Embodiment P92. A substrate comprising: (a) a plurality of overlapping amplification clusters on a surface of the substrate, wherein: (i) an overlapping amplification cluster comprises amplicons of a first template polynucleotide comprising a first adapter sequence, and amplicons of a second template polynucleotide comprising a second adapter sequence, wherein the first and second template polynucleotides are not substantially complementary to each other; (ii) said first adapter sequence comprises a first platform primer sequence and a first sequencing primer sequence; (iii) said second adapter sequence comprises a second platform primer sequence and a second sequencing primer sequence; (iv) said first platform primer sequence comprises a sequence complementary to a first amplification primer attached to said surface; (v) said second platform primer sequence comprises a sequence complementary to a second amplification primer attached to said surface; (vi) the first platform primer sequence is different from said second platform primer sequence, said first sequencing primer sequence is different from said second sequencing primer sequence and said first amplification primer is different from said second amplification primer; and (b) a plurality of first sequencing primers hybridized to the first adapter sequences of the overlapping amplification clusters.

Embodiment P93. The substrate of Embodiment P92, wherein the first template polynucleotide further comprises a third adapter sequence, wherein the third adapter sequence comprises: i) a first platform primer sequence complementary to a first amplification primer attached to the surface, and ii) a third sequencing primer sequence; and wherein the second template polynucleotide further comprises a fourth adapter sequence, wherein the fourth adapter sequence comprises: i) a second platform primer sequence complementary to a second amplification primer attached to the surface, and ii) a fourth sequencing primer sequence.

ADDITIONAL EMBODIMENTS

The present disclosure provides the following additional illustrative embodiments.

Embodiment 1. A method of sequencing different populations of polynucleotides immobilized on a solid support, said method comprising: contacting a first population of polynucleotides annealed to a first sequencing primer with a first sequencing solution comprising a plurality of modified nucleotides comprising a reversible terminator and monitoring the sequential incorporation of complementary nucleotides to generate a first sequencing read, wherein the reversible terminator is removed prior to the introduction of the next complementary nucleotide; contacting a second population of polynucleotides annealed to a second sequencing primer with a second sequencing solution comprising a plurality of modified nucleotides comprising a reversible terminator and monitoring the sequential incorporation of complementary nucleotides to generate a second sequencing read, wherein the reversible terminator is removed prior to the introduction of the next complementary nucleotide; contacting a third population of polynucleotides annealed to a third sequencing primer with a third sequencing solution comprising a plurality of modified nucleotides comprising a reversible terminator and monitoring the sequential incorporation of complementary nucleotides to generate a third sequencing read, wherein the reversible terminator is removed prior to the introduction of the next complementary nucleotide; wherein the first sequencing primer, second sequencing primer, and third sequencing primer are different.

Embodiment 2. The method of Embodiment 1, comprising sequencing a plurality of different populations of polynucleotides within overlapping optically resolvable features.

Embodiment 3. The method of Embodiment 1 or 2, wherein the first population of polynucleotides, the second population of polynucleotides, and the third population of polynucleotides are not substantially complementary.

Embodiment 4. The method of any one of Embodiments 1 to 3, wherein monitoring the sequential incorporation of complementary nucleotides comprises a sequencing-by-synthesis, sequencing-by-ligation, or sequencing-by-binding process.

Embodiment 5. The method of any one of Embodiments 1 to 3, wherein monitoring the sequential incorporation of complementary nucleotides comprises incorporating one or more modified nucleotides into the sequencing primer with a polymerase to create an extension strand, and detecting the one or more incorporated nucleotides so as to identify each incorporated nucleotide in said extension strand, thereby generating one or more sequencing reads.

Embodiment 6. The method of any one of Embodiments 1 to 3, wherein monitoring the sequential incorporation of complementary nucleotides comprises incorporating one or more modified nucleotides into the first sequencing primer with a polymerase to create an extension strand, and detecting the one or more incorporated nucleotides in a first optically resolvable feature; incorporating one or more modified nucleotides into the second sequencing primer with a polymerase to create an extension strand, and detecting the one or more incorporated nucleotides in a second optically resolvable feature; incorporating one or more modified nucleotides into the third sequencing primer with a polymerase to create an extension strand, and detecting the one or more incorporated nucleotides in a third optically resolvable feature; and incorporating one or more modified nucleotides into the fourth sequencing primer with a polymerase to create an extension strand, and detecting the one or more incorporated nucleotides in a fourth optically resolvable feature; wherein the optically resolvable features overlap.

Embodiment 7. A method of sequencing a plurality of template polynucleotides on a solid support, said method comprising: (a) amplifying a first template polynucleotide comprising a first adapter sequence and a second adapter sequence, and amplifying a second template polynucleotide comprising a third adapter sequence and a fourth adapter sequence to generate a plurality of overlapping amplification clusters on the solid support, wherein said first adapter sequence comprises a first platform primer binding sequence and a first sequencing primer binding sequence; said second adapter sequence comprises a second platform primer binding sequence and a second sequencing primer binding sequence; said third adapter sequence comprises the first platform primer binding sequence and a third sequencing primer binding sequence; said fourth adapter sequence comprises the second platform primer binding sequence and a fourth sequencing primer binding sequence; (b) sequentially sequencing said overlapping amplification clusters by i) hybridizing a first sequencing primer to the first sequencing primer binding sequence and generating a first sequencing read; ii) hybridizing a second sequencing primer to the second sequencing primer binding sequence and generating a second sequencing read; iii) hybridizing a third sequencing primer to the third sequencing primer binding sequence and generating a third sequencing read; iv) hybridizing a fourth sequencing primer to the fourth sequencing primer binding sequence and generating a fourth sequencing read.

Embodiment 8. The method of Embodiment 7, wherein amplifying comprises hybridizing the first template polynucleotide to a first immobilized oligonucleotide and hybridizing the second template polynucleotide to a second immobilized oligonucleotide and extending the first and second immobilized oligonucleotide to form a plurality of first amplification products and plurality of second amplification products.

Embodiment 9. The method of Embodiment 7 or 8, wherein amplifying the first template polynucleotide and the second template polynucleotide occurs simultaneously.

Embodiment 10. A method of amplifying a plurality of template polynucleotides, the method comprising: (a) contacting a solid support with a first template polynucleotide comprising a first adapter sequence thereby forming a first complex attached to said solid support and contacting the solid support with a second template polynucleotide comprising a second adapter sequence thereby forming a second complex attached to said solid support, wherein: said first adapter sequence comprises a first platform primer binding sequence complementary to a first amplification primer, and a first sequencing primer binding sequence, and said second adapter sequence comprises the first platform primer binding sequence and a second sequencing primer binding sequence; said first complex comprises a first amplification primer attached to the solid support hybridized to said first adapter sequence; and said second complex comprises a second amplification primer attached to the solid support hybridized to said second adapter sequence, wherein the first and second amplification primer comprise the same sequence; and said first sequencing primer binding sequence is different from said second sequencing primer binding sequence; (b) amplifying the first template polynucleotide and the second template polynucleotide to form a plurality of first amplification products and plurality of second amplification products that form overlapping amplification clusters on the solid support.

Embodiment 11. The method of Embodiment 10, further comprising sequentially sequencing said first and second amplification products, said sequencing comprising: (i) hybridizing and extending a first sequencing primer to the first amplification product, incorporating one or more modified nucleotides into the sequencing primer with a polymerase to create an extension strand, and detecting the one or more incorporated nucleotides so as to identify each incorporated nucleotide in said extension strand, thereby generating a first sequencing read; and (ii) hybridizing and extending a second sequencing primer to the second amplification product, incorporating one or more modified nucleotides into the sequencing primer with a polymerase to create an extension strand, and detecting the one or more incorporated nucleotides so as to identify each incorporated nucleotide in said extension strand, thereby generating a second sequencing read.

Embodiment 12. The method of Embodiment 10, further comprising sequentially sequencing said first and second amplification products, said sequencing comprising: hybridizing a first sequencing primer to the first amplification product and contacting the sequencing primer with a sequencing solution comprising one or more modified nucleotides comprising a reversible terminator, and monitoring the sequential incorporation of complementary nucleotides in a first optically resolvable feature, wherein the reversible terminator is removed prior to the introduction of the next complementary nucleotide; and hybridizing a second sequencing primer to the second amplification product and contacting the sequencing primer with a sequencing solution comprising one or more modified nucleotides comprising a reversible terminator, and monitoring the sequential incorporation of complementary nucleotides in a second optically resolvable feature, wherein the reversible terminator is removed prior to the introduction of the next complementary nucleotide; wherein said first and second optically resolvable features overlap.

Embodiment 13. The method of any one of Embodiments 10 to 12, further comprising contacting the solid support with a third template polynucleotide comprising a third adapter sequence thereby forming a third complex attached to said solid support and contacting said solid support with a fourth template polynucleotide comprising a fourth adapter sequence thereby forming a fourth complex attached to said solid support, wherein (i) said third adapter sequence comprises the first platform primer binding sequence and a third sequencing primer binding sequence; (ii) said fourth adapter sequence comprises the second platform primer binding sequence and a fourth sequencing primer binding sequence; and amplifying the third template polynucleotide and the fourth template polynucleotide to form a plurality of third amplification products and plurality of fourth amplification products that form overlapping amplification clusters on the solid support.

Embodiment 14. The method of Embodiment 13, further comprising sequentially sequencing said third and fourth amplification products, said sequencing comprising: (i) hybridizing and extending a third sequencing primer to the third amplification product, incorporating one or more modified nucleotides into the sequencing primer with a polymerase to create an extension strand, and detecting the one or more incorporated nucleotides so as to identify each incorporated nucleotide in said extension strand, thereby generating a third sequencing read; and (ii) hybridizing and extending a fourth sequencing primer to the fourth amplification product, incorporating one or more modified nucleotides into the sequencing primer with a polymerase to create an extension strand, and detecting the one or more incorporated nucleotides so as to identify each incorporated nucleotide in said extension strand, thereby generating a fourth sequencing read.

Embodiment 15. The method of Embodiment 13, further comprising sequentially sequencing said third and fourth amplification products, said sequencing comprising: hybridizing a third sequencing primer to the third amplification product and contacting the sequencing primer with a sequencing solution comprising one or more modified nucleotides comprising a reversible terminator, and monitoring the sequential incorporation of complementary nucleotides in a third optically resolvable feature wherein the reversible terminator is removed prior to the introduction of the next complementary nucleotide; and hybridizing a fourth sequencing primer to the fourth amplification product and contacting the sequencing primer with a sequencing solution comprising one or more modified nucleotides comprising a reversible terminator, and monitoring the sequential incorporation of complementary nucleotides in a fourth optically resolvable feature, wherein the reversible terminator is removed prior to the introduction of the next complementary nucleotide; wherein said third and fourth optically resolvable features overlap.

Embodiment 16. The method of Embodiment 15, wherein the first, second, third, and fourth optically resolvable features overlap.

Embodiment 17. The method of any one of Embodiments 12 to 16, wherein the overlapping optically resolvable features overlap by at least 25%, at least 50%, or at least 75%.

Embodiment 18. The method of any one of Embodiments 12 to 17, wherein said optically resolvable feature comprises an area of about 0.5 µm$^2$ to about 1.5 µm$^2$.

Embodiment 19. A method for amplifying polynucleotides, said method comprising: contacting a solid support with a first population of polynucleotides comprising a first sequencing primer binding sequence thereby forming a first complex, and contacting the solid support with a second population of polynucleotides comprising a second sequencing primer binding sequence thereby forming a second complex, wherein said first complex comprises a first polynucleotide comprising said first sequencing primer binding sequence hybridized to a first oligonucleotide attached to the solid support and wherein said second complex comprises a second polynucleotide comprising said second sequencing primer binding sequence hybridized to a second oligonucleotide attached to the solid support; and contacting said first complex with a polymerase and extending the first oligonucleotide thereby forming a plurality of first amplification products and contacting said second complex with said polymerase and extending the second oligonucleotide thereby forming a plurality of second amplification products.

Embodiment 20. The method of Embodiment 19, wherein said solid support further comprises a first plurality of oligonucleotides comprising said first oligonucleotide attached to the solid support and a second plurality of oligonucleotides comprising said second oligonucleotide attached to the solid support.

Embodiment 21. The method of Embodiment 19 or 20, wherein the first population of polynucleotides and the second population of polynucleotides are each single-stranded prior to forming said first complex and second complex.

Embodiment 22. The method of any one of Embodiments 19 to 21, comprising contacting a solid support with 3, 4, 5, 6, 7, 8, 9, 10, 11, or 12 different populations of polynucleotides wherein each of said different populations have a different sequencing primer binding sequence relative to each different population, and each of said different populations have a common sequencing primer binding sequence within each population.

Embodiment 23. The method of any one of Embodiments 19 to 22, wherein the first population of polynucleotides each further comprise a first platform primer binding sequence complementary to the first plurality of oligonucleotides attached to the solid support and the second population of polynucleotides each further comprise the second platform primer binding sequence complementary to the second plurality of oligonucleotides attached to the solid support.

Embodiment 24. The method of any one of Embodiments 19 to 23, wherein the polynucleotides of the first population of polynucleotides each comprise a first sequencing primer binding sequence and a third sequencing primer binding sequence.

Embodiment 25. The method of any one of Embodiments 19 to 24, wherein the polynucleotides of the second population of polynucleotides each comprise a second sequencing primer binding sequence and a fourth sequencing primer binding sequence.

Embodiment 26. The method of any one of Embodiments 19 to 25, wherein contacting the first complex and the second complex with the polymerase comprises bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, emulsion PCR, or combinations thereof.

Embodiment 27. The method of any one of Embodiments 19 to 26, wherein contacting the first complex and the second complex with the polymerase comprises bridge polymerase chain reaction (bPCR) amplification, solid-phase rolling circle amplification (RCA), or solid-phase exponential rolling circle amplification (eRCA).

Embodiment 28. The method of any one of Embodiments 19 to 27, further comprising sequencing the plurality of first amplification products or complements thereof and sequencing the plurality of second amplification products or complements thereof.

Embodiment 29. The method of Embodiment 28, wherein sequencing comprises a sequencing-by-synthesis or sequencing-by-binding process.

Embodiment 30. The method of Embodiment 28, wherein sequencing comprises hybridizing a first sequencing primer to the plurality of first amplification products and a second sequencing primer to the plurality of second amplification products, or complements thereof, and contacting the first sequencing primer and the second sequencing primer with a sequencing solution comprising one or more modified nucleotides comprising a reversible terminator, and monitoring the sequential incorporation of complementary nucleotides to generate one or more sequencing reads, wherein the reversible terminator is removed prior to the introduction of the next complementary nucleotide.

Embodiment 31. The method of Embodiment 28, wherein sequencing comprises hybridizing a first sequencing primer to the plurality of first amplification products and a second sequencing primer to the plurality of second amplification products, or complements thereof, incorporating one or more modified nucleotides comprising a reversible terminator into the first sequencing primer with the polymerase to create a first extension strand and incorporating one or more modified nucleotides comprising a reversible terminator into the second sequencing primer with the polymerase to create a second extension strand, and detecting the one or more incorporated nucleotides so as to identify each incorporated nucleotide in said extension strand, thereby generating one or more sequencing reads, wherein the reversible terminator is removed prior to the introduction of the next complementary nucleotide.

Embodiment 32. The method of Embodiment 28, wherein sequencing comprises hybridizing a first sequencing primer to the plurality of first amplification products and a second sequencing primer to the plurality of second amplification products, or complements thereof, incorporating one or more modified nucleotides into the first sequencing primer with the polymerase to create a first extension strand and detecting the one or more incorporated nucleotides in a first optically resolvable feature; and incorporating one or more modified nucleotides into the second sequencing primer with the polymerase to create a second extension strand, and detecting the one or more incorporated nucleotides in a second optically resolvable feature; wherein the first and second optically resolvable features overlap.

Embodiment 33. The method of Embodiment 32, wherein the method further comprises incorporating a dideoxy nucleotide triphosphate (ddNTP) into the first extension strand prior to hybridizing the second sequencing primer.

Embodiment 34. The method of Embodiment 32 or 33, wherein the optically resolvable features overlap by at least 25%, at least 50%, or at least 75%.

Embodiment 35. The method of any one of Embodiments 32 to 34, wherein said optically resolvable feature comprises an area of about 0.5 µm² to about 1.5 µm².

Embodiment 36. The method of any one of Embodiments 1 to 9 or 11 to 18 or 28 to 35, wherein the sequencing primer is a sequence selected from the group consisting of SEQ ID NO:1 to SEQ ID NO:96, or a complement thereof.

Embodiment 37. The method of any one of Embodiments 1 to 9 or 11 to 18 or 28 to 36, comprising generating about 500 million (M) to about $3\times10^{11}$ sequencing reads.

Embodiment 38. The method of any one of Embodiments 1 to 37, wherein the solid support is a multiwell container or an unpatterned solid support.

Embodiment 39. The method of any one of Embodiments 1 to 38, wherein the solid support comprises a plurality of oligonucleotides immobilized to a polymer.

Embodiment 40. The method of any one of Embodiments 1 to 39, wherein the solid support comprises a plurality of particles.

Embodiment 41. The method of any one of Embodiments 1 to 40, wherein the plurality of oligonucleotides is present at a density of about 100 oligonucleotides per µm² to about 1,000,000 oligonucleotides per µm².

Embodiment 42. The method of any one of Embodiments 1 to 41, wherein each template polynucleotide is not reseeded, reamplified, or both reseeded and reamplified after generating each sequencing read.

Embodiment 43. The method of any one of Embodiments 2 to 42, wherein the method generates a total number of sequencing reads greater than the number of optically resolvable features on the solid support.

Embodiment 44. The method of any one of Embodiments 2 to 42, wherein the method generates a total number of sequencing reads greater than 100% of the optically resolvable features on the solid support.

Embodiment 45. A substrate comprising: (a) a plurality of amplification clusters on a solid support, wherein: (i) one or more amplification clusters comprises one or more copies of a first template polynucleotide comprising a first adapter sequence, and one or more copies of a second template polynucleotide comprising a second adapter sequence, wherein the first and second template polynucleotides are not substantially complementary to each other; and (ii) said first adapter sequence comprises a first platform primer binding sequence and a first sequencing primer binding sequence; and said second adapter sequence comprises the first platform primer binding sequence and a second sequencing primer binding sequence, wherein said first sequencing primer binding sequence is different from said second sequencing primer binding sequence and wherein said first platform primer binding sequence comprises a sequence complementary to a first amplification primer attached to said solid support; and (b) a plurality of first sequencing primers hybridized to the first adapter sequences of the amplification clusters.

Embodiment 46. A kit comprising the substrate of Embodiment 45.

Embodiment 47. A kit comprising an adapter composition, said adapter composition comprising: a first adapter comprising a first platform primer binding sequence and a first sequencing primer binding sequence; a second adapter comprising a second platform primer binding sequence and a second sequencing primer binding sequence; a third adapter comprising the third platform primer binding sequence and a third sequencing primer binding sequence, wherein the first sequencing primer binding sequence, second sequencing primer binding sequence, and the third sequencing primer binding sequence are different.

Embodiment 48. The kit of Embodiment 47, further comprising a fourth adapter, comprising the second platform primer binding sequence and a fourth sequencing primer binding sequence.

Embodiment 49. The kit of Embodiment 47 or 48, wherein each adapter is in a separate container.

Embodiment 50. The kit of Embodiment 47 or 48, wherein each adapter is in a single container.

Embodiment 51. The kit of Embodiment 49, further comprising 4 or more different sequencing primers.

What is claimed is:

1. A method of sequencing different populations of polynucleotides immobilized on a solid support, wherein the solid support is a multiwell container, said method comprising:

contacting a first population of polynucleotides annealed to a first sequencing primer with a first sequencing solution comprising a plurality of modified nucleotides comprising a reversible terminator and monitoring the sequential incorporation of complementary nucleotides to generate a first sequencing read, wherein the reversible terminator is removed prior to the introduction of the next complementary nucleotide, wherein the first sequencing primer comprises SEQ ID NO: 1;

contacting a second population of polynucleotides annealed to a second sequencing primer with a second sequencing solution comprising a plurality of modified nucleotides comprising a reversible terminator and monitoring the sequential incorporation of complementary nucleotides to generate a second sequencing read, wherein the reversible terminator is removed prior to the introduction of the next complementary nucleotide; and contacting a third population of polynucleotides annealed to a third sequencing primer with a third sequencing solution comprising a plurality of modified nucleotides comprising a reversible terminator and monitoring the sequential incorporation of complementary nucleotides to generate a third sequencing read, wherein the reversible terminator is removed prior to the introduction of the next complementary nucleotide;

wherein the first sequencing primer, second sequencing primer, and third sequencing primer are different.

2. The method of claim 1, comprising sequencing a plurality of different populations of polynucleotides within overlapping optically resolvable features.

3. The method of claim 2, wherein the first population of polynucleotides, the second population of polynucleotides, and the third population of polynucleotides are not substantially complementary.

4. The method of claim 1, wherein monitoring the sequential incorporation of complementary nucleotides comprises a sequencing-by-synthesis, sequencing-by-ligation, or sequencing-by-binding process.

5. The method of claim 1, wherein monitoring the sequential incorporation of complementary nucleotides comprises incorporating one or more modified nucleotides into the sequencing primer with a polymerase to create an extension strand, and detecting the one or more incorporated nucleotides so as to identify each incorporated nucleotide in said extension strand, thereby generating one or more sequencing reads.

6. The method of claim 1, wherein monitoring the sequential incorporation of complementary nucleotides comprises
   incorporating one or more modified nucleotides into the first sequencing primer with a polymerase to create an extension strand, and detecting the one or more incorporated nucleotides in a first optically resolvable feature;
   incorporating one or more modified nucleotides into the second sequencing primer with a polymerase to create an extension strand, and detecting the one or more incorporated nucleotides in a second optically resolvable feature; and
   incorporating one or more modified nucleotides into the third sequencing primer with a polymerase to create an extension strand, and detecting the one or more incorporated nucleotides in a third optically resolvable feature; wherein the first, second, and third optically resolvable features overlap.

7. The method of claim 1, comprising generating about 500 million (M) to about $3 \times 10^{11}$ sequencing reads.

8. The method of claim 1, wherein the multiwell container solid comprises a plurality of oligonucleotides immobilized to a polymer.

9. The method of claim 1, wherein the multiwell container comprises a plurality of particles.

10. The method of claim 1, wherein the multiwell container comprises a plurality of oligonucleotides at a density of about 100 oligonucleotides per $\mu m^2$ to about 1,000,000 oligonucleotides per $\mu m^2$.

11. The method of claim 1, wherein each template polynucleotide is not reseeded, reamplified, or both reseeded and reamplified after generating each sequencing read.

12. The method of claim 2, wherein the method generates a total number of sequencing reads greater than the number of optically resolvable features on the multiwell container.

13. The method of claim 2, wherein the method generates a total number of sequencing reads greater than 100% of the optically resolvable features on the multiwell container.

14. The method of claim 1, wherein the first population of polynucleotides, the second population of polynucleotides, and the third population of polynucleotides each comprise a platform primer binding sequence, wherein said platform primer binding sequence is the same.

15. The method of claim 1, wherein the first population of polynucleotides comprises a first and a second sequencing primer binding sequence, and the second population of polynucleotides comprises a first and a third sequencing primer binding sequence.

16. The method of claim 1, wherein the first population of polynucleotides comprises a first and a second sequencing primer binding sequence, and the second population of polynucleotides comprises a third and a fourth sequencing primer binding sequence.

17. The method of claim 6, wherein the optically resolvable features overlap by at least 25%.

18. The method of claim 6, wherein the optically resolvable features overlap by between at least 25% to 75%.

19. The method of claim 1, comprising monitoring the sequential incorporation of 5 or more complementary nucleotides prior to contacting a population of polynucleotides with a different sequencing solution.

20. The method of claim 1, comprising monitoring the sequential incorporation of 5 to 100 complementary nucleotides prior to contacting a population of polynucleotides with a different sequencing solution.

21. A method of sequencing different polynucleotides immobilized on a solid support, wherein the solid support is a multiwell container, said method comprising:
   contacting a first polynucleotide annealed to a first sequencing primer with a first sequencing solution comprising a plurality of modified nucleotides comprising a reversible terminator, and incorporating one or more modified nucleotides into the first sequencing primer with a polymerase to create a first extension strand, and detecting the one or more incorporated nucleotides so as to identify each incorporated nucleotide in the first extension strand, thereby generating a first sequencing read, wherein the first sequencing primer comprises SEQ ID NO: 1;
   contacting a second polynucleotide annealed to a second sequencing primer with a second sequencing solution comprising a plurality of modified nucleotides comprising a reversible terminator and incorporating one or more modified nucleotides into the second sequencing primer with a polymerase to create a second extension strand, and detecting the one or more incorporated nucleotides so as to identify each incorporated nucleotide in the second extension strand, thereby generating a second sequencing read; and
   contacting a third polynucleotide annealed to a third sequencing primer with a third sequencing solution comprising a plurality of modified nucleotides comprising a reversible terminator and incorporating one or more modified nucleotides into the third sequencing primer with a polymerase to create a third extension strand, and detecting the one or more incorporated nucleotides so as to identify each incorporated nucleotide in the third extension strand, thereby generating a third sequencing read;

wherein the first sequencing primer, second sequencing primer, and third sequencing primer are different.

* * * * *